(12) United States Patent
Welsh et al.

(10) Patent No.: US 10,851,096 B2
(45) Date of Patent: Dec. 1, 2020

(54) ARYL AND HETEROARYL AMIDES FOR USE AS ANTI-PROLIFERATIVE, ANTI-THROMBOTIC, AND ANTI-VIRAL AGENTS

(71) Applicants: Rutgers, The State University of New Jersey, New Brunswick, NJ (US); The Curators of the University of Missouri, Columbia, MO (US)

(72) Inventors: William J. Welsh, New Brunswick, NJ (US); Raymond Birge, New Brunswick, NJ (US); Vladyslav Kholodovych, New Brunswick, NJ (US); Youyi Peng, New Brunswick, NJ (US); Thomas Walter Comollo, New Brunswick, NJ (US); Stanley G. Kimani, New Brunswick, NJ (US); Kamlendra Singh, Columbia, MO (US)

(73) Assignees: Rutgers, The State University of New Jersey, New Brunswick, NJ (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/311,136

(22) PCT Filed: Jun. 16, 2017

(86) PCT No.: PCT/US2017/037895
§ 371 (c)(1),
(2) Date: Dec. 18, 2018

(87) PCT Pub. No.: WO2017/222930
PCT Pub. Date: Dec. 28, 2017

(65) Prior Publication Data
US 2019/0127361 A1    May 2, 2019

Related U.S. Application Data

(60) Provisional application No. 62/352,499, filed on Jun. 20, 2016.

(51) Int. Cl.
C07D 417/12 (2006.01)
C07D 413/12 (2006.01)
(Continued)

(52) U.S. Cl.
CPC ............ *C07D 417/12* (2013.01); *A61K 31/42* (2013.01); *A61K 31/496* (2013.01); *A61P 7/02* (2018.01);
(Continued)

(58) Field of Classification Search
CPC ......................... C07D 261/08; C07D 295/192; C07D 409/14; C07D 413/12; C07D 413/14; C07D 417/12; C07D 417/14
See application file for complete search history.

(56) References Cited

U.S. PATENT DOCUMENTS 3,987,179 A   10/1976 Nadelson
2004/0266840 A1   12/2004 Singh et al.
(Continued)

FOREIGN PATENT DOCUMENTS

WO    2004019882 A2    3/2004

OTHER PUBLICATIONS

Chemical Abstracts, RN 1180216-81-2 (public availability Sep. 4, 2009).*
(Continued)

*Primary Examiner* — Valerie Rodriguez-Garcia
(74) *Attorney, Agent, or Firm* — Viksnins Harris Padys Malen LLP

(57) ABSTRACT

Certain compounds of formula I: I and salts including pharmaceutically acceptable salts thereof are disclosed. Also
(Continued)

disclosed are pharmaceutical compositions comprising a compound of formula I, processes for preparing compounds of formula I, intermediates useful for preparing compounds of formula I and therapeutic methods using a compound of formula I.

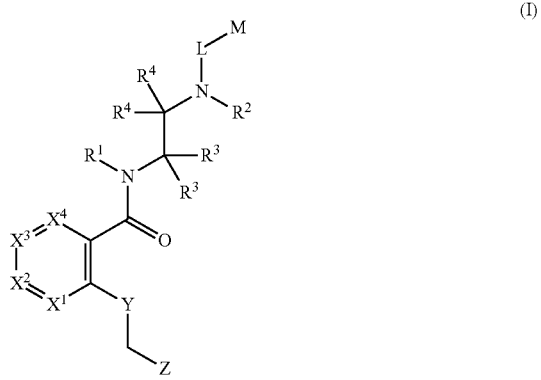

(I)

18 Claims, 15 Drawing Sheets

(51) Int. Cl.
```
C07D 261/08      (2006.01)
A61K 31/42       (2006.01)
C07D 295/192     (2006.01)
A61K 31/496      (2006.01)
A61P 7/02        (2006.01)
A61P 9/00        (2006.01)
A61P 31/18       (2006.01)
A61P 35/00       (2006.01)
C07D 409/14      (2006.01)
C07D 413/14      (2006.01)
C07D 417/14      (2006.01)
```
(52) U.S. Cl.
CPC ............... *A61P 9/00* (2018.01); *A61P 31/18* (2018.01); *A61P 35/00* (2018.01); *C07D 261/08* (2013.01); *C07D 295/192* (2013.01); *C07D 409/14* (2013.01); *C07D 413/12* (2013.01); *C07D 413/14* (2013.01); *C07D 417/14* (2013.01)

(56) References Cited

U.S. PATENT DOCUMENTS

2010/0184766 A1   7/2010   Kunzer et al.
2014/0128410 A1   5/2014   Cai et al.

OTHER PUBLICATIONS

CAS Registry Search, 1-300, May 10, 2016.

Cohen, P., et al., "Delayed apoptotic cell clearance and lupus-like autoimmunity in mice lacking the c-mer membrane tyrosine kinase", Journal of Experimental Medicine 196(1),135-140 (2002).
Duncan, J., et al., "An RCS-Like Retinal Dystrophy Phenotype in Mer Knockout Mice", Invest Ophthalmol Vis Sci 44 (2), 826-838 (2003).
Graham, D., et al., "The TAM family: phosphatidylserine-sensing receptor tyrosine kinases gone awry in cancer", Nature Reviews Cancer 14(12), 769-785 (2014).
Hamel, R., et al., "Biology of Zika Virus Infection in Human Skin Cells", Journal of Virology 89 (17), 8880-8896 (2015).
Keating, A., et al., "Inhibition of Mer and Axl Receptor Tyrosine Kinases in Astrocytoma Cells Leads to Increased Apoptosis and Improved Chemosensitivity", Molecular Cancer Therapeutics 9(5), 1298-1307 (2010).
Kimani, S., et al., "Small molecule inhibitors block Gas6-inducible TAM activation and tumorigenicity", Sci Rep 7, 43908 (2017).
Lemke, G., "Biology of the TAM Receptors", Cold Spring Harbor Perspectives in Biology 5(11), a009076 (2013).
Linger, R., et al., "Mer or Axl Receptor Tyrosine Kinase Inhibition Promotes Apoptosis, Blocks Growth, and Enhances Chemosensitivity of Human Non-Small Cell Lung Cancer", Oncogene 32(29), 3420-3431 (2013).
Linger, R., et al., "Mer receptor tyrosine kinase is a therapeutic target in pre-B-cell acute lymphoblastic leukemia", Blood 122(9), 1599-1609 (2013).
Linger, R., et al., "TAM Receptor Tyrosine Kinases: Biologic Functions, Signaling, and Potential Therapeutic Targeting in Human Cancer", Advances in Cancer Research 100, 35-83 (2008).
Lu, Q., et al., "Homeostatic regulation of the immune system by receptor tyrosine kinases of the Tyro 3 family", Science 293(5528), 306-311 (2001).
Nowakowski, et al., "Expression Analysis Highlights AXL as a Candidate Zika Virus Entry Receptor in Neural Stem Cells", Cell Stem Cell 18, 1-6 (2016).
Patent Cooperation Treaty, International Searching Authority, Search Report and Written Opinion for PCT/US2017/37895, 8 pages, dated Sep. 13, 2017.
PubChem, PubChem CID: 1124072, BAS 02257413, 1-12, deposited on Jul. 10, 2005.
Rothlin, C., et al., "TAM Receptor Signaling in Immune Homeostasis", Annual Review of Immunology 33, 355-391 (2015).
Rothlin, C., et al., "TAM Receptors Are Pleiotropic Inhibitors of the Innate Immune Response", Cell 131(6), 1124-1136 (2007).
Scott, R., et al., "Phagocytosis and clearance of apoptotic cells is mediated by MER", Nature 411(6834), 207-211 (2001).
Seitz, H., et al., "Macrophages and Dendritic Cells Use Different Axl/Mertk/Tyro3 Receptors in Clearance of Apoptotic Cells", Journal of Immunology 178(9), 5635-5642 (2007).
Verma, A., et al., "Targeting Axl and Mer Kinases in Cancer", Molecular Cancer Therapeutics 10(10), 1763-1773 (2011).
Zhang, N., et al., "Activation of the AXL kinase causes resistance to EGFR-targeted therapy in lung cancer", Nature Genetics 44(8), 852-860 (2012).
Nakamura, H., et al., "Synthesis and biological evaluation of benzamides and benzamidines as selective inhibitors of VEGFR tyrosine kinases", Biorganic & Medicinal Chemisty Letters 16(19), 5127-5131 (2006).

\* cited by examiner

1M

1N

1O

1P

1Q

1R

1S

ARYL AND HETEROARYL AMIDES FOR USE AS ANTI-PROLIFERATIVE, ANTI-THROMBOTIC, AND ANTI-VIRAL AGENTS

CROSS-REFERENCE TO RELATED APPLICATIONS

This application is a 35 U.S.C. § 371 application of International Application No. PCT/US2017/037895, filed Jun. 16, 2017, which claims the benefit of priority of U.S. Application Ser. No. 62/352,499, filed Jun. 20, 2016, which application is herein incorporated by reference.

BACKGROUND

The TAM receptors (Tyro-3, Axl, and Mer) are a family of three homologous type I receptor tyrosine kinases (RTKs) that have complex and multifactorial roles in physiological and pathophysiological processes. (Mer and MerTK are used interchangeably throughout this document.) All three TAMs have a highly conserved intracellular kinase domain and a less conserved extracellular region characterized by two tandem immunoglobulin-like (Ig) domains and two tandem fibronectin type III repeats (Graham D. K., et al., *Nature reviews Cancer* 2014 December; 14(12): 769-785; Lemke G., Biology of the TAM receptors. *Cold Spring Harbor perspectives in biology* 2013 November; 5(11): a009076; Verma A., et al., *Molecular cancer therapeutics* 2011 October; 10(10): 1763-1773). The main ligands for TAMs are the vitamin K-dependent soluble proteins Growth arrest-specific 6 (Gas6) and Protein S (Pros1), that interact with the tandem Ig1 (major contact) and Ig2 (minor contact) domains to trigger receptor dimerization and activation. The crystal structure of the Axl Ig1/Ig2 duet, in complex with Gas6 LG1 and LG2 has been solved by X-ray crystallography at 3.3 Å resolution (PDB Ref. Code 2C5D), confirming the main features of the ligand-receptor interface necessary for high affinity ligand binding.

Functionally, TAM receptors are not essential for embryonic development and triple knockout of Tyro, Axl, and Mer have surprisingly unremarkable phenotypes through postnatal life. However, in adulthood, particularly after puberty, triple knockout mice develop widespread systemic inflammation characterized, in part, by the loss of negative regulation of Toll-like receptors (TLRs)s in myeloid-derived cells (Rothlin C. V., et al., *Annual review of immunology* 2015; 33: 355-391; Rothlin C. V., et al., *Cell* 2007 Dec. 14; 131(6): 1124-113), and constitutive elevation in pro-inflammatory cytokines that drive age-dependent autoimmunity (Lu Q., Lemke G., *Science* 2001 Jul. 13; 293(5528): 306-311). Subsequent studies showed that TAMs have specialized functions as homeostatic receptors that function in the clearance of apoptotic cells and the resolution of inflammation (reviewed in Graham D. K., *Nature reviews Cancer*). Single knockouts of Tyro-3, Axl, or Mer share some of the aforementioned effects of enhanced inflammation and hyper-activation of immune subsets, albeit with milder phenotypic outcomes, due in part to the non-overlapping expression of TAMs in different immune subsets such as macrophages (M1 versus M2), dendritic cells (DCs), Natural Killer cells (NK cells), epithelial subsets, and lymphocytes such as CD4+ T cells (Seitz H. M., et al., *Journal of immunology* 2007 May 1; 178(9): 5635-5642). Mice that lack Mer show significant impairment in macrophage (M2)-dependent clearance of apoptotic cells in peripheral tissues (Cohen P. L., et al., *The Journal of experimental medicine* 2002 Jul. 1; 196(1): 135-140; Scott R. S., et al., *Nature* 2001 May 10; 411(6834): 207-211) as well as retinitis pigmentosa as a consequence of defective clearance of disposed rod outer segments by retinal pigmented epithelial cells (RPEs) in the retina (Duncan J. L., et al., *Invest Ophthalmol Vis Sci* 2003 February; 44(2): 826-838; Finnemann S. C., et al., *Advances in experimental medicine and biology* 2006; 572: 499-503).

In addition to their homeostatic roles in apoptotic cell clearance and tissue homeostasis under physiological conditions, all three TAM receptors are frequently overexpressed in human cancers, and clinically associated with aggressive tumor progression and poor survival outcome (reviewed in Graham D. K., *Nature reviews Cancer*). Overexpression of TAMs can drive conventional oncogenic signaling and survival pathways in both hematopoietic and solid cancers (Linger R. M., et al., Advances in cancer research 2008; 100: 35-83; Linger R. M., et al., Blood 2013 Aug. 29; 122(9): 1599-1609), and can also induce intrinsic drug resistance (Keating A. K., et al., *Molecular cancer therapeutics* 2010 May; 9(5): 1298-1307; Linger R. M., et al., *Oncogene* 2013 Jul. 18; 32(29): 3420-3431) that includes acquired resistance to first-line TKIs for EGFR (Gefitinib) and Met (BMS 777607) (Zhang Z., et al., Lee *Nature genetics* 2012 August; 44(8): 852-860). Moreover, TAMs (particularly Axl and Mer) are expressed on tumor-infiltrating myeloid-derived cells such as macrophages, DCs, and NK cells, and have been identified as suppressors of anti-tumor immunity. Indeed, inhibition of TAM expression/function, either via genetic ablation or via targeted TKI-based therapeutics, improves overall tumor immunity, suggesting that TAMs may act as checkpoint inhibitors akin to CTLA-4, PD-1, and PD-L1. TAM antagonists, therefore, may have opportunistic dual target specificity, initially to target overexpressed/activated TAMs on cancer cells, and secondarily as immune checkpoint inhibitors on infiltrating innate immune cells to block tolerance.

Coincident with clinical evidence linking TAMs with poor patient outcomes in cancer, there has been great interest in recent years to develop TAM therapeutics in the form of small molecule TKIs, antagonistic monoclonal antibodies (mAbs), and fusion proteins (Axl-Fc) that act as receptor traps to neutralize TAM ligands, each of which has distinct modes of action and specific strengths and weaknesses. Here we describe a fourth approach to inhibit TAM receptors by virtue of the development and characterization of novel small molecule inhibitors (SMIs) that block binding of the Gas6 LG domain to the major Ig1 domain in Axl in the extracellular region. Employing methods in rational (computer-aided) drug design, we discovered and characterized a focused series of SMIs that target a hydrophobic pocket near the major interaction site between the LG domain of Gas6 and the Ig1 domain of Axl and inhibit native receptors and Axl reporter lines with sub-micromolar activities. Additionally, these compounds inhibit Gas6-inducible motility and invasion in Axl-expressing cell lines, and suppress tumor growth in mouse xenograft models of lung cancer. These observations confirm that the Ig1 domain/Gas6 interface is an attractive target for developing small-molecule Ig1 inhibitors, and offer a novel approach to target TAMs in pathophysiological conditions.

Accordingly, there is a need for therapeutic agents and methods that treat cancer or stimulate immune responses in patients with HIV or treat other diseases or conditions such as thrombosis, platelet aggregation, or a viral infection (e.g., Zika virus).

SUMMARY OF INVENTION

One embodiment provides a method for treating cancer, a viral infection, a thrombotic event, or platelet aggregation in a mammal in need there of comprising administering to the mammal in need thereof a compound of formula I:

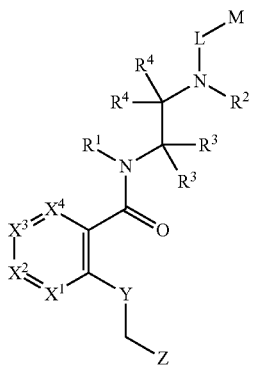

wherein:

$X^1$ is N or $CR^{a1}$, $X^2$ is N or $CR^{a2}$, $X^3$ is N or $CR^{a3}$, $X^4$ is N or $CR^{a4}$ provided no more than two of $X^1$, $X^2$, $X^3$, or $X^4$ is N;

each $R^{a1}$, $R^{a2}$, $R^{a3}$, and $R^{a4}$ is independently hydrogen, halogen, $(C_1-C_4)$alkyl, $(C_1-C_4)$haloalkyl, —$O(C_1-C_4)$alkyl, or —$O(C_1-C_4)$haloalkyl;

Y is S, S(=O), S(=O)$_2$, or O;

Z is phenyl, 5-membered heteroaryl, or 6-membered heteroaryl, wherein any phenyl, 5-membered heteroaryl, or 6-membered heteroaryl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl;

$R^1$ is hydrogen or $(C_1-C_4)$alkyl and $R^2$ is hydrogen or $(C_1-C_4)$alkyl, or $R^1$ and $R^2$ together with atoms to which they are attached form a piperazinyl, wherein the piperazinyl is optionally substituted with one or more halogen, $(C_1-C_4)$alkyl, $(C_1-C_4)$haloalkyl, —$O(C_1-C_4)$alkyl, or —$O(C_1-C_4)$haloalkyl;

each $R^3$ is independently hydrogen or $(C_1-C_4)$alkyl;

each $R^4$ is independently hydrogen or $(C_1-C_4)$alkyl;

L is absent, $L^1$, or -$L^2C(=O)NR^bL^3$-;

$L^1$ is —$(C_1-C_6)$alkyl-optionally substituted with one or more halogen or oxo;

$L^2$ is absent or —$(C_1-C_6)$alkyl-optionally substituted with one or more halogen;

$L^3$ is absent or —$(C_1-C_6)$alkyl-optionally substituted with one or more halogen;

$R^b$ is hydrogen or $(C_1-C_4)$alkyl; and

M is aryl, 5-10-membered heteroaryl, or 5-10-membered heterocycle, wherein any aryl, 5-10-membered heteroaryl, or 5-10-membered heterocycle of M is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl;

or a pharmaceutically acceptable salt thereof.

One embodiment provides a novel compound of formula I:

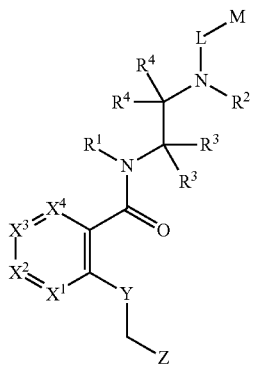

wherein:

$X^1$ is N or $CR^{a1}$, $X^2$ is N or $CR^{a2}$, $X^3$ is N or $CR^{a3}$, $X^4$ is N or $CR^{a4}$ provided no more than two of $X^1$, $X^2$, $X^3$, or $X^4$ is N;

each $R^{a1}$, $R^{a2}$, $R^{a3}$, and $R^{a4}$ is independently hydrogen, halogen, $(C_1-C_4)$alkyl, $(C_1-C_4)$haloalkyl, —$O(C_1-C_4)$alkyl, or —$O(C_1-C_4)$haloalkyl;

Y is S, S(=O), S(=O)$_2$, or O;

Z is a 5-membered heteroaryl, or 6-membered heteroaryl, wherein any 5-membered heteroaryl, or 6-membered heteroaryl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl;

$R^1$ is hydrogen or $(C_1-C_4)$alkyl, $R^2$ is hydrogen or $(C_1-C_4)$alkyl and L is absent; or $R^1$ and $R^2$ together with the atoms to which they are attached form a piperazine and L is absent or -$L^2C(=O)NR^bL^3$-, wherein the piperizinyl is optionally substituted with one or more halogen, $(C_1-C_4)$alkyl, $(C_1-C_4)$haloalkyl, —$O(C_1-C_4)$alkyl, or —$O(C_1-C_4)$haloalkyl;

each $R^3$ is independently hydrogen or $(C_1-C_4)$alkyl;

each $R^4$ is independently hydrogen or $(C_1-C_4)$alkyl;

$L^2$ is —$(C_1-C_6)$alkyl-optionally substituted with one or more halogen;

$L^3$ is absent or —$(C_1-C_6)$alkyl-optionally substituted with one or more halogen;

$R^b$ is hydrogen or $(C_1-C_4)$alkyl; and

M is aryl, 5-10-membered heteroaryl, or a 5-10 membered heterocycle, wherein any aryl, 5-10-membered heteroaryl, or 5-10 membered heterocycle of M is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl;

or a salt thereof.

One embodiment provides a pharmaceutical composition comprising a compound of formula I or a pharmaceutically acceptable salt thereof as described herein, and a pharmaceutically acceptable carrier.

One embodiment provides a method of treating cancer, a viral infection, a thrombotic event, or platelet aggregation in an animal (e.g., a mammal such as a human) comprising administering to the animal in need thereof a compound of formula I or a pharmaceutically acceptable salt thereof as described herein.

One embodiment provides a compound of formula I or a pharmaceutically acceptable salt thereof as described herein for use in medical therapy.

One embodiment provides a compound of formula I or a pharmaceutically acceptable salt thereof as described herein for the prophylactic or therapeutic treatment of cancer, a viral infection, a thrombotic event, or platelet aggregation.

One embodiment provides the use of a compound of formula I or a pharmaceutically acceptable salt thereof as described herein to prepare a medicament for treating cancer, a viral infection, a thrombotic event, or platelet aggregation in an animal (e.g., a mammal such as a human).

One embodiment provides a biomarker comprising a labeled compound of formula I or a pharmaceutically acceptable salt thereof as described herein to prepare a medicament for treating cancer, a viral infection, a thrombotic event, or platelet aggregation in an animal (e.g., a mammal such as a human).

One embodiment provides a method for diagnosing a disease or condition comprising administering biomarker comprising a labeled compound of formula I or a pharmaceutically acceptable salt thereof as described herein to an animal (e.g., a mammal such as a human).

One embodiment provides processes and intermediates disclosed herein that are useful for preparing a compound of formula I or a salt thereof.

DETAILED DESCRIPTION

Figure 1:
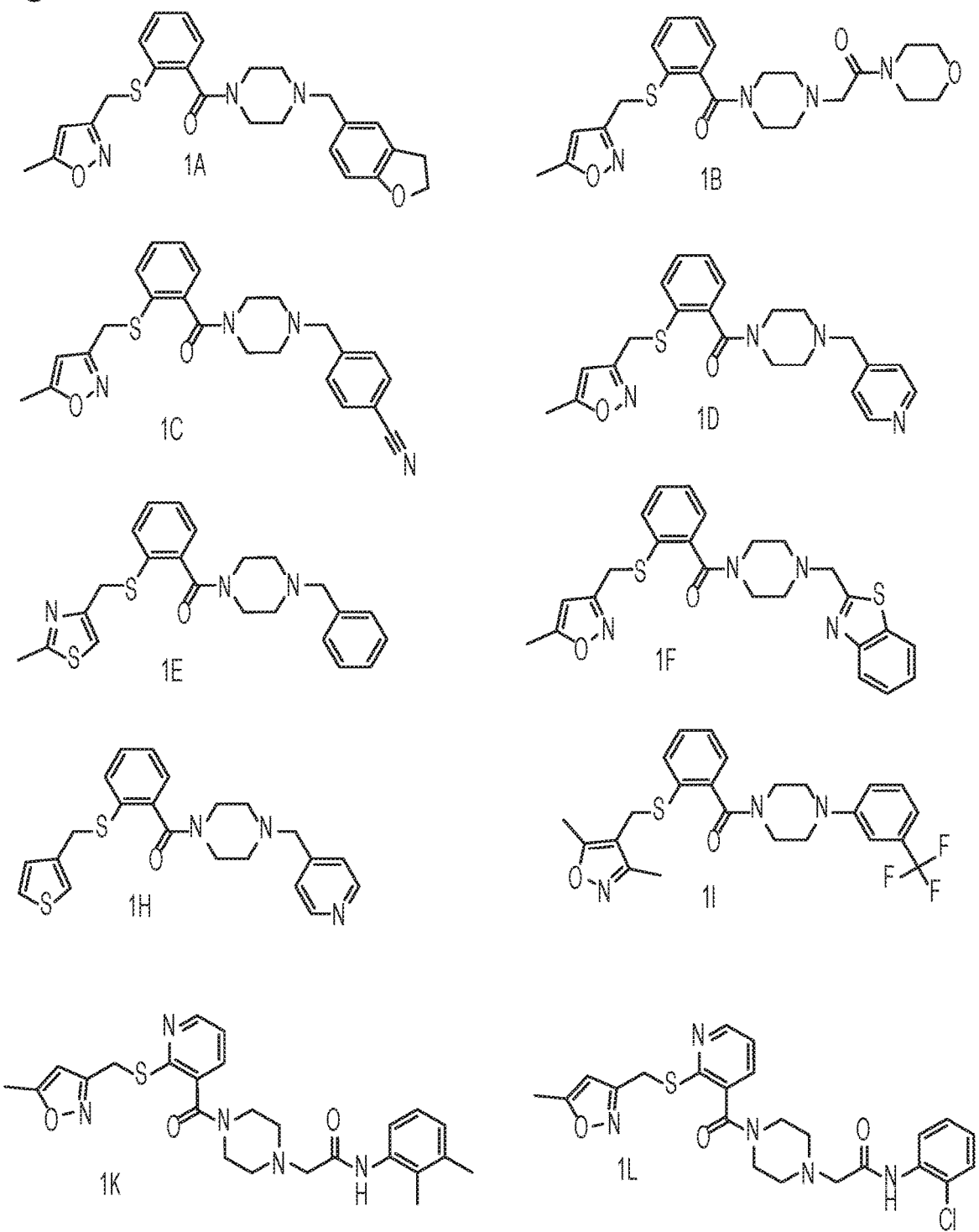
FIG. 1 illustrates certain compounds.
Figure 1:
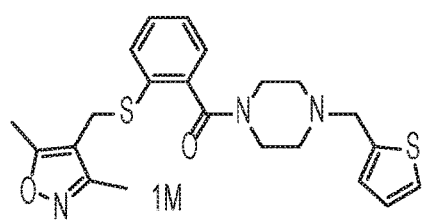
Figure 1:
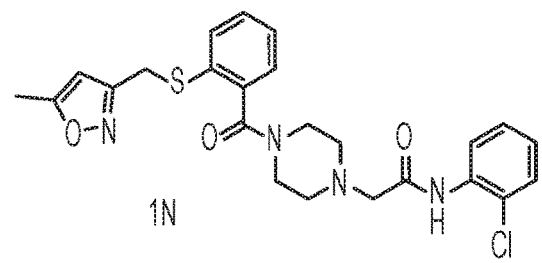
Figure 1:
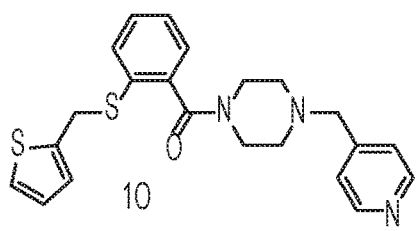
Figure 1:
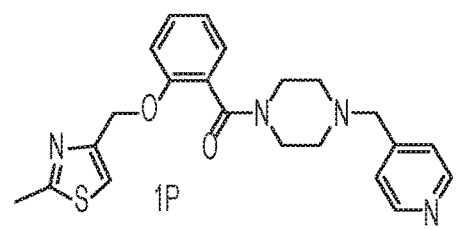
Figure 1:
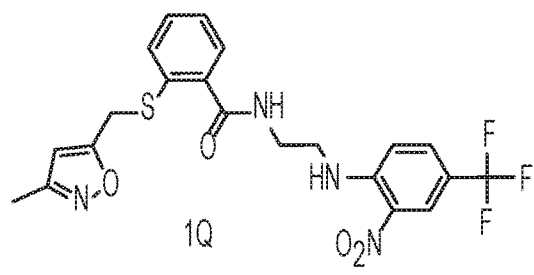
Figure 1:
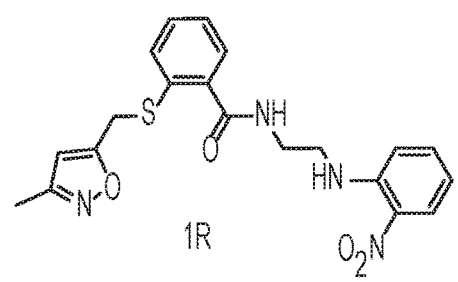
Figure 1:
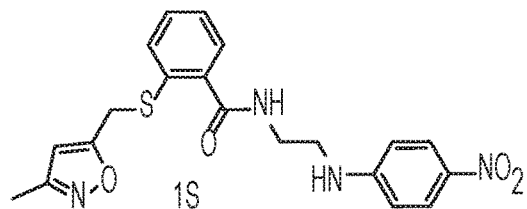

The following definitions are used, unless otherwise described.

The term "halo" or "halogen" as used herein refers to fluoro, chloro, bromo and iodo.

The term "alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms. As used herein alkyl groups may used as linkers (e.g., linking two or more fragments of a compound of formula I).

The term "haloalkyl" as used herein refers to an alkyl as defined herein, wherein one or more hydrogen atoms are each replaced by a halo substituent. For example, a ($C_1$-$C_6$) haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "aryl" as used herein refers to a single aromatic ring or a bicyclic or multicyclic ring. For example, an aryl group can have 6 to 20 carbon atoms, 6 to 14 carbon atoms, 6 to 12 carbon atoms, or 6 to 10 carbon atoms. Aryl includes a phenyl radical or an ortho-fused bicyclic or multicyclic radical having about 9 to 14 atoms or 9-10 atoms in which at least one ring is aromatic (e.g., an aryl fused to one or more aryl or carbocycle). Such bicyclic or multicyclic rings may be optionally substituted with one or more (e.g., 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Exemplary aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2 or 3 rings) wherein a heteroaryl group, as defined above, can be fused with one or more heteroaryls (e.g., naphthyridinyl), carbocycles (e.g., 5,6,7,8-tetrahydroquinolyl) or aryls (e.g., indazolyl) to form a multiple condensed ring. Such multiple condensed rings may be optionally substituted with one or more (e.g., 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl, thianaphthenyl, pyrrolopyridinyl and pyrazolopyridinyl.

The term "heterocyclyl" or "heterocycle" as used herein refers to a single saturated or partially unsaturated ring or a multiple condensed ring. The term includes single saturated or partially unsaturated rings (e.g., 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g., ring systems comprising 2 or 3 rings) wherein a heterocycle group (as defined above) can be connected to two adjacent atoms (fused heterocycle) with one or more heterocycles (e.g., decahydronapthyridinyl), heteroaryls (e.g., 1,2,3,4-tetrahydronaphthyridinyl), carbocycles (e.g., decahydroquinolyl) or aryls. It is to be understood that the point of attachment of a heterocycle multiple condensed ring, as defined above, can be at any position of the ring including a heterocyle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, tetrahydropyrimidinyl-2-one, imidazolidinyl-2-one, pyrrolidinyl-2-one, 2,3-dihydropyrano[4,3,2-de]quinolonyl, 2,5-benzo[d][1,3]dioxolyl and chromanyl-4-one.

The term "carbocycle" or "carbocyclyl" refers to a saturated (i.e., cycloalkyl) or partially unsaturated (e.g., cycloalkenyl, cycloalkadienyl, etc.) ring having 3 to 7 carbon atoms as a monocycle or a mutlicyclic ring system. In one embodiment the carbocycle is a monocycle comprising 3-6 ring carbons (i.e. ($C_3$-$C_6$)carbocycle). Carbocycle includes multicyclic carbocyles having 7 to 12 carbon atoms as a bicyclic ring, and up to about 20 carbon atoms as a polycycle provided that the largest single ring of a multicyclic carbocycle is 7 carbon atoms. The term "spirobicyclic carbocycle" refers to a carbocycle bicyclic ring system wherein the rings of the bicyclic ring system are connected to a single carbon atom (e.g., spiropentane, spiro [4,5]decane, spiro[4.5]decane, etc.). The term "fused-bicyclic carbocycle" refers to a carbocycle bicyclic ring system wherein the rings of the bicyclic ring system are connected to two adjacent carbon atoms such as a bicyclo [4,5], [5,5], [5,6] or [6,6] system, or 9 or 10 ring atoms arranged as a bicyclo [5,6] or [6,6] system (e.g., decahydronaphthalene, norsabinane, norcarane). The term "bridged-bicyclic carbocycle" refers to a carbocycle bicyclic ring system wherein the rings of the bicyclic ring system are connected to two non-adjacent carbon (e.g., norbornane, bicyclo[2.2.2]octane, etc). The "carbocycle" or "carbocyclyl" may be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "patient" as used herein refers to any animal including mammals such as humans, higher non-human primates, rodents, domestic and farm animals such as cows, horses, pigs, sheep, dogs and cats. In one embodiment, the patient is a human patient. In one embodiment, the mammal is a human. In one embodiment, the patient is a human patient.

The phrase "therapeutically effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

Specific embodiments listed below for radicals, substituents, and ranges, are for illustration only; they do not exclude other defined embodiments or values or other values within defined ranges for the radicals and substituents. It is to be understood that two or more embodiments may be combined. The embodiments listed herein below (and subsets thereof) are embodiments for compounds of formula I (including the compounds of formula I as used in the methods described herein) and all related formulas (e.g., compounds of formulas Ia, Ib, Ic, Id).

It is also to be understood that the embodiments listed herein below (or subsets thereof) can be excluded from compounds of formula I (including the compounds of formula I as used in the methods described herein) and all related formulas (e.g., compounds of formulas Ia, Ib, Ic, Id).

In one embodiment Y is S, S(=O), S(=O)$_2$;

In one embodiment Y is S.

In one embodiment Y is O.

In one embodiment $X^1$ is $CR^{a1}$, $X^2$ is $CR^{a2}$, $X^3$ is $CR^{a3}$, and $X^4$ is $CR^{a4}$.

In one embodiment $X^1$ is CH, $X^2$ is CH, $X^3$ is CH, and $X^4$ is CH.

In one embodiment $X^1$ is N, $X^2$ is $CR^{a2}$, $X^3$ is $CR^{a3}$, and $X^4$ is $CR^{a4}$.

In one embodiment $X^1$ is N, $X^2$ is CH, $X^3$ is CH, and $X^4$ is CH.

In one embodiment $X^1$ is N, $X^2$ is $CR^{a2}$, $X^3$ is N, and $X^4$ is $CR^{a4}$.

In one embodiment $X^1$ is N, $X^2$ is CH, $X^3$ is N, and $X^4$ is CH.

In one embodiment Z is a 5-membered heteroaryl or 6-membered heteroaryl, wherein any 5-membered heteroaryl or 6-membered heteroaryl of Z is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl.

In one embodiment Z is an isoxazolyl, wherein any isoxazolyl of Z is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl.

In one embodiment Z is isoxazol-3-yl, isoxazol-4-yl, or isoxazol-5-yl, wherein any isoxazol-3-yl, isoxazol-4-yl, or isoxazol-5-yl of Z is optionally substituted with one or more (C$_1$-C$_4$)alkyl.

In one embodiment Z is:

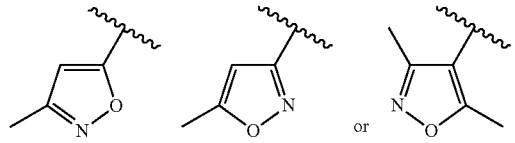

In one embodiment $R^1$ is hydrogen or (C$_1$-C$_4$)alkyl and $R^2$ is hydrogen or (C$_1$-C$_4$)alkyl.

In one embodiment $R^1$ is hydrogen and $R^2$ is hydrogen.

In one embodiment $R^1$ and $R^2$ together with the atoms to which they are attached form a piperazinyl, wherein the piperazinyl is optionally substituted with one or more halogen, (C$_1$-C$_4$)alkyl, (C$_1$-C$_4$)haloalkyl, —O(C$_1$-C$_4$)alkyl, or —O(C$_1$-C$_4$)haloalkyl.

In one embodiment $R^1$ and $R^2$ together with the atoms to which they are attached form a piperizinyl.

In one embodiment each $R^3$ is hydrogen and each $R^4$ is hydrogen.

In one embodiment L is absent, —(C$_1$-C$_6$)alkyl-, or -L$^2$C(=O)NR$^b$L$^3$-.

In one embodiment L$^2$ is —(C$_1$-C$_6$)alkyl-, and L$^3$ is absent or —(C$_1$-C$_6$)alkyl-.

In one embodiment $R^b$ is hydrogen, methyl or ethyl.

In one embodiment L is absent.

In one embodiment L is —(C$_1$-C$_6$)alkyl.

In one embodiment L is absent, —(CH$_2$)—, —CH$_2$C(=O)NHCH$_2$—, —CH$_2$C(=O)N(CH$_2$CH$_3$)CH$_2$—, or —CH$_2$C(=O)NH—.

In one embodiment M is phenyl, benzothiazolyl, pyridinyl, benzoxazolyl, thiazolyl, benzoimidazolyl, or pyrimidinyl, wherein any phenyl, benzothiazolyl, pyridinyl, benzoxazolyl, thiazolyl, benzoimidazolyl, or pyrimidinyl of M is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl.

In one embodiment M is phenyl, morpholinyl, benzothiazolyl, pyridinyl, thiophenyl, dihydrobenzofuranyl, or benzoimidazolyl, wherein any phenyl, morpholinyl, benzothiazolyl, pyridinyl, thiophenyl, dihydrobenzofuranyl, or benzoimidazolyl of M is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl.

In one embodiment M is:

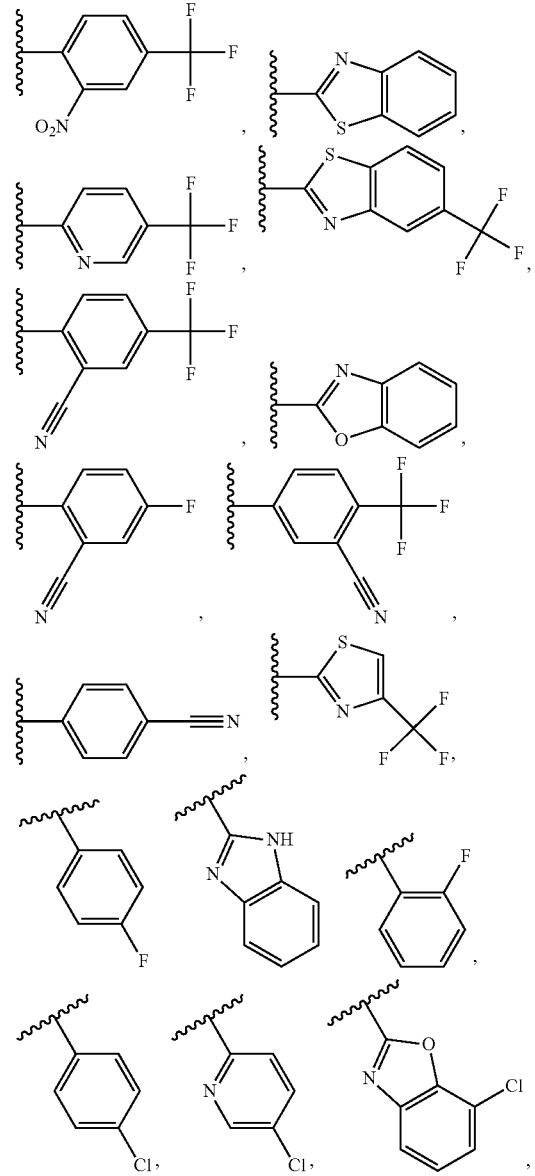

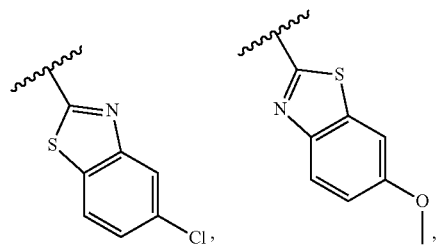
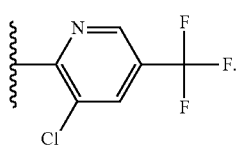
In one embodiment the residue:
-L-M
of the compound of formula I is:
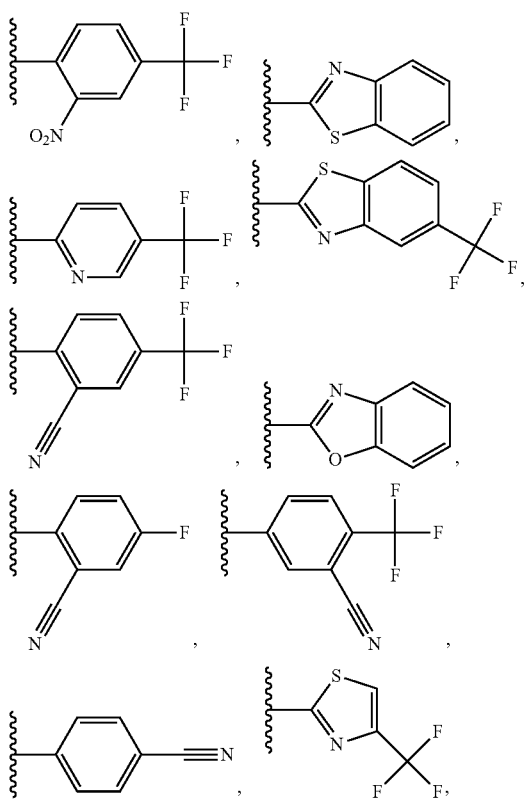
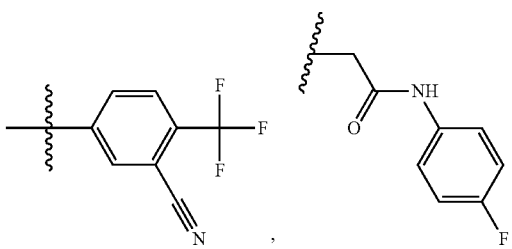
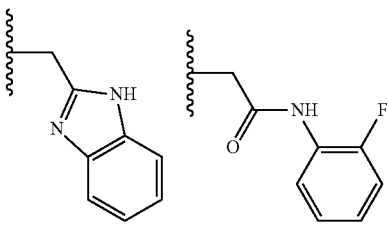
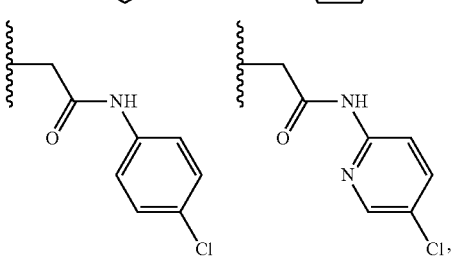
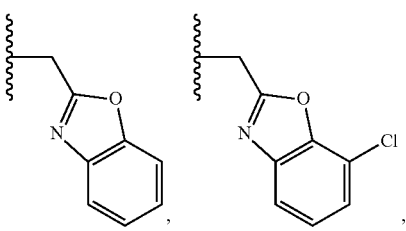
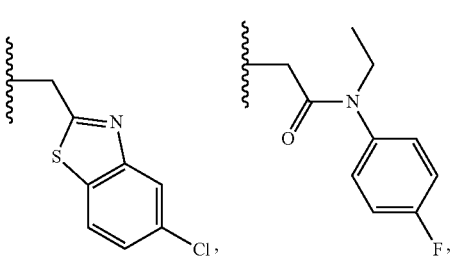
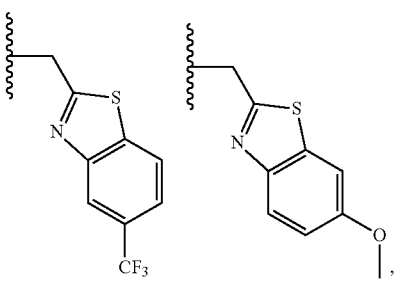
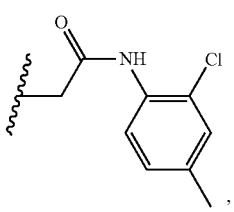

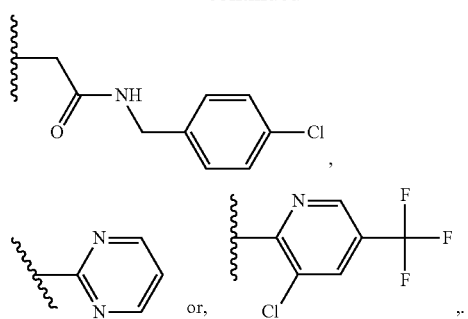
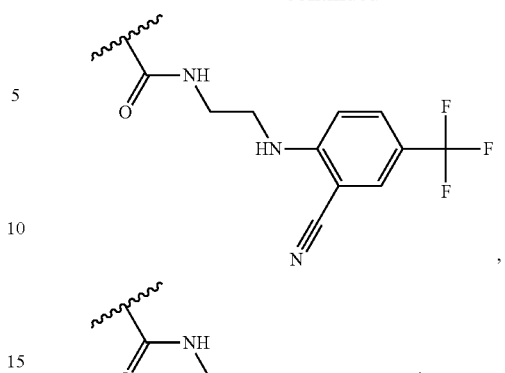
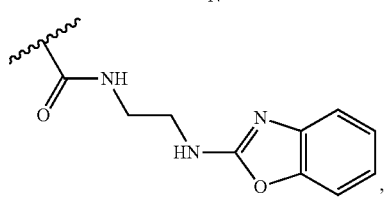
In one embodiment the residue:
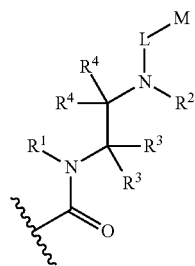
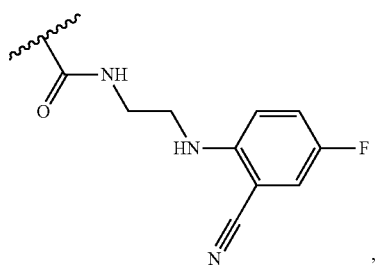
of the compound of formula I is:
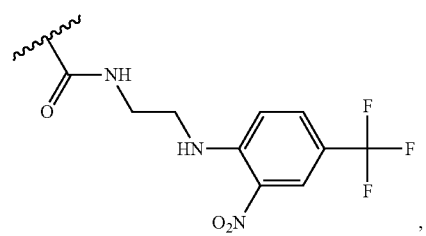
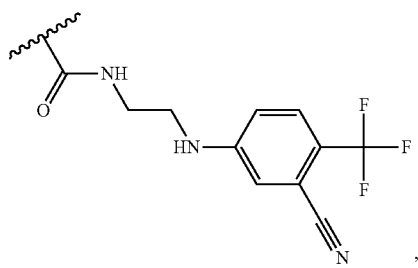
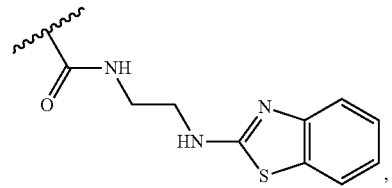
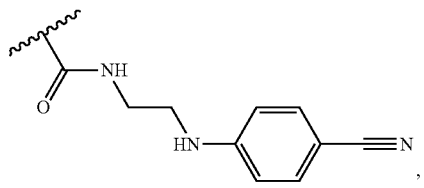
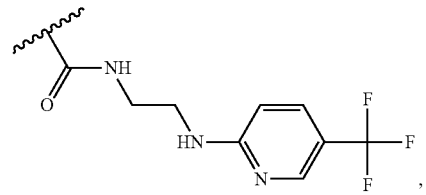
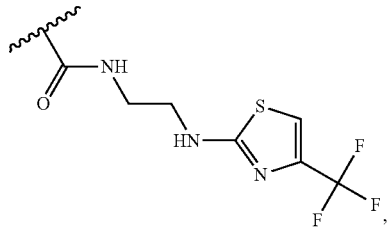
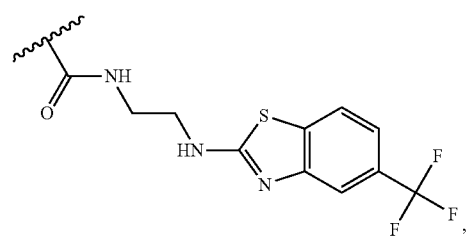
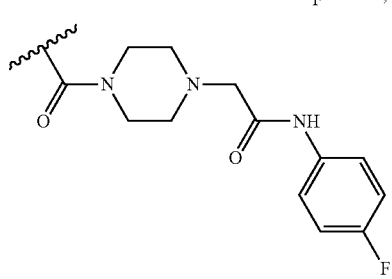

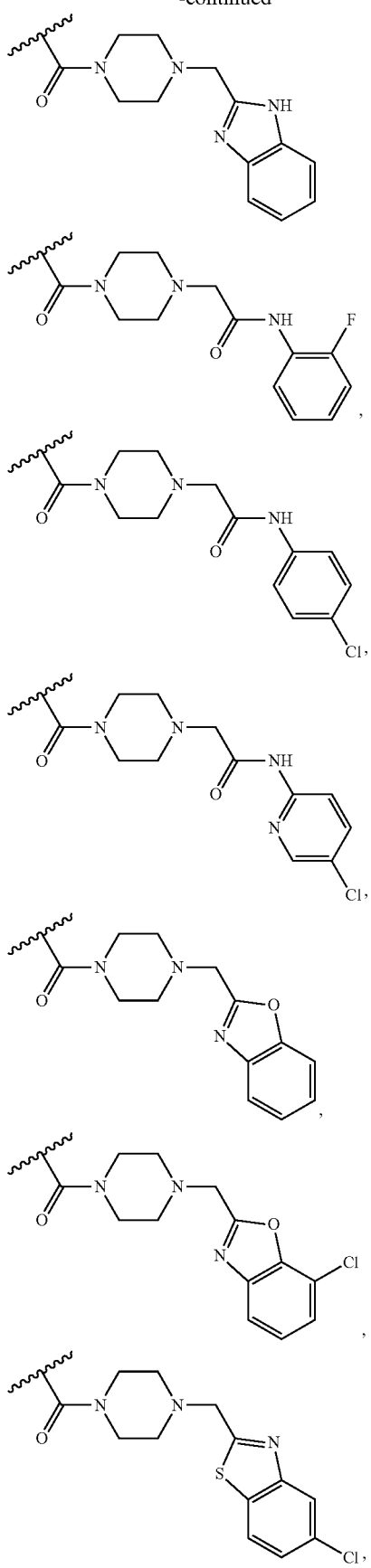
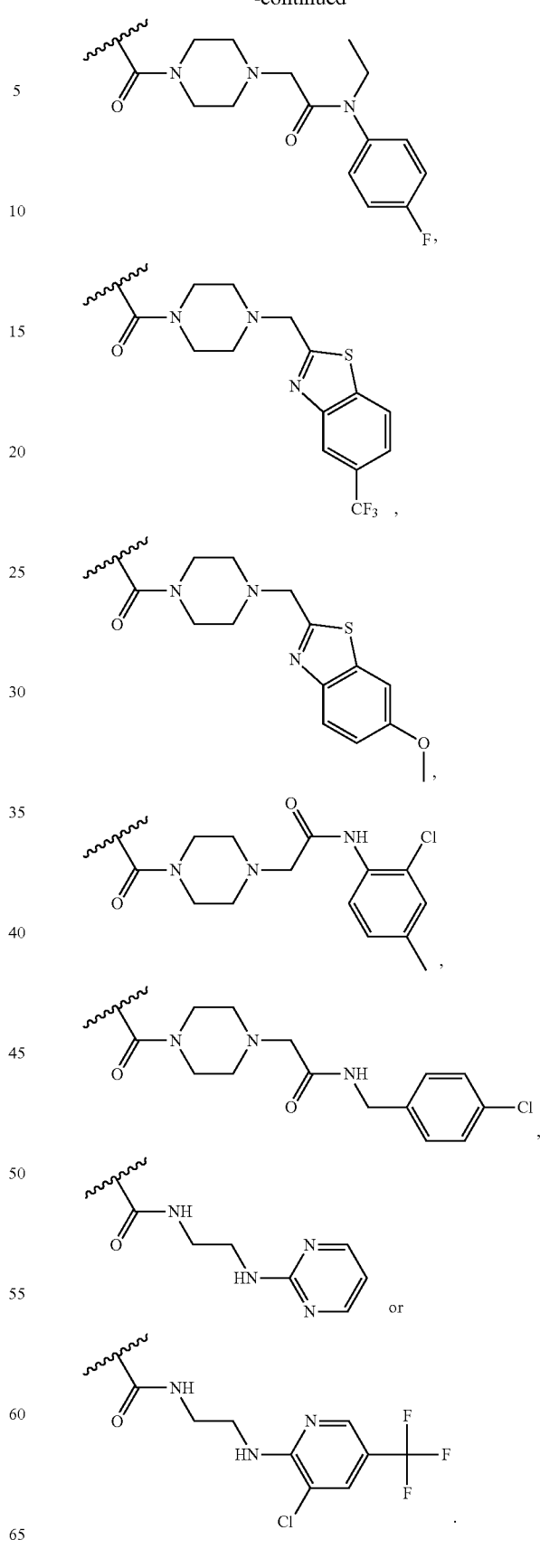

In one embodiment a compound of formula I is:
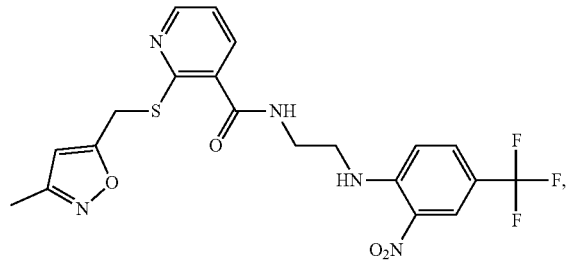
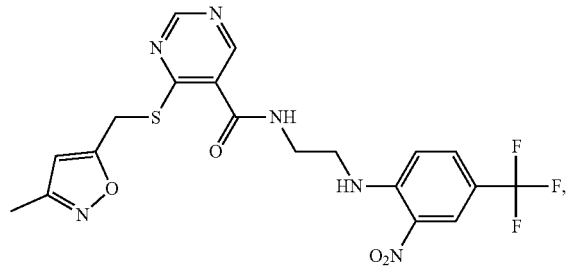
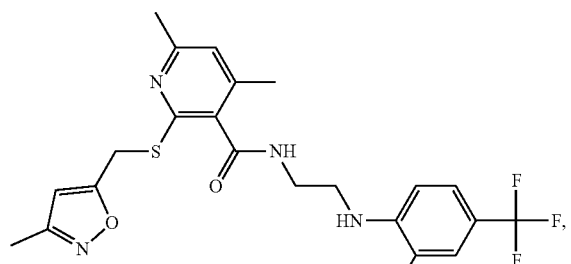
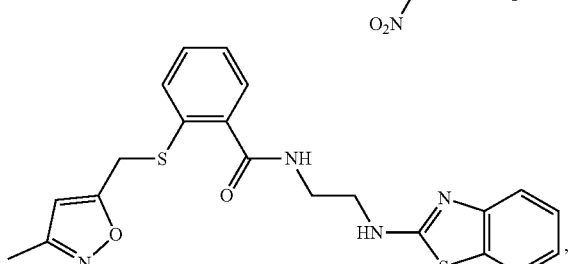
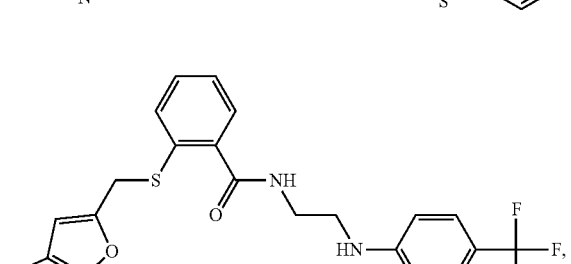
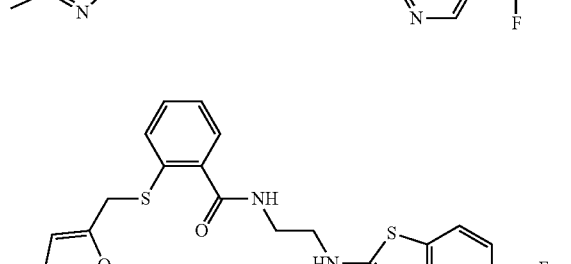
-continued
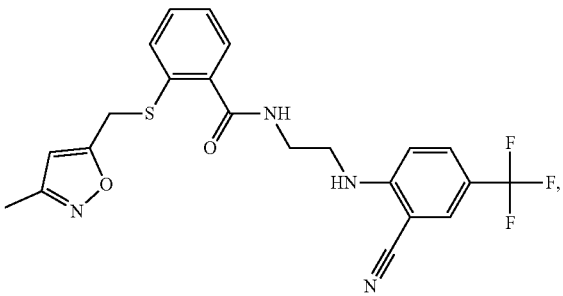
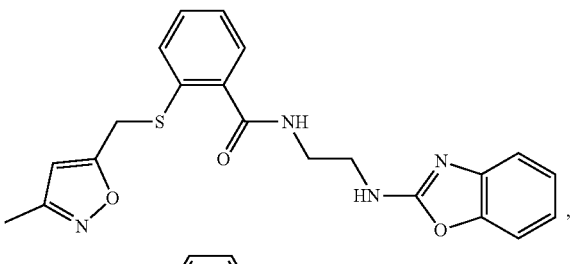
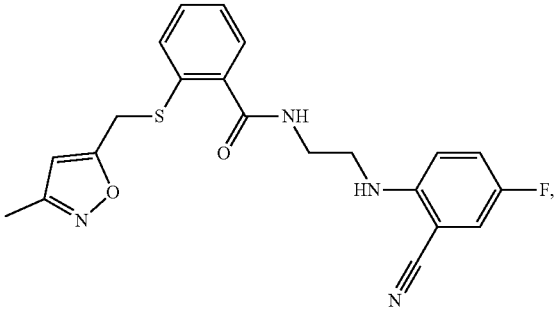
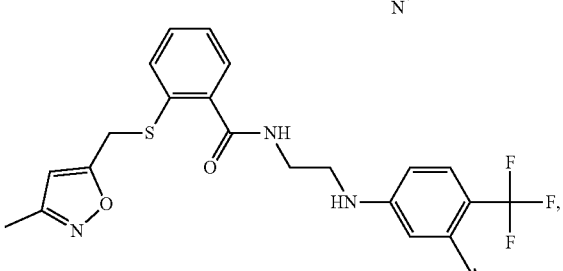
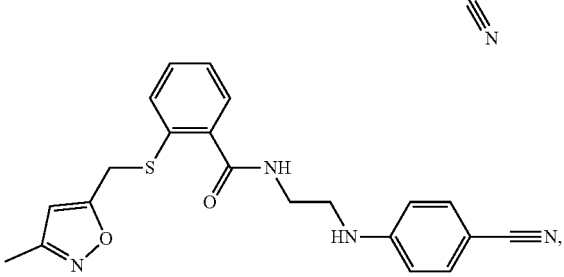
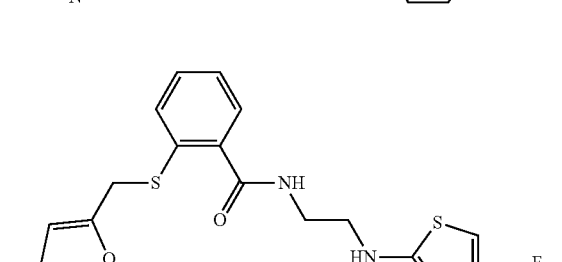

21
-continued
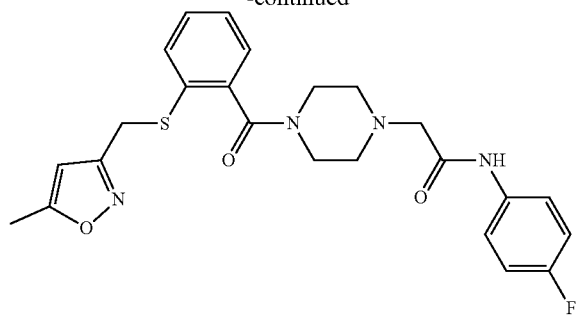
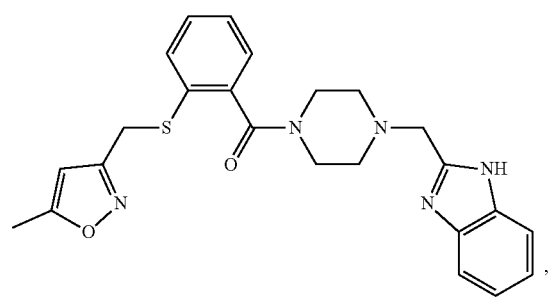
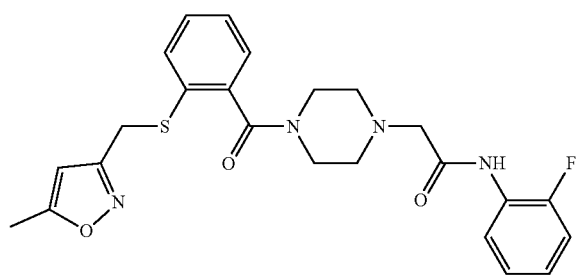
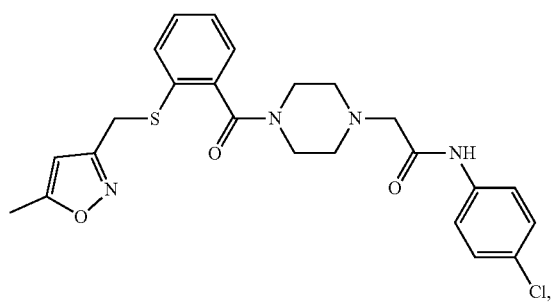
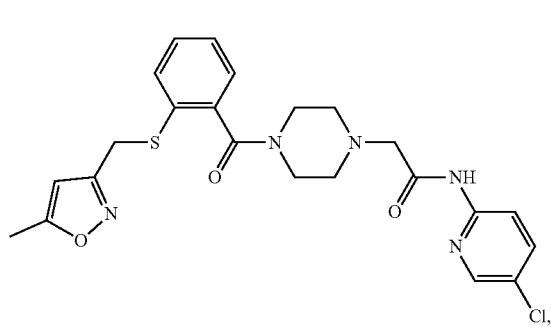
22
-continued
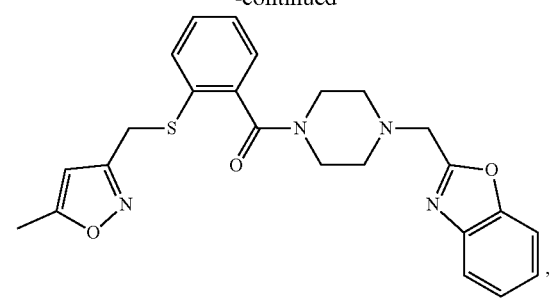
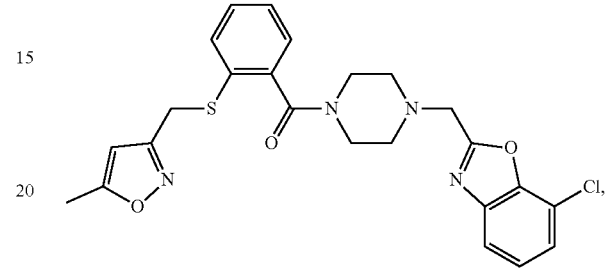
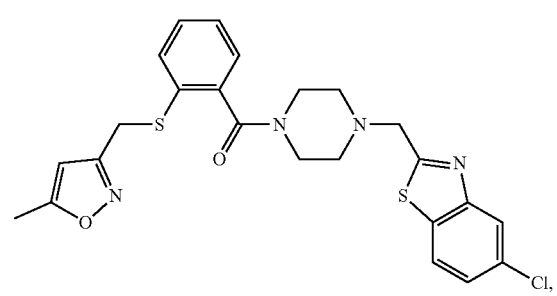
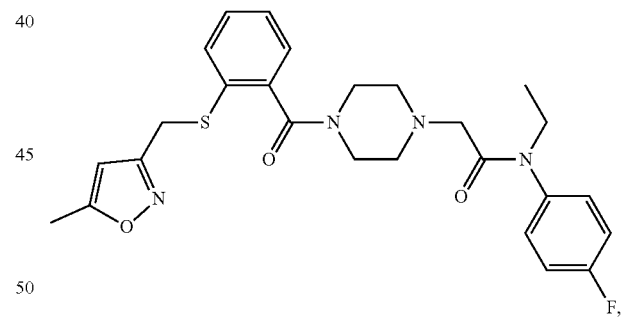
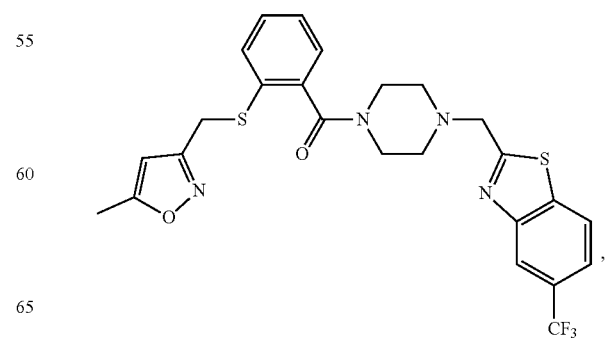

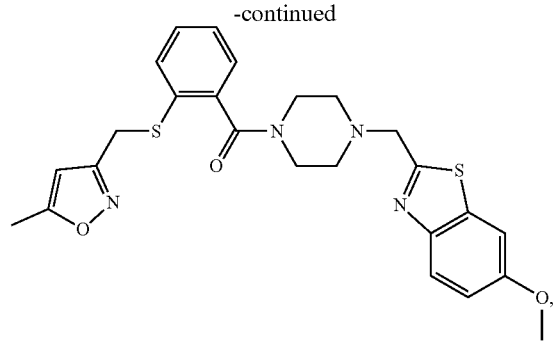
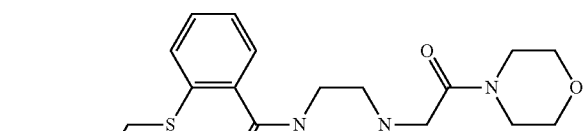
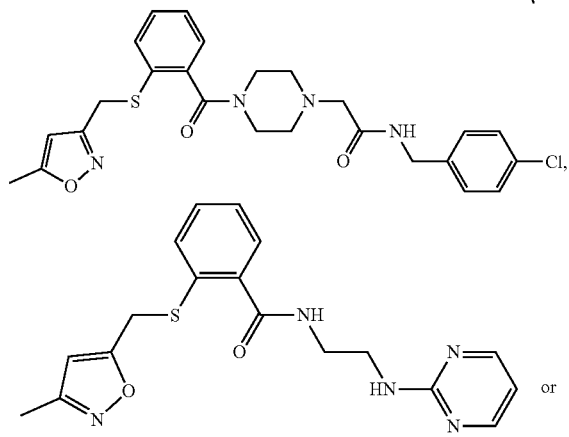
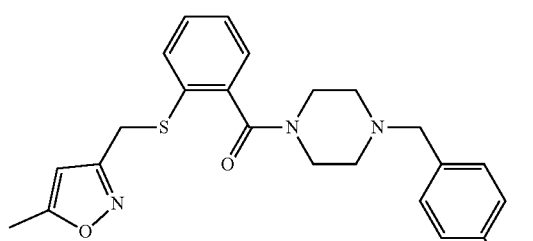
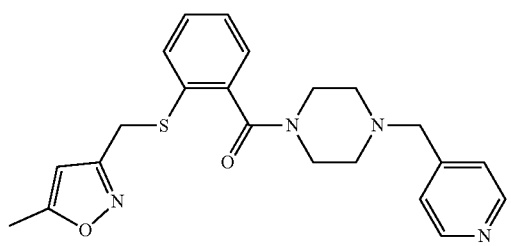
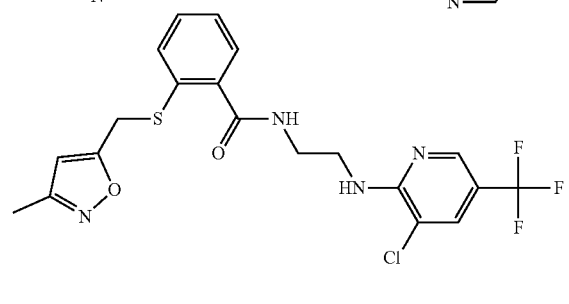
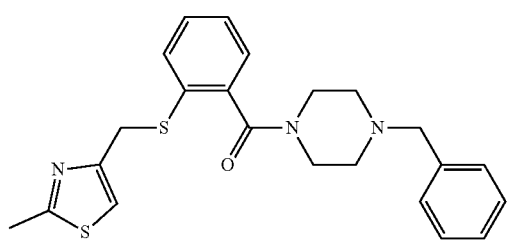
or
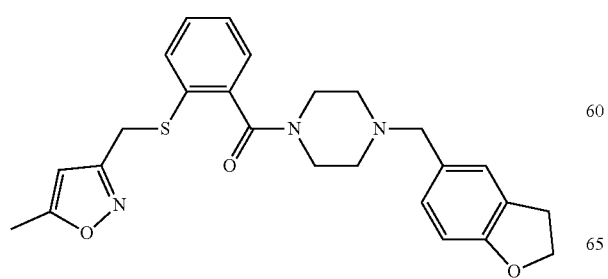
or a salt thereof.
In one embodiment a compound of formula I is:
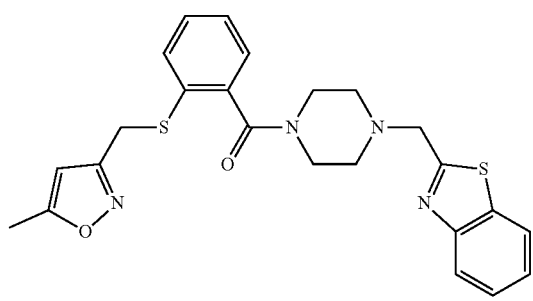

1H
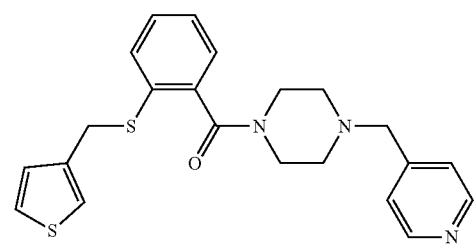
1I
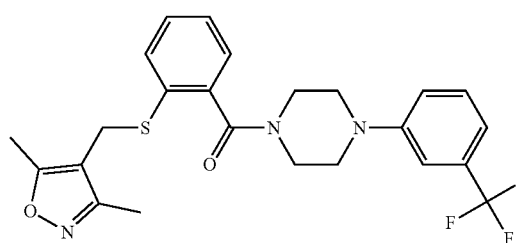
1K
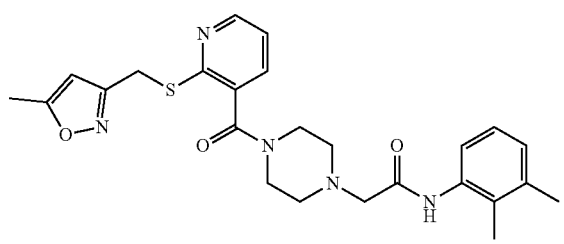
1L
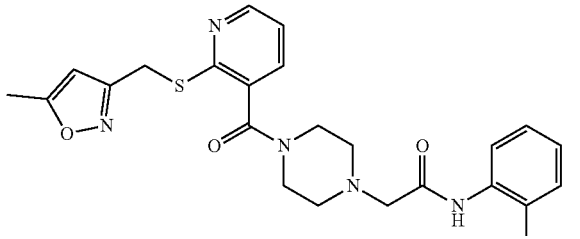
1M
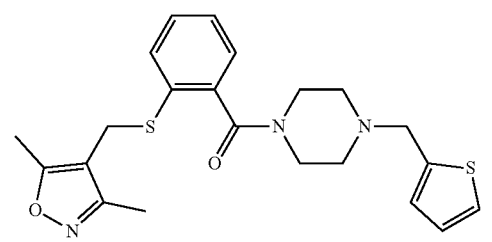
1N
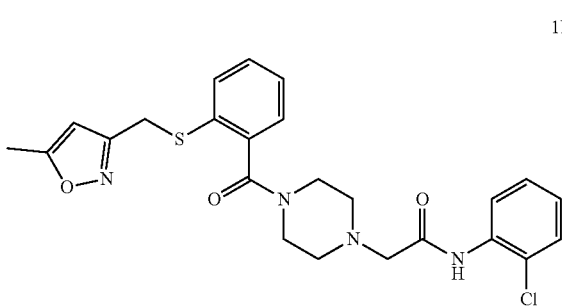
1O
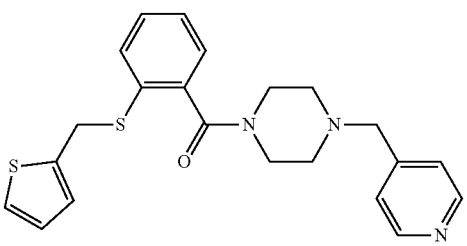
1P
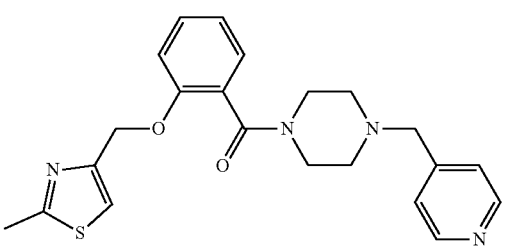
1Q
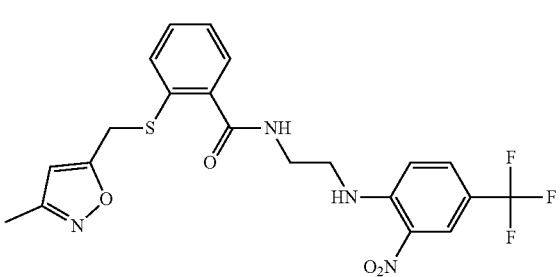
1R
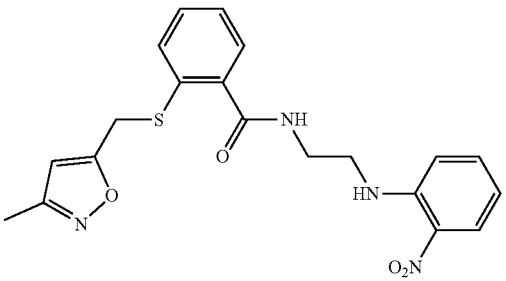
1S
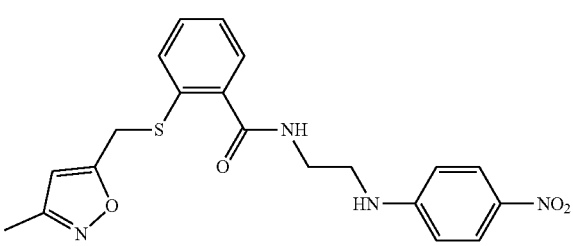
or a salt thereof.
One embodiment provides a pharmaceutical composition comprising a compound of formula I:

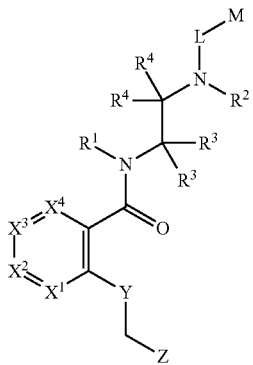

I wherein:
$X^1$ is N or $CR^{a1}$, $X^2$ is N or $CR^{a2}$, $X^3$ is N or $CR^{a3}$, $X^4$ is N or $CR^{a4}$ provided no more than two of $X^1$, $X^2$, $X^3$, or $X^4$ is N;

each $R^{a1}$, $R^{a2}$, $R^{a3}$, and $R^{a4}$ is independently hydrogen, halogen, $(C_1-C_4)$alkyl, $(C_1-C_4)$haloalkyl, —O$(C_1-C_4)$alkyl, or —O$(C_1-C_4)$haloalkyl;

Y is S, S(=O), S(=O)$_2$, or O;

Z is phenyl, 5-membered heteroaryl, or 6-membered heteroaryl, wherein any phenyl, 5-membered heteroaryl, or 6-membered heteroaryl of Z is optionally substituted with one or more halogen, NO$_2$, CN, —OH, $(C_1-C_4)$alkyl, $(C_1-C_4)$haloalkyl, —O$(C_1-C_4)$alkyl, or —O$(C_1-C_4)$haloalkyl;

$R^1$ is hydrogen or $(C_1-C_4)$alkyl and $R^2$ is hydrogen or $(C_1-C_4)$alkyl, or $R^1$ and $R^2$ together with atoms to which they are attached form a piperazinyl, wherein the piperazinyl is optionally substituted with one or more halogen, $(C_1-C_4)$alkyl, $(C_1-C_4)$haloalkyl, —O$(C_1-C_4)$alkyl, or —O$(C_1-C_4)$haloalkyl;

each $R^3$ is independently hydrogen or $(C_1-C_4)$alkyl;
each $R^4$ is independently hydrogen or $(C_1-C_4)$alkyl;
L is absent, $L^1$, or -$L^2$C(=O)NR$^b$L$^3$-;
$L^1$ is —$(C_1-C_6)$alkyl-optionally substituted with one or more halogen or oxo;
$L^2$ is absent or —$(C_1-C_6)$alkyl-optionally substituted with one or more halogen;
$L^3$ is absent or —$(C_1-C_6)$alkyl-optionally substituted with one or more halogen;
$R^b$ is hydrogen or $(C_1-C_4)$alkyl; and
M is aryl, 5-10-membered heteroaryl, or 5-10-membered heterocycle wherein any aryl, 5-10-membered heteroaryl, or 5-10-membered heterocycle of M is optionally substituted with one or more halogen, NO$_2$, CN, —OH, $(C_1-C_4)$alkyl, $(C_1-C_4)$haloalkyl, —O$(C_1-C_4)$alkyl, or —O$(C_1-C_4)$haloalkyl;

or a pharmaceutically acceptable salt thereof; and
a pharmaceutically acceptable carrier provided the compound is not [2-[[(3,5-dimethyl-4-isoxazolyl)methyl]thio]phenyl](4-phenyl-1-piperazinyl)-methanone or a pharmaceutically acceptable salt thereof.

In one embodiment $R^1$ and $R^2$ together with the atoms to which they are attached form a piperazine and L is absent or -$L^2$C(=O)NR$^b$L$^3$-, wherein the piperizinyl is optionally substituted with one or more halogen, $(C_1-C_4)$alkyl, $(C_1-C_4)$haloalkyl, —O$(C_1-C_4)$alkyl, or —O$(C_1-C_4)$haloalkyl.

In one embodiment $R^1$ and $R^2$ together with the atoms to which they are attached form a piperizinyl and L is -$L^2$C(=O)NR$^b$L$^3$-, wherein the piperizinyl is optionally substituted with one or more halogen, $(C_1-C_4)$alkyl, $(C_1-C_4)$haloalkyl, —O$(C_1-C_4)$alkyl, or —O$(C_1-C_4)$haloalkyl.

In one embodiment $R^1$ and $R^2$ together with the atoms to which they are attached form a piperizinyl and L is -$L^2$C(=O)NR$^b$L$^3$-.

One embodiment provides a compound of formula Ia:

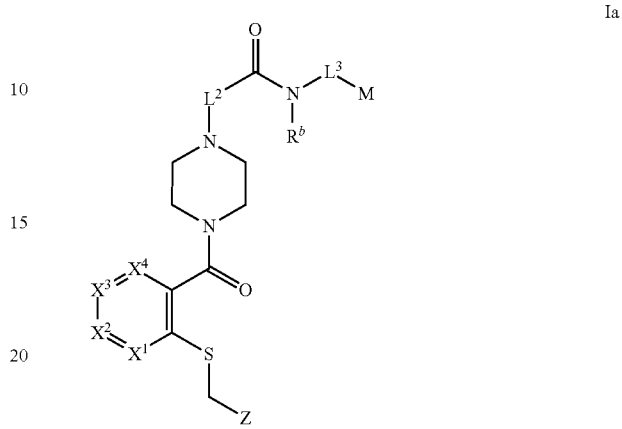

Ia or a salt thereof.

In one embodiment $L^2$ is —CH$_2$—.
In one embodiment $L^3$ is absent or —$(C_1-C_6)$alkyl-.
In one embodiment $L^3$ is absent or —CH$_2$—.
In one embodiment $R^b$ is hydrogen, methyl or ethyl.
In one embodiment $R^1$ and $R^2$ together with the atoms to which they are attached form a piperizinyl and L is absent.
In one embodiment $R^1$ and $R^2$ together with the atoms to which they are attached form a piperizinyl and L is absent.

One embodiment provides a compound of formula Ib:

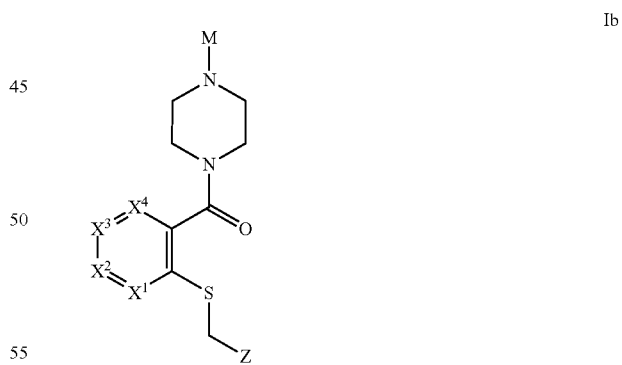

Ib or a salt thereof.

In one embodiment $R^3$ is hydrogen and each $R^4$ is hydrogen.

In one embodiment $R^1$ is hydrogen or $(C_1-C_4)$alkyl and $R^2$ is hydrogen or $(C_1-C_4)$alkyl and L is absent.

In one embodiment $R^1$ is hydrogen and $R^2$ is hydrogen and L is absent.

One embodiment provides a compound of formula Ic:

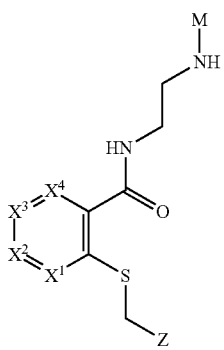

or a salt thereof.

In one embodiment Z is a 5-membered heteroaryl, wherein any 5-membered heteroaryl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is a 5-membered heteroaryl, wherein any 5-membered heteroaryl of Z is substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is a 6-membered heteroaryl, wherein any 6-membered heteroaryl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is a 5-membered heteroaryl wherein the heteroaryl ring includes atoms selected from carbon, oxygen and nitrogen, and wherein any 5-membered heteroaryl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is a 5-membered heteroaryl wherein the heteroaryl ring includes atoms selected from carbon, oxygen and nitrogen, and wherein any 5-membered heteroaryl of Z is substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is an isoxazolyl, wherein any isoxazolyl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is an isoxazolyl, wherein any isoxazolyl of Z is substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is isoxazol-3-yl, isoxazol-4-yl, or isoxazol-5-yl, wherein any isoxazol-3-yl, isoxazol-4-yl, or isoxazol-5-yl of Z is optionally substituted with one or more $(C_1-C_4)$alkyl.

In one embodiment Z is isoxazol-3-yl, isoxazol-4-yl, or isoxazol-5-yl, wherein any isoxazol-3-yl, isoxazol-4-yl, or isoxazol-5-yl of Z is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment Z is:

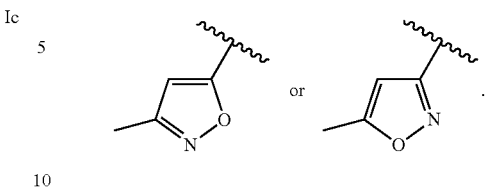

In one embodiment M is phenyl, benzothiazolyl, pyridinyl, benzoxazolyl, thiazolyl, benzoimidazolyl, or pyrimidinyl, wherein any phenyl, benzothiazolyl, pyridinyl, benzoxazolyl, thiazolyl, benzoimidazolyl, or pyrimidinyl of M is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment M is phenyl, benzothiazolyl, pyridinyl, benzoxazolyl, thiazolyl, or pyrimidinyl, wherein any phenyl, benzothiazolyl, pyridinyl, benzoxazolyl, thiazolyl, or pyrimidinyl of M is optionally substituted with one or more halogen, $NO_2$, CN, —OH, $(C_1-C_4)$alkyl, $(C_1-C_4)$haloalkyl, —$O(C_1-C_4)$alkyl, or —$O(C_1-C_4)$haloalkyl.

In one embodiment M is:

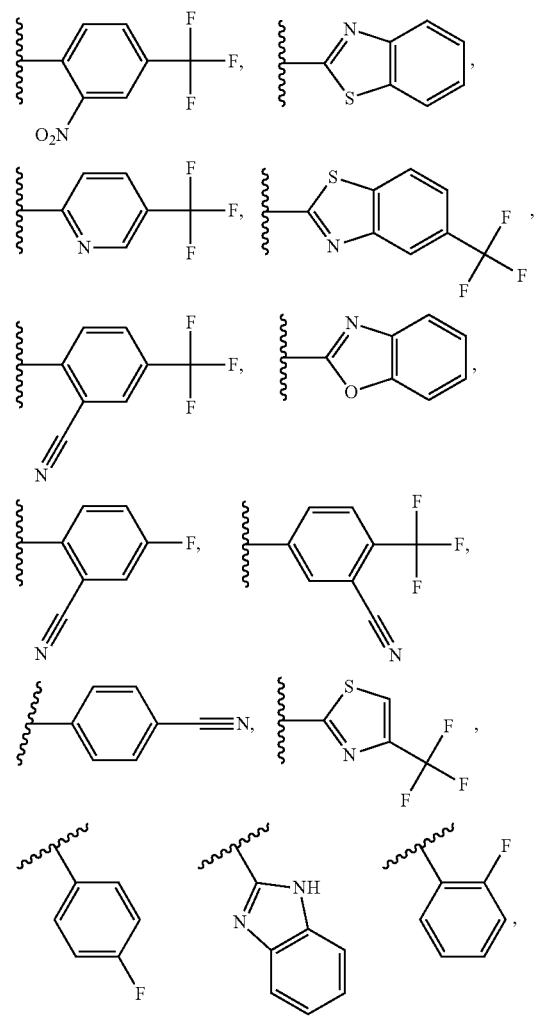

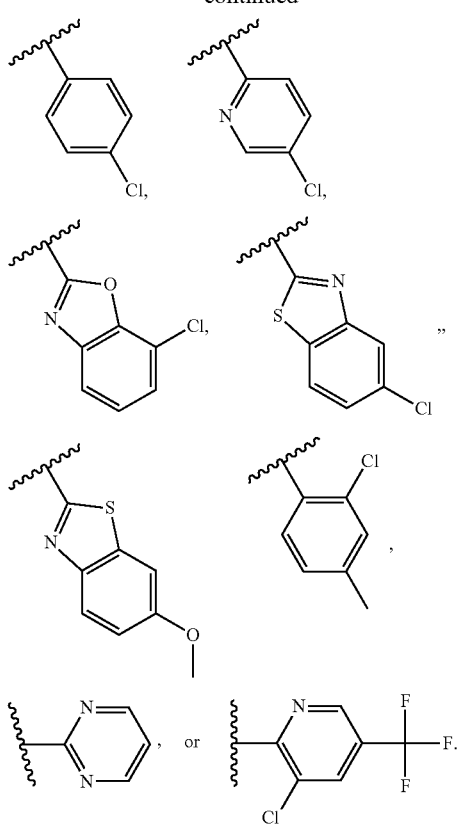
In one embodiment the residue:
-L-M
of the compound of formula I is:
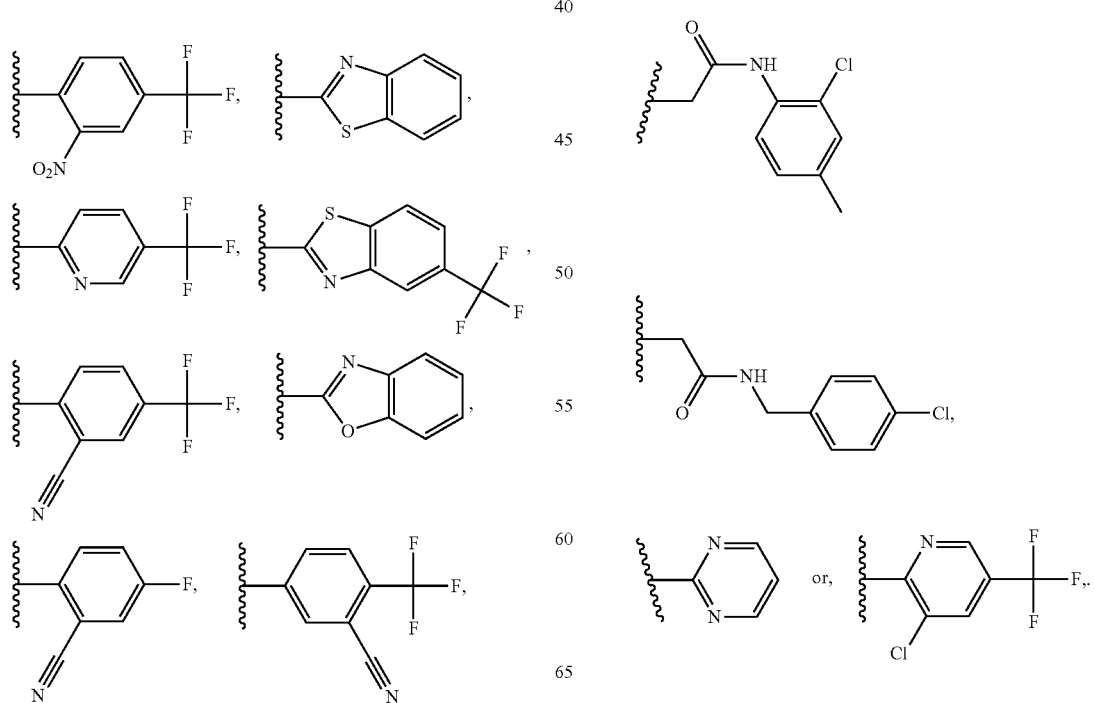

In one embodiment the residue:
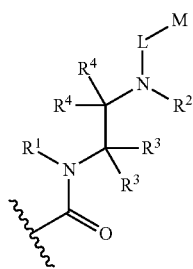
of the compound of formula I is:
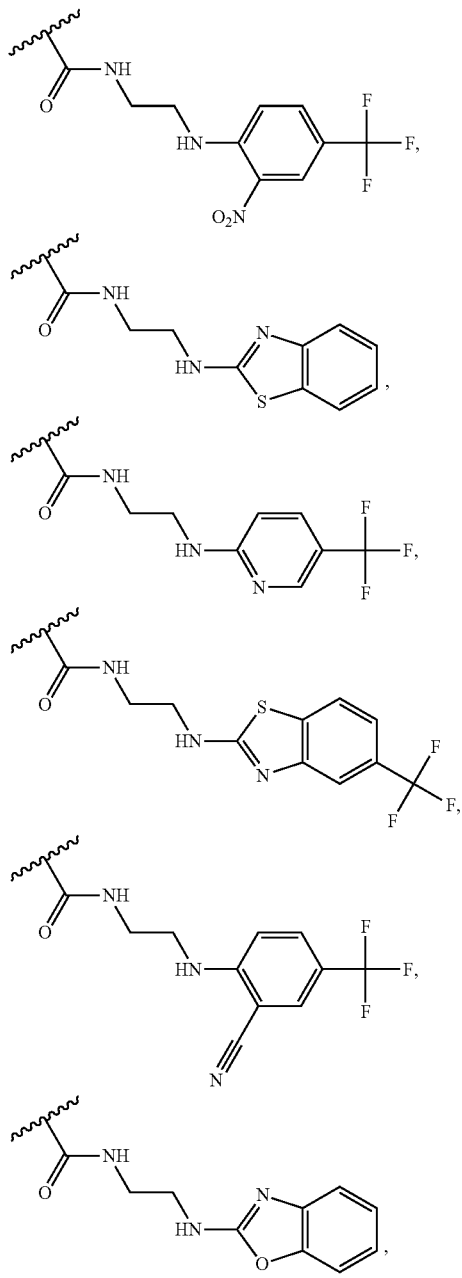
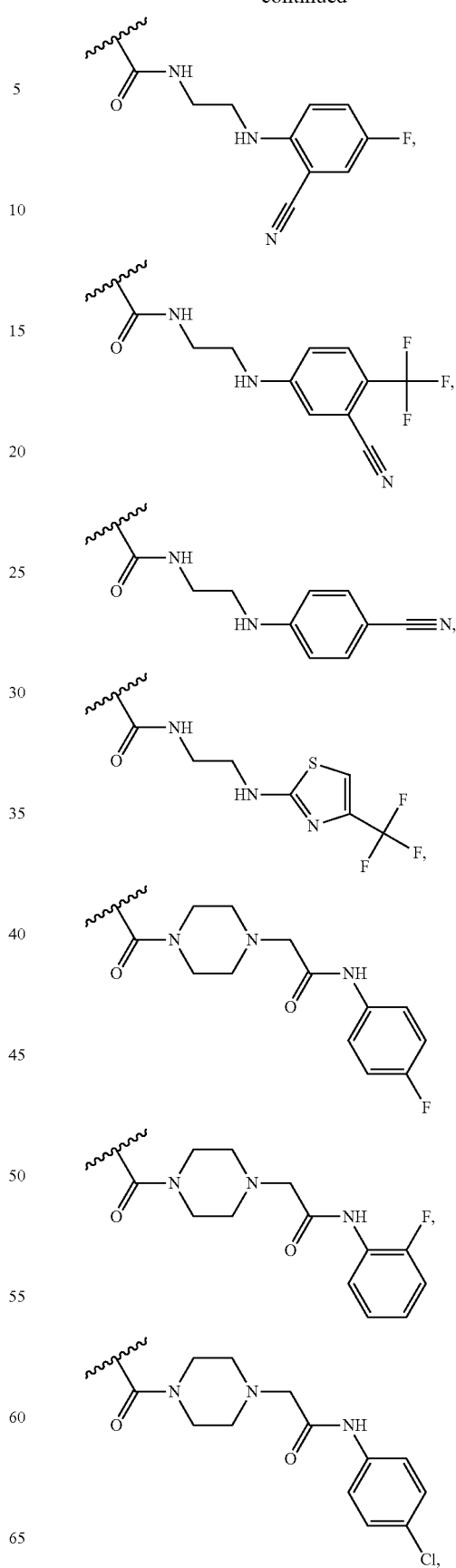

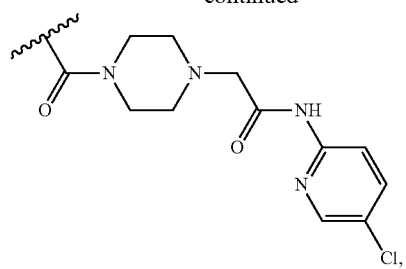
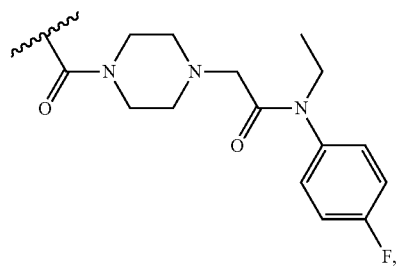
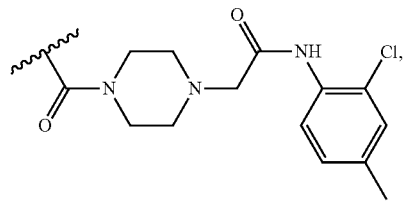
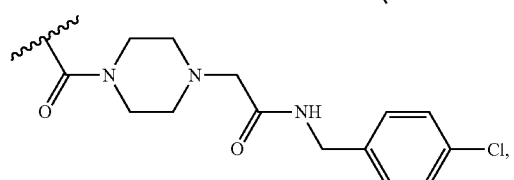
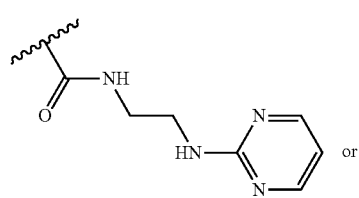
or
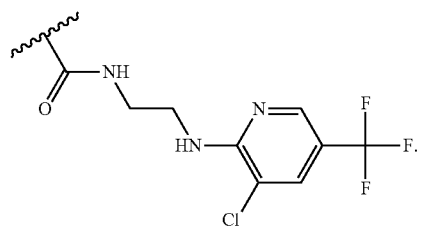
One embodiment provides a compound that is:
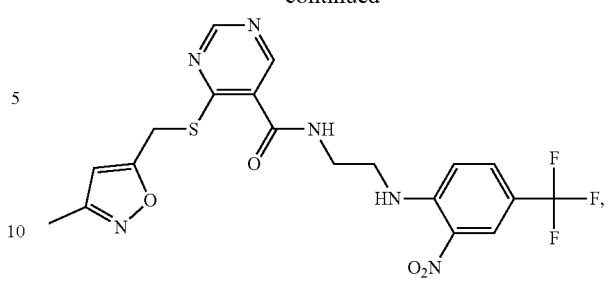
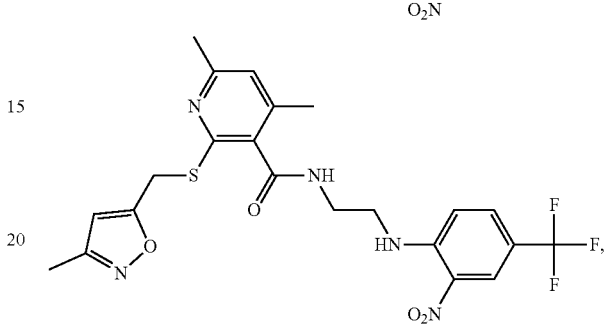
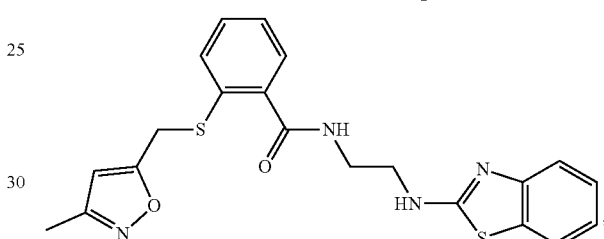
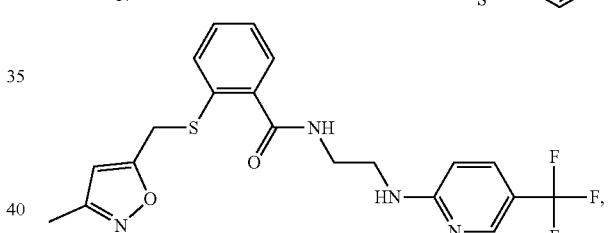
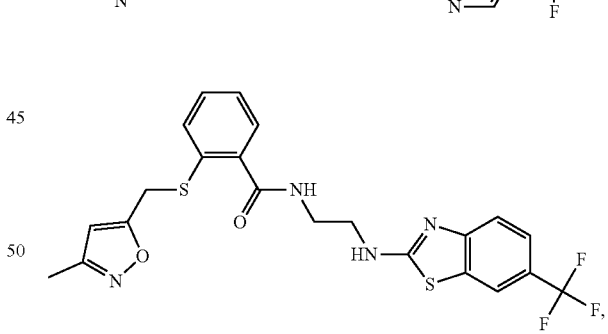
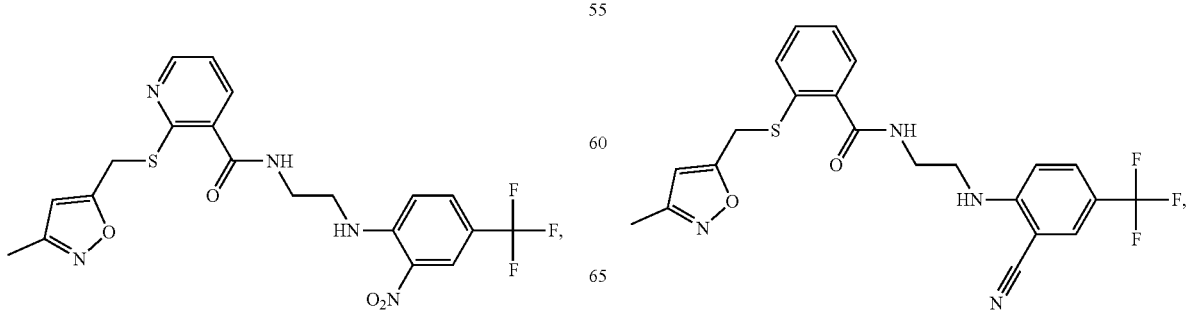

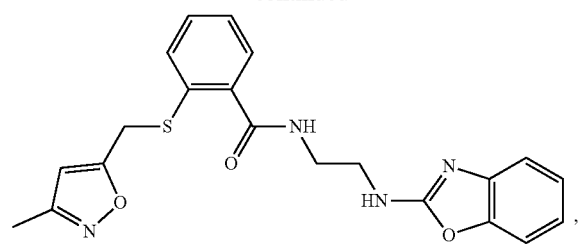
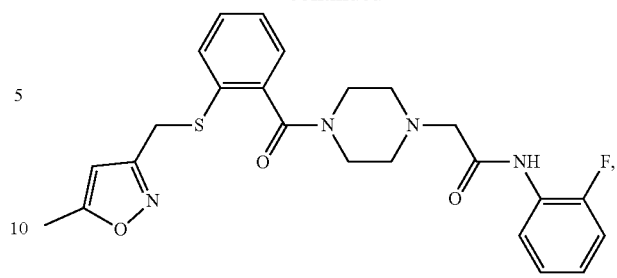
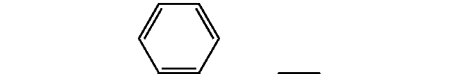

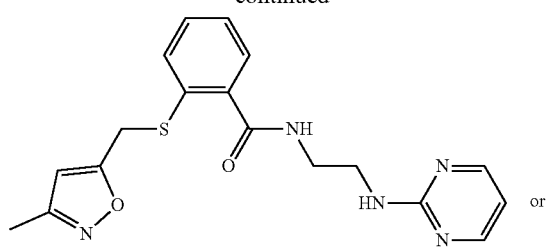

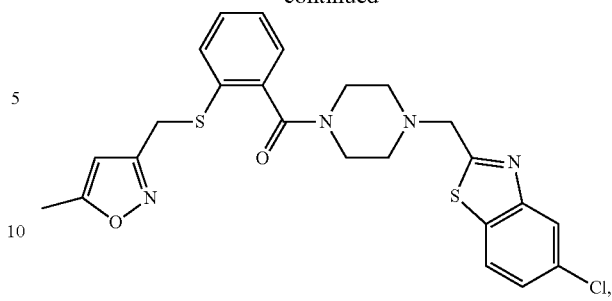

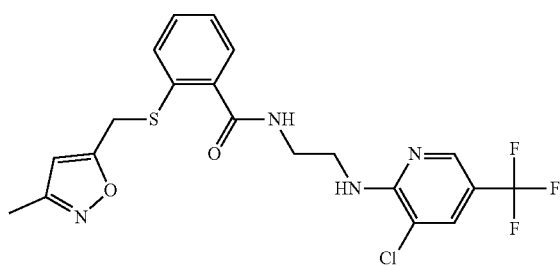

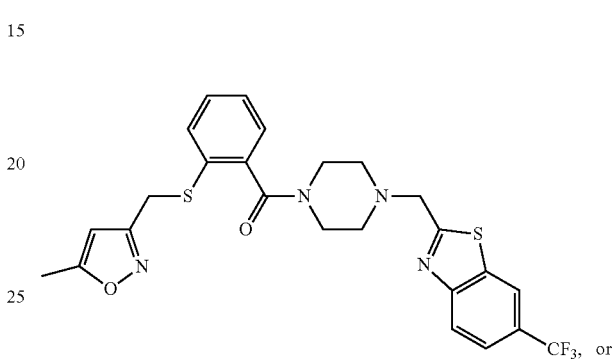

or a salt thereof.

One embodiment provides a compound that is:

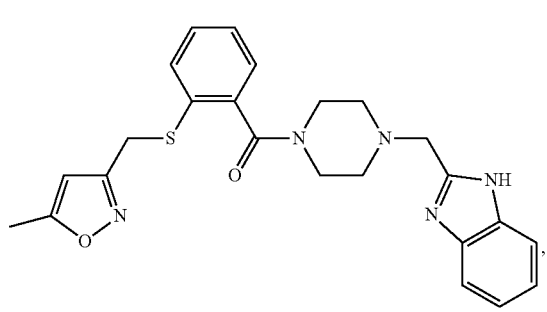

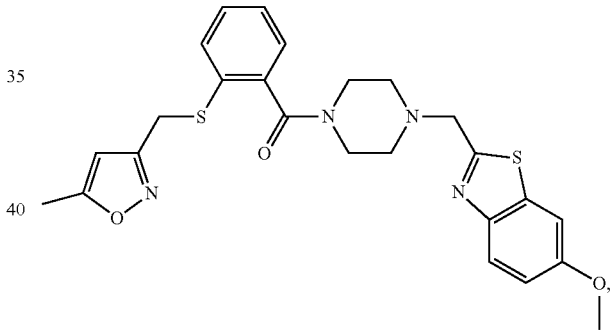

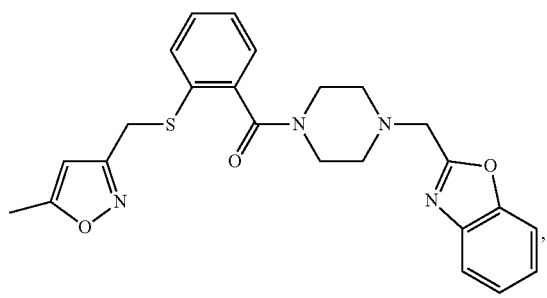

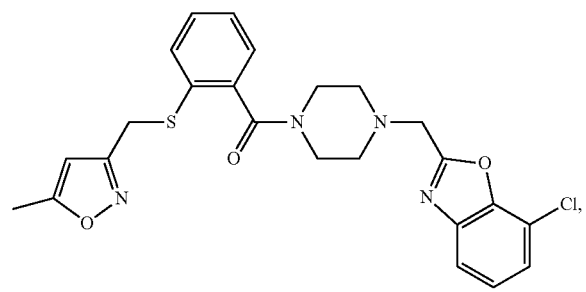

or a salt thereof.

In one embodiment the compounds of formula I or any related formula (e.g., formula Ia, Ib, Ic) do not include the following compounds or any subset thereof:

2-[[(2-methyl-4-thiazolyl)methyl]thio]-N-[2-[[3-(trifluoromethyl)-2-pyridinyl]amino]ethyl]-benzamide

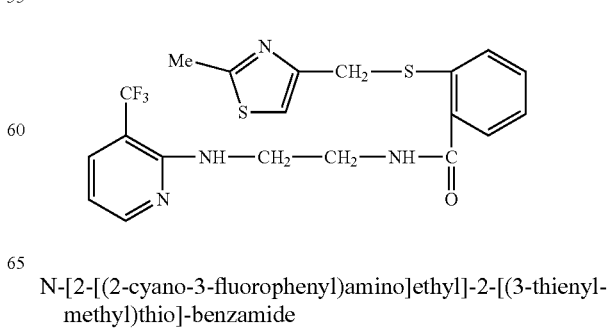

N-[2-[(2-cyano-3-fluorophenyl)amino]ethyl]-2-[(3-thienylmethyl)thio]-benzamide

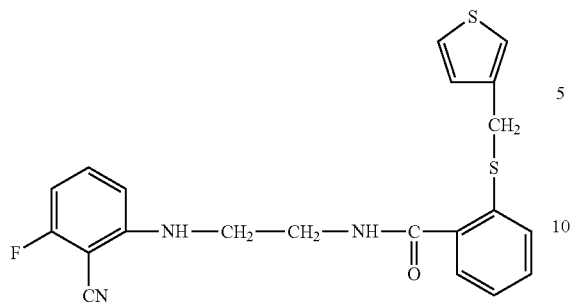

N-[2-[[3-chloro-5-(trifluoromethyl)-2-pyridinyl]amino]
ethyl]-2-[[(2-methyl-4-thiazolyl)methyl]thio]-benzamide

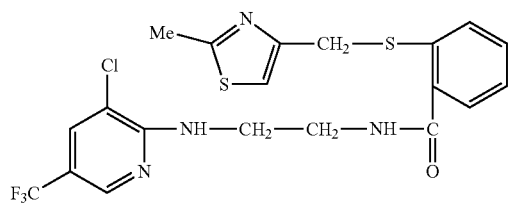 [SMILES: Cc1nc(CSc2ccccc2C(=O)NCCNc2ncc(C(F)(F)F)cc2Cl)cs1]

2-[[(3-methyl-5-isoxazolyl)methyl]thio]-N-[2-[[2-nitro-4-
(trifluoromethyl)phenyl]amino]ethyl]-benzamide

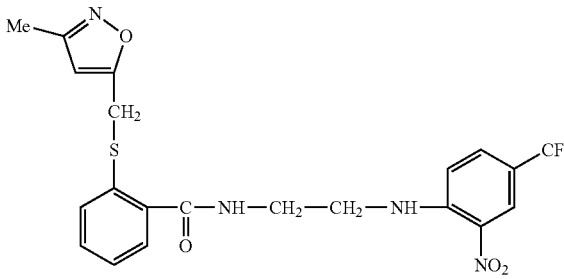 [SMILES: Cc1cc(CSc2ccccc2C(=O)NCCNc2ccc(C(F)(F)F)cc2[N+](=O)[O-])on1]

N-[2-[(3-cyano-2-pyridinyl)amino]ethyl]-2-[(2-thienylm-
ethyl)thio]-benzamide

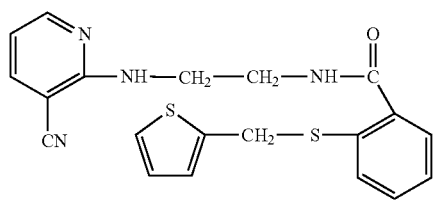

2-[[(5-methyl-3-isoxazolyl)methyl]thio]-N-[2-[(2-nitrophe-
nyl)amino]ethyl]-3-pyridinecarboxamide

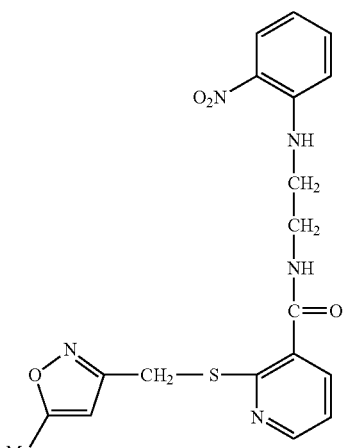

N-[2-[(3,5-dichloro-2-pyridinyl)amino]ethyl]-2-[[(3-
methyl-1,2,4-oxadiazol-5-yl)methyl]thio]-benzamide

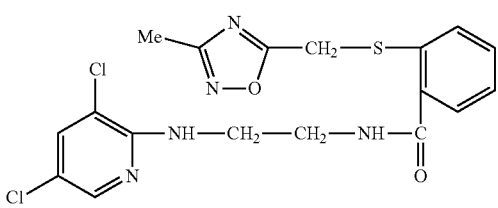 [SMILES: Cc1noc(CSc2ccccc2C(=O)NCCNc2ncc(Cl)cc2Cl)n1]

2-[[(2-methyl-4-thiazolyl)methyl]thio]-N-[2-[(4-nitrophe-
nyl)amino]ethyl]-benzamide

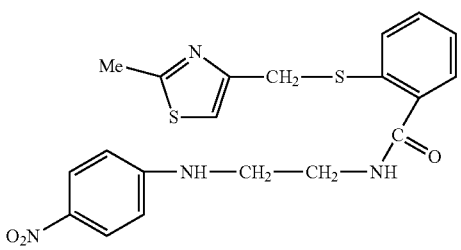 [SMILES: Cc1nc(CSc2ccccc2C(=O)NCCNc2ccc([N+](=O)[O-])cc2)cs1]

N-[2-(2-benzothiazolylamino)ethyl]-2-[(2-thienylmethyl)
thio]-benzamide

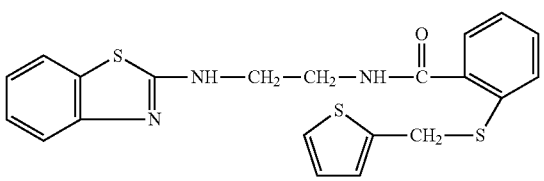 [SMILES: O=C(NCCNc1nc2ccccc2s1)c1ccccc1SCc1cccs1]

N-[2-[(3-cyano-2-pyridinyl)amino]ethyl]-2-[(4-thiazolylm-
ethyl)thio]-benzamide

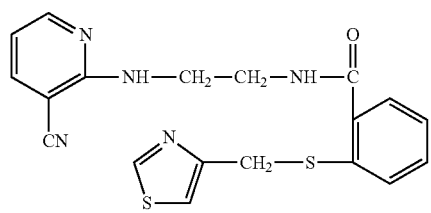 [SMILES: N#Cc1cccnc1NCCNC(=O)c1ccccc1SCc1cscn1]

2-[[(3-methyl-5-isoxazolyl)methyl]thio]-N-[2-[(6-methyl-3-pyridazinyl)amino]ethyl]-benzamide

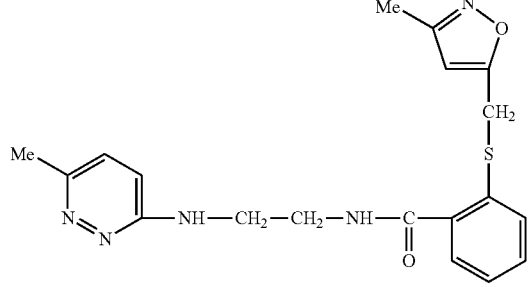

2-[[(3,5-dimethyl-4-isoxazolyl)methyl]thio]-N-[2-[[3-(trifluoromethyl)-2-pyridinyl]amino]ethyl]-3-pyridinecarboxamide

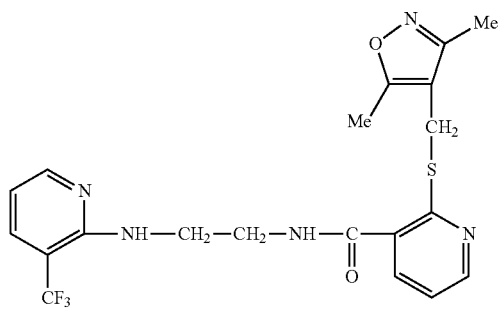

2-[[(3-methyl-5-isoxazolyl)methyl]thio]-N-[2-[(2-nitrophenyl)amino]ethyl]-benzamide

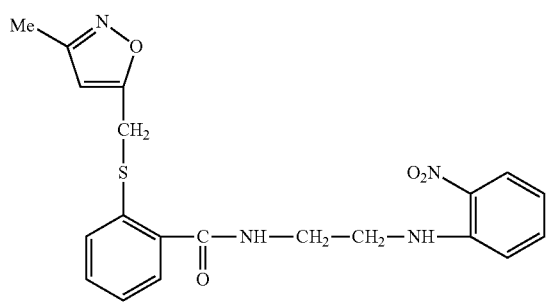 [SMILES: Cc1cc(CSc2ccccc2C(=O)NCCNc2ccccc2[N+](=O)[O-])on1]

N-[2-[(2-nitrophenyl)amino]ethyl]-2-[(3-thienylmethyl)thio]-benzamide

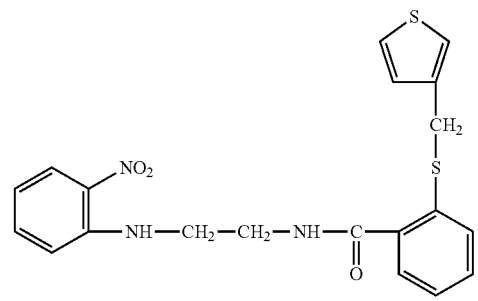 [SMILES: O=C(NCCNc1ccccc1[N+](=O)[O-])c1ccccc1SCc1ccsc1]

2-[[(3,5-dimethyl-4-isoxazolyl)methyl]thio]-N-[1-methyl-2-(methylphenylamino)ethyl]-3-pyridinecarboxamide

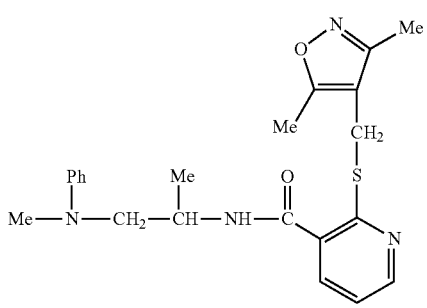 [SMILES: Cc1noc(C)c1CSc1ncccc1C(=O)NC(C)CN(C)c1ccccc1]

N-[2-[(2-cyano-3-fluorophenyl)amino]ethyl]-2-[[(5-methyl-1,2,4-oxadiazol-3-yl)methyl]thio]-benzamide

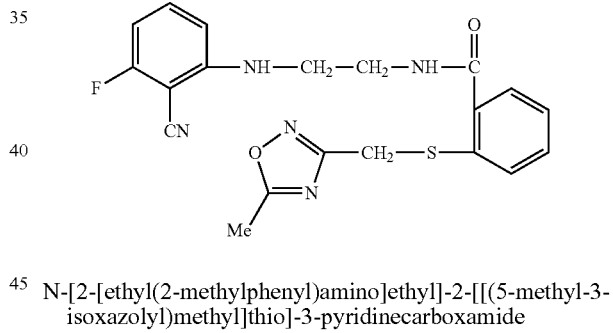

N-[2-[ethyl(2-methylphenyl)amino]ethyl]-2-[[(5-methyl-3-isoxazolyl)methyl]thio]-3-pyridinecarboxamide

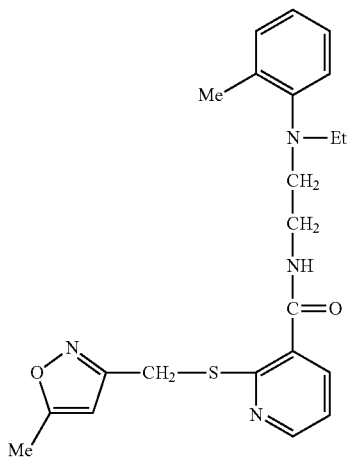 [SMILES: CCN(CCNC(=O)c1cccnc1SCc1cc(C)on1)c1ccccc1C]

2-[[(3-methyl-1,2,4-oxadiazol-5-yl)methyl]thio]-N-[2-[(2-nitrophenyl)amino]ethyl]-benzamide

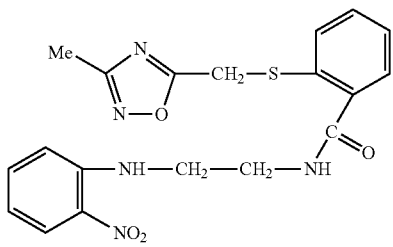 [SMILES: Cc1noc(CSc2ccccc2C(=O)NCCNc2ccccc2[N+](=O)[O-])n1]

2-[[(2-methyl-4-thiazolyl)methyl]thio]-N-[2-(2-pyrazinylamino)ethyl]-benzamide

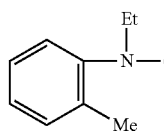

N-[2-[ethyl(2-methylphenyl)amino]ethyl]-2-[[(3-methyl-1,2,4-oxadiazol-5-yl)methyl]thio]-benzamide

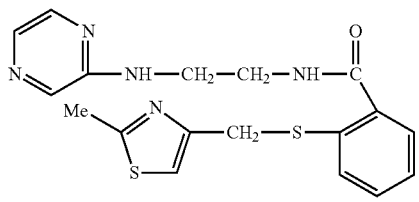 [SMILES: Cc1nc(CSc2ccccc2C(=O)NCCNc2cnccn2)cs1]

N-[1-methyl-2-(methylphenylamino)ethyl]-2-[(2-thienylmethyl)thio]-benzamide

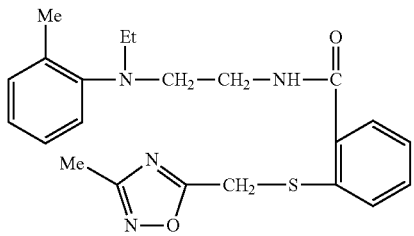 [SMILES: CCN(CCNC(=O)c1ccccc1SCc1nc(C)no1)c1ccccc1C]

2-[[(3,5-dimethyl-4-isoxazolyl)methyl]thio]-N-[2-[ethyl(2-methylphenyl)amino]ethyl]-3-pyridinecarboxamide

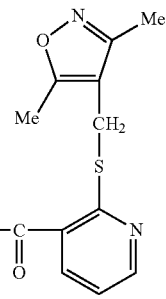

2-[[(5-methyl-3-isoxazolyl)methyl]thio]-N-[2-(methylphenylamino)propyl]-3-pyridinecarboxamide

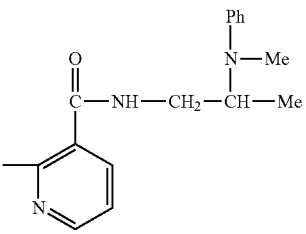

2-[[(2-methyl-4-thiazolyl)methyl]thio]-N-[2-(4-quinazolinylamino)ethyl]-benzamide

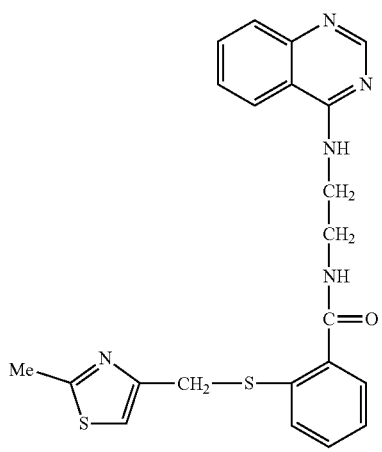

2-[[(3,5-dimethyl-4-isoxazolyl)methyl]thio]-N-[2-(2-pyrimidinylamino)ethyl]-benzamide

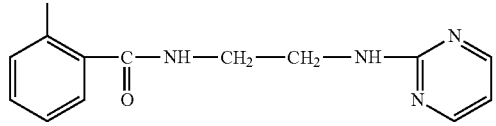

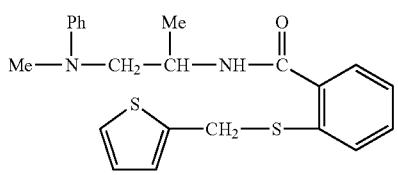 [SMILES: CC(CN(C)c1ccccc1)NC(=O)c1ccccc1SCc1cccs1]

2-[[(3,5-dimethyl-4-isoxazolyl)methyl]thio]-N-[2-[[2-nitro-4-(trifluoromethyl)phenyl]amino]ethyl]-3-pyridinecarboxamide

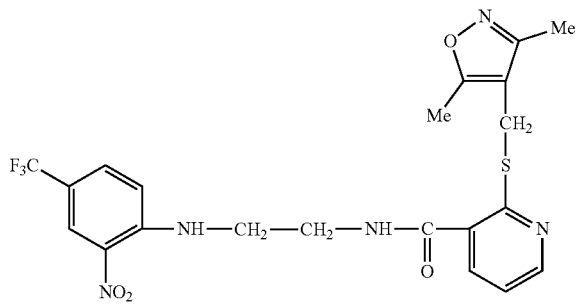 [SMILES: Cc1noc(C)c1CSc1ncccc1C(=O)NCCNc1ccc(C(F)(F)F)cc1[N+](=O)[O-]]

N-[2-(methylphenylamino)propyl]-2-[(4-thiazolylmethyl)thio]-benzamide

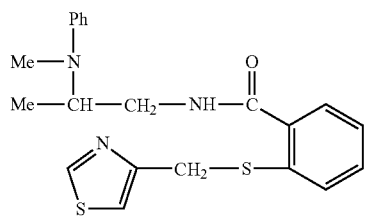

N-[2-[(3,5-dichloro-2-pyridinyl)amino]ethyl]-2-[(4-thiazolylmethyl)thio]-benzamide

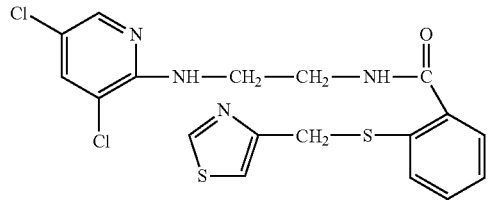 [SMILES: O=C(NCCNc1ncc(Cl)cc1Cl)c1ccccc1SCc1cscn1]

N-[2-[ethyl(3-methylphenyl)amino]ethyl]-2-[[(3-methyl-1,2,4-oxadiazol-5-yl)methyl]thio]-benzamide

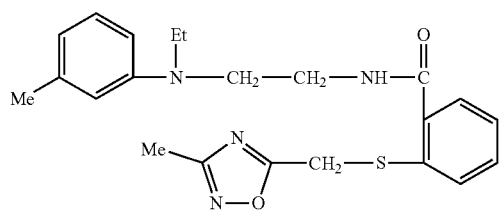 [SMILES: CCN(CCNC(=O)c1ccccc1SCc1nc(C)no1)c1cccc(C)c1]

2-[[(5-methyl-1,2,4-oxadiazol-3-yl)methyl]thio]-N-[2-[(4-nitrophenyl)amino]ethyl]-benzamide

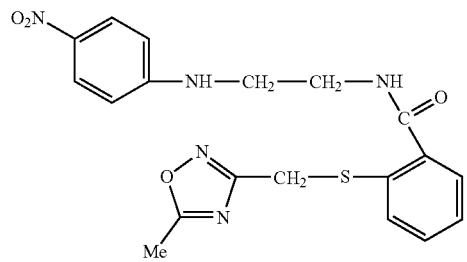 [SMILES: Cc1nc(CSc2ccccc2C(=O)NCCNc2ccc([N+](=O)[O-])cc2)no1]

N-[2-[(2-cyano-3-fluorophenyl)amino]ethyl]-2-[[(3-methyl-1,2,4-oxadiazol-5-yl)methyl]thio]-benzamide

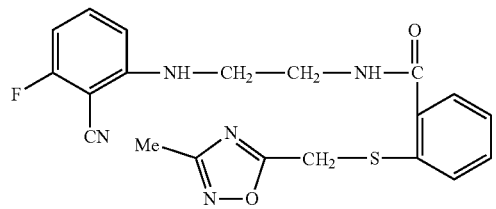 [SMILES: Cc1noc(CSc2ccccc2C(=O)NCCNc2cccc(F)c2C#N)n1]

2-[[(3,5-dimethyl-4-isoxazolyl)methyl]thio]-N-[2-[(5-methyl[1,2,4]triazolo[1,5-a]pyrimidin-7-yl)amino]ethyl]-benzamide

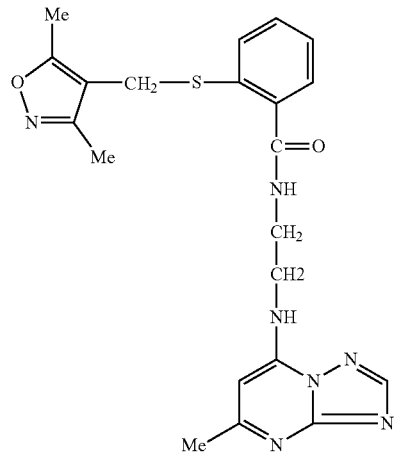 [SMILES: Cc1cc(NCCNC(=O)c2ccccc2SCc2c(C)noc2C)n2ncnc2n1]

N-[2-(methylphenylamino)propyl]-2-[(2-thienylmethyl)thio]-benzamide

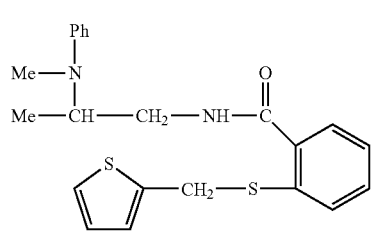 [SMILES: CC(CNC(=O)c1ccccc1SCc1cccs1)N(C)c1ccccc1]

2-[[(5-methyl-1,2,4-oxadiazol-3-yl)methyl]thio]-N-[2-[(2-nitrophenyl)amino]ethyl]-benzamide

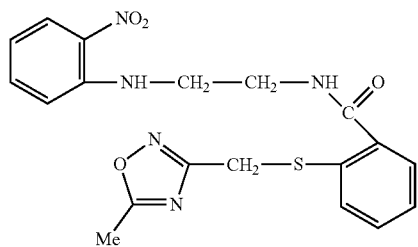 [SMILES: Cc1nc(CSc2ccccc2C(=O)NCCNc2ccccc2[N+](=O)[O-])no1]

2-[[(5-methyl-1,2,4-oxadiazol-3-yl)methyl]thio]-N-[2-(methylphenylamino)propyl]-benzamide

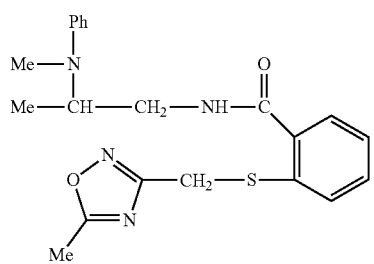 [SMILES: Cc1nc(CSc2ccccc2C(=O)NCC(C)N(C)c2ccccc2)no1]

2-[[(3-methyl-5-isoxazolyl)methyl]thio]-N-[2-[(4-nitrophenyl)amino]ethyl]-benzamide

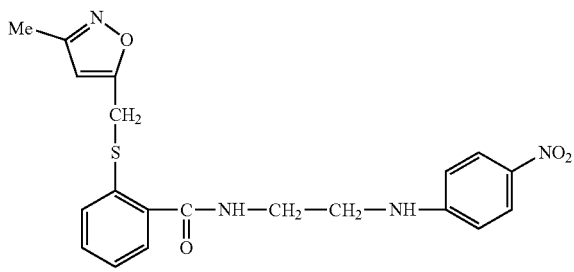 [SMILES: Cc1cc(CSc2ccccc2C(=O)NCCNc2ccc([N+](=O)[O-])cc2)on1]

N-[2-[(2-cyano-3-fluorophenyl)amino]ethyl]-2-[[(3,5-dimethyl-4-isoxazolyl)methyl]thio]-3-pyridinecarboxamide

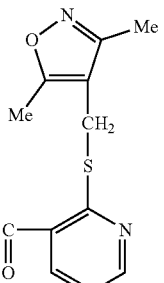

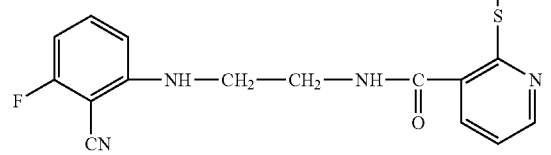

2-[[(2-methyl-4-thiazolyl)methyl]thio]-N-[2-[(2-nitrophenyl)amino]ethyl]-benzamide

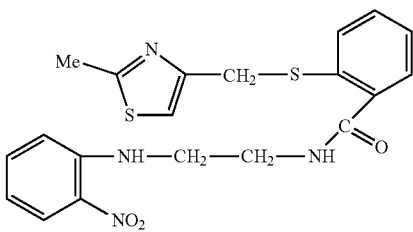 [SMILES: Cc1nc(CSc2ccccc2C(=O)NCCNc2ccccc2[N+](=O)[O-])cs1]

N-[2-[(3-cyano-2-pyridinyl)amino]ethyl]-2-[(5-methyl-1,2,4-oxadiazol-3-yl)methoxy]-benzamide

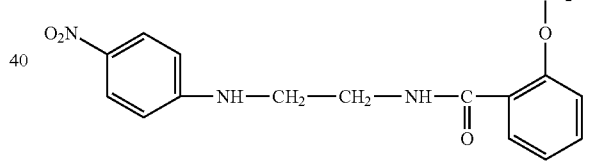

2-[(3,5-dimethyl-4-isoxazolyl)methoxy]-N-[2-[(4-nitrophenyl)amino]ethyl]-benzamide 2-[(3,5-dimethyl-4-isoxazolyl)methoxy]-N-[2-[ethyl(2-methylphenyl)amino]ethyl]-benzamide

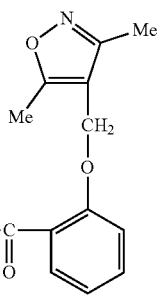

2-[(3,5-dimethyl-4-isoxazolyl)methoxy]-N-[2-[ethyl(3-methylphenyl)amino]ethyl]-benzamide

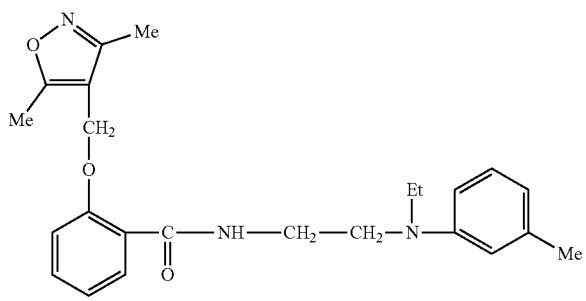 [SMILES: CCN(CCNC(=O)c1ccccc1OCc1c(C)noc1C)c1cccc(C)c1]

N-[2-[(3-cyano-2-pyridinyl)amino]ethyl]-2-[(3,5-dimethyl-4-isoxazolyl)methoxy]-benzamide

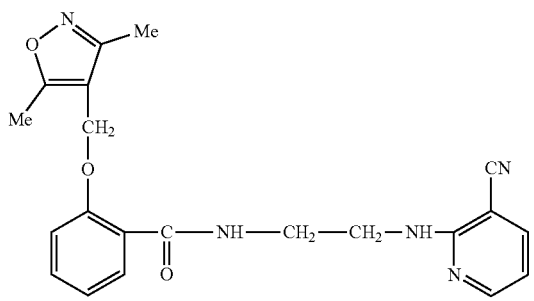 [SMILES: Cc1noc(C)c1COc1ccccc1C(=O)NCCNc1ncccc1C#N]

N-[2-[[3-chloro-5-(trifluoromethyl)-2-pyridinyl]amino]ethyl]-2-[(3,5-dimethyl-4-isoxazolyl)methoxy]-benzamide

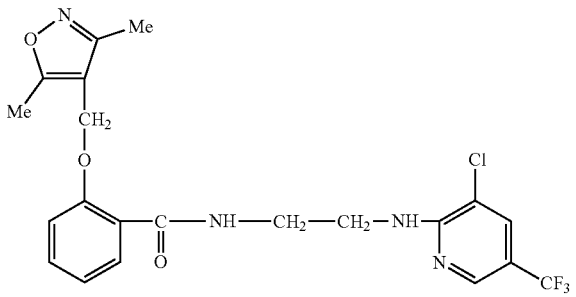 [SMILES: Cc1noc(C)c1COc1ccccc1C(=O)NCCNc1ncc(C(F)(F)F)cc1Cl]

N-[2-(methylphenylamino)ethyl]-2-(4-thiazolylmethoxy)-benzamide

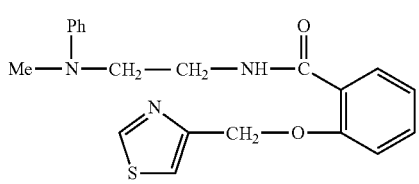

N-[2-(methylphenylamino)propyl]-2-(4-thiazolylmethoxy)-benzamide

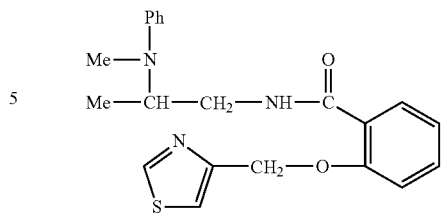

2-[(5-methyl-1,2,4-oxadiazol-3-yl)methoxy]-N-[2-[(2-nitrophenyl)amino]ethyl]-benzamide

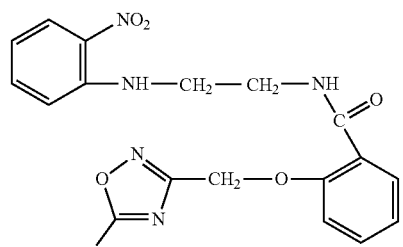

2-[(3,5-dimethyl-4-isoxazolyl)methoxy]-N-[2-(2-pyrimidinylamino)ethyl]-benzamide

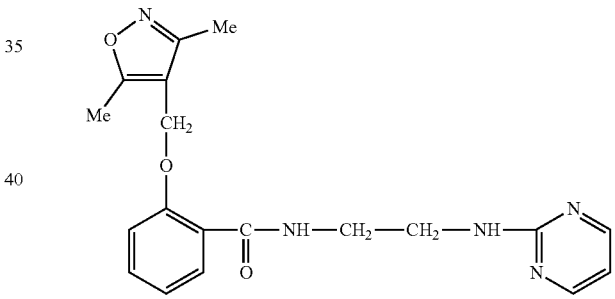

2-[(3,5-dimethyl-4-isoxazolyl)methoxy]-N-[1-methyl-2-(methylphenylamino)ethyl]-benzamide

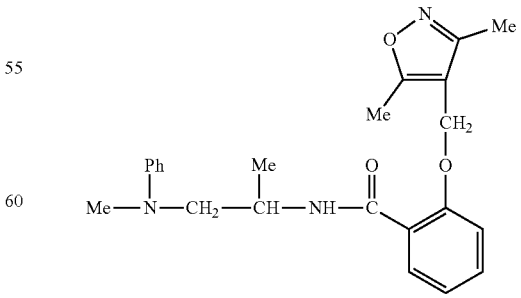

2-[(3,5-dimethyl-4-isoxazolyl)methoxy]-N-[2-[(6-methyl-3-pyridazinyl)amino]ethyl]-benzamide

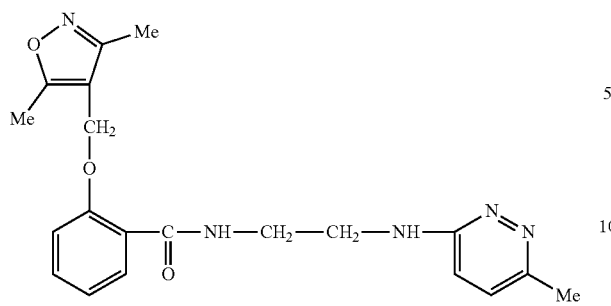

2-[(2-methyl-4-thiazolyl)methoxy]-N-[2-[[2-nitro-4-(trifluoromethyl)phenyl]amino]ethyl]-benzamide

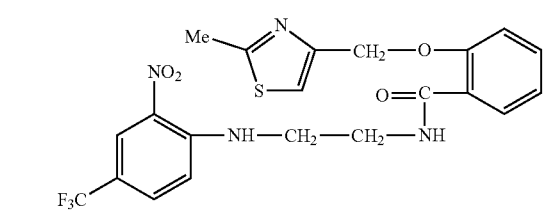 [SMILES: Cc1nc(COc2ccccc2C(=O)NCCNc2ccc(C(F)(F)F)cc2[N+](=O)[O-])cs1]

1-Piperazineacetamide, N-(4-fluorophenyl)-4-[2-[(4-thiazolylmethyl)thio]benzoyl]-1-Piperazineacetamide

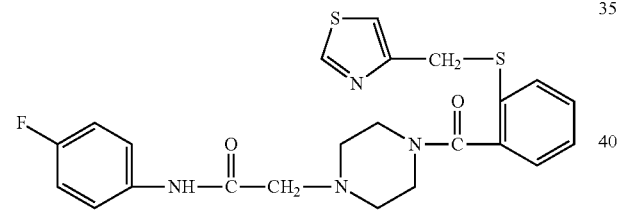

1-Piperazineacetamide, 4-[2-[[(3,5-dimethyl-4-isoxazolyl)methyl]thio]benzoyl]-N-(4-fluorophenyl)-1-piperazineacetamide

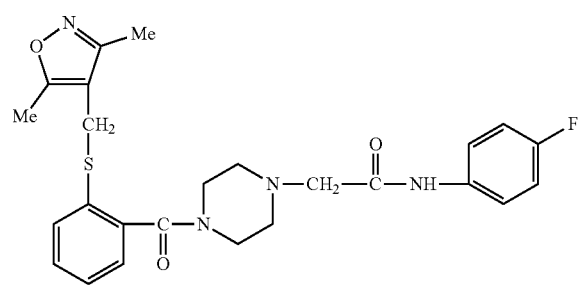 [SMILES: Cc1noc(C)c1CSc1ccccc1C(=O)N1CCN(CC(=O)Nc2ccc(F)cc2)CC1]

N-(2,3-dimethylphenyl)-4-[[2-[[(5-methyl-3-isoxazolyl)methyl]thio]-3-pyridinyl]carbonyl]-1-piperazineacetamide

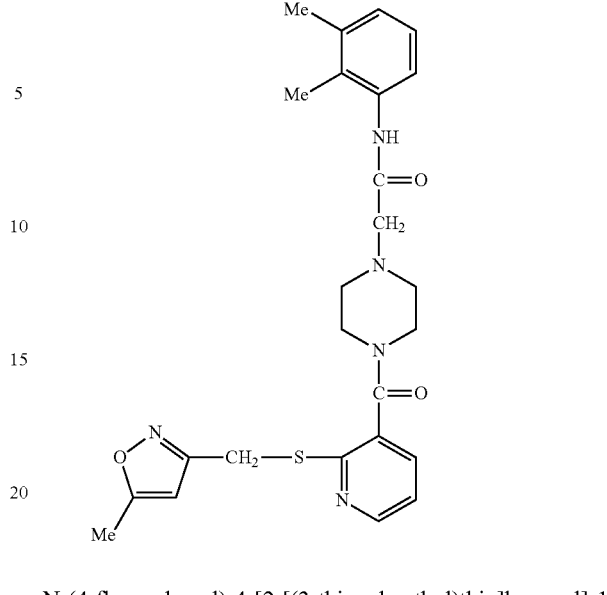

N-(4-fluorophenyl)-4-[2-[(3-thienylmethyl)thio]benzoyl]-1-piperazineacetamide

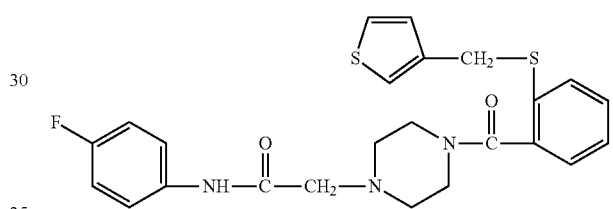

N-(2-chlorophenyl)-4-[2-[(3-thienylmethyl)thio]benzoyl]-1-piperazineacetamide

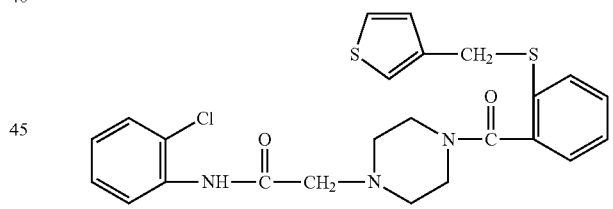

N-(2,3-dimethylphenyl)-4-[2-[[(5-methyl-3-isoxazolyl)methyl]thio]benzoyl]-1-piperazineacetamide

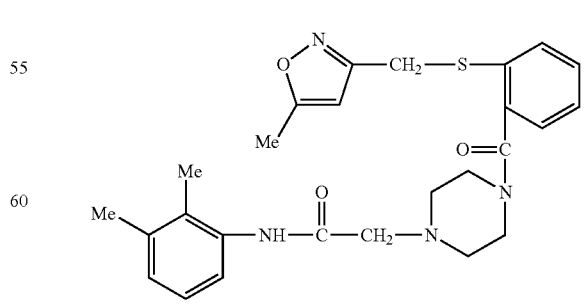

N-(2-ethylphenyl)-4-[2-[(4-thiazolylmethyl)thio]benzoyl]-1-piperazineacetamide

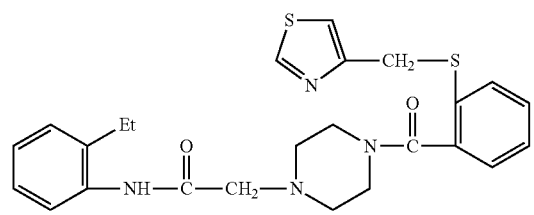 [SMILES: CCc1ccccc1NC(=O)CN1CCN(C(=O)c2ccccc2SCc2cscn2)CC1]

N-(2-chlorophenyl)-4-[2-[(2-thienylmethyl)thio]benzoyl]-1-piperazineacetamide

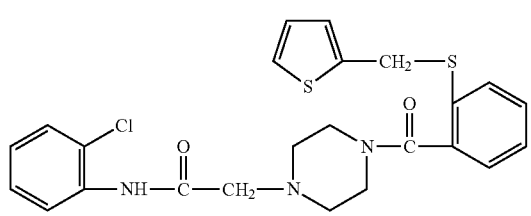 [SMILES: O=C(CN1CCN(C(=O)c2ccccc2SCc2cccs2)CC1)Nc1ccccc1Cl]

N-phenyl-4-[2-[(3-thienylmethyl)thio]benzoyl]-1-piperazineacetamide

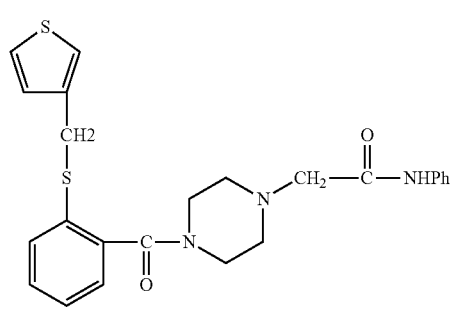

N-(2-chlorophenyl)-4-[[2-[[(5-methyl-3-isoxazolyl)methyl]thio]-3-pyridinyl]carbonyl]-1-piperazineacetamide

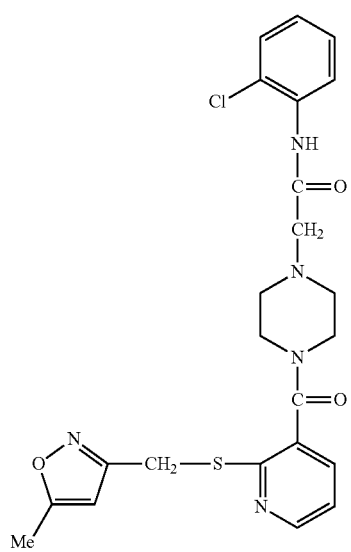 [SMILES: Cc1cc(CSc2ncccc2C(=O)N2CCN(CC(=O)Nc3ccccc3Cl)CC2)no1]

N-(5-methyl-3-isoxazolyl)-4-[2-[(3-thienylmethyl)thio]benzoyl]-1-piperazineacetamide

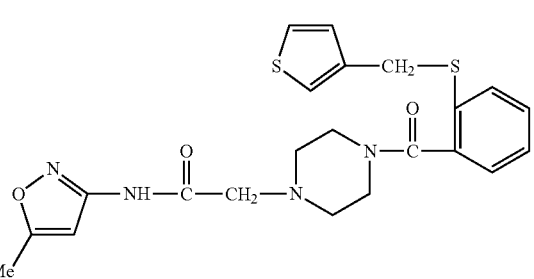

4-[[2-[[(3,5-dimethyl-4-isoxazolyl)methyl]thio]-3-pyridinyl]carbonyl]-N-(5-methyl-3-isoxazolyl)-1-piperazineacetamide

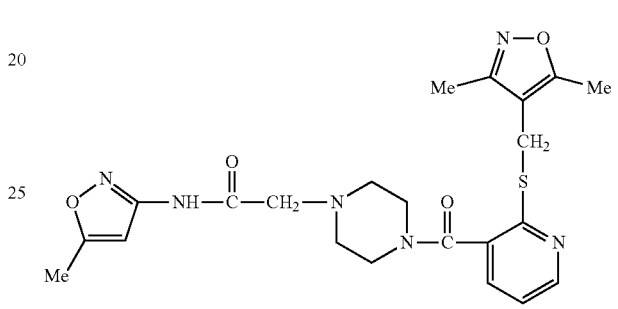

N-(5-methyl-3-isoxazolyl)-4-[2-[(4-thiazolylmethyl)thio]benzoyl]-1-piperazineacetamide

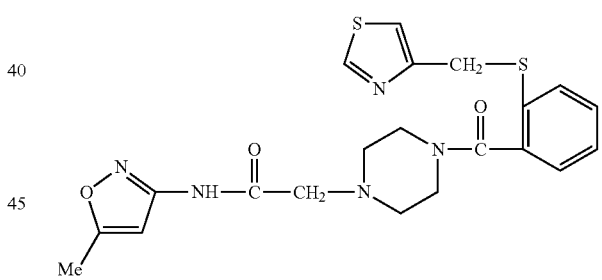

N-(2-ethylphenyl)-4-[2-[(3-thienylmethyl)thio]benzoyl]-1-piperazineacetamide

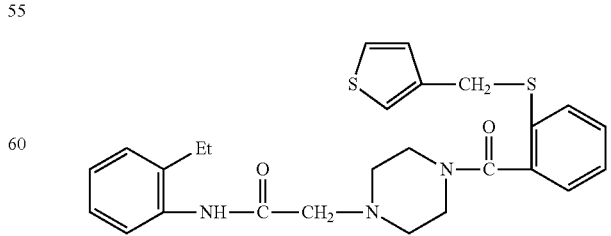

N-(2-chlorophenyl)-4-[2-[[(5-methyl-3-isoxazolyl)methyl]thio]benzoyl]-1-piperazineacetamide

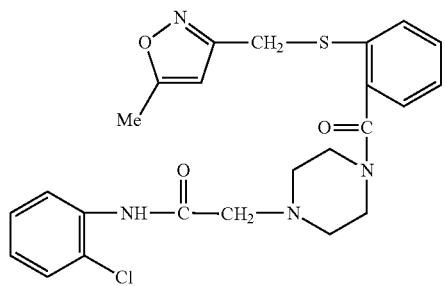 [SMILES: Cc1cc(CSc2ccccc2C(=O)N2CCN(CC(=O)Nc3ccccc3Cl)CC2)no1]

N-(2,3-dimethylphenyl)-4-[2-[(2-thienylmethyl)thio]benzoyl]-1-piperazineacetamide

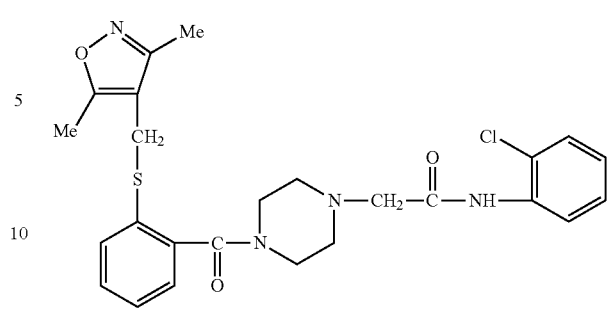

4-[2-[[(3,5-dimethyl-4-isoxazolyl)methyl]thio]benzoyl]-N-phenyl-1-piperazineacetamide

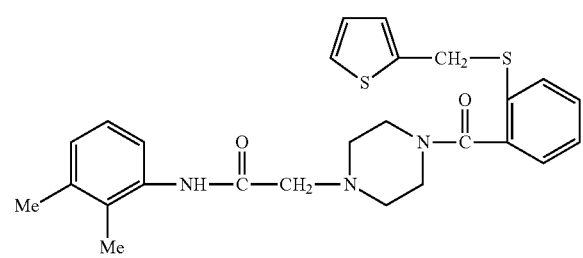 [SMILES: Cc1cccc(NC(=O)CN2CCN(C(=O)c3ccccc3SCc3cccs3)CC2)c1C]

4-[2-[[(3,5-dimethyl-4-isoxazolyl)methyl]thio]benzoyl]-N-(2-ethylphenyl)-1-piperazineacetamide

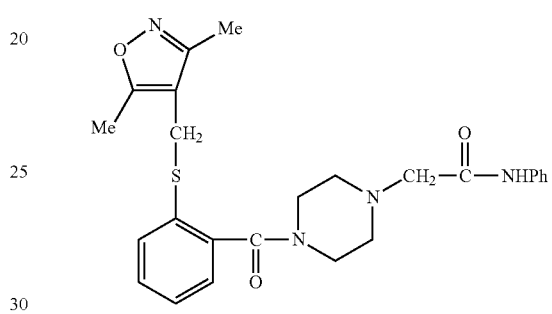

N-(2,3-dimethylphenyl)-4-[2-[(4-thiazolylmethyl)thio]benzoyl]-1-piperazineacetamide

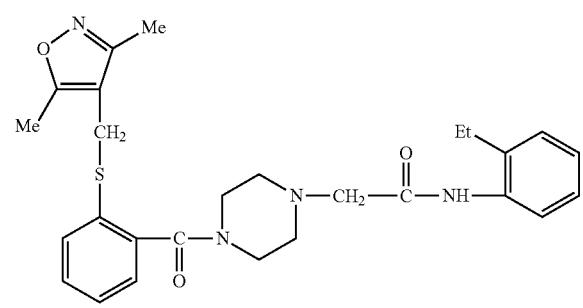 [SMILES: CCc1ccccc1NC(=O)CN1CCN(C(=O)c2ccccc2SCc2c(C)noc2C)CC1]

N-phenyl-4-[2-[(2-thienylmethyl)thio]benzoyl]-1-piperazineacetamide

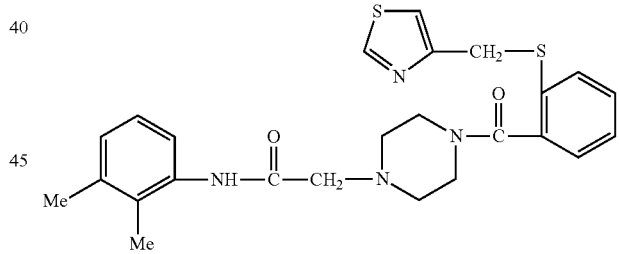

N-(2,3-dimethylphenyl)-4-[2-[(2-thienylmethyl)thio]benzoyl]-1-piperazineacetamide

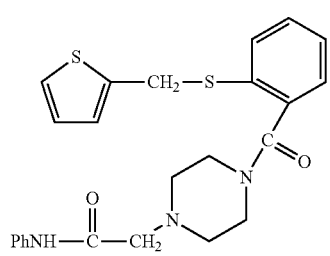

N-(2-chlorophenyl)-4-[2-[[(3,5-dimethyl-4-isoxazolyl)methyl]thio]benzoyl]-1-piperazineacetamide

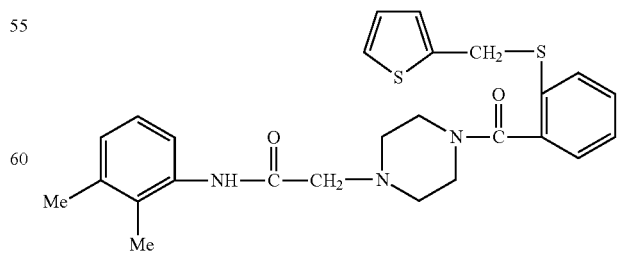

N-(4-fluorophenyl)-4-[2-[[(3-methyl-5-isoxazolyl)methyl]thio]benzoyl]-1-piperazineacetamide

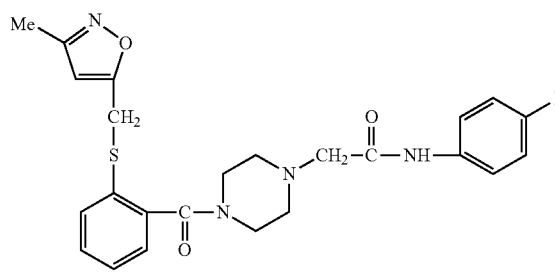

N-phenyl-4-[2-[(4-thiazolylmethyl)thio]benzoyl]-1-piperazineacetamide

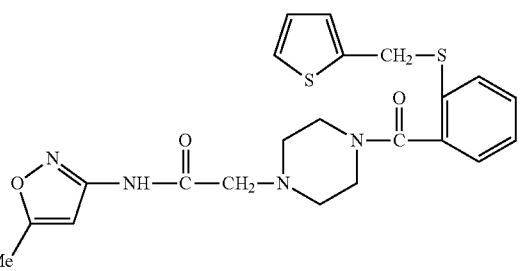

N-(3-fluorophenyl)-4-[2-[(2-methyl-4-thiazolyl)methoxy]benzoyl]-1-piperazineacetamide

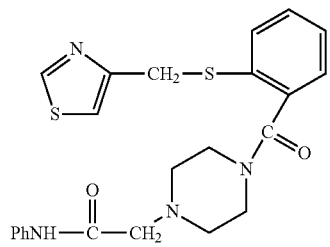

4-[[2-[[(5-methyl-3-isoxazolyl)methyl]thio]-3-pyridinyl]carbonyl]-N-(4-methylphenyl)-1-piperazineacetamide

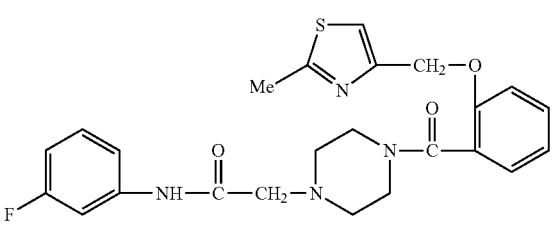

N-(2,6-dimethylphenyl)-4-[2-[(5-methyl-1,2,4-oxadiazol-3-yl)methoxy]benzoyl]-1-piperazineacetamide

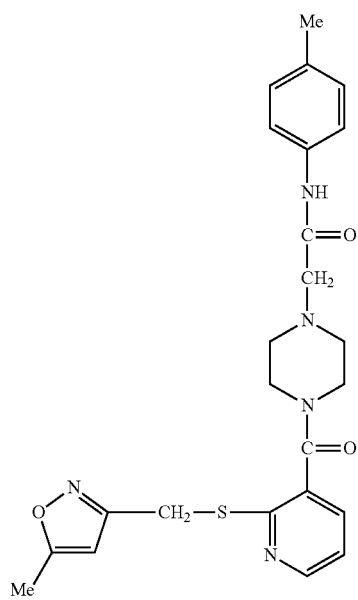 [SMILES: Cc1ccc(NC(=O)CN2CCN(C(=O)c3cccnc3SCc3cc(C)on3)CC2)cc1]

N-(5-methyl-3-isoxazolyl)-4-[2-[(2-thienylmethyl)thio]benzoyl]-1-piperazineacetamide

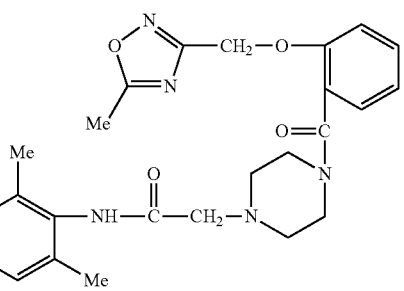

N-(2-ethylphenyl)-4-[2-[(2-methyl-4-thiazolyl)methoxy]benzoyl]-1-piperazineacetamide

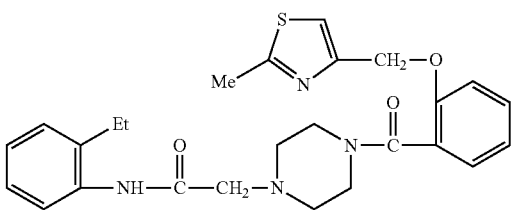

N-(2,6-dimethylphenyl)-4-[2-[(2-methyl-4-thiazolyl)methoxy]benzoyl]-1-piperazineacetamide

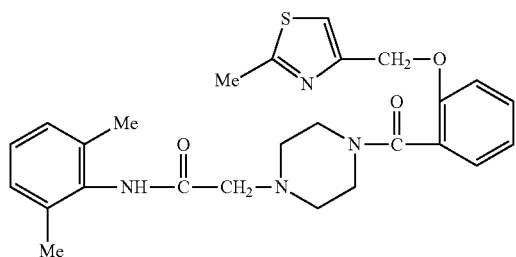 [SMILES: Cc1nc(COc2ccccc2C(=O)N2CCN(CC(=O)Nc3c(C)cccc3C)CC2)cs1]

N-(2,3-dimethylphenyl)-4-[2-[(5-methyl-1,2,4-oxadiazol-3-yl)methoxy]benzoyl]-1-piperazineacetamide

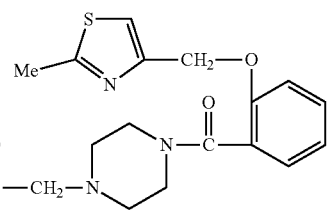

N-(5-methyl-3-isoxazolyl)-4-[2-[(2-methyl-4-thiazolyl)methoxy]benzoyl]-1-piperazineacetamide

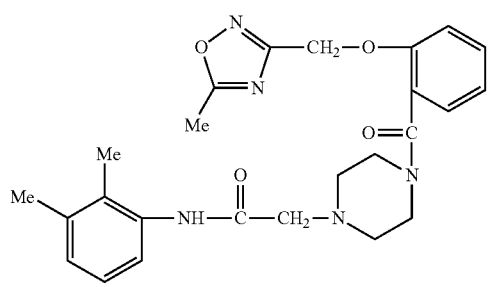 [SMILES: Cc1nc(COc2ccccc2C(=O)N2CCN(CC(=O)Nc3cccc(C)c3C)CC2)no1]

N-(2-chlorophenyl)-4-[2-[(2-methyl-4-thiazolyl)methoxy]benzoyl]-1-piperazineacetamide N-(2,3-dimethylphenyl)-4-[2-[(2-methyl-4-thiazolyl)methoxy]benzoyl]-1-piperazineacetamide

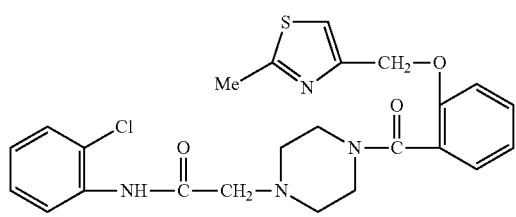 [SMILES: Cc1nc(COc2ccccc2C(=O)N2CCN(CC(=O)Nc3ccccc3Cl)CC2)cs1]

N-(3-fluorophenyl)-4-[2-[(5-methyl-1,2,4-oxadiazol-3-yl)methoxy]benzoyl]-1-piperazineacetamide

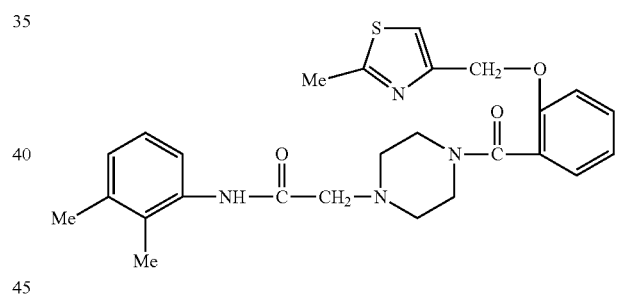

4-[2-[(3,5-dimethyl-4-isoxazolyl)methoxy]benzoyl]-N-(2-ethylphenyl)-1-piperazineacetamide

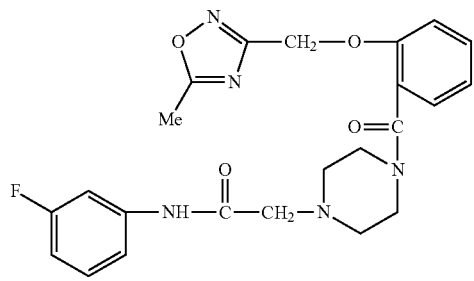 [SMILES: Cc1nc(COc2ccccc2C(=O)N2CCN(CC(=O)Nc3cccc(F)c3)CC2)no1]

N-(4-methylphenyl)-4-[2-[(2-methyl-4-thiazolyl)methoxy]benzoyl]-1-piperazineacetamide

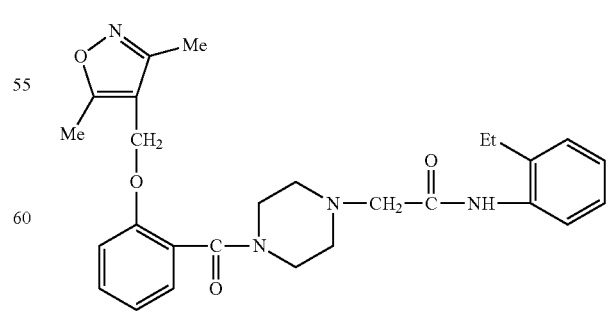

N-(4-fluorophenyl)-4-[2-[(5-methyl-1,2,4-oxadiazol-3-yl)methoxy]benzoyl]-1-piperazineacetamide

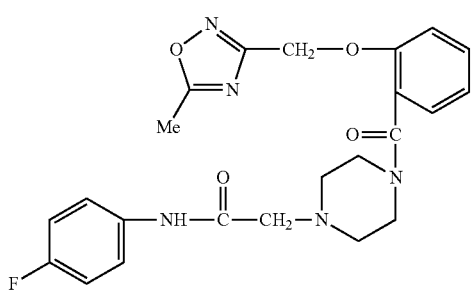 [SMILES: Cc1nc(COc2ccccc2C(=O)N2CCN(CC(=O)Nc3ccc(F)cc3)CC2)no1]

N-(4-fluorophenyl)-4-[2-[(2-methyl-4-thiazolyl)methoxy]
benzoyl]-1-piperazineacetamide

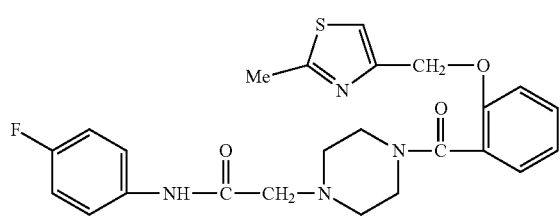 [SMILES: Cc1nc(COc2ccccc2C(=O)N2CCN(CC(=O)Nc3ccc(F)cc3)CC2)cs1]

4-[2-[(5-methyl-1,2,4-oxadiazol-3-yl)methoxy]benzoyl]-N-
(4-methylphenyl)-1-piperazineacetamide

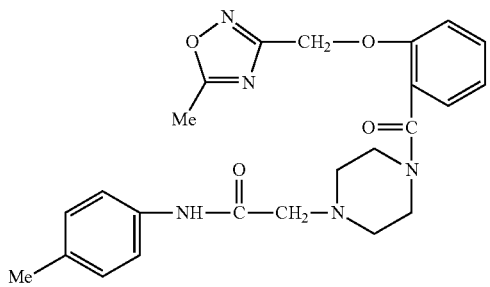 [SMILES: Cc1ccc(NC(=O)CN2CCN(C(=O)c3ccccc3OCc3noc(C)n3)CC2)cc1]

N-(2-ethylphenyl)-4-[2-[(5-methyl-1,2,4-oxadiazol-3-yl)
methoxy]benzoyl]-1-piperazineacetamide

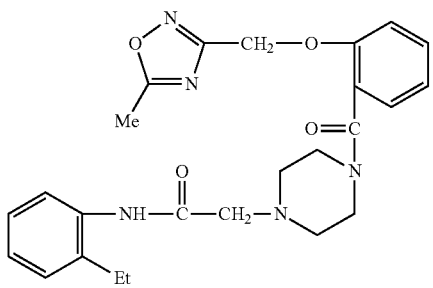 [SMILES: CCc1ccccc1NC(=O)CN1CCN(C(=O)c2ccccc2OCc2noc(C)n2)CC1]

[2-[[(3,5-dimethyl-4-isoxazolyl)methyl]thio]phenyl](4-phe-
nyl-1-piperazinyl)-methanone

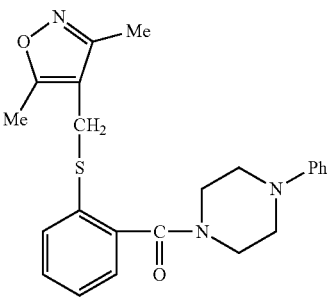 [SMILES: Cc1noc(C)c1CSc1ccccc1C(=O)N1CCN(c2ccccc2)CC1]

[4-(3-hydroxyphenyl)-1-piperazinyl][2-[[(5-methyl-3-isox-
azolyl)methyl]thio]-3-pyridinyl]-methanone

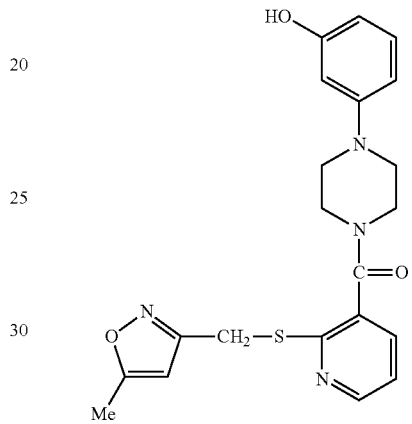

[2-[[(3,5-dimethyl-4-isoxazolyl)methyl]thio]-3-pyridinyl]
(4-thiazolo[5,4-b]pyridin-2-yl-1-piperazinyl)-methanone

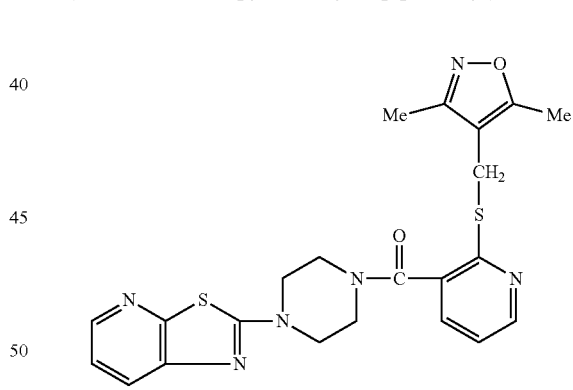

[4-(5-chloro-2-pyridinyl)-1-piperazinyl][2-[[(5-methyl-1,2,
4-oxadiazol-3-yl)methyl]thio]phenyl]-methanone

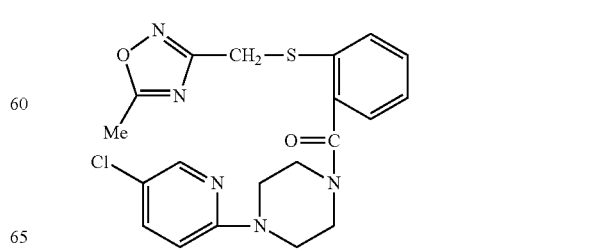

[2-[[(2-methyl-4-thiazolyl)methyl]thio]phenyl][4-(5-methyl[1,2,4]triazolo[1,5-a]pyrimidin-7-yl)-1-piperazinyl]-methanone

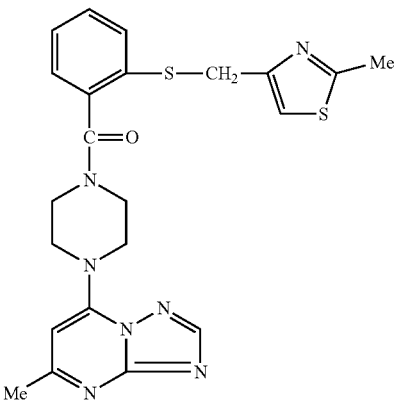 [SMILES: Cc1cc(N2CCN(C(=O)c3ccccc3SCc3csc(C)n3)CC2)n2ncnc2n1]

[4-(5-chloro-2-pyridinyl)-1-piperazinyl][2-[(4-thiazolylmethyl)thio]phenyl]-methanone

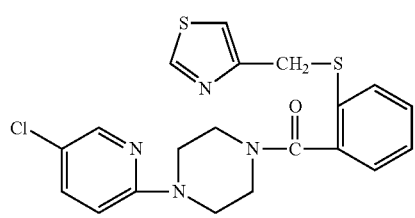 [SMILES: O=C(c1ccccc1SCc1cscn1)N1CCN(c2ccc(Cl)cn2)CC1]

[4-(5-chloro-2-pyridinyl)-1-piperazinyl][2-[[(2-methyl-4-thiazolyl)methyl]thio]phenyl]-methanone

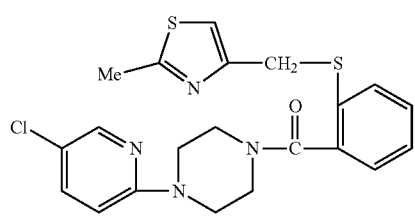 [SMILES: Cc1nc(CSc2ccccc2C(=O)N2CCN(c3ccc(Cl)cn3)CC2)cs1]

[4-[3-chloro-5-(trifluoromethyl)-2-pyridinyl]-1-piperazinyl][2-[[(5-methyl-1,2,4-oxadiazol-3-yl)methyl]thio]phenyl]-methanone

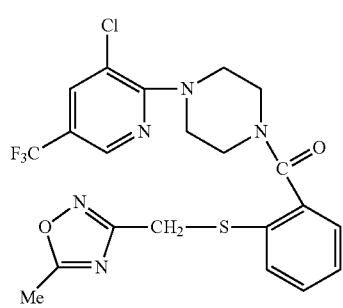 [SMILES: Cc1nc(CSc2ccccc2C(=O)N2CCN(c3ncc(C(F)(F)F)cc3Cl)CC2)no1]

[2-[[(2-methyl-4-thiazolyl)methyl]thio]phenyl][4-(2-pyrimidinyl)-1-piperazinyl]-methanone

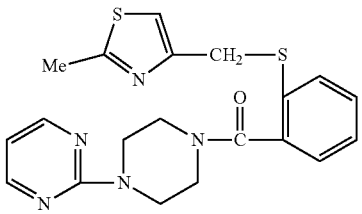 [SMILES: Cc1nc(CSc2ccccc2C(=O)N2CCN(c3ncccn3)CC2)cs1]

[2-[[(2-methyl-4-thiazolyl)methyl]thio]phenyl][4-(2-nitrophenyl)-1-piperazinyl]-methanone

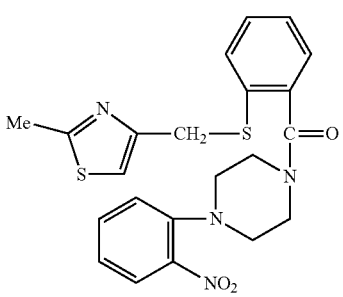 [SMILES: Cc1nc(CSc2ccccc2C(=O)N2CCN(c3ccccc3[N+](=O)[O-])CC2)cs1]

[2-[[(3-methyl-5-isoxazolyl)methyl]thio]phenyl](4-thieno[2,3-d]pyrimidin-4-yl-1-piperazinyl)-methanone

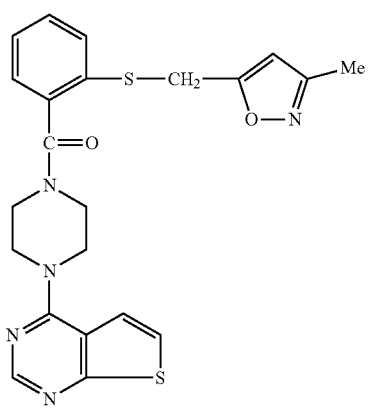 [SMILES: Cc1cc(CSc2ccccc2C(=O)N2CCN(c3ncnc4sccc34)CC2)on1]

[2-[[(3-methyl-5-isoxazolyl)methyl]thio]phenyl][4-(2-pyridinyl)-1-piperazinyl]-methanone

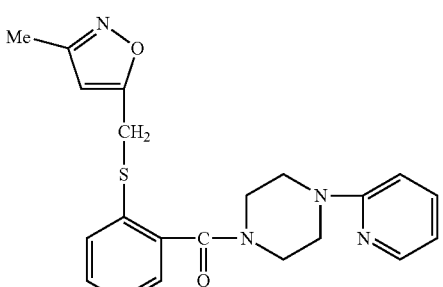

[2-[[(3-methyl-5-isoxazolyl)methyl]thio]phenyl](4-thiazolo[5,4-b]pyridin-2-yl-1-piperazinyl)-methanone

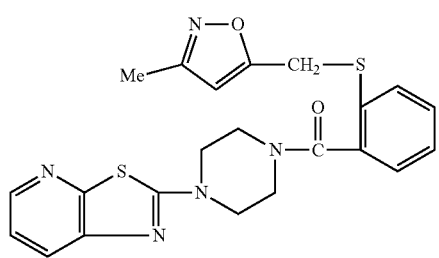 [SMILES: Cc1cc(CSc2ccccc2C(=O)N2CCN(c3nc4cccnc4s3)CC2)on1]

[2-[[(3-methyl-1,2,4-oxadiazol-5-yl)methyl]thio]phenyl][4-[5-(trifluoromethyl)-2-pyridinyl]-1-piperazinyl]-methanone

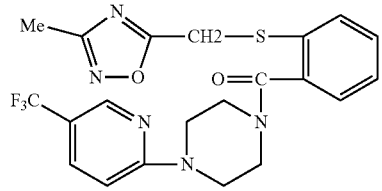 [SMILES: Cc1noc(CSc2ccccc2C(=O)N2CCN(c3ccc(C(F)(F)F)cn3)CC2)n1]

[2-[[(5-methyl-1,2,4-oxadiazol-3-yl)methyl]thio]phenyl][4-(3-methylphenyl)-1-piperazinyl]-methanone

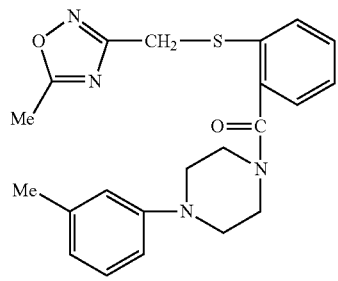 [SMILES: Cc1cccc(N2CCN(C(=O)c3ccccc3SCc3noc(C)n3)CC2)c1]

6-[4-[2-[[(5-methyl-1,2,4-oxadiazol-3-yl)methyl]thio]benzoyl]-1-piperazinyl]-3-Pyridinecarbonitrile

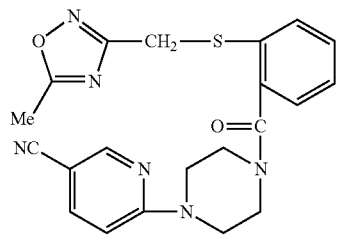 [SMILES: Cc1nc(CSc2ccccc2C(=O)N2CCN(c3ccc(C#N)cn3)CC2)no1]

[4-(2-pyrazinyl)-1-piperazinyl][2-[(4-thiazolylmethyl)thio]phenyl]-methanone

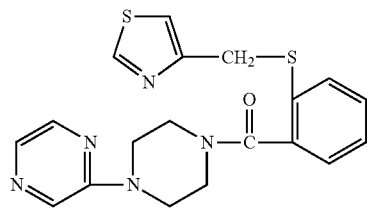 [SMILES: O=C(c1ccccc1SCc1cscn1)N1CCN(c2cnccn2)CC1]

2-[4-[2-[(4-thiazolylmethyl)thio]benzoyl]-1-piperazinyl]-4-Pyridinecarbonitrile,

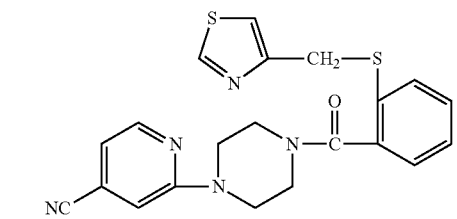 [SMILES: N#Cc1ccnc(N2CCN(C(=O)c3ccccc3SCc3cscn3)CC2)c1]

[2-[[(3,5-dimethyl-4-isoxazolyl)methyl]thio]phenyl][4-(2-ethoxyphenyl)-1-piperazinyl]-methanone

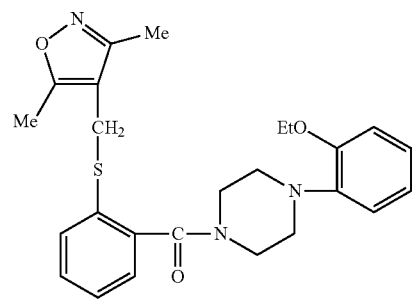

[4-(2-pyridinyl)-1-piperazinyl][2-[(2-thienylmethyl)thio]phenyl]-methanone

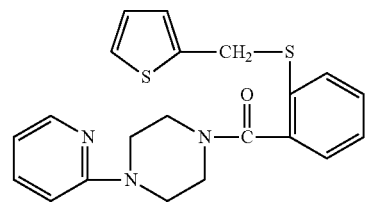 [SMILES: O=C(c1ccccc1SCc1cccs1)N1CCN(c2ccccn2)CC1]

[2-[[(2-methyl-4-thiazolyl)methyl]thio]phenyl](4-thieno[2,3-d]pyrimidin-4-yl-1-piperazinyl)-methanone

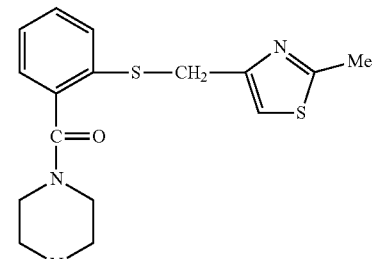

[4-(5-chloro-2-pyridinyl)-1-piperazinyl][2-[[(3-methyl-5-isoxazolyl)methyl]thio]phenyl]-methanone

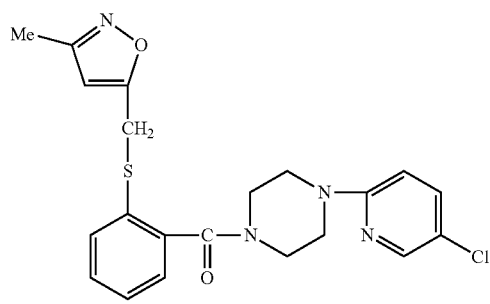 [SMILES: Cc1cc(CSc2ccccc2C(=O)N2CCN(c3ccc(Cl)cn3)CC2)on1]

[2-[[(3,5-dimethyl-4-isoxazolyl)methyl]thio]-3-pyridinyl][4-(2-pyridinyl)-1-piperazinyl]-methanone

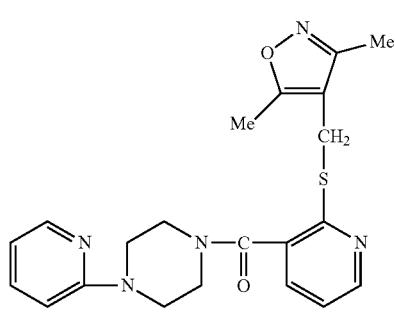 [SMILES: Cc1noc(C)c1CSc1ncccc1C(=O)N1CCN(c2ccccn2)CC1]

[4-(3-chlorophenyl)-1-piperazinyl][2-[[(3-methyl-5-isoxazolyl)methyl]thio]phenyl]-methanone

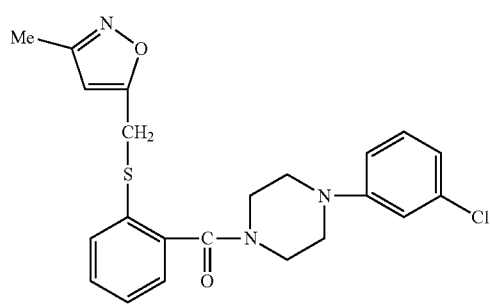 [SMILES: Cc1cc(CSc2ccccc2C(=O)N2CCN(c3cccc(Cl)c3)CC2)on1]

[2-[[(3,5-dimethyl-4-isoxazolyl)methyl]thio]-3-pyridinyl][4-[3-(trifluoromethyl)phenyl]-1-piperazinyl]-methanone

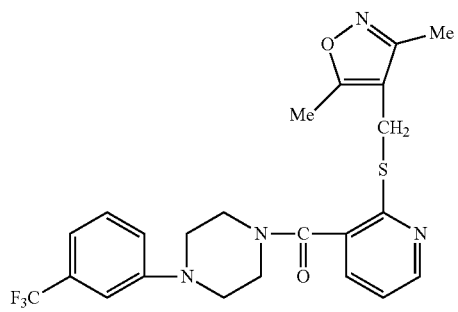 [SMILES: Cc1noc(C)c1CSc1ncccc1C(=O)N1CCN(c2cccc(C(F)(F)F)c2)CC1]

[2-[[(3,5-dimethyl-4-isoxazolyl)methyl]thio]phenyl][4-(2,3-dimethylphenyl)-1-piperazinyl]-methanone

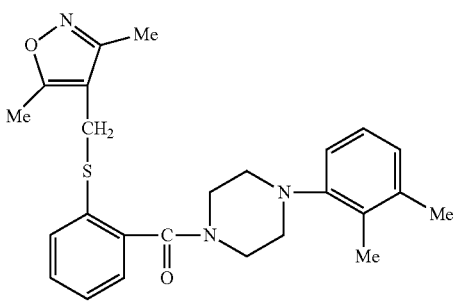 [SMILES: Cc1cccc(N2CCN(C(=O)c3ccccc3SCc3c(C)noc3C)CC2)c1C]

[4-(4-hydroxyphenyl)-1-piperazinyl][2-[[(2-methyl-4-thiazolyl)methyl]thio]phenyl]-methanone

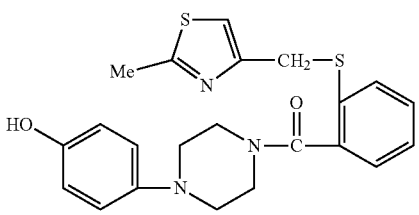 [SMILES: Cc1nc(CSc2ccccc2C(=O)N2CCN(c3ccc(O)cc3)CC2)cs1]

[2-[[(5-methyl-3-isoxazolyl)methyl]thio]-3-pyridinyl][4-(3-methylphenyl)-1-piperazinyl]-methanone

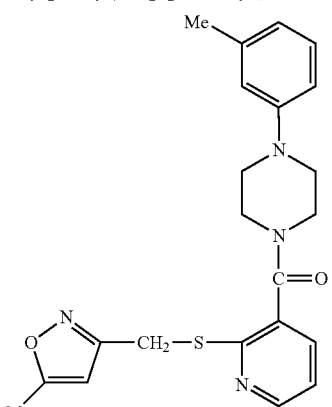

[4-(2,6-dimethyl-4-pyrimidinyl)-1-piperazinyl][2-[[(5-methyl-3-isoxazolyl)methyl]thio]-3-pyridinyl]-methanone

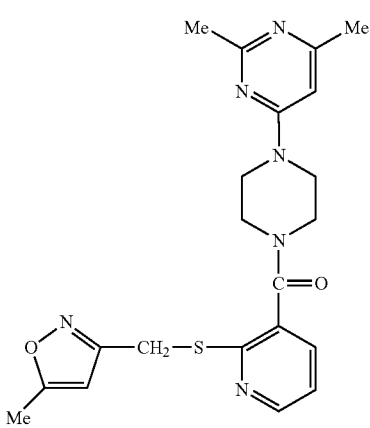 [SMILES: Cc1cc(N2CCN(C(=O)c3cccnc3SCc3cc(C)on3)CC2)nc(C)n1]

71

[4-(5-chloro-2-pyridinyl)-1-piperazinyl][2-[[(3-methyl-1,2,4-oxadiazol-5-yl)methyl]thio]phenyl]-methanone

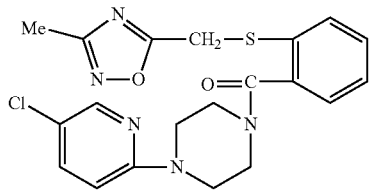 [SMILES: Cc1noc(CSc2ccccc2C(=O)N2CCN(c3ccc(Cl)cn3)CC2)n1]

[4-(4-chloro-2-nitrophenyl)-1-piperazinyl][2-[[(5-methyl-1,2,4-oxadiazol-3-yl)methyl]thio]phenyl]-methanone

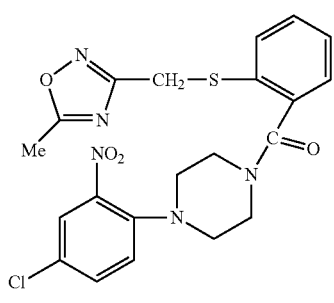 [SMILES: Cc1nc(CSc2ccccc2C(=O)N2CCN(c3ccc(Cl)cc3[N+](=O)[O-])CC2)no1]

[4-(2-pyrazinyl)-1-piperazinyl][2-[(2-thienylmethyl)thio]phenyl]-methanone

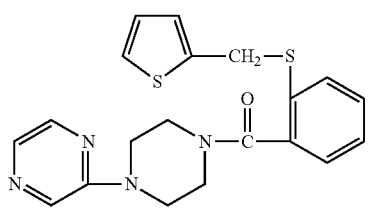 [SMILES: O=C(c1ccccc1SCc1cccs1)N1CCN(c2cnccn2)CC1]

[4-(6-chloro-2-pyridinyl)-1-piperazinyl][2-[(3-thienylmethyl)thio]phenyl]-methanone

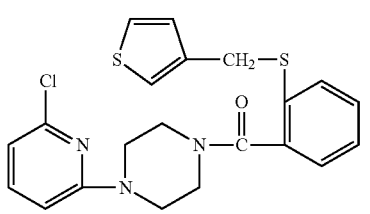 [SMILES: O=C(c1ccccc1SCc1ccsc1)N1CCN(c2cccc(Cl)n2)CC1]

[2-[[(5-methyl-3-isoxazolyl)methyl]thio]-3-pyridinyl][4-[3-(trifluoromethyl)phenyl]-1-piperazinyl]-methanone

72

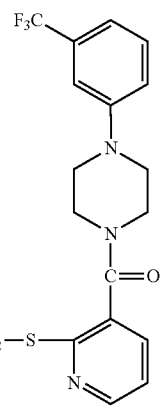

[2-[[(3,5-dimethyl-4-isoxazolyl)methyl]thio]phenyl][4-[5-(trifluoromethyl)-2-pyridinyl]-1-piperazinyl]-methanone

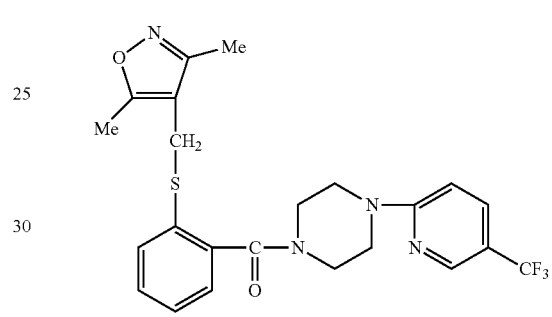

[2-[[(5-methyl-1,2,4-oxadiazol-3-yl)methyl]thio]phenyl][4-(2-thiazolyl)-1-piperazinyl]-methanone

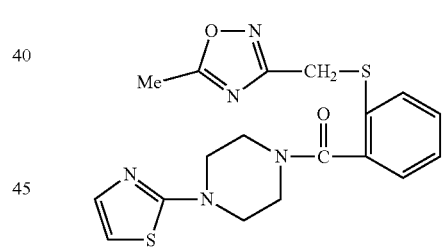

[4-(5-chloro-2-methylphenyl)-1-piperazinyl][2-[[(3,5-dimethyl-4-isoxazolyl)methyl]thio]-3-pyridinyl]-methanone

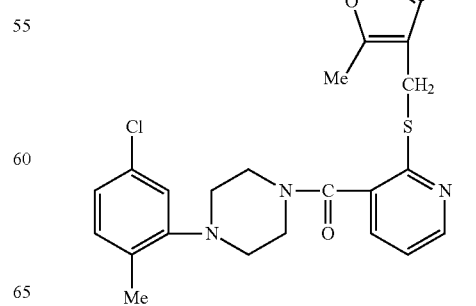

[2-[[(3-methyl-5-isoxazolyl)methyl]thio]phenyl](4-phenyl-1-piperazinyl)-methanone

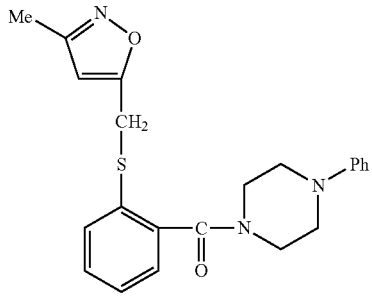 [SMILES: Cc1cc(CSc2ccccc2C(=O)N2CCN(c3ccccc3)CC2)on1]

[2-[[(3-methyl-1,2,4-oxadiazol-5-yl)methyl]thio]phenyl][4-(4-nitrophenyl)-1-piperazinyl]-methanone

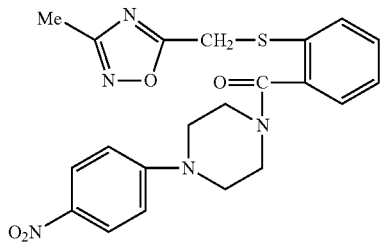 [SMILES: Cc1noc(CSc2ccccc2C(=O)N2CCN(c3ccc([N+](=O)[O-])cc3)CC2)n1]

[2-[[(3,5-dimethyl-4-isoxazolyl)methyl]thio]phenyl][4-[3-(trifluoromethyl)phenyl]-1-piperazinyl]-methanone

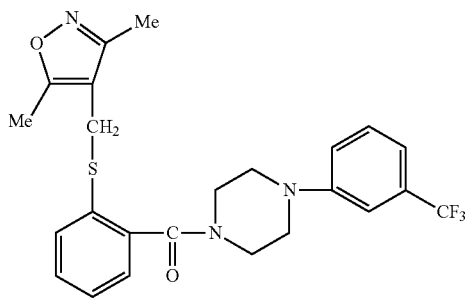 [SMILES: Cc1noc(C)c1CSc1ccccc1C(=O)N1CCN(c2cccc(C(F)(F)F)c2)CC1]

[2-[(4-thiazolylmethyl)thio]phenyl][4-[5-(trifluoromethyl)-2-pyridinyl]-1-piperazinyl]-methanone

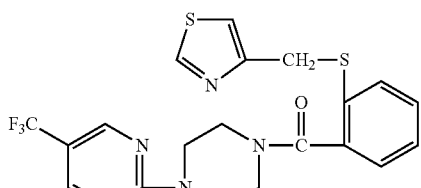

[2-[[(5-methyl-3-isoxazolyl)methyl]thio]-3-pyridinyl](4-thieno[2,3-d]pyrimidin-4-yl-1-piperazinyl)-methanone

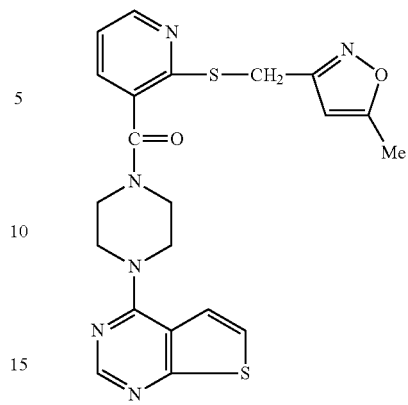

[2-[[(3,5-dimethyl-4-isoxazolyl)methyl]thio]phenyl][4-(4-methoxyphenyl)-1-piperazinyl]-methanone

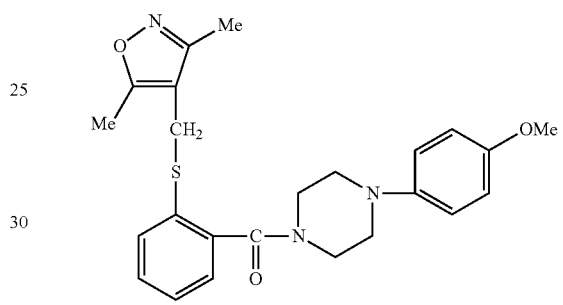

[4-(2,6-dimethyl-4-pyrimidinyl)-1-piperazinyl][2-[(2-thienylmethyl)thio]phenyl]-methanone

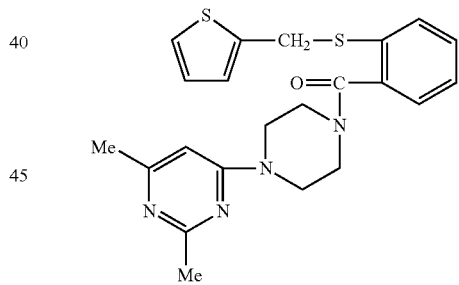

[2-[[(3,5-dimethyl-4-isoxazolyl)methyl]thio]-3-pyridinyl][4-(5-nitro-2-pyridinyl)-1-piperazinyl]-methanone

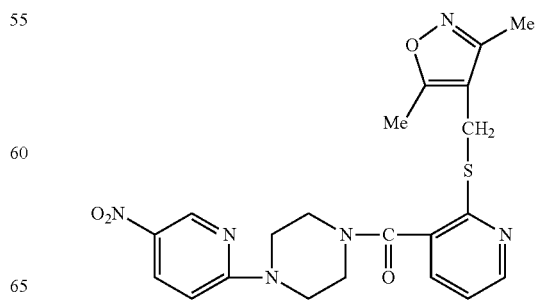

[4-(2-chlorophenyl)-1-piperazinyl][2-[[(2-methyl-4-thiaz-olyl)methyl]thio]phenyl]-methanone

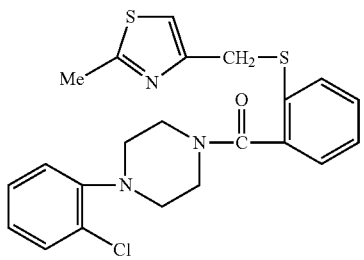 [SMILES: Cc1nc(CSc2ccccc2C(=O)N2CCN(c3ccccc3Cl)CC2)cs1]

[2-[[(3,5-dimethyl-4-isoxazolyl)methyl]thio]-3-pyridinyl][4-(3-nitrophenyl)-1-piperazinyl]-methanone

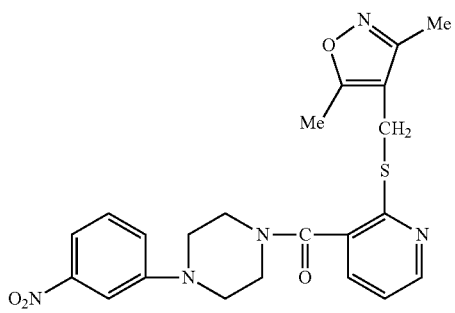 [SMILES: Cc1noc(C)c1CSc1ncccc1C(=O)N1CCN(c2cccc([N+](=O)[O-])c2)CC1]

[4-(2-chlorophenyl)-1-piperazinyl][2-[[(3,5-dimethyl-4-isoxazolyl)methyl]thio]phenyl]-methanone

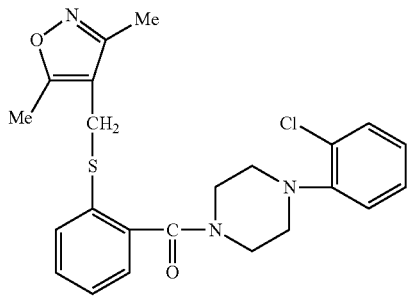

[4-(2-hydroxyphenyl)-1-piperazinyl][2-[(2-thienylmethyl)thio]phenyl]-methanone

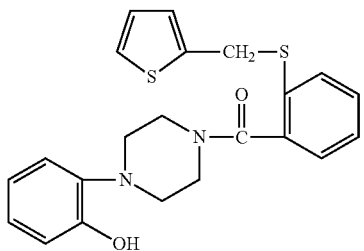 [SMILES: O=C(c1ccccc1SCc1cccs1)N1CCN(c2ccccc2O)CC1]

2-[(3-thienylmethyl)thio]phenyl][4-[5-(trifluoromethyl)-2-pyridinyl]-1-piperazinyl]-methanone

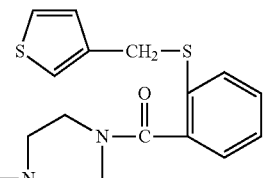

[2-[(2-furanylmethyl)thio]phenyl][4-(2-pyrimidinyl)-1-piperazinyl]-methanone

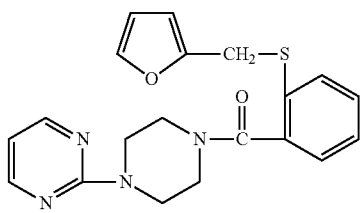 [SMILES: O=C(c1ccccc1SCc1ccco1)N1CCN(c2ncccn2)CC1]

[2-[[(3,5-dimethyl-4-isoxazolyl)methyl]thio]-3-pyridinyl][4-(4-nitrophenyl)-1-piperazinyl]-methanone

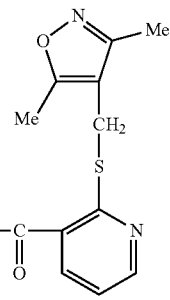

[4-(5-chloro-2-pyridinyl)-1-piperazinyl][2-[(2-thienylmethyl)thio]phenyl]-methanone

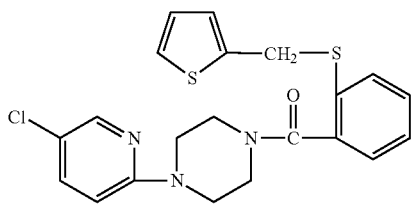 [SMILES: O=C(c1ccccc1SCc1cccs1)N1CCN(c2ccc(Cl)cn2)CC1]

[2-[[(3,5-dimethyl-4-isoxazolyl)methyl]thio]-3-pyridinyl][4-(2-pyrazinyl)-1-piperazinyl]-methanone

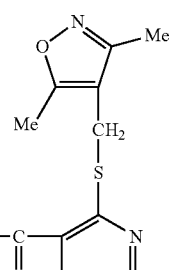

77

[2-[[(5-methyl-3-isoxazolyl)methyl]thio]-3-pyridinyl][4-(2-pyridinyl)-1-piperazinyl]-methanone

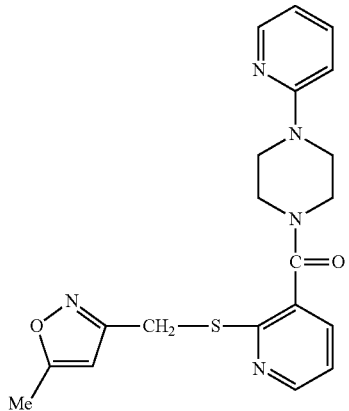 [SMILES: Cc1cc(CSc2ncccc2C(=O)N2CCN(c3ccccn3)CC2)no1]

[2-[(4-thiazolylmethyl)thio]phenyl][4-(2-thiazolyl)-1-piperazinyl]-methanone

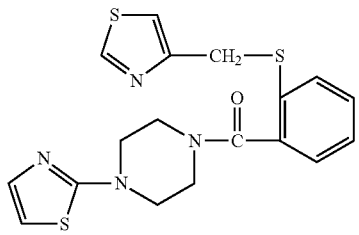 [SMILES: O=C(c1ccccc1SCc1cscn1)N1CCN(c2nccs2)CC1]

[2-[[(3,5-dimethyl-4-isoxazolyl)methyl]thio]phenyl][4-(2-methoxyphenyl)-1-piperazinyl]-methanone

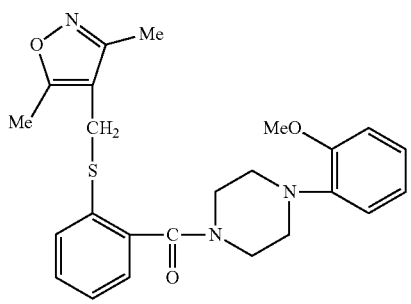 [SMILES: COc1ccccc1N1CCN(C(=O)c2ccccc2SCc2c(C)noc2C)CC1]

[2-[[(3,5-dimethyl-4-isoxazolyl)methyl]thio]-3-pyridinyl][4-(3-methylphenyl)-1-piperazinyl]-

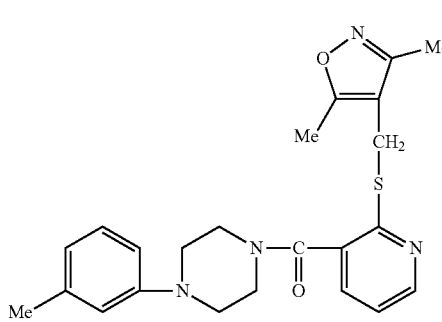

78

[4-(3-methylphenyl)-1-piperazinyl][2-[(4-thiazolylmethyl)thio]phenyl]-methanone

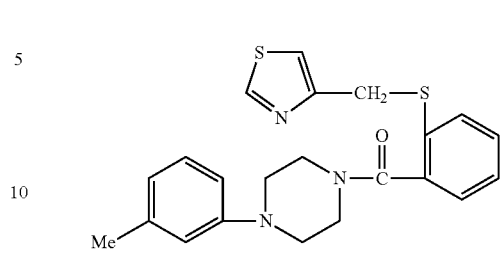

[2-[[(3,5-dimethyl-4-isoxazolyl)methyl]thio]-3-pyridinyl][4-(3-hydroxyphenyl)-1-piperazinyl]-methanone

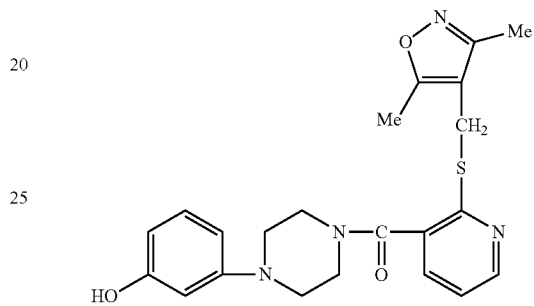

[2-[[(3,5-dimethyl-4-isoxazolyl)methyl]thio]phenyl][4-(1-methyl-1H-imidazol-2-yl)-1-piperazinyl]-methanone

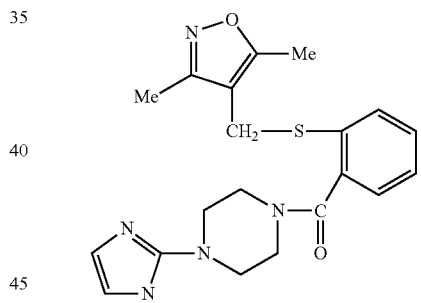

[4-(5-chloro-2-pyridinyl)-1-piperazinyl][2-[[(3,5-dimethyl-4-isoxazolyl)methyl]thio]phenyl]-methanone

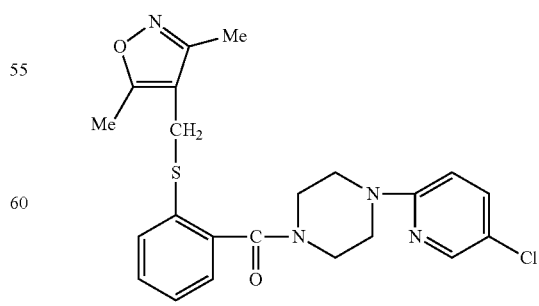

[2-[[(5-methyl-3-isoxazolyl)methyl]thio]-3-pyridinyl](4-thiazolo[5,4-b]pyridin-2-yl-1-piperazinyl)-methanone

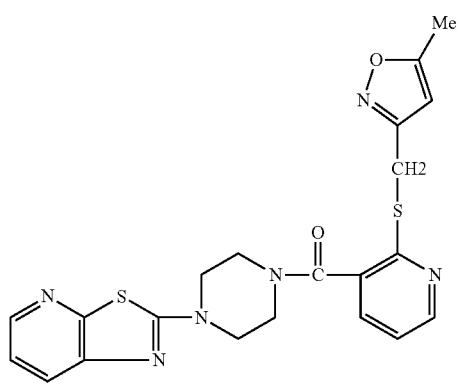 [SMILES: Cc1cc(CSc2ncccc2C(=O)N2CCN(c3nc4cccnc4s3)CC2)no1]

[4-(2-hydroxyphenyl)-1-piperazinyl][2-[[(3-methyl-5-isoxazolyl)methyl]thio]phenyl]-methanone

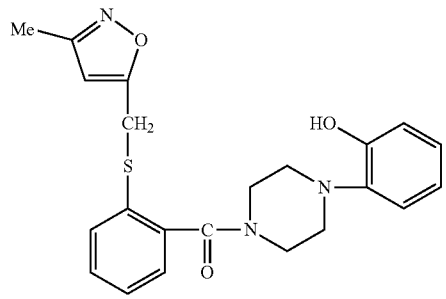 [SMILES: Cc1cc(CSc2ccccc2C(=O)N2CCN(c3ccccc3O)CC2)on1]

[4-[6-methyl-2-(1-methylethyl)-4-pyrimidinyl]-1-piperazinyl][2-[(2-thienylmethyl)thio]phenyl]-methanone

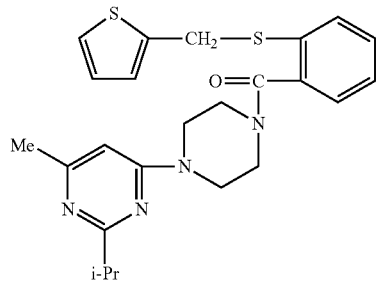 [SMILES: Cc1cc(N2CCN(C(=O)c3ccccc3SCc3cccs3)CC2)nc(C(C)C)n1]

[4-(2-pyrimidinyl)-1-piperazinyl][2-[(4-thiazolylmethyl)thio]phenyl]-methanone

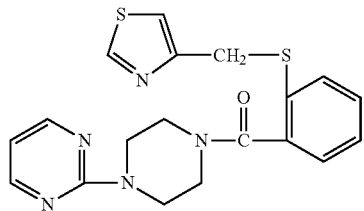 [SMILES: O=C(c1ccccc1SCc1cscn1)N1CCN(c2ncccn2)CC1]

[4-(3-chlorophenyl)-1-piperazinyl][2-[[(3,5-dimethyl-4-isoxazolyl)methyl]thio]-3-pyridinyl]-methoanone

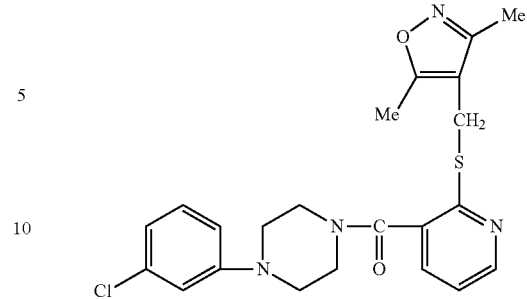

[2-[[(3,5-dimethyl-4-isoxazolyl)methyl]thio]-3-pyridinyl][4-(2-thiazolyl)-1-piperazinyl]-methanone

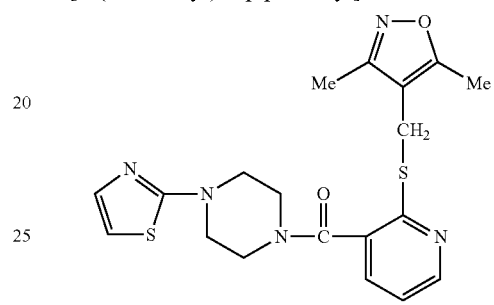

[4-(3-hydroxyphenyl)-1-piperazinyl][2-[[(3-methyl-5-isoxazolyl)methyl]thio]phenyl]-methanone

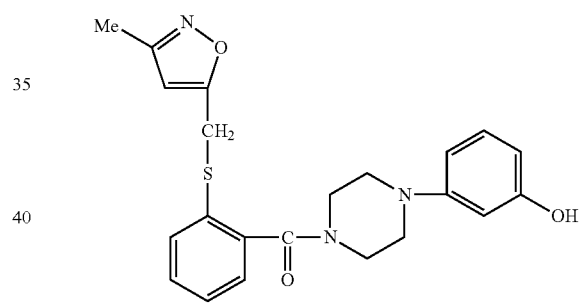

[2-[[(3,5-dimethyl-4-isoxazolyl)methyl]thio]phenyl](4-thieno[2,3-d]pyrimidin-4-yl-1-piperazinyl) methanone-

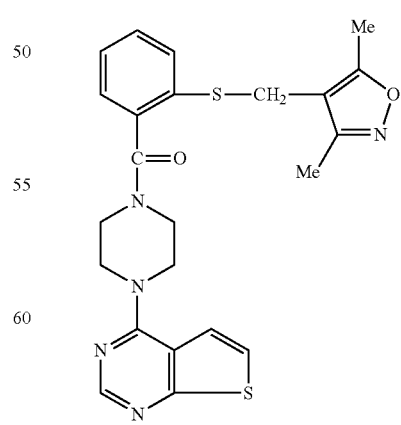

[4-(2-hydroxyphenyl)-1-piperazinyl][2-[[(5-methyl-3-isoxazolyl)methyl]thio]-3-pyridinyl]-methanone

81

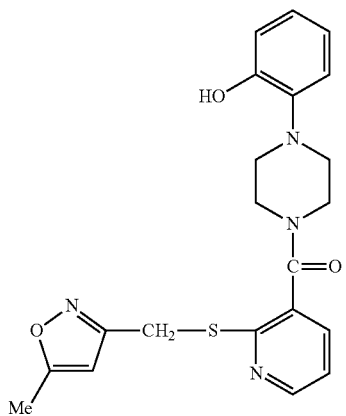 [SMILES: Cc1cc(CSc2ncccc2C(=O)N2CCN(c3ccccc3O)CC2)no1]

[2-[[(3-methyl-5-isoxazolyl)methyl]thio]phenyl][4-(2-pyrimidinyl)-1-piperazinyl]-methanone

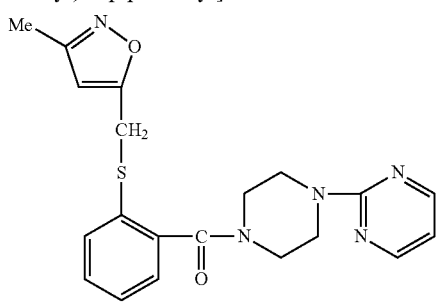

[2-[[(3-methyl-5-isoxazolyl)methyl]thio]phenyl][4-(5-nitro-2-pyridinyl)-1-piperazinyl]-methanone

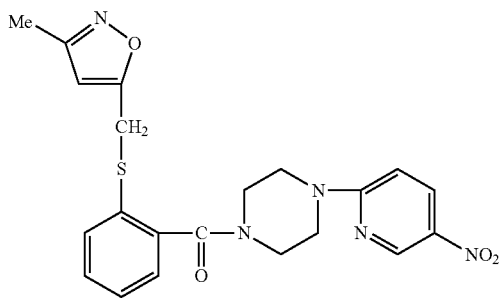 [SMILES: Cc1cc(CSc2ccccc2C(=O)N2CCN(c3ccc([N+](=O)[O-])cn3)CC2)on1]

[2-[[(3,5-dimethyl-4-isoxazolyl)methyl]thio]phenyl][4-(2,6-dimethyl-4-pyrimidinyl)-1-piperazinyl]-methanone

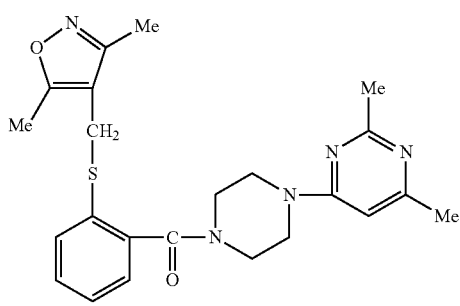 [SMILES: Cc1cc(N2CCN(C(=O)c3ccccc3SCc3c(C)noc3C)CC2)nc(C)n1]

[4-(5-chloro-2-pyridinyl)-1-piperazinyl][2-[[(5-methyl-3-isoxazolyl)methyl]thio]-3-pyridinyl]-methanone

82

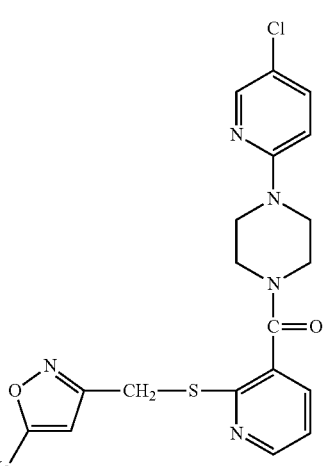

[4-(3-chlorophenyl)-1-piperazinyl][2-[(2-thienylmethyl)thio]phenyl]-methanone

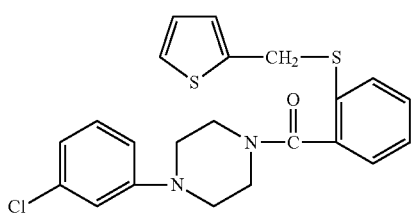 [SMILES: O=C(c1ccccc1SCc1cccs1)N1CCN(c2cccc(Cl)c2)CC1]

[4-(2-hydroxyphenyl)-1-piperazinyl][2-[(3-thienylmethyl)thio]phenyl]-methanone

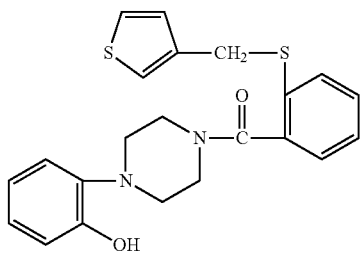 [SMILES: O=C(c1ccccc1SCc1ccsc1)N1CCN(c2ccccc2O)CC1]

[4-(2-fluorophenyl)-1-piperazinyl][2-[(2-thienylmethyl)thio]phenyl]-methanone

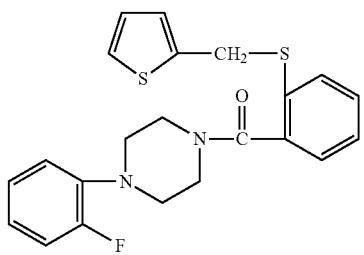 [SMILES: O=C(c1ccccc1SCc1cccs1)N1CCN(c2ccccc2F)CC1]

[4-(2-benzothiazolyl)-1-piperazinyl][2-[[(3-methyl-5-isoxazolyl)methyl]thio]phenyl]-3-furancarboxylic acid

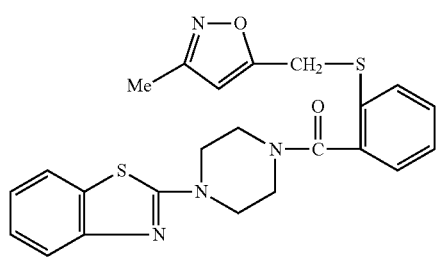 [SMILES: Cc1cc(CSc2ccccc2C(=O)N2CCN(c3nc4ccccc4s3)CC2)on1]

[2-[(4-thiazolylmethyl)thio]phenyl][4-[3-(trifluoromethyl)phenyl]-1-piperazinyl]-methanone MF

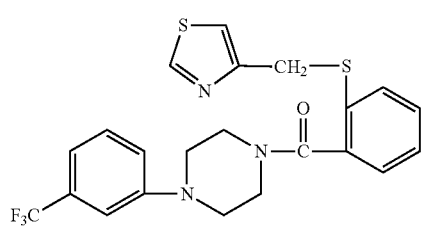 [SMILES: O=C(c1ccccc1SCc1cscn1)N1CCN(c2cccc(C(F)(F)F)c2)CC1]

[4-(2-chlorophenyl)-1-piperazinyl][2-[(4-thiazolylmethyl)thio]phenyl]-methanone

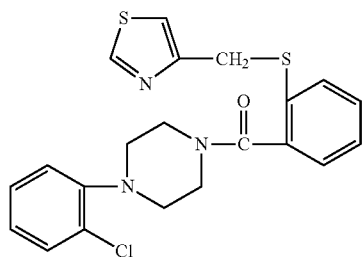 [SMILES: O=C(c1ccccc1SCc1cscn1)N1CCN(c2ccccc2Cl)CC1]

[4-(4-chloro-2-nitrophenyl)-1-piperazinyl][2-[[(3,5-dimethyl-4-isoxazolyl)methyl]thio]phenyl]-methanone

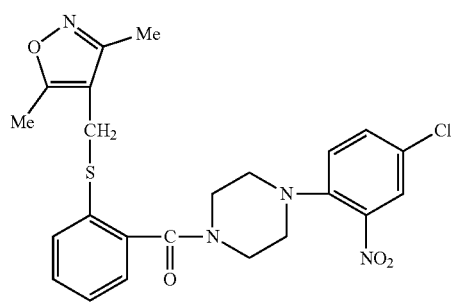 [SMILES: Cc1noc(C)c1CSc1ccccc1C(=O)N1CCN(c2ccc(Cl)cc2[N+](=O)[O-])CC1]

[4-(3-chlorophenyl)-1-piperazinyl][2-[[(3,5-dimethyl-4-isoxazolyl)methyl]thio]phenyl]-methanone

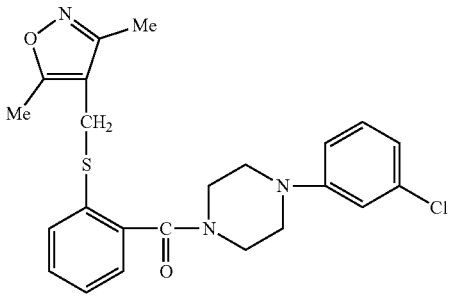 [SMILES: Cc1noc(C)c1CSc1ccccc1C(=O)N1CCN(c2cccc(Cl)c2)CC1]

[4-(1-methyl-1H-pyrazolo[3,4-d]pyrimidin-4-yl)-1-piperazinyl][2-[(3-thienylmethyl)thio]phenyl]-methanone

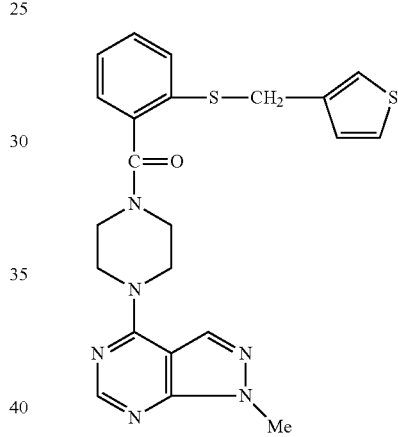

[2-[[(3,5-dimethyl-4-isoxazolyl)methyl]thio]phenyl][4-(3-hydroxyphenyl)-1-piperazinyl]-methanone

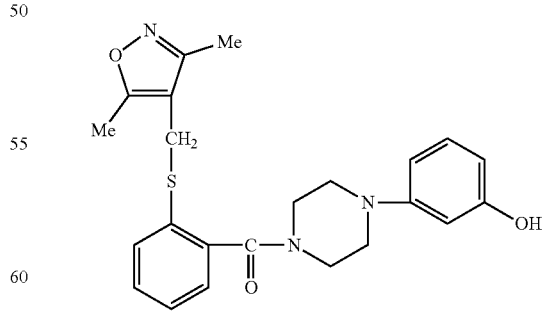

2-[4-[[2-[[(5-methyl-3-isoxazolyl)methyl]thio]-3-pyridinyl]carbonyl]-1-piperazinyl]-3-pyridinecarbonitrile,

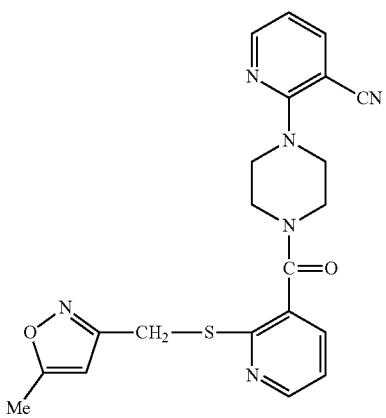 [SMILES: Cc1cc(CSc2ncccc2C(=O)N2CCN(c3ncccc3C#N)CC2)no1]

[2-[[(3,5-dimethyl-4-isoxazolyl)methyl]thio]phenyl][4-(2-hydroxyphenyl)-1-piperazinyl]-methanone

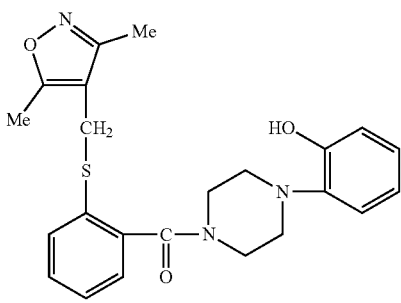 [SMILES: Cc1noc(C)c1CSc1ccccc1C(=O)N1CCN(c2ccccc2O)CC1]

[4-(2,6-dimethyl-4-pyrimidinyl)-1-piperazinyl][2-[(4-thiazolylmethyl)thio]phenyl]-methanone

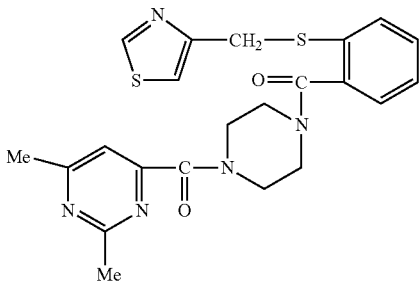 [SMILES: Cc1cc(C(=O)N2CCN(C(=O)c3ccccc3SCc3cscn3)CC2)nc(C)n1]

[4-(5-chloro-2-pyridinyl)-1-piperazinyl][2-[[(3,5-dimethyl-4-isoxazolyl)methyl]thio]-3-pyridinyl]-methanone

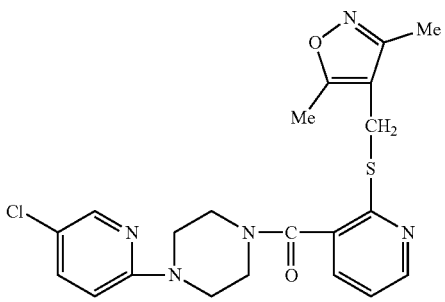 [SMILES: Cc1noc(C)c1CSc1ncccc1C(=O)N1CCN(c2ccc(Cl)cn2)CC1]

[2-[[(5-methyl-1,2,4-oxadiazol-3-yl)methyl]thio]phenyl](4-phenyl-1-piperazinyl)-methanone

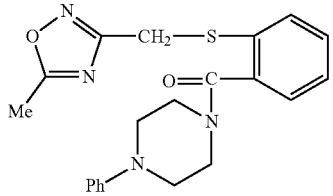 [SMILES: Cc1nc(CSc2ccccc2C(=O)N2CCN(c3ccccc3)CC2)no1]

[2-[[(3-methyl-5-isoxazolyl)methyl]thio]phenyl][4-[5-(trifluoromethyl)-2-pyridinyl]-1-piperazinyl]-methanone

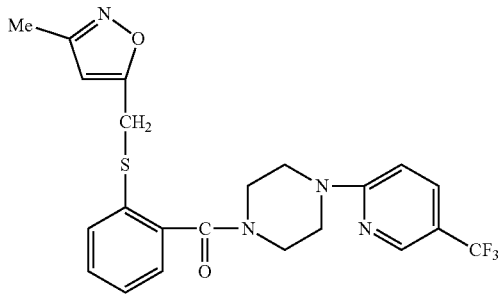 [SMILES: Cc1cc(CSc2ccccc2C(=O)N2CCN(c3ccc(C(F)(F)F)cn3)CC2)on1]

[4-(2-methoxyphenyl)-1-piperazinyl][2-[(2-thienylmethyl)thio]phenyl]-methanone

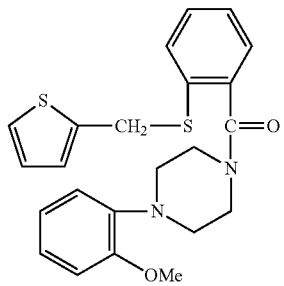 [SMILES: COc1ccccc1N1CCN(C(=O)c2ccccc2SCc2cccs2)CC1]

[4-(2-thiazolyl)-1-piperazinyl][2-[(2-thienylmethyl)thio]phenyl]-methanone

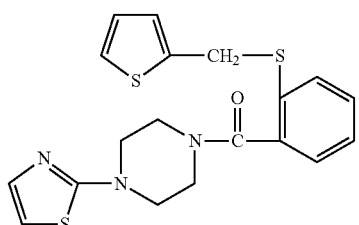

[2-[[(5-methyl-3-isoxazolyl)methyl]thio]-3-pyridinyl](4-phenyl-1-piperazinyl)-methanone

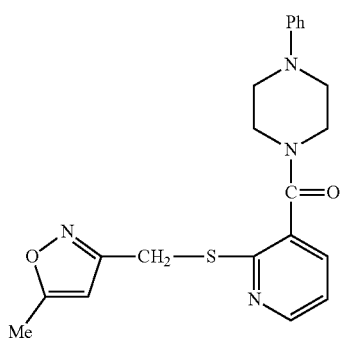 [SMILES: Cc1cc(CSc2ncccc2C(=O)N2CCN(c3ccccc3)CC2)no1]

(4-thieno[2,3-d]pyrimidin-4-yl-1-piperazinyl)[2-[(2-thienylmethyl)thio]phenyl]-methanone

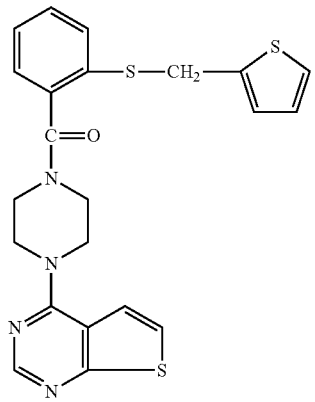 [SMILES: O=C(c1ccccc1SCc1cccs1)N1CCN(c2ncnc3sccc23)CC1]

[4-(2-hydroxyphenyl)-1-piperazinyl][2-[[(2-methyl-4-thiazolyl)methyl]thio]phenyl]-methanone

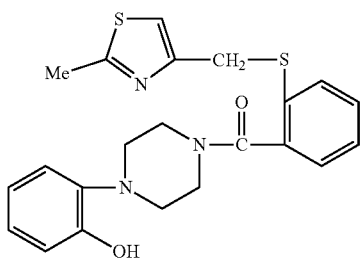 [SMILES: Cc1nc(CSc2ccccc2C(=O)N2CCN(c3ccccc3O)CC2)cs1]

[4-(4-chloro-2-nitrophenyl)-1-piperazinyl][2-[[(3,5-dimethyl-4-isoxazolyl)methyl]thio]-3-pyridinyl]-methanone

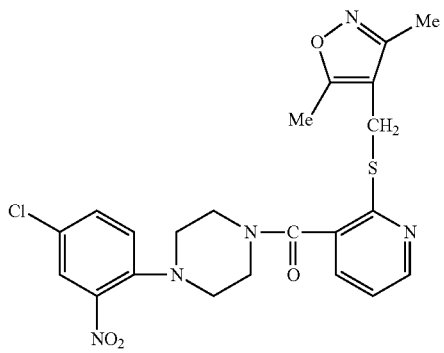 [SMILES: Cc1noc(C)c1CSc1ncccc1C(=O)N1CCN(c2ccc(Cl)cc2[N+](=O)[O-])CC1]

[4-(2-pyrimidinyl)-1-piperazinyl][2-[(2-thienylmethyl)thio]phenyl]-methanone

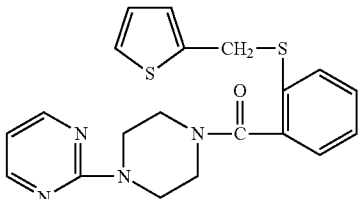

[4-(5-bromo-2-pyrimidinyl)-1-piperazinyl][2-[[(3,5-dimethyl-4-isoxazolyl)methyl]thio]phenyl]-methanone

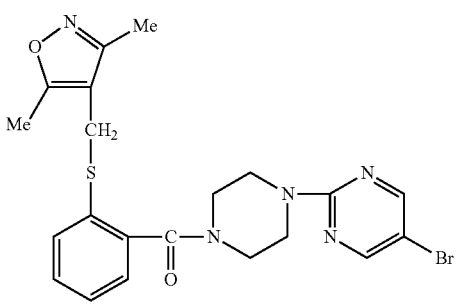 [SMILES: Cc1noc(C)c1CSc1ccccc1C(=O)N1CCN(c2ncc(Br)cn2)CC1]

[2-[[(3-methyl-5-isoxazolyl)methyl]thio]phenyl][4-(3-nitrophenyl)-1-piperazinyl]-methanone

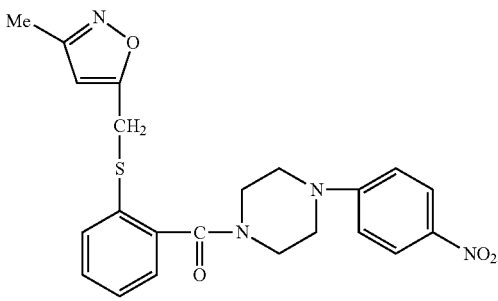

[2-[[(3,5-dimethyl-4-isoxazolyl)methyl]thio]phenyl][4-(3-methoxyphenyl)-1-piperazinyl]-methanone

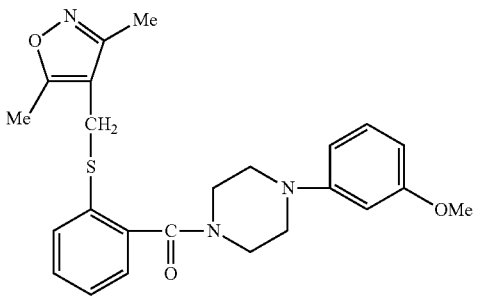 [SMILES: COc1cccc(N2CCN(C(=O)c3ccccc3SCc3c(C)noc3C)CC2)c1]

[4-[3-chloro-5-(trifluoromethyl)-2-pyridinyl]-1-piperazinyl][2-[(4-thiazolylmethyl)thio]phenyl]-methanone

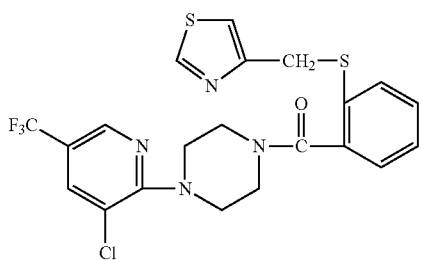 [SMILES: O=C(c1ccccc1SCc1cscn1)N1CCN(c2ncc(C(F)(F)F)cc2Cl)CC1]

[2-[[(3,5-dimethyl-4-isoxazolyl)methyl]thio]phenyl][4-(2-thiazolyl)-1-piperazinyl]methanone-

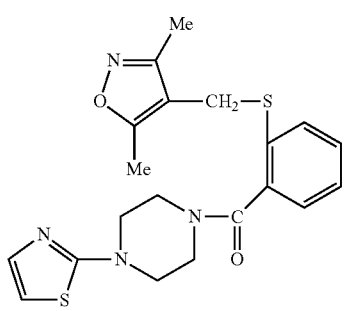 [SMILES: Cc1noc(C)c1CSc1ccccc1C(=O)N1CCN(c2nccs2)CC1]

[4-(3-hydroxyphenyl)-1-piperazinyl][2-[(2-thienylmethyl)thio]phenyl]-methanone

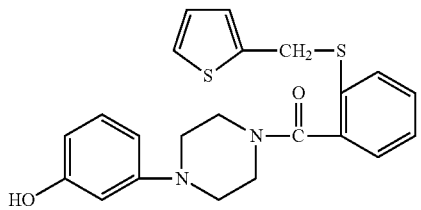 [SMILES: O=C(c1ccccc1SCc1cccs1)N1CCN(c2cccc(O)c2)CC1]

[2-[[(3,5-dimethyl-4-isoxazolyl)methyl]thio]phenyl][4-(2-pyridinyl)-1-piperazinyl]-methanone

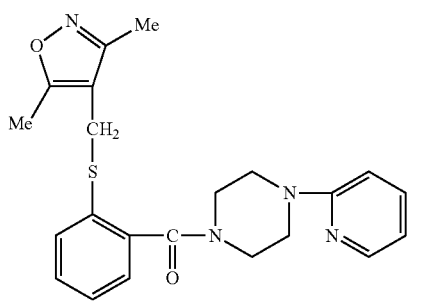 [SMILES: Cc1noc(C)c1CSc1ccccc1C(=O)N1CCN(c2ccccn2)CC1]

[4-(2,6-dimethyl-4-pyrimidinyl)-1-piperazinyl][2-[[(3-methyl-5-isoxazolyl)methyl]thio]phenyl]-methanone

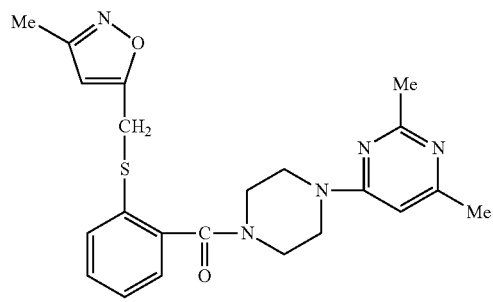 [SMILES: Cc1cc(CSc2ccccc2C(=O)N2CCN(c3cc(C)nc(C)n3)CC2)on1]

[2-[[(3,5-dimethyl-4-isoxazolyl)methyl]thio]-3-pyridinyl][4-(2,6-dimethyl-4-pyrimidinyl)-1-piperazinyl]-methanone

[4-(5-bromo-2-pyrimidinyl)-1-piperazinyl][2-[[(5-methyl-3-isoxazolyl)methyl]thio]-3-pyridinyl]-methanone

[2-[[(3,5-dimethyl-4-isoxazolyl)methyl]thio]phenyl][4-(2-pyrimidinyl)-1-piperazinyl]-methanone

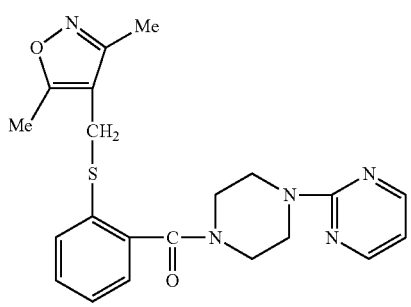 [SMILES: Cc1noc(C)c1CSc1ccccc1C(=O)N1CCN(c2ncccn2)CC1]

[2-[[(3,5-dimethyl-4-isoxazolyl)methyl]thio]-3-pyridinyl](4-thieno[2,3-d]pyrimidin-4-yl-1-piperazinyl)-methanone

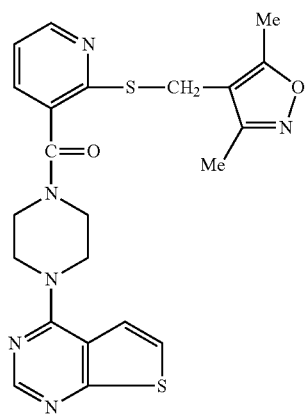 [SMILES: Cc1noc(C)c1CSc1ncccc1C(=O)N1CCN(c2ncnc3sccc23)CC1]

[2-[[(3,5-dimethyl-4-isoxazolyl)methyl]thio]-3-pyridinyl][4-(3-methoxyphenyl)-1-piperazinyl]-methanone

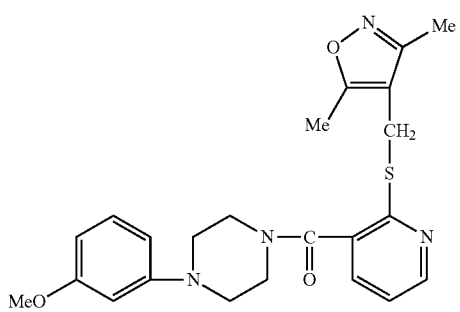 [SMILES: COc1cccc(N2CCN(C(=O)c3cccnc3SCc3c(C)noc3C)CC2)c1]

[4-(2,3-dimethylphenyl)-1-piperazinyl][2-[[(3-methyl-5-isoxazolyl)methyl]thio]phenyl]-methanone

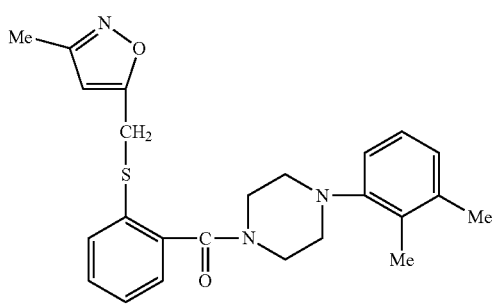 [SMILES: Cc1cc(CSc2ccccc2C(=O)N2CCN(c3cccc(C)c3C)CC2)on1]

[4-[(4-chlorophenyl)methyl]-1-piperazinyl][2-[[(5-methyl-1,2,4-oxadiazol-3-yl)methyl]thio]phenyl]-methanone

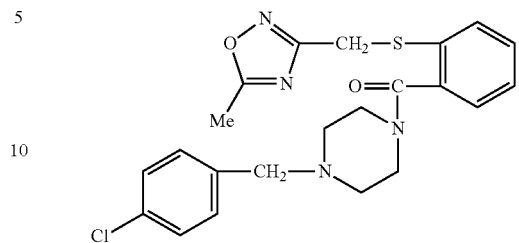

(4-phenyl-1-piperazinyl)[2-[(2-thienylmethyl)thio]phenyl]-methanone

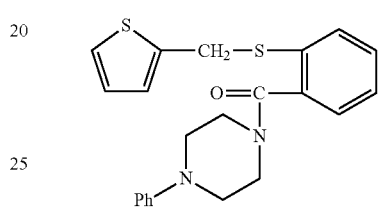

[2-[[(3,5-dimethyl-4-isoxazolyl)methyl]thio]phenyl](4-thiazolo[5,4-b]pyridin-2-yl-1-piperazinyl)-methanone

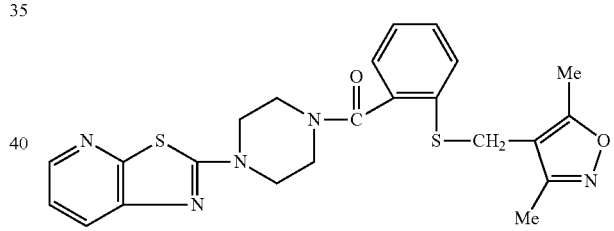

[4-(4-chloro-2-nitrophenyl)-1-piperazinyl][2-[[(3-methyl-1,2,4-oxadiazol-5-yl)methyl]thio]phenyl]-methanone

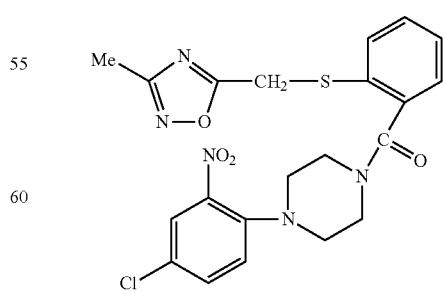

[4-(2-fluorophenyl)-1-piperazinyl][2-[[(5-methyl-1,2,4-oxadiazol-3-yl)methyl]thio]phenyl]-methanone

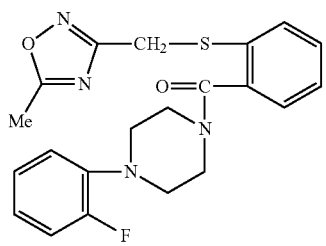 [SMILES: Cc1nc(CSc2ccccc2C(=O)N2CCN(c3ccccc3F)CC2)no1]

[2-[[(3-methyl-1,2,4-oxadiazol-5-yl)methyl]thio]phenyl][4-(5-nitro-2-pyridinyl)-1-piperazinyl]-methanone

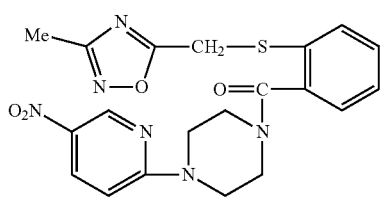 [SMILES: Cc1noc(CSc2ccccc2C(=O)N2CCN(c3ccc([N+](=O)[O-])cn3)CC2)n1]

[2-[[(5-methyl-1,2,4-oxadiazol-3-yl)methyl]thio]phenyl][4-[5-(trifluoromethyl)-2-pyridinyl]-1-piperazinyl]-methanone

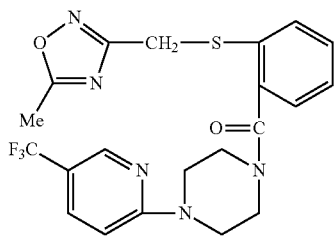 [SMILES: Cc1nc(CSc2ccccc2C(=O)N2CCN(c3ccc(C(F)(F)F)cn3)CC2)no1]

[2-[[(3,5-dimethyl-4-isoxazolyl)methyl]thio]phenyl][4-(4-nitrophenyl)-1-piperazinyl]-methanone

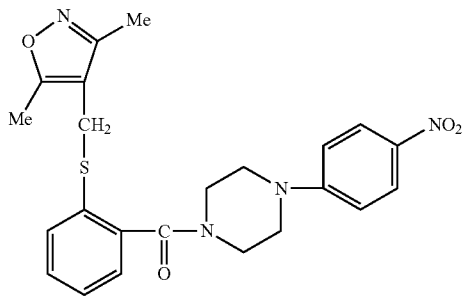 [SMILES: Cc1noc(C)c1CSc1ccccc1C(=O)N1CCN(c2ccc([N+](=O)[O-])cc2)CC1]

[4-(4-chlorophenyl)-1-piperazinyl][2-[[(2-methyl-4-thiazolyl)methyl]thio]phenyl]-methanone

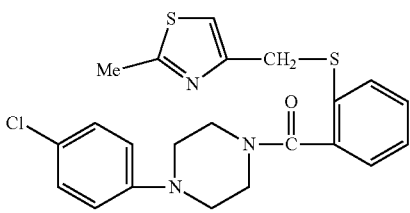 [SMILES: Cc1nc(CSc2ccccc2C(=O)N2CCN(c3ccc(Cl)cc3)CC2)cs1]

[4-(3-hydroxyphenyl)-1-piperazinyl][2-[[(2-methyl-4-thiazolyl)methyl]thio]phenyl]-methanone

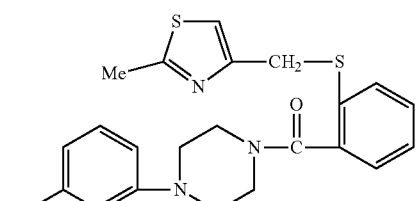

[4-(3,5-dichloro-2-pyridinyl)-1-piperazinyl][2-[(2-thienylmethyl)thio]phenyl]-methanone

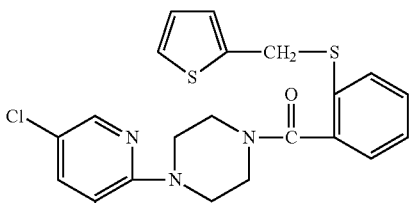

2-[4-[[2-[[(5-methyl-3-isoxazolyl)methyl]thio]-3-pyridinyl]carbonyl]-1-piperazinyl]-4-pyridinecarbonitrile

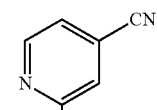
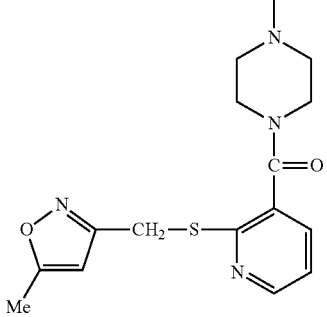

[4-(2,3-dimethylphenyl)-1-piperazinyl][2-[[(2-methyl-4-thiazolyl)methyl]thio]phenyl]-methanone

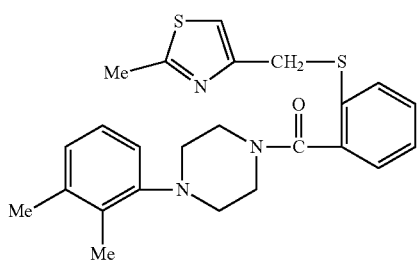 [SMILES: Cc1nc(CSc2ccccc2C(=O)N2CCN(c3cccc(C)c3C)CC2)cs1]

[2-[[(3,5-dimethyl-4-isoxazolyl)methyl]thio]-3-pyridinyl][4-(2-methoxyphenyl)-1-piperazinyl]-methanone

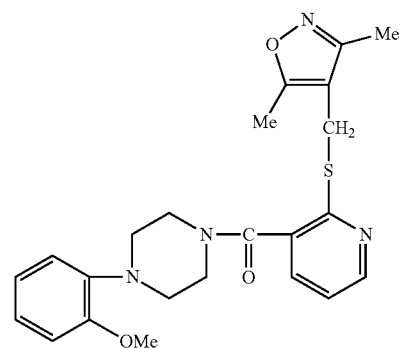 [SMILES: COc1ccccc1N1CCN(C(=O)c2cccnc2SCc2c(C)noc2C)CC1]

[4-(4-chlorophenyl)-1-piperazinyl][2-[[(3-methyl-5-isoxazolyl)methyl]thio]phenyl]-methanone

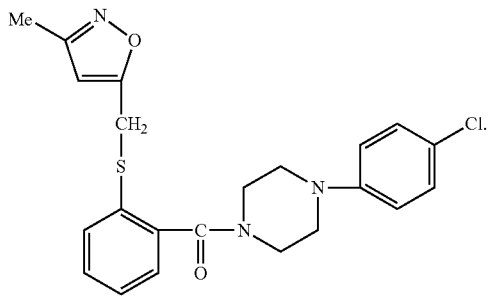 [SMILES: Cc1cc(CSc2ccccc2C(=O)N2CCN(c3ccc(Cl)cc3)CC2)on1]

[2-[[(3-methyl-1,2,4-oxadiazol-5-yl)methyl]thio]phenyl][4-(3-methylphenyl)-1-piperazinyl]-methanone

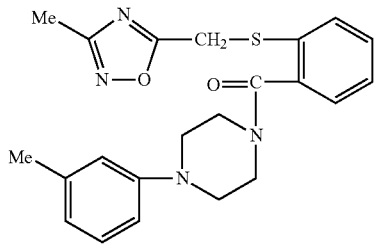 [SMILES: Cc1cccc(N2CCN(C(=O)c3ccccc3SCc3nc(C)no3)CC2)c1]

[2-[[(3-methyl-1,2,4-oxadiazol-5-yl)methyl]thio]phenyl][4-[3-(trifluoromethyl)phenyl]-1-piperazinyl]-methanone

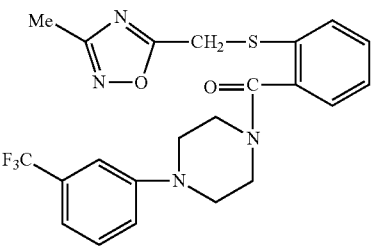 [SMILES: Cc1noc(CSc2ccccc2C(=O)N2CCN(c3cccc(C(F)(F)F)c3)CC2)n1]

[2-[[(5-methyl-3-isoxazolyl)methyl]thio]-3-pyridinyl][4-(2-pyrimidinyl)-1-piperazinyl]-methanone

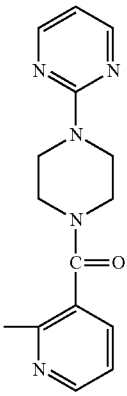

[4-(2-methoxyphenyl)-1-piperazinyl][2-[[(3-methyl-1,2,4-oxadiazol-5-yl)methyl]thio]phenyl]-methanone

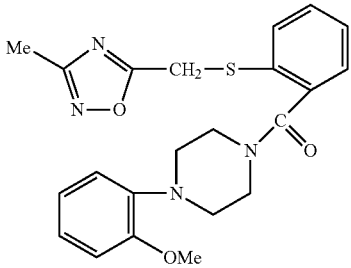 [SMILES: COc1ccccc1N1CCN(C(=O)c2ccccc2SCc2nc(C)no2)CC1]

[2-[(3,5-dimethyl-4-isoxazolyl)methoxy]phenyl][4-(2,3-dimethylphenyl)-1-piperazinyl]-methanone

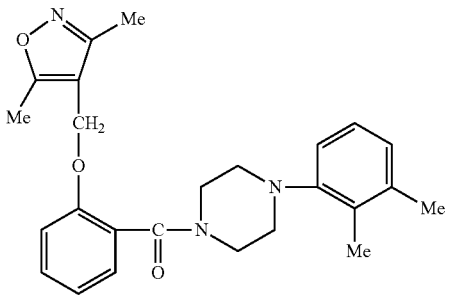 [SMILES: Cc1cccc(N2CCN(C(=O)c3ccccc3OCc3c(C)noc3C)CC2)c1C]

[2-[(5-methyl-1,2,4-oxadiazol-3-yl)methoxy]phenyl][4-[2-nitro-4-(trifluoromethyl)phenyl]-1-piperazinyl]-methanone

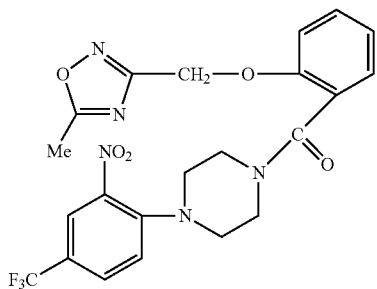 [SMILES: Cc1nc(COc2ccccc2C(=O)N2CCN(c3ccc(C(F)(F)F)cc3[N+](=O)[O-])CC2)no1]

[2-(4-thiazolylmethoxy)phenyl][4-(2-thiazolyl)-1-piperazinyl]-methanone

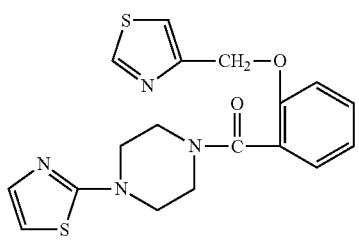 [SMILES: O=C(c1ccccc1OCc1cscn1)N1CCN(c2nccs2)CC1]

[2-[(3,5-dimethyl-4-isoxazolyl)methoxy]phenyl](4-thiazolo[5,4-b]pyridin-2-yl-1-piperazinyl)-methanone

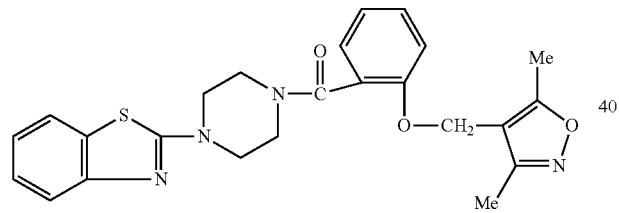

[2-[(3,5-dimethyl-4-isoxazolyl)methoxy]phenyl][4-(2-pyrazinyl)-1-piperazinyl]-methanone

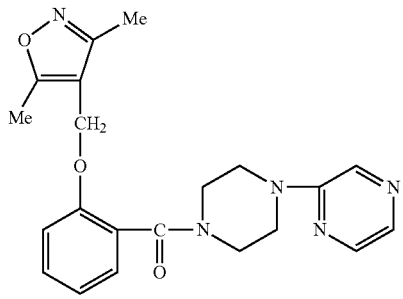 [SMILES: Cc1noc(C)c1COc1ccccc1C(=O)N1CCN(c2cnccn2)CC1]

[2-[(3,5-dimethyl-4-isoxazolyl)methoxy]phenyl](4-thieno[2,3-d]pyrimidin-4-yl-1-piperazinyl)-methanone

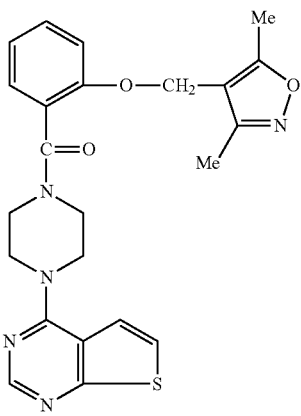 [SMILES: Cc1noc(C)c1COc1ccccc1C(=O)N1CCN(c2ncnc3sccc23)CC1]

[4-(2-fluorophenyl)-1-piperazinyl][2-[(3-phenyl-1,2,4-oxadiazol-5-yl)methoxy]phenyl]-methanone

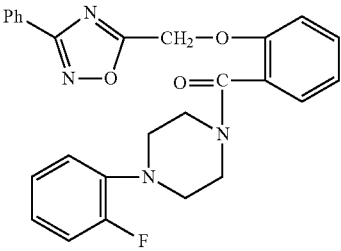 [SMILES: O=C(c1ccccc1OCc1nc(-c2ccccc2)no1)N1CCN(c2ccccc2F)CC1]

[4-(3-chlorophenyl)-1-piperazinyl][2-[(3,5-dimethyl-4-isoxazolyl)methoxy]phenyl]-methanone

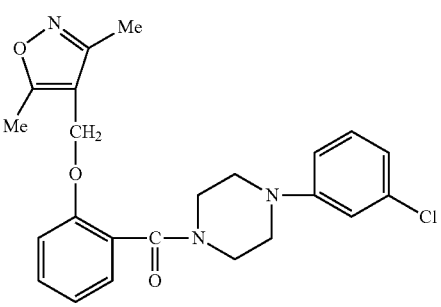 [SMILES: Cc1noc(C)c1COc1ccccc1C(=O)N1CCN(c2cccc(Cl)c2)CC1]

[2-[(2-methyl-4-thiazolyl)methoxy]phenyl](4-phenyl-1-piperazinyl)-methanone

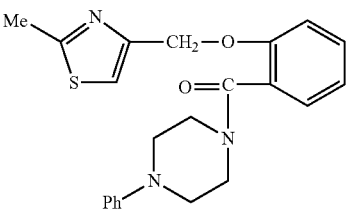 [SMILES: Cc1nc(COc2ccccc2C(=O)N2CCN(c3ccccc3)CC2)cs1]

[2-[(3,5-dimethyl-4-isoxazolyl)methoxy]phenyl][4-(2-nitrophenyl)-1-piperazinyl]-methanone

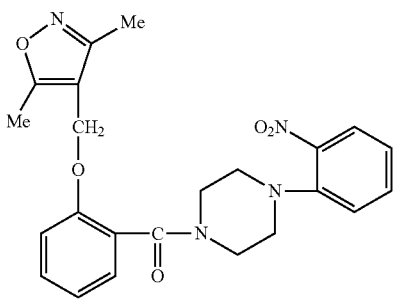 [SMILES: Cc1noc(C)c1COc1ccccc1C(=O)N1CCN(c2ccccc2[N+](=O)[O-])CC1]

2-[4-[2-[(3,5-dimethyl-4-isoxazolyl)methoxy]benzoyl]-1-piperazinyl]-3-pyridinecarbonitrile

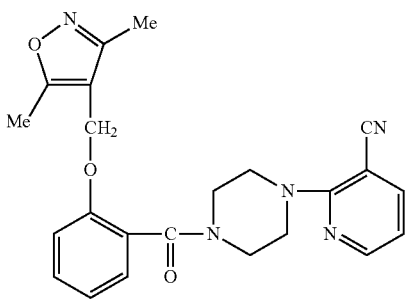 [SMILES: Cc1noc(C)c1COc1ccccc1C(=O)N1CCN(c2ncccc2C#N)CC1]

[4-(4-fluorophenyl)-1-piperazinyl][2-[[3-(4-methylphenyl)-1,2,4-oxadiazol-5-yl]methoxy]phenyl]-methanone

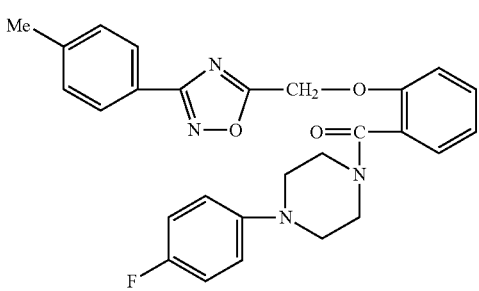 [SMILES: Cc1ccc(-c2noc(COc3ccccc3C(=O)N3CCN(c4ccc(F)cc4)CC3)n2)cc1]

[2-[(3,5-dimethyl-4-isoxazolyl)methoxy]phenyl][4-(5-methyl[1,2,4]triazolo[1,5-a]pyrimidin-7-yl)-1-piperazinyl]-methanone

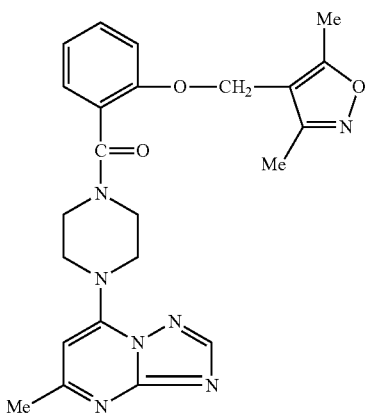 [SMILES: Cc1cc(N2CCN(C(=O)c3ccccc3OCc3c(C)noc3C)CC2)n2ncnc2n1]

[4-(2-methoxyphenyl)-1-piperazinyl][2-[[3-(4-methylphenyl)-1,2,4-oxadiazol-5-yl]methoxy]phenyl]-methanone

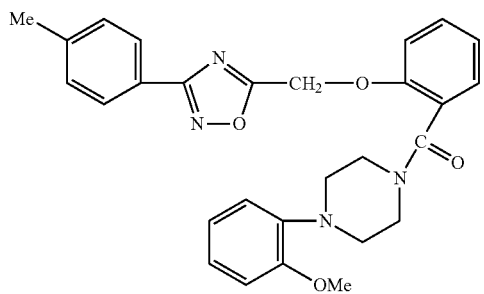 [SMILES: COc1ccccc1N1CCN(C(=O)c2ccccc2OCc2nc(-c3ccc(C)cc3)no2)CC1]

[2-[(3,5-dimethyl-4-isoxazolyl)methoxy]phenyl][4-(2-methoxyphenyl)-1-piperazinyl]-methanone

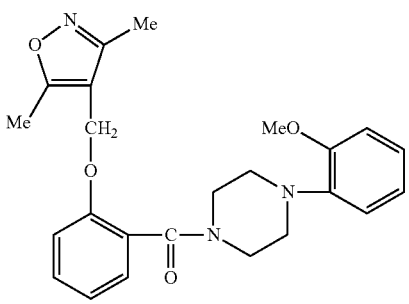 [SMILES: COc1ccccc1N1CCN(C(=O)c2ccccc2OCc2c(C)noc2C)CC1]

[4-(3,5-dichloro-2-pyridinyl)-1-piperazinyl][2-(4-thiazolylmethoxy)phenyl]-methanone

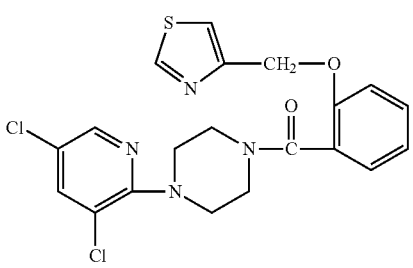 [SMILES: O=C(c1ccccc1OCc1cscn1)N1CCN(c2ncc(Cl)cc2Cl)CC1]

[2-[(3,5-dimethyl-4-isoxazolyl)methoxy]phenyl][4-(2-ethoxyphenyl)-1-piperazinyl]-methanone

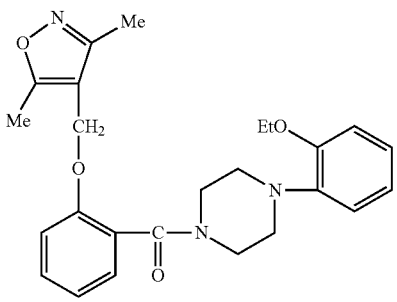 [SMILES: CCOc1ccccc1N1CCN(C(=O)c2ccccc2OCc2c(C)noc2C)CC1]

[2-[(3,5-dimethyl-4-isoxazolyl)methoxy]phenyl][4-(4-pyridinyl)-1-piperazinyl]-methanone

101

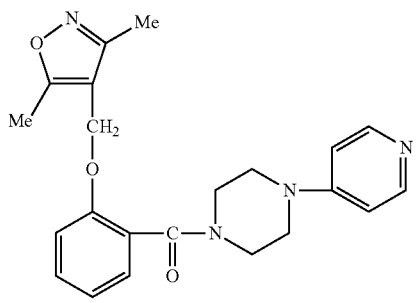 [SMILES: Cc1noc(C)c1COc1ccccc1C(=O)N1CCN(c2ccncc2)CC1]

2-fluoro-6-[4-[2-(4-thiazolylmethoxy)benzoyl]-1-piperazinyl]-benzonitrile

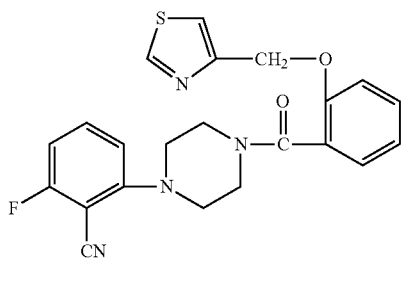 [SMILES: N#Cc1c(F)cccc1N1CCN(C(=O)c2ccccc2OCc2cscn2)CC1]

[4-(4-chlorophenyl)-1-piperazinyl][2-[(5-methyl-1,2,4-oxadiazol-3-yl)methoxy]phenyl]-methanone

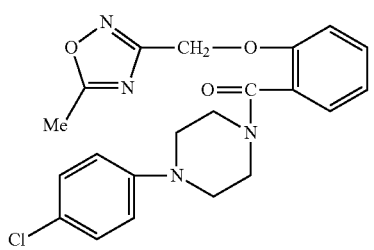 [SMILES: Cc1nc(COc2ccccc2C(=O)N2CCN(c3ccc(Cl)cc3)CC2)no1]

[2-[(5-methyl-1,2,4-oxadiazol-3-yl)methoxy]phenyl][4-(2-pyrimidinyl)-1-piperazinyl]-methanone

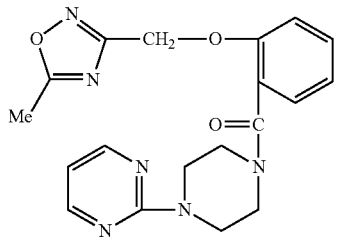 [SMILES: Cc1nc(COc2ccccc2C(=O)N2CCN(c3ncccn3)CC2)no1]

[2-[(3,5-dimethyl-4-isoxazolyl)methoxy]phenyl][4-(3-hydroxyphenyl)-1-piperazinyl]-methanone

102

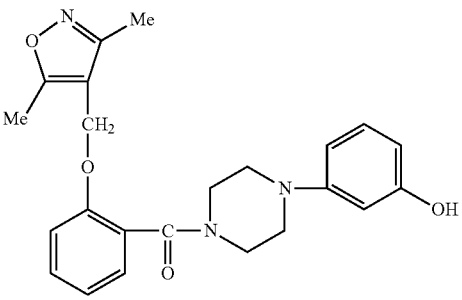 [SMILES: Cc1noc(C)c1COc1ccccc1C(=O)N1CCN(c2cccc(C(F)(F)F)c2)CC1]

[2-[(3,5-dimethyl-4-isoxazolyl)methoxy]phenyl][4-[3-(trifluoromethyl)phenyl]-1-piperazinyl]-methanone

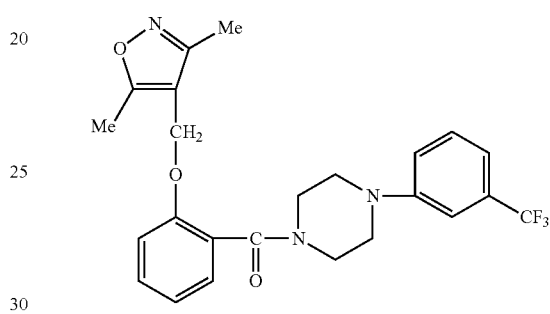

[2-[(2-methyl-4-thiazolyl)methoxy]phenyl][4-[5-(trifluoromethyl)-2-pyridinyl]-1-piperazinyl]-methanone

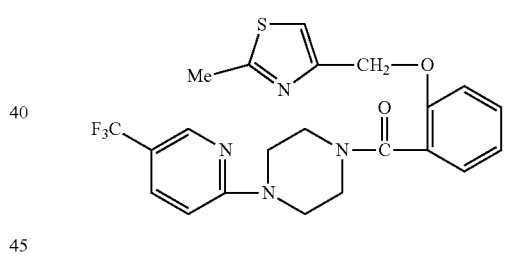

[2-[(3,5-dimethyl-4-isoxazolyl)methoxy]phenyl][4-(2-fluorophenyl)-1-piperazinyl]-methanone

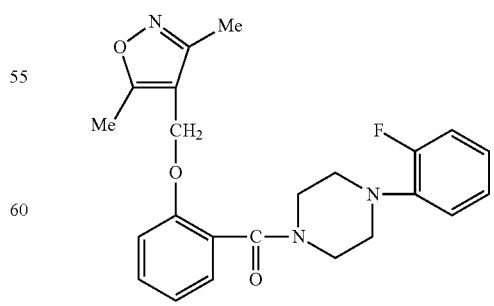

[2-[(3,5-dimethyl-4-isoxazolyl)methoxy]phenyl][4-(2-pyridinyl)-1-piperazinyl]-methanone

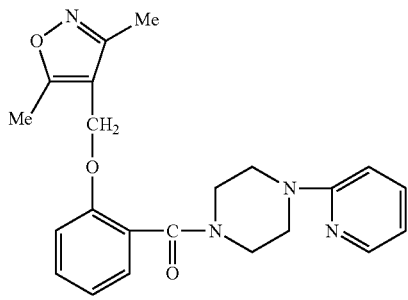 [SMILES: Cc1noc(C)c1COc1ccccc1C(=O)N1CCN(c2ccccn2)CC1]

[4-(5-chloro-2-methylphenyl)-1-piperazinyl][2-(4-thiazolylmethoxy)phenyl]-methanone

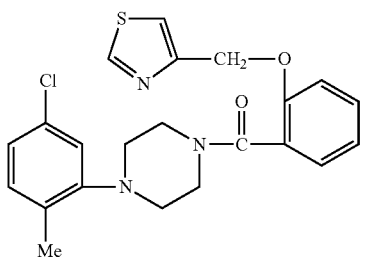 [SMILES: Cc1ccc(Cl)cc1N1CCN(C(=O)c2ccccc2OCc2cscn2)CC1]

[4-(2-chlorophenyl)-1-piperazinyl][2-[(3,5-dimethyl-4-isoxazolyl)methoxy]phenyl]-methanone

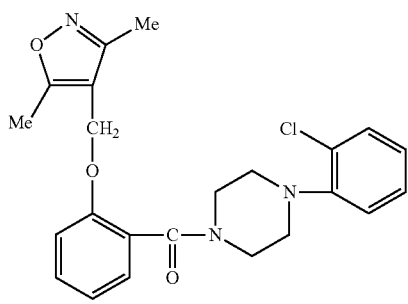 [SMILES: Cc1noc(C)c1COc1ccccc1C(=O)N1CCN(c2ccccc2Cl)CC1]

[4-(2-ethoxyphenyl)-1-piperazinyl][2-(4-thiazolylmethoxy)phenyl]-methanone

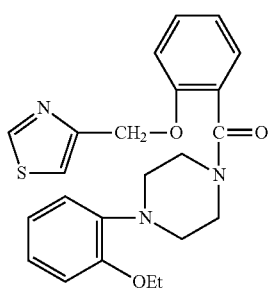 [SMILES: CCOc1ccccc1N1CCN(C(=O)c2ccccc2OCc2cscn2)CC1]

[2-[(3,5-dimethyl-4-isoxazolyl)methoxy]phenyl][4-(2-hydroxyphenyl)-1-piperazinyl]-methanone

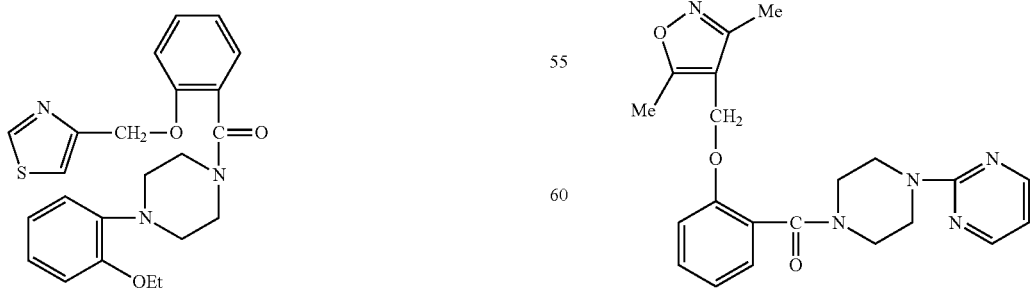

[2-[(3,5-dimethyl-4-isoxazolyl)methoxy]phenyl][4-(4-nitrophenyl)-1-piperazinyl]-methanone

[2-[(3,5-dimethyl-4-isoxazolyl)methoxy]phenyl][4-(4-methoxyphenyl)-1-piperazinyl]-methanone

[2-[(3,5-dimethyl-4-isoxazolyl)methoxy]phenyl][4-(2-pyrimidinyl)-1-piperazinyl]-methanone

[2-[(5-methyl-1,2,4-oxadiazol-3-yl)methoxy]phenyl][4-(4-nitrophenyl)-1-piperazinyl]-methanone

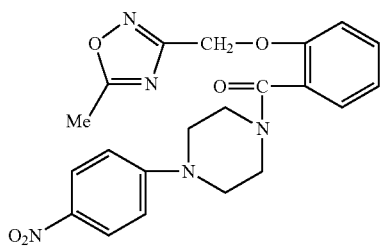 [SMILES: Cc1nc(COc2ccccc2C(=O)N2CCN(c3ccc([N+](=O)[O-])cc3)CC2)no1]

[4-(4-hydroxyphenyl)-1-piperazinyl][2-(4-thiazolyl-methoxy)phenyl]-methanone

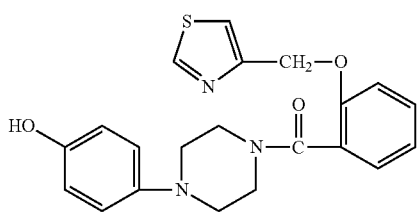 [SMILES: O=C(c1ccccc1OCc1cscn1)N1CCN(c2ccc(O)cc2)CC1]

[2-[(3,5-dimethyl-4-isoxazolyl)methoxy]phenyl][4-[5-(trifluoromethyl)-2-pyridinyl]-1-piperazinyl]-methanone

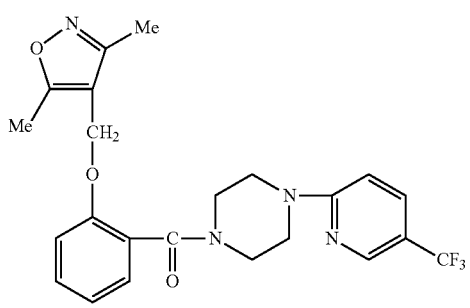 [SMILES: Cc1noc(C)c1COc1ccccc1C(=O)N1CCN(c2ccc(C(F)(F)F)cn2)CC1]

[2-[(5-methyl-1,2,4-oxadiazol-3-yl)methoxy]phenyl](4-thieno[2,3-d]pyrimidin-4-yl-1-piperazinyl)-methanone

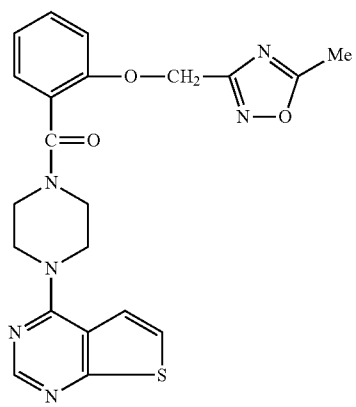 [SMILES: Cc1nc(COc2ccccc2C(=O)N2CCN(c3ncnc4sccc34)CC2)no1]

[2-[(3,5-dimethyl-4-isoxazolyl)methoxy]phenyl][4-(4-fluorophenyl)-1-piperazinyl]-methanone

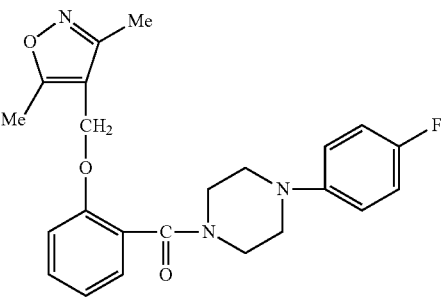 [SMILES: Cc1noc(C)c1COc1ccccc1C(=O)N1CCN(c2ccc(F)cc2)CC1]

[2-[(3,5-dimethyl-4-isoxazolyl)methoxy]phenyl][4-(3-methoxyphenyl)-1-piperazinyl]-methanone

[4-(3-methylphenyl)-1-piperazinyl][2-(4-thiazolylmethoxy)phenyl]-methanone

[4-(2,3-dimethylphenyl)-1-piperazinyl][2-[(5-methyl-1,2,4-oxadiazol-3-yl)methoxy]phenyl]-methanone

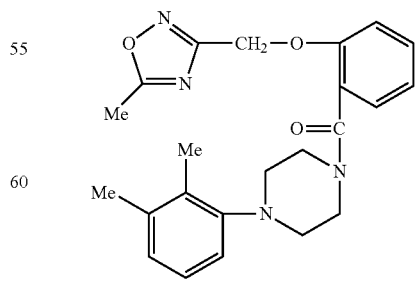

[4-(5-chloro-2-pyridinyl)-1-piperazinyl][2-[(3,5-dimethyl-4-isoxazolyl)methoxy]phenyl]-methanone

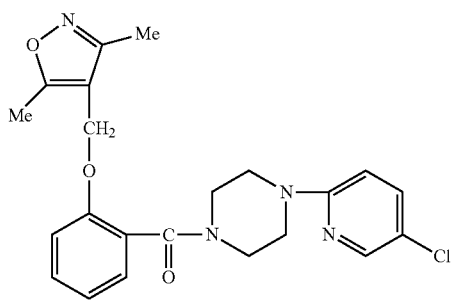 [SMILES: Cc1noc(C)c1COc1ccccc1C(=O)N1CCN(c2ccc(Cl)cn2)CC1]

[2-[(3,5-dimethyl-4-isoxazolyl)methoxy]phenyl](4-phenyl-1-piperazinyl)-methanone

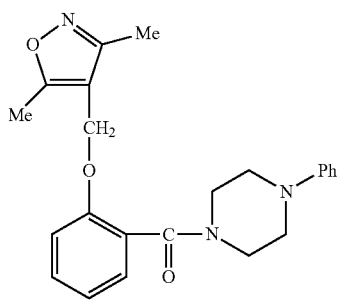 [SMILES: Cc1noc(C)c1COc1ccccc1C(=O)N1CCN(c2ccccc2)CC1]

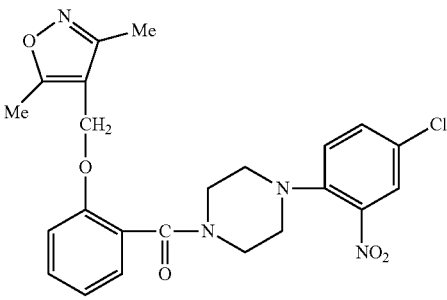 [SMILES: Cc1noc(C)c1COc1ccccc1C(=O)N1CCN(c2ccc(Cl)cc2[N+](=O)[O-])CC1]

[2-[(3,5-dimethyl-4-isoxazolyl)methoxy]phenyl][4-[6-methyl-2-(1-methylethyl)-4-pyrimidinyl]-1-piperazinyl]-methanone

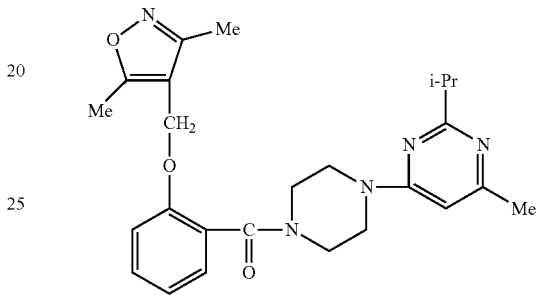

[4-(2-ethoxyphenyl)-1-piperazinyl][2-[(2-methyl-4-thiazolyl)methoxy]phenyl]-methanone

[2-[(2-methyl-4-thiazolyl)methoxy]phenyl][4-[3-(trifluoromethyl)phenyl]-1-piperazinyl]-methanone

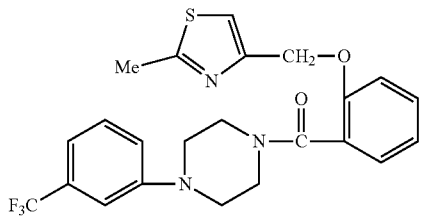

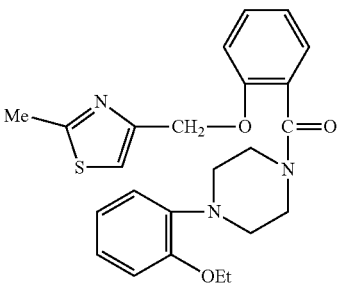 [SMILES: CCOc1ccccc1N1CCN(C(=O)c2ccccc2OCc2csc(C)n2)CC1]

[2-[(3,5-dimethyl-4-isoxazolyl)methoxy]phenyl][4-(2,6-dimethyl-4-pyrimidinyl)-1-piperazinyl]-methanone

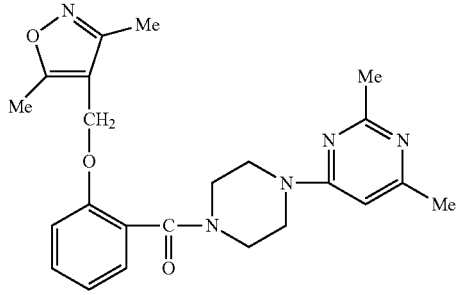

[4-(4-chloro-2-nitrophenyl)-1-piperazinyl][2-[(3,5-dimethyl-4-isoxazolyl)methoxy]phenyl]-methanone or salt thereof.

One embodiment provides a novel compound of formula Id:

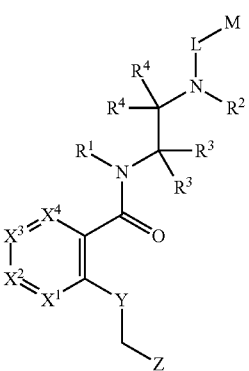

wherein:

X$^1$ is N or CR$^{a1}$, X$^2$ is N or CR$^{a2}$, X$^3$ is N or CR$^{a3}$, X$^4$ is N or CR$^{a4}$ provided no more than two of X$^1$, X$^2$, X$^3$, or X$^4$ is N;

each R$^{a1}$, R$^{a2}$, R$^{a3}$, and R$^{a4}$ is independently hydrogen, halogen, (C$_1$-C$_4$)alkyl, (C$_1$-C$_4$)haloalkyl, —O(C$_1$-C$_4$)alkyl, or —O(C$_1$-C$_4$)haloalkyl;

Y is S, S(=O), S(=O)$_2$, or O;

Z is a 5-membered heteroaryl, or 6-membered heteroaryl, wherein any 5-membered heteroaryl, or 6-membered heteroaryl of Z is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl;

R$^1$ and R$^2$ together with the atoms to which they are attached form a piperazine, wherein the piperizinyl is optionally substituted with one or more halogen, (C$_1$-C$_4$)alkyl, (C$_1$-C$_4$)haloalkyl, —O(C$_1$-C$_4$)alkyl, or —O(C$_1$-C$_4$)haloalkyl;

each R$^3$ is independently hydrogen or (C$_1$-C$_4$)alkyl;

each R$^4$ is independently hydrogen or (C$_1$-C$_4$)alkyl;

L is —(C$_1$-C$_4$)alkyl-optionally substituted with one or more halogen; and

M is 9-10-membered heteroaryl wherein any 9-10-membered heteroaryl of M is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl;

or a salt thereof.

In one embodiment M is a 9-membered heteroaryl optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl.

In one embodiment M is a 9-membered heteroaryl wherein the heteroaryl ring includes 1-3 nitrogen, oxygen and sulfur atoms wherein the heteroaryl is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl.

In one embodiment M is a 1H-benzoimidazolyl, benzooxazolyl, or benzolthiazolyl wherein any 1H-benzoimidazolyl, benzooxazolyl, or benzolthiazolyl of M is optionally substituted with one or more halogen, NO$_2$, CN, —OH, (C$_1$-C$_4$)alkyl, (C$_1$-C$_4$)haloalkyl, —O(C$_1$-C$_4$)alkyl, or —O(C$_1$-C$_4$)haloalkyl In one embodiment the moiety L is —CH$_2$—

In one embodiment the moiety M is:

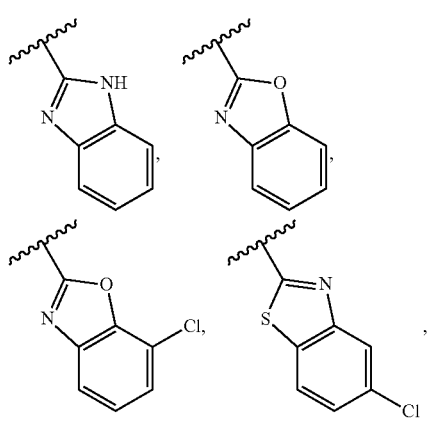

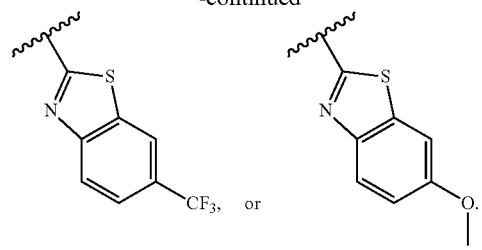

In one embodiment the moiety -L-M of the compound of formula I is:

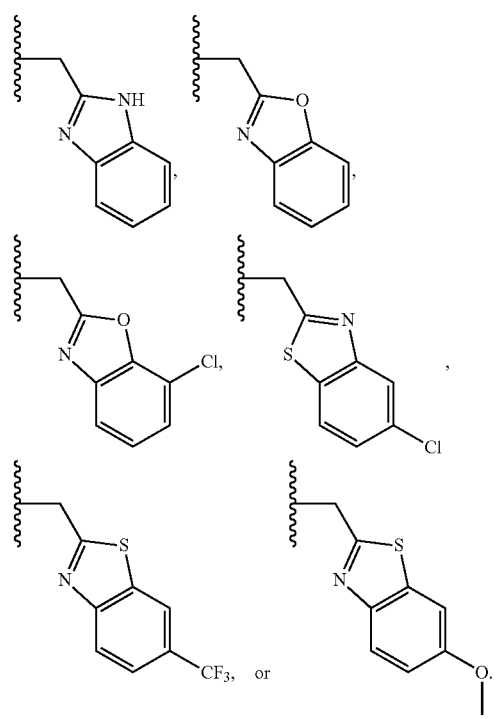

In one embodiment a salt is a pharmaceutically acceptable salt.

Processes for preparing compounds of formula I are provided as embodiments of the invention.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. In one embodiment the compounds of formula I can be administered to the mammal (e.g., human patient) as a prodrug of the compound of formula I.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, or 10 to 750 mg, or 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of the compounds disclosed herein and one or more other active therapeutic agents are both present in the body of the patient.

In some embodiments, one or more of the compounds disclosed herein are co-administered with one or more active therapeutic agents by combining the compounds disclosed herein with the other therapeutic agents in a unitary dosage form for simultaneous or sequential administration to a patient. Thus, this combination therapy may be administered as a simultaneous or sequential regimen. When administered sequentially, the combination may be administered in two or more administrations.

The expression and function of TAM (Tyro-3, Axl, and Mer) receptor tyrosine kinases and ligands have been noted in several tumor types. Accordingly, the compounds of formula I (or salts thereof) described herein may be useful for treating cancer in an animal (e.g., a mammal such as a human including a human patient).

Accordingly, one embodiment provides a method to treat a cancer selected from the cancers discussed in the paragraphs directly below.

Axl ectopic expression or overexpression has been noted in acute myeloid leukemia[1-4], chronic myeloid leukemia[1], B-cell chronic lymphoid leukemia[5], lung cancer[6-10], glioblastoma[11-13], breast cancer[14-17], colorectal cancer[18-20], gastric cancer[21,22], pancreatic cancer[23-25], esophageal cancer[26], melanoma[27-31], squamous cell skin cancer[32], prostate cancer[33,34], endometrial cancer[35], ovarian cancer[36-38], oral squamous carcinoma[39], thyroid cancer[40-43], bladder cancer[44], renal cancer[45-47], schwannoma[48], mesothelioma[49,50], Kaposi sarcoma[51], and osteosarcoma[52,53].

Axl prognostic significance has been noted in acute myeloid leukemia[23], lung cancer[54], glioblastoma[12], osteosarcoma[52], oral squamous cell carcinoma[39], breast cancer[17], head and neck cancer[55], colorectal cancer[20], pancreatic cancer[23,24], esophageal cancer[26], ovarian cancer[38], gastric cancer[21,56], bladder cancer[4];

Axl function roles have been noted in prostate cancer[34], ovarian cancer[57], breast cancer[16,58], thyroid cancer[43], lung cancer[10,59], pancreatic cancer[23,25], melanoma[28,30], hepatocellular carcinoma[60,61], glioblastoma[11,13], mesothelioma[49], osteosarcoma[53,62], schwannoma[48], Kaposi's sarcoma[51], and esophageal cancer[26].

Axl metastatic roles have been noted in breast cancer[16,17,58,59,63,64], lung cancer[7,59], melanoma[29-31], prostate cancer[34,65], pancreatic cancer[23,24], ovarian cancer[37], hepatocellular carcinoma[60,61], thyroid cancer[43], bladder cancer[44,66], Kaposi's sarcoma[12], mesothelioma[49], esophageal cancer[26], glioblastoma[11,67], colorectal cancer[19], cervical cancer[19], neuroblastoma[68], and osteosarcoma[62].

Axl roles in chemoresistance have been noted in breast cancer[16,17,58,59,63,64], lung cancer[7,59], melanoma[29-31], prostate cancer[34,65], pancreatic cancer[23,24], ovarian cancer[37], hepatocellular carcinoma[60,61], thyroid cancer[43], bladder cancer[44,66], Kaposi's sarcoma[12], mesothelioma[49], esophageal cancer[26], glioblastoma[11,67], colorectal cancer[19], cervical cancer[19], neuroblastoma[68], and osteosarcoma[62].

MerTK ectopic expression or overexpression has been noted in acute myeloid leukemia[3,73,74], T-cell acute lymphoid leukemia[73,75,76], B-cell acute lymphoid leukemia[77,78], lung cancer[10], glioma[13,79], melanoma[30,31,80,81], prostate cancer[33,82], schwannoma[48], mantle cell lymphoma[83], and rhabdomyosarcoma[84].

MerTK prognostic significance has been noted in gastric cancer[21,56].

MerTK function roles have been noted in acute myeloid leukemia[74], B-cell acute leukemia[78], T-cell acute leukemia[76,85,86], glioma[13,87], lung cancer[10], and melanoma[31,81].

MerTK metastatic roles have been noted in glioblastoma[67,79,87], and melanoma[31,81] MerTK roles in chemoresistance have been noted in B-cell acute leukemia[78], T-cell acute leukemia[76,85], glioma[13,79], lung cancer[10], pancreatic cancer[24], and breast cancer[58].

Tyro3 ectopic expression or overexpression has been noted in acute myeloid leukemia[3,88], multiple myeloma[89], lung cancer[890], melanoma[30,91,92], prostate cancer[33], endometrial cancer[35], thyroid cancer[43], and schwannoma[48].

Tyro3 function roles have been noted in melanoma[91], and thyroid cancer[43].

Tyro3 metastatic roles have been noted in melanoma[91], and thyroid cancer[43].

Gas6 ectopic expression or overexpression has been noted in acute myeloid leukemia[93], acute lymphoid leukemia[93], chronic myeloid leukemia[93], myeloma[93], glioblastoma[12], breast cancer[94], gastric cancer[22], endometrial cancer[35], ovarian cancer[36,95], thyroid cancer[42], renal cancer[47], and schwannoma[48].

Gas6 prognostic significance has been noted in acute myeloid leukemia[96], lung cancer[54], glioblastoma[12], and renal cancer[47].

Gas6 function roles have been noted in lymphoma[97], breast cancer[97], prostate cancer[33,98], colorectal cancer[97], pancreatic cancer[97], thyroid cancer[43], schwannoma[48], gastric cancer[22], osteosarcoma[52], and renal cancer[99].

Gas6 metastatic roles have been noted in breast cancer[97], prostate cancer[33,100], pancreatic cancer[97], hepatocellular carcinoma[60], gastric cancer[22], osteosarcoma[52], and renal cancer[99].

Gas6 roles in chemoresistance have been noted in B-cell acute leukemia[101].

Protein S ectopic expression or overexpression has been noted in acute myeloid leukemia[102], thyroid cancer[103,104], colorectal cancer[105], pancreatic cancer[106], brain tumors[107], lung cancer[90,108], prostate cancer[109], ovarian cancer[110], and osteosarcom[109].

Protein S prognostic significance has been noted in prostate cancer[109].

Protein S metastatic roles have been noted in prostate cancer[109]

1. Neubauer, A. et al. Recent progress on the role of Axl, a receptor tyrosine kinase, in malignant transformation of myeloid leukemias. Leuk Lymphoma 25, 91-96, doi: 10.3109/10428199709042499 (1997).
2. Rochlitz, C. et al. Axl expression is associated with adverse prognosis and with expression of Bcl2 and CD34 in de novo acute myeloid leukemia (AML): results from a multicenter trial of the Swiss Group for Clinical Cancer Research (SAKK). Leukemia 13, 1352-1358 (1999).
3. Ben-Batalla, I. et al. Axl, a prognostic and therapeutic target in acute myeloid leukemia mediates paracrine crosstalk of leukemia cells with bone marrow stroma. Blood 122, 2443-2452, doi:10.1182/blood-2013-03-491431 [pii] (2013).
4. Park, I. K. et al. Inhibition of the receptor tyrosine kinase Axl impedes activation of the FLT3 internal tandem duplication in human acute myeloid leukemia: implications for Axl as a potential therapeutic target. Blood 121, 2064-2073, doi:10.1182/blood-2012-07-444018 (2013).
5. Ghosh, A. K. et al. The novel receptor tyrosine kinase Axl is constitutively active in B-cell chronic lymphocytic leukemia and acts as a docking site of nonreceptor kinases: implications for therapy. Blood 117, 1928-1937, doi:10.1182/blood-2010-09-305649 (2011).
6. Wimmel, A., Glitz, D., Kraus, A., Roeder, J. & Schuermann, M. Axl receptor tyrosine kinase expression in human lung cancer cell lines correlates with cellular adhesion. European journal of cancer 37, 2264-2274 (2001).
7. Shieh, Y. S. et al. Expression of axl in lung adenocarcinoma and correlation with tumor progression. Neoplasia 7, 1058-1064 (2005).
8. Rikova, K. et al. Global survey of phosphotyrosine signaling identifies oncogenic kinases in lung cancer. Cell 131, 1190-1203, doi:S0092-8674(07)01522-X [pii], 10.1016/j.cell.2007.11.025 (2007).
9. Cui, Z. L. et al. YES-associated protein 1 promotes adenocarcinoma growth and metastasis through activation of the receptor tyrosine kinase Axl. International journal of immunopathology and pharmacology 25, 989-1001, doi:16 [pii] (2012).
10. Linger, R. M. et al. Mer or Axl receptor tyrosine kinase inhibition promotes apoptosis, blocks growth and enhances chemosensitivity of human non-small cell lung cancer. Oncogene 32, 3420-3431, doi:10.1038/onc.2012.355 (2013).
11. Vajkoczy, P. et al. Dominant-negative inhibition of the Axl receptor tyrosine kinase suppresses brain tumor cell growth and invasion and prolongs survival. Proc Natl Acad Sci USA 103, 57995804, doi:10.1073/pnas.0510923103 (2006).
12. Hutterer, M. et al. Axl and growth arrest-specific gene 6 are frequently overexpressed in human gliomas and predict poor prognosis in patients with glioblastoma multiforme. Clin Cancer Res 14, 130-138, doi:10.1158/1078-0432.CCR-07-0862 (2008).
13. Keating, A. K. et al. Inhibition of Mer and Axl receptor tyrosine kinases in astrocytoma cells leads to increased apoptosis and improved chemosensitivity. Molecular cancer therapeutics 9, 12981307, doi:10.1158/1535-7163.MCT-09-0707 (2010).
14. Berclaz, G. et al. Estrogen dependent expression of the receptor tyrosine kinase axl in normal and malignant human breast. Ann Oncol 12, 819-824 (2001).
15. Meric, F. et al. Expression profile of tyrosine kinases in breast cancer. Clin Cancer Res 8, 361-367 (2002).
16. Zhang, Y. X. et al. AXL is a potential target for therapeutic intervention in breast cancer progression. Cancer research 68, 1905-1915, doi:10.1158/0008-5472.CAN-07-2661 (2008).
17. Gjerdrum, C. et al. Axl is an essential epithelial-to-mesenchymal transition-induced regulator of breast cancer metastasis and patient survival. Proc Natl Acad Sci USA 107, 1124-1129, doi:10.1073/pnas.0909333107 (2010).
18. Craven, R. J. et al. Receptor tyrosine kinases expressed in metastatic colon cancer. Int J Cancer 60, 791-797 (1995).
19. Mudduluru, G., Vajkoczy, P. & Allgayer, H. Myeloid zinc finger 1 induces migration, invasion, and in vivo metastasis through Axl gene expression in solid cancer. Molecular cancer research: MCR 8, 159-169, doi: 10.1158/1541-7786.MCR-09-0326 (2010).
20. Dunne, P. D. et al. AXL is a key regulator of inherent and chemotherapy-induced invasion and predicts a poor clinical outcome in early-stage colon cancer. Clin Cancer Res 20, 164-175, doi:10.1158/1078-0432.CCR-13-1354, 1078-0432.CCR-13-1354 [pii] (2014).
21. Lin, W. C. et al. tie-1 protein tyrosine kinase: a novel independent prognostic marker for gastric cancer. Clin Cancer Res 5, 1745-1751 (1999).
22. Sawabu, T. et al. Growth arrest-specific gene 6 and Axl signaling enhances gastric cancer cell survival via Akt pathway. Molecular carcinogenesis 46, 155-164, doi: 10.1002/mc.20211 (2007).
23. Koorstra, J. B. et al. The Axl receptor tyrosine kinase confers an adverse prognostic influence in pancreatic cancer and represents a new therapeutic target. Cancer biology & therapy 8, 618-626 (2009).

24. Song, X. et al. Overexpression of receptor tyrosine kinase Axl promotes tumor cell invasion and survival in pancreatic ductal adenocarcinoma. Cancer 117, 734-743, doi:10.1002/cncr.25483 (2011).
25. Leconet, W. et al. Preclinical validation of AXL receptor as a target for antibody-based pancreatic cancer immunotherapy. Oncogene, doi:10.1038/onc.2013.487, onc2013487 [pii] (2013).
26. Hector, A. et al. The Axl receptor tyrosine kinase is an adverse prognostic factor and a therapeutic target in esophageal adenocarcinoma. Cancer biology & therapy 10, 1009-1018, doi:10.4161/cbt.10.10.13248 (2010).
27. Quong, R. Y. et al. Protein kinases in normal and transformed melanocytes. Melanoma Res 4, 313-319 (1994).
28. van Ginkel, P. R. et al. Expression of the receptor tyrosine kinase Axl promotes ocular melanoma cell survival. Cancer research 64, 128-134 (2004).
29. Sensi, M. et al. Human cutaneous melanomas lacking MITF and melanocyte differentiation antigens express a functional Axl receptor kinase. The Journal of investigative dermatology 131, 2448-2457, doi:10.1038/jid.2011.218 (2011).
30. Tworkoski, K. et al. Phosphoproteomic screen identifies potential therapeutic targets in melanoma. Molecular cancer research: MCR 9, 801-812, doi:10.1158/1541-7786.MCR-10-0512 (2011).
31. Tworkoski, K. A. et al. MERTK controls melanoma cell migration and survival and differentially regulates cell behavior relative to AXL. Pigment Cell Melanoma Res 26, 527-541, doi:10.1111/pcmr.12110 (2013).
32. Green, J. et al. Overexpression of the Axl tyrosine kinase receptor in cutaneous SCC-derived cell lines and tumours. Br J Cancer 94, 1446-1451, doi:6603135 [pii], 10.1038/sj.bjc.6603135 (2006).
33. Shiozawa, Y. et al. GAS6/AXL axis regulates prostate cancer invasion, proliferation, and survival in the bone marrow niche. Neoplasia 12, 116-127 (2010).
34. Paccez, J. D. et al. The receptor tyrosine kinase Axl is an essential regulator of prostate cancer proliferation and tumor growth and represents a new therapeutic target. Oncogene 32, 689698, doi:10.1038/onc.2012.89 (2013).
35. Sun, W. S., Fujimoto, J. & Tamaya, T. Coexpression of growth arrest-specific gene 6 and receptor tyrosine kinases Axl and Sky in human uterine endometrial cancers. Ann Oncol 14, 898-906 (2003).
36. Sun, W., Fujimoto, J. & Tamaya, T. Coexpression of Gas6/Axl in human ovarian cancers. Oncology 66, 450-457, doi:10.1159/000079499, 79499 [pii] (2004).
37. Rankin, E. B. et al. AXL is an essential factor and therapeutic target for metastatic ovarian cancer. Cancer research 70, 7570-7579, doi:10.1158/0008-5472.CAN-10-1267 (2010).
38. Chen, P. X., Li, Q. Y. & Yang, Z. Axl and prostasin are biomarkers for prognosis of ovarian adenocarcinoma. Ann Diagn Pathol 17, 425-429, doi:10.1016/j.anndiagpath.2013.01.005, S1092-9134(13)00035-X [pii] (2013).
39. Lee, C. H. et al. Axl is a prognostic marker in oral squamous cell carcinoma. Ann Surg Oncol 19 Suppl 3, S500-508, doi:10.1245/s10434-011-1985-8 (2012).
40. Tanaka, K. et al. Expression profile of receptor-type protein tyrosine kinase genes in the human thyroid. Endocrinology 139, 852-858, doi:10.1210/endo.139.3.5791 (1998).
41. Ito, T. et al. Expression of the Axl receptor tyrosine kinase in human thyroid carcinoma. Thyroid 9, 563-567 (1999).
42. Ito, M. et al. Expression of receptor-type tyrosine kinase, Axl, and its ligand, Gas6, in pediatric thyroid carcinomas around chernobyl. Thyroid 12, 971-975, doi:10.1089/105072502320908303 (2002).
43. Avilla, E. et al. Activation of TYRO3/AXL tyrosine kinase receptors in thyroid cancer. Cancer research 71, 1792-1804, doi:10.1158/0008-5472.CAN-10-2186 (2011).
44. Yeh, C. Y. et al. Transcriptional activation of the Axl and PDGFR-alpha by c-Met through a ras- and Src-independent mechanism in human bladder cancer. BMC cancer 11, 139, doi:10.1186/1471-2407-11-139 (2011).
45. Chung, B. I., Malkowicz, S. B., Nguyen, T. B., Libertino, J. A. & McGarvey, T. W. Expression of the proto-oncogene Axl in renal cell carcinoma. DNA Cell Biol 22, 533-540, doi:10.1089/104454903607089 46 (2003).
46. Dalgin, G. S., Holloway, D. T., Liou, L. S. & DeLisi, C. Identification and characterization of renal cell carcinoma gene markers. Cancer Inform 3, 65-92 (2007).
47. Gustafsson, A. et al. Differential expression of Axl and Gas6 in renal cell carcinoma reflecting tumor advancement and survival. Clin Cancer Res 15, 4742-4749, doi:10.1158/1078-0432.CCR08-2514, 1078-0432.CCR-08-2514 [pii] (2009).
48. Ammoun, S. et al. Axl/Gas6/NFkappaB signalling in schwannoma pathological proliferation, adhesion and survival. Oncogene 33, 336-346, doi:10.1038/onc.2012.587 (2014).
49. Ou, W. B. et al. AXL regulates mesothelioma proliferation and invasiveness. Oncogene 30, 16431652, doi:10.1038/onc.2010.555 (2011).
50. Pinato, D. J. et al. The expression of Axl receptor tyrosine kinase influences the tumour phenotype and clinical outcome of patients with malignant pleural mesothelioma. Br J Cancer 108, 621-628, doi:10.1038/bjc.2013.9, bjc20139 [pii] (2013).
51. Liu, R. et al. Induction, regulation, and biologic function of Axl receptor tyrosine kinase in Kaposi sarcoma. Blood 116, 297-305, doi:10.1182/blood-2009-12-257154 (2010).
52. Han, J. et al. Gas6/Axl mediates tumor cell apoptosis, migration and invasion and predicts the clinical outcome of osteosarcoma patients. Biochemical and biophysical research communications 435, 493-500, doi:10.1016/j.bbrc.2013.05.019 (2013).
53. Zhang, Y. et al. Knockdown of AXL receptor tyrosine kinase in osteosarcoma cells leads to decreased proliferation and increased apoptosis. International journal of immunopathology and pharmacology 26, 179-188 (2013).
54. Ishikawa, M. et al. Higher expression of receptor tyrosine kinase Axl, and differential expression of its ligand, Gas6, predict poor survival in lung adenocarcinoma patients. Ann Surg Oncol 20 Suppl 3, S467-476, doi:10.1245/s10434-012-2795-3 (2013).
55. Giles, K. M. et al. Axl mediates acquired resistance of head and neck cancer cells to the epidermal growth factor receptor inhibitor erlotinib. Molecular cancer therapeutics 12, 25412558, doi:10.1158/1535-7163.MCT-13-0170, 1535-7163.MCT-13-0170 [pii] (2013).
56. Wu, C. W. et al. Clinical significance of AXL kinase family in gastric cancer. Anticancer Res 22, 1071-1078 (2002).
57. Jiao, Y., Ou, W., Meng, F., Zhou, H. & Wang, A. Targeting HSP90 in ovarian cancers with multiple receptor tyrosine kinase coactivation. Molecular cancer 10, 125, doi:10.1186/1476-4598-10-125 (2011).

58. Zhao, Y. et al. Differential expression of Axl and correlation with invasion and multidrug resistance in cancer cells. Cancer investigation 30, 287-294, doi: 10.3109/07357907.2012.657816 (2012).
59. Li, Y. et al. Axl as a potential therapeutic target in cancer: role of Axl in tumor growth, metastasis and angiogenesis. Oncogene 28, 3442-3455, doi:10.1038/onc.2009.212 (2009).
60. He, L. et al. Differential expression of Axl in hepatocellular carcinoma and correlation with tumor lymphatic metastasis. Molecular carcinogenesis 49, 882-891, doi: 10.1002/mc.20664 (2010).
61. Xu, M. Z. et al. AXL receptor kinase is a mediator of YAP-dependent oncogenic functions in hepatocellular carcinoma. Oncogene 30, 1229-1240, doi:10.1038/onc.2010.504 (2011).
62. Rettew, A. N. et al. Multiple receptor tyrosine kinases promote the in vitro phenotype of metastatic human osteosarcoma cell lines. Oncogenesis 1, e34, doi:10.1038/oncsis.2012.34 (2012).
63. Holland, S. J. et al. Multiple roles for the receptor tyrosine kinase axl in tumor formation. Cancer research 65, 9294-9303, doi: 10.1158/0008-5472.CAN-05-0993 (2005).
64. Vuoriluoto, K. et al. Vimentin regulates EMT induction by Slug and oncogenic H-Ras and migration by governing Axl expression in breast cancer. Oncogene 30, 1436-1448, doi:10.1038/onc.2010.509 (2011).
65. Mishra, A. et al. Hypoxia stabilizes GAS6/Axl signaling in metastatic prostate cancer. Molecular cancer research: MCR 10, 703-712, doi:10.1158/1541-7786.MCR-11-0569 (2012).
66. Sayan, A. E. et al. Fra-1 controls motility of bladder cancer cells via transcriptional upregulation of the receptor tyrosine kinase AXL. Oncogene 31, 1493-1503, doi: 10.1038/onc.2011.336 (2012).
67. Rogers, A. E. et al. Mer receptor tyrosine kinase inhibition impedes glioblastoma multiforme migration and alters cellular morphology. Oncogene 31, 4171-4181, doi:10.1038/onc.2011.588 (2012).
68. Duijkers, F. A., Meijerink, J. P., Pieters, R. & van Noesel, M. M. Downregulation of Axl in nonMYCN amplified neuroblastoma cell lines reduces migration. Gene 521, 62-68, doi:10.1016/j.gene.2013.03.029 (2013).
69. Hong, C. C. et al. Receptor tyrosine kinase AXL is induced by chemotherapy drugs and overexpression of AXL confers drug resistance in acute myeloid leukemia. Cancer letters 268, 314-324, doi:10.1016/j.canlet.2008.04.017 (2008).
70. Macleod, K. et al. Altered ErbB receptor signaling and gene expression in cisplatin-resistant ovarian cancer. Cancer research 65, 6789-6800, doi:10.1158/0008-5472.CAN-04-2684 (2005).
71. Lay, J. D. et al. Sulfasalazine suppresses drug resistance and invasiveness of lung adenocarcinoma cells expressing AXL. Cancer research 67, 3878-3887, doi:10.1158/00085472.CAN-06-3191 (2007).
72. Hong, J., Peng, D., Chen, Z., Sehdev, V. & Belkhiri, A. ABL regulation by AXL promotes cisplatin resistance in esophageal cancer. Cancer research 73, 331-340, doi: 10.1158/0008-5472.CAN-123151 (2013).
73. Graham, D. K., Dawson, T. L., Mullaney, D. L., Snodgrass, H. R. & Earp, H. S. Cloning and mRNA expression analysis of a novel human protooncogene, c-mer. Cell Growth Differ 5, 647-657 (1994).
74. 74 Lee-Sherick, A. B. et al. Aberrant Mer receptor tyrosine kinase expression contributes to leukemogenesis in acute myeloid leukemia. Oncogene 32, 5359-5368, doi:10.1038/onc.2013.40 (2013).
75. Graham, D. K. et al. Ectopic expression of the protooncogene Mer in pediatric T-cell acute lymphoblastic leukemia. Clin Cancer Res 12, 2662-2669, doi:10.1158/1078-0432.ccr-05-2208 (2006).
76. Brandao, L. N. et al. Inhibition of MerTK increases chemosensitivity and decreases oncogenic potential in T-cell acute lymphoblastic leukemia. Blood cancer journal 3, e101, doi:10.1038/bcj.2012.46 (2013).
77. Yeoh, E. J. et al. Classification, subtype discovery, and prediction of outcome in pediatric acute lymphoblastic leukemia by gene expression profiling. Cancer cell 1, 133-143 (2002).
78. Linger, R. M. et al. Mer receptor tyrosine kinase is a therapeutic target in pre-B-cell acute lymphoblastic leukemia. Blood 122, 1599-1609, doi:10.1182/blood-2013-01-478156 (2013).
79. Wang, Y. et al. Mer receptor tyrosine kinase promotes invasion and survival in glioblastoma multiforme. Oncogene 32, 872-882, doi:10.1038/onc.2012.104 (2013).
80. Gyorffy, B. & Lage, H. A Web-based data warehouse on gene expression in human malignant melanoma. The Journal of investigative dermatology 127, 394-399, doi: 5700543 [pii], 10.1038/sj.jid.5700543 (2007).
81. Schlegel, J. et al. MERTK receptor tyrosine kinase is a therapeutic target in melanoma. J Clin Invest 123, 2257-2267, doi:10.1172/JCI67816 (2013).
82. Wu, Y. M., Robinson, D. R. & Kung, H. J. Signal pathways in up-regulation of chemokines by tyrosine kinase MER/NYK in prostate cancer cells. Cancer research 64, 7311-7320, doi:10.1158/0008-5472.CAN-04-0972 (2004).
83. Ek, S., Hogerkorp, C. M., Dictor, M., Ehinger, M. & Borrebaeck, C. A. Mantle cell lymphomas express a distinct genetic signature affecting lymphocyte trafficking and growth regulation as compared with subpopulations of normal human B cells. Cancer research 62, 4398-4405 (2002).
84. Khan, J. et al. cDNA microarrays detect activation of a myogenic transcription program by the PAX3-FKHR fusion oncogene. Proc Natl Acad Sci USA 96, 13264-13269 (1999).
85. Keating, A. K. et al. Lymphoblastic leukemia/lymphoma in mice overexpressing the Mer (MerTK) receptor tyrosine kinase. Oncogene 25, 6092-6100, doi:10.1038/sj.onc.1209633 (2006).
86. Fan, L. et al. [Expression of Mer on Jurkat cells and its anti-apoptosis effect]. Ai zheng=Aizheng=Chinese journal of cancer 26, 698-702 (2007).
87. Knubel, K. H. et al. MerTK inhibition is a novel therapeutic approach for glioblastoma multiforme. Oncotarget 5, 1338-1351 (2014).
88. Crosier, P. S., Hall, L. R., Vitas, M. R., Lewis, P. M. & Crosier, K. E. Identification of a novel receptor tyrosine kinase expressed in acute myeloid leukemic blasts. Leuk Lymphoma 18, 443449, doi:10.3109/10428199509059643 (1995).
89. De Vos, J. et al. Identifying intercellular signaling genes expressed in malignant plasma cells by using complementary DNA arrays. Blood 98, 771-780 (2001).
90. Wimmel, A. et al. Synthesis and secretion of the anticoagulant protein S and coexpression of the Tyro3 receptor in human lung carcinoma cells. Cancer 86, 43-49, doi:10.1002/(SICI)10970142(19990701)86:1<43::AID-CNCR8>3.0.CO; 2-D [pii] (1999).

91. Zhu, S. et al. A genomic screen identifies TYRO3 as a MITF regulator in melanoma. Proc Natl Acad Sci USA 106, 17025-17030, doi:10.1073/pnas.0909292106 (2009).
92. Demarest, S. J. et al. Evaluation of Tyro3 expression, Gas6-mediated Akt phosphorylation, and the impact of anti-Tyro3 antibodies in melanoma cell lines. Biochemistry 52, 3102-3118, doi:10.1021/bi301588c (2013).
93. Dirks, W. et al. Expression of the growth arrest-specific gene 6 (GAS6) in leukemia and lymphoma cell lines. Leuk Res 23, 643-651, doi:S0145-2126(99)00075-2 [pii] (1999).
94. Mc Cormack, O. et al. Growth arrest-specific gene 6 expression in human breast cancer. Br J Cancer 98, 1141-1146, doi:10.1038/sj.bjc.6604260, 6604260 [pii] (2008).
95. Buehler, M. et al. Meta-analysis of microarray data identifies GAS6 expression as an independent predictor of poor survival in ovarian cancer. BioMed research international 2013, 238284, doi:10.1155/2013/238284 (2013).
96. Whitman, S. P. et al. GAS6 expression identifies high-risk adult AML patients: potential implications for therapy. Leukemia, doi:10.1038/leu.2013.371, leu2013371 [pii] (2013).
97. Loges, S. et al. Malignant cells fuel tumor growth by educating infiltrating leukocytes to produce the mitogen Gas6. Blood 115, 2264-2273, doi:10.1182/blood-2009-06-228684 (2010).
98. Sainaghi, P. P. et al. Gas6 induces proliferation in prostate carcinoma cell lines expressing the Axl receptor. J Cell Physiol 204, 36-44, doi:10.1002/jcp.20265 (2005).
99. Gustafsson, A., Bostrom, A. K., Ljungberg, B., Axelson, H. & Dahlback, B. Gas6 and the receptor tyrosine kinase Axl in clear cell renal cell carcinoma. PLoS One 4, e7575, doi:10.1371/journal.pone.0007575 (2009).
100. Lee, Y., Lee, M. & Kim, S. Gas6 induces cancer cell migration and epithelial-mesenchymal transition through upregulation of MAPK and Slug. Biochemical and biophysical research communications 434, 8-14, doi: 10.1016/j.bbrc.2013.03.082, S0006-291X(13)00546-9 [pii] (2013).
101. Shiozawa, Y., Pedersen, E. A. & Taichman, R. S. GAS6/Mer axis regulates the homing and survival of the E2A/PBX1-positive B-cell precursor acute lymphoblastic leukemia in the bone marrow niche. Experimental hematology 38, 132-140, doi:10.1016/j.exphem.2009.11.002 (2010).
102. Abe, A. et al. Establishment and characterization of an immature human megakaryoblastic cell line, MEG-A2. Leukemia 9, 341-349 (1995).
103. Chung, K. W., Kim, S. W. & Kim, S. W. Gene expression profiling of papillary thyroid carcinomas in Korean patients by oligonucleotide microarrays. Journal of the Korean Surgical Society 82, 271-280, doi:10.4174/jkss.2012.82.5.271 (2012).
104. Griffith, O. L., Melck, A., Jones, S. J. & Wiseman, S. M. Meta-analysis and meta-review of thyroid cancer gene expression profiling studies identifies important diagnostic biomarkers. Journal of clinical oncology: official journal of the American Society of Clinical Oncology 24, 5043-5051, doi:10.1200/JCO.2006.06.7330 (2006).
105. Sierko, E., Wojtukiewicz, M. Z., Zawadzki, R., Zimnoch, L. & Kisiel, W. Expression of protein C (PC), protein S (PS) and thrombomodulin (TM) in human colorectal cancer. Thrombosis research 125, e71-75, doi: 10.1016/j.thromres.2009.09.011 (2010).
106. Odegaard, O. R., Lindahl, A. K., Try, K., Kvalheim, G. & Sorbo, J. H. Recurrent venous thrombosis during warfarin treatment related to acquired protein S deficiency. Thrombosis research 66, 729-734 (1992).
107. Phillips, D. J. et al. Protein S, an antithrombotic factor, is synthesized and released by neural tumor cells. Journal of neurochemistry 61, 344-347 (1993).
108. Wojtukiewicz, M. Z. et al. Abnormal regulation of coagulation/fibrinolysis in small cell carcinoma of the lung. Cancer 65, 481-485 (1990).
109. Saraon, P. et al. Proteomic profiling of androgen-independent prostate cancer cell lines reveals a role for protein S during the development of high grade and castration-resistant prostate cancer. J Biol Chem 287, 34019-34031, doi:10.1074/jbc.M112.384438 (2012).
110. Faca, V. M. et al. Proteomic analysis of ovarian cancer cells reveals dynamic processes of protein secretion and shedding of extra-cellular domains. PLoS One 3, e2425, doi:10.1371/journal.pone.0002425 (2008).
111. Maillard, C., Berruyer, M., Serre, C. M., Dechavanne, M. & Delmas, P. D. Protein-S, a vitamin K dependent protein, is a bone matrix component synthesized and secreted by osteoblasts. Endocrinology 130, 1599-1604, doi:10.1210/endo. 130.3.1531628 (1992).

The invention will now be illustrated by the following non-limiting Examples.

Example 1

Materials and Methods

Identification of Small Molecule Inhibitor (SMI)-Binding Pockets in the Axl Ig1 Domain:

The crystal structure of soluble Gas6/Axl complex (PDB Ref. Code 2C5D, Sasaki T, et al. *The EMBO Journal* 2006 Jan. 11; 25(1): 80-87) was used to identify possible SMI binding sites. The potential inhibitor binding sites were visually evaluated for their size and shape for virtual screening of drug-like compounds from our library of compounds. A pocket near the major Axl-Gas6 interaction site was selected for docking of library compounds.

Virtual Screening of Library Compounds:

In silico (virtual) screening of the library of drug-like compounds was performed to identify and rank a focused series of top hits in terms of their propensity to bind in a groove defined by the interface between Axl Ig1 and Gas6 LG1.

Antibodies and Reagents:

Antibodies used were as follows: anti-phosphorylated hAxl (Cell Signaling), hAxl (Santa Cruz), anti-phosphorylated STAT1 (BD Bioscience), anti-phosphorylated hAkt (Santa Cruz), anti-hGas6 (R&D), anti-γ-carboxylation (Sekisui Diagnostics), anti-6x-Histidine epitope (Novus Biologicals), GAPDH (Millipore) and anti-(3-Actin (Cell Signaling). The secondary antibodies used for immunoblot analysis were horseradish peroxidase-conjugated anti-mouse and anti-rabbit from Jackson ImmunoResearch.

Human Gas6 Conditioned Medium:

Stable HEK 293 cells secreting human Gas6 (clone 7.4.1) were allowed to achieve 70% confluence in a 10-cm plate. The complete medium with 10% FBS was then changed into serum free media in the presence of 10 g/mL vitamin K1 (Phytonadione injectable emulsion from Hospira). After 72 hours, the Gas6 conditioned medium was collected, and validated for the presence of Gas6 and γ-carboxylation (by immunoblot) and activity of Gas6 (via activation of pSTAT1 in hAxl/γR1 cells).

Detection of Activation of TAM Receptors:

Stable hAxl/IFN-γR1 CHO reporter cell lines (containing human Axl extracellular domains and transmembrane and intracellular domains of human IFN-γR1) were serum starved for 5 hrs±small molecule inhibitors and then stimulated with human Gas6 conditioned media±small molecule inhibitors for 30 minutes. For H1299 human non-small cell lung carcinoma and MDA-MB-231 human breast adenocarcinoma cell lines, the cells were serum starved overnight±small molecule inhibitors and stimulated with human Gas6 conditioned media±small molecule inhibitors for 30 minutes. Whole cell lysates of hAxl/IFN-γR1, H1299 and MDA-MB-231 cells were prepared using HNTG buffer (20 mM HEPES, pH 7.5, 150 mM NaCl, 10% glycerol, 1% Triton X-100, 1 mM PMSF, 1 mM $Na_3VO_4$, 10 mM $Na_2MoO_4$, 1 mM EDTA, 10 mM NaF and 20 μg/mL aprotinin). The resulting lysates were resolved on SDS-PAGE gel and immunoblotted with respective antibodies.

Competitive Inhibition Assay:

400 nM His tagged-sAxl were co-incubated with increasing amounts of compound 1A (0, 5, 10 or 20 μM) in a 50 μl reaction mixture of Tris-Nacl Buffer (20 mM Tris.HCl, 150 mM NaCl, pH 8.0), and incubated at 37° C. for 60 minutes, with intermittent mixing. Thereafter, equal amount of hGas6 (100 nM) was added to each tube and incubated at 37° C. for another 60 minutes, with intermittent mixing. To each of the tubes, 1 μg of 6×-His antibody was added and the mixture was incubated overnight at 4° C. on a rotary mixer. After overnight incubation, 30 μl of Protein A/G PLUS agarose beads (Santa Cruz) were added into each of the tubes and incubated for an hour at 4° C. The mixtures were centrifuged and the pellets were then washed four times in ice-cold Nonidet P-40 buffer (20 mM Tris.HCl, 150 mM NaCl, pH 8.0 and 1% Nonidet P-40). Pellets were re-suspended in 30 μl of 2× sample loading dye and boiled for 5 min at 95° C. The samples were fractionated by SDS-PAGE and bound Gas6 was analyzed by immunoblotting.

Colony Forming Assays:

H1299 cells were plated in 6 well plates at a very low density (~250 cells/well). Next day, the cells were treated with the SMIs at different concentrations. The cells were incubated with the drugs for 14 days. After 14 days, colonies were stained with 0.25% crystal violet in 95% ethanol. Colonies consisting of more than 50 cells were counted.

Cytotoxicity Assays:

H1299 cells were plated at 3500 cells/200 μl in 96 well plates. 24 h after plating, erlotinib, compound 1Q or compound 1I were added at the indicated concentrations. 72 h after treatment, cells MTS reagent was added (Promega) to the cells. Color change was monitored at 490 nm. For the combination study, the concentration of compound was kept constant at 10 μM whereas different concentrations of erlotinib were added. MTS assay was performed according to the manufacturer's instructions.

Real-Time Migration Assay Using the RTCA DP Xcelligence System:

H1299 and MDA-MB-231 cells lines were seeded in complete medium and allowed to attain ~80% confluence and then serum starved overnight in medium containing 0.5% FBS. The cells were then detached by Accutase (Sigma), counted and resuspended in serum-free RPMI-1640 medium. In the lower chamber of the CIM plate, 1×RPMI-1640 containing 10% FBS was added as a chemoattractant. In the top chamber, 50 μl of 1×RPMI-1640 was added to all wells. Both chambers were assembled, loaded in the Xcelligence system, and run for 30 min for equilibration or background readings. One hundred microliters of each cell line suspended in 1×RPMI-1640 (40,000 cells/100 μl)±Gas6±small molecule inhibitors then were added in triplicates in upper chamber wells. Readings for changes in the cell index (CI) were taken every 10 min for 24 h and migration was shown as a change in cell index versus time.

Mouse Xenograft Studies:

500,000 H1299 cells in 100 μl of PBS were injected subcutaneously into the right flank of 4-6 week NOD/SCIDg mice. Once tumors were palpable, the mice were randomized into 3 groups, each group had 6 mice: control mice were treated with vehicle (DMSO) intraperitoneally (IP) and the treatment groups with compound 1I (day 1, day 2, day 3 and day 4) or with compound 1Q (day 1, day 2, day 3, day 4, day 7 and day 8) at a dose of 100 mg/kg IP. Similar studies were conducted on compound 1Q dosed at 300 mg/kg in mice. Tumor size and body weights were measured three times a week and the tumor volume calculated.

Quantification of Immunoblot Intensities:

Immunoblot data were obtained within a linear range of exposure, and intensities were quantified by ImageJ. The levels of hAxl/IFN-γR1 cells lines activation were measured by pSTAT1 whereas the levels of H1299 and MDA-MB-231 cell lines activation were measured by pAxl signal intensities. Blots were normalized to intensities of respective β-actin or GAPDH protein loading controls. The levels of pSTAT1 or pAxl activation induced by Gas6±small molecule inhibitors were plotted as a fold of enhancement or reduction over intensities induced by Gas6 alone.

Data Analysis:

All experiments were repeated at least three times. Statistical analysis was done by GraphPad Prism. Descriptive statistics for quantitative variables were summarized using mean±standard deviation. Differences between groups were tested by T-test or one-way ANOVA followed by Tukey post-hoc test. Differences with a P value of <0.05 were considered statistically significant.

Results

Identification of Small Molecule Inhibitors (SMIs) in a Functional Cell Based Reporter Bioassay:

A series of compounds that function as Axl Ig1 Gas6 LG inhibitors has been discovered. These drug-like molecules have been identified and developed employing rational (computer-based) drug design strategies based on the known X-ray crystal structure of human Axl in a complex with human Gas6, where two potential target sites were postulated (PDB Ref. Code 2C5D).

Figure 2A:
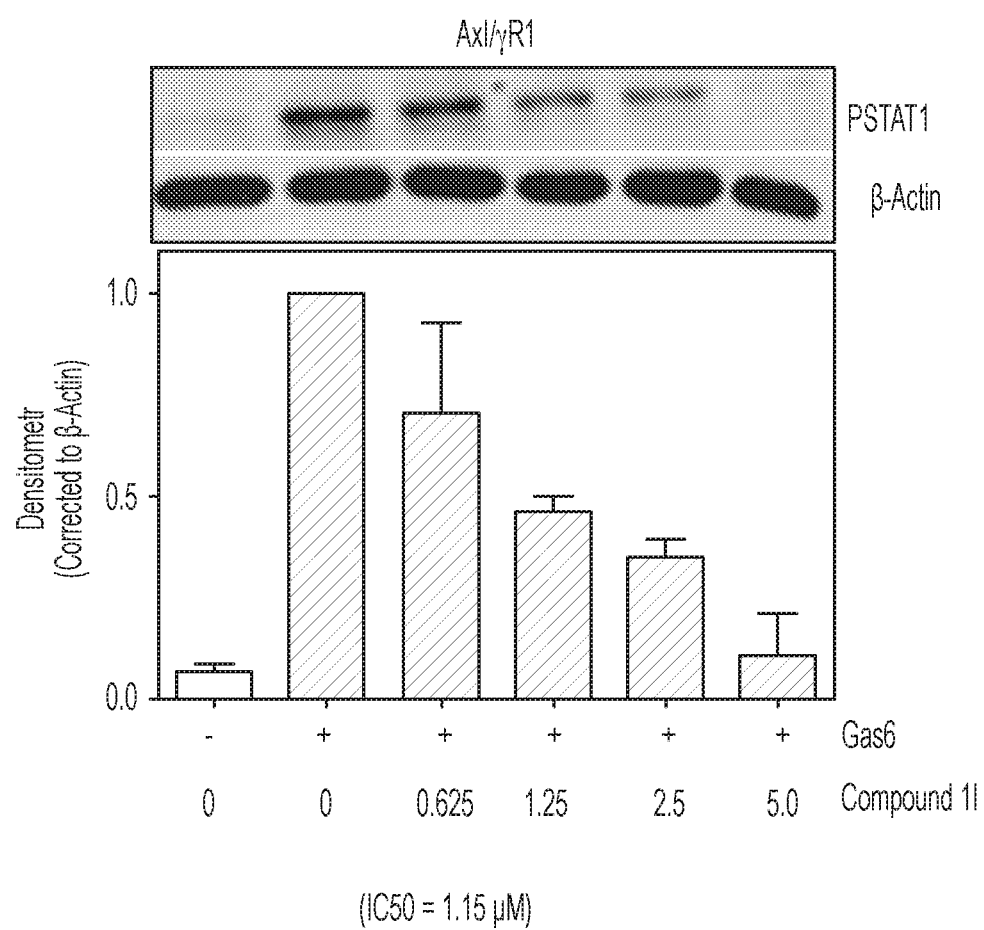
FIG. 2A illustrates results of dose-response assays to estimate the IC50 value of compound 1I.
Figure 2B:
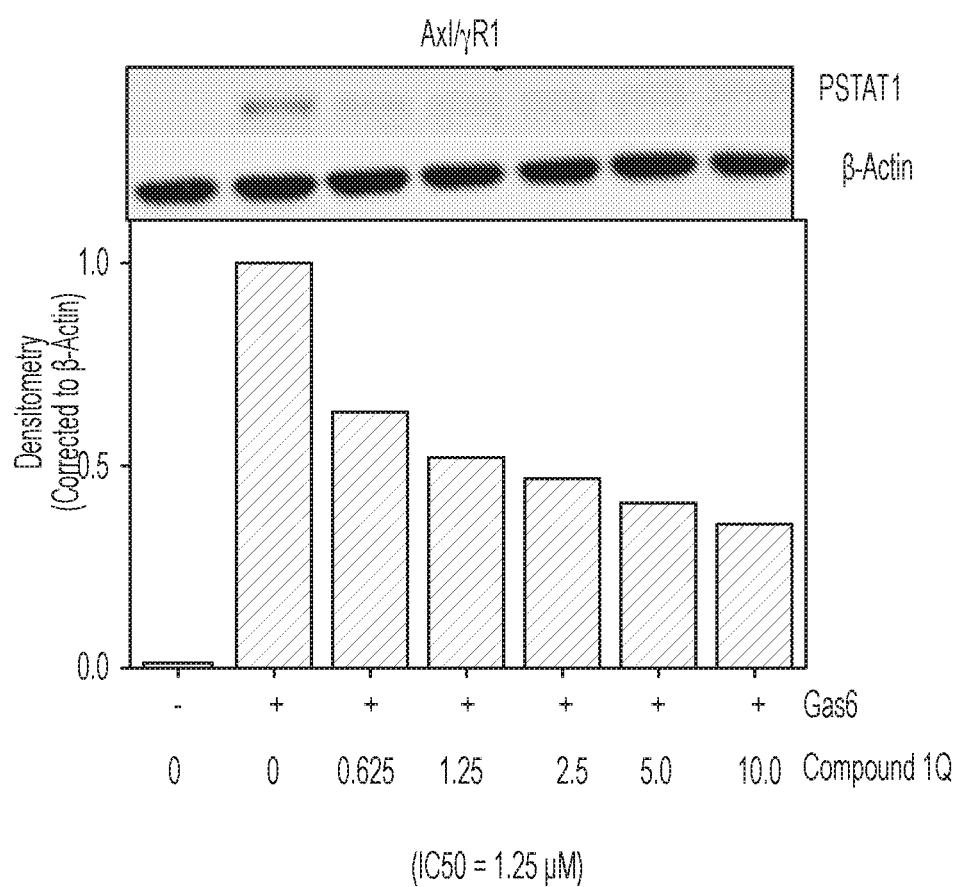
FIG. 2B illustrates results of dose-response assays to estimate the IC50 value of compound 1Q.

To evaluate the inhibitor activity of the compounds, an Axl reporter system was used that recapitulates Axl activation in a cell-based assay. Within successive rounds of iterative workflow of computational design and biological assay, Axl-Gas6 inhibitors designated compounds 1I and 1Q (FIG. 1) were found that exhibit potent anti-Axl activity with an apparent EC50 in the low micro-molar range (FIGS. 2A, 2B). Cytotoxicity assays using normal (non-cancerous) cells revealed that these compounds have no discernible cellular toxicity. Further iterations of computational inhibitor design and biological evaluation led to the discovery of additional compounds.

To ascertain whether these compounds inhibited Axl by preventing Gas6/Axl protein-protein interaction, or conversely inhibited receptor dimerization, compounds 1I and 1Q were tested in a pull-down assay to determine if they compete with Gas6-Axl binding. When His-tagged soluble Axl Ig1/Ig2 recombinant proteins were co-incubated with purified recombinant Gas6 (Amgen), compounds 1I and 1Q were able to inhibit in vitro the Axl/Gas6 interaction in a dose-dependent manner (FIG. 2A, 2B).

Figure 3:
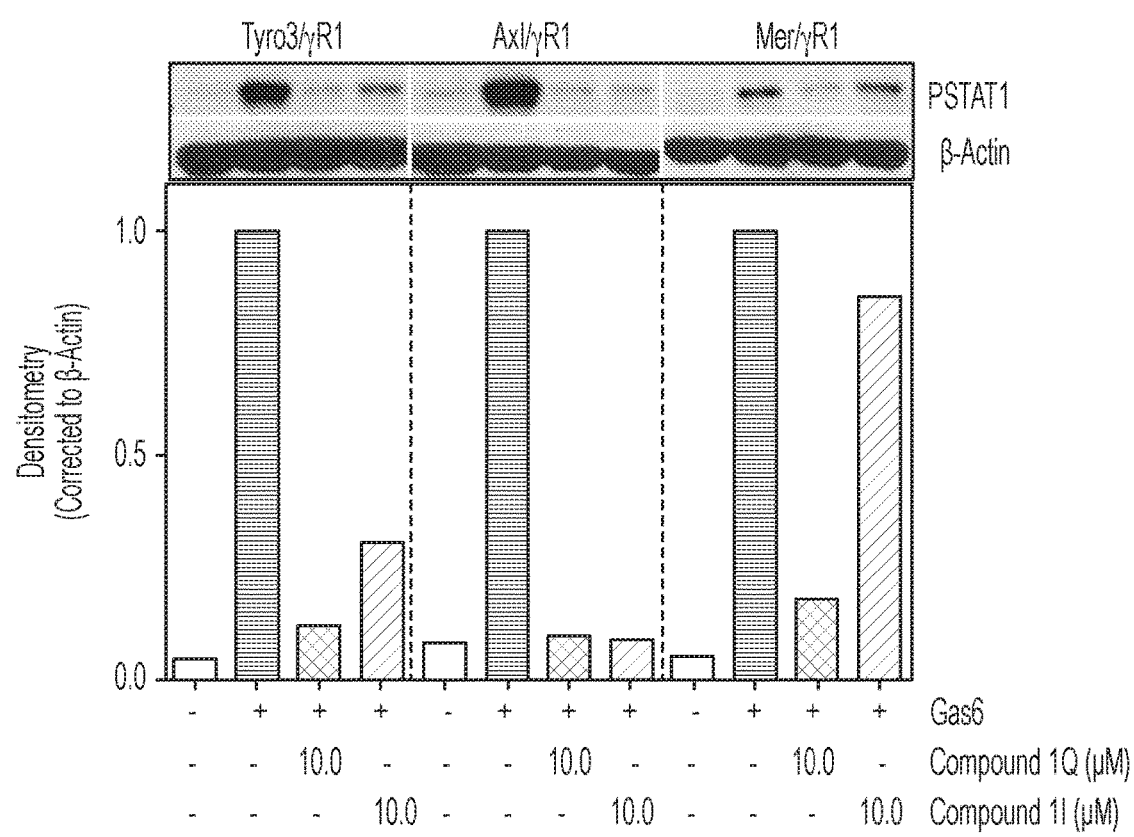
FIG. 3 establishes that both compounds 1Q and 1I act on all three of the TAM receptor kinases: Tyro3, Axl, Mer.

Having in vitro evidence using recombinant proteins and cell-based evidence using reporter hAxl-γR1 lines, compounds were tested to determine whether the inhibitors had specificity towards Axl, or whether they were pan-TAM inhibitors. Towards this goal, homology modeling against the published Axl Ig1/Ig2-Gas6 LG1 domain structure described above by Sasate and colleagues was performed (Sasaki T, et al. *The EMBO Journal* 2006 Jan. 11; 25(1): 80-87). The extracellular sequence homology of the three TAMs (Tyro3, Axl, Mer) in their Ig1/Ig2 Gas6 interaction regions reveals 36% overall identity. Subsequent homology-based 3-D modeling predictions of the Ig1/Ig2 duets of all three TAM receptors when aligned against the X-ray crystal structure of the minimum Axl-Gas6 complex (PDB entry 2C5D) chain C sequence (which corresponds to Axl's Ig1 and Ig2 domains) was used to explore the similarity of the site in Mer and Tyro3. The shape and biochemical properties of the binding site are conserved. Consistent with this notion, when Mer-γR1 and Tyro-3-γR1 cells were treated with 10 μM compound, compounds 1I and 1Q had similar blocking activity on all three TAM lines (FIG. 3). These data suggest that the subject inhibitors act at the interface between Gas6 and TAM Ig-1 block assemblages of ligand-receptors pan-TAM inhibitors.

Figure 4:
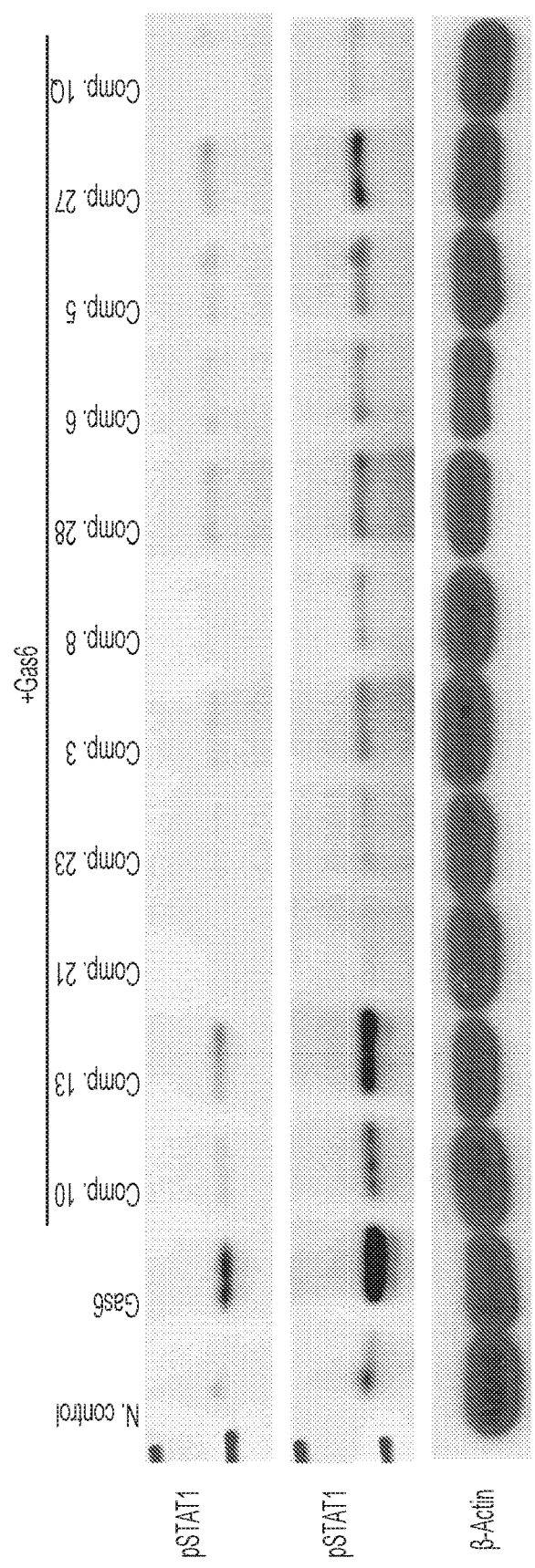
FIG. 4 shows the inhibition of Gas6-induced activation of hAxl/γR1 reporter cells by certain test compounds (10 μM).
Figure 4:
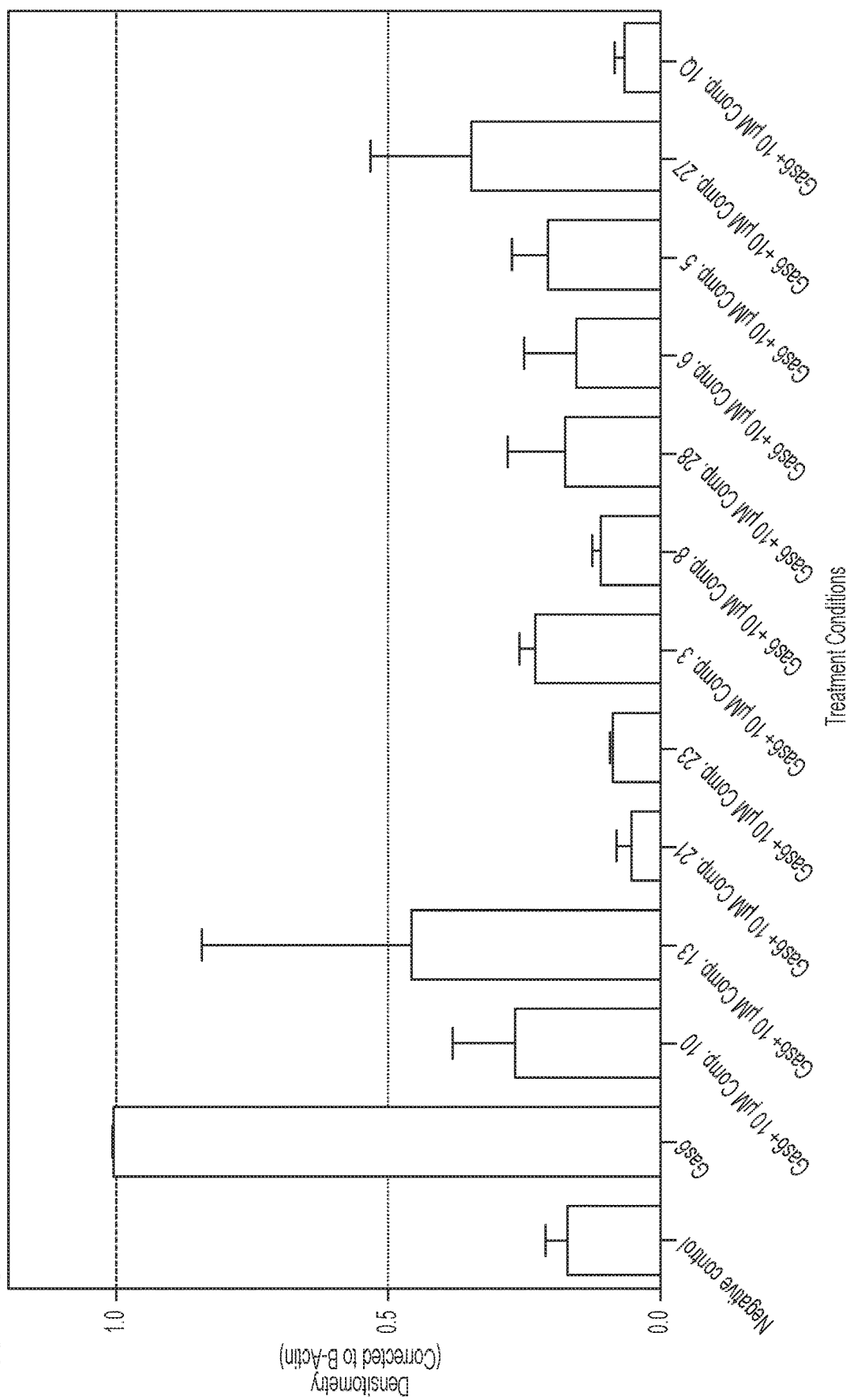

The development of compounds 1I and 1Q by virtual docking and refinement indicates that it is possible to generate TAM Ig1-Gas6 LG inhibition by small molecules that target this ligand/receptor pair. To obtain more efficacious inhibitors, structural and cheminformatics analyses suggested further chemical modifications (FIG. 1). After further iterative rounds of structure/function chemical modifications and virtual docking in 3D space, a new series of drug-like compounds was tested on the hAxl/IFN-γR1 reporter cell lines. Among these, for example, compound 1I (IC50=1.15 μM, FIG. 2A) and compound 1Q (IC50=1.25 μM, FIG. 2B), showed Axl-inhibitory activity with favorable IC50 values. Similar to the pan-TAM inhibitory profile of compound IT (FIG. 3A), these compounds showed specificity of pan-TAMs capable of inhibiting Mer and Tyro3 in addition to Axl (FIG. 3). Potent inhibition of Gas6-induced hAxl/γR1 reporter cells was also obtained for a representative subset of novel composition-of-matter compounds (FIG. 4). Taken together, these data establish proof-of principle that small molecules can effectively inhibit Axl extracellular domain-Gas6 interfaces, providing alternative strategies to tyrosine kinase inhibitors (TKIs) in order to block TAM receptor activation.

Figure 5A:
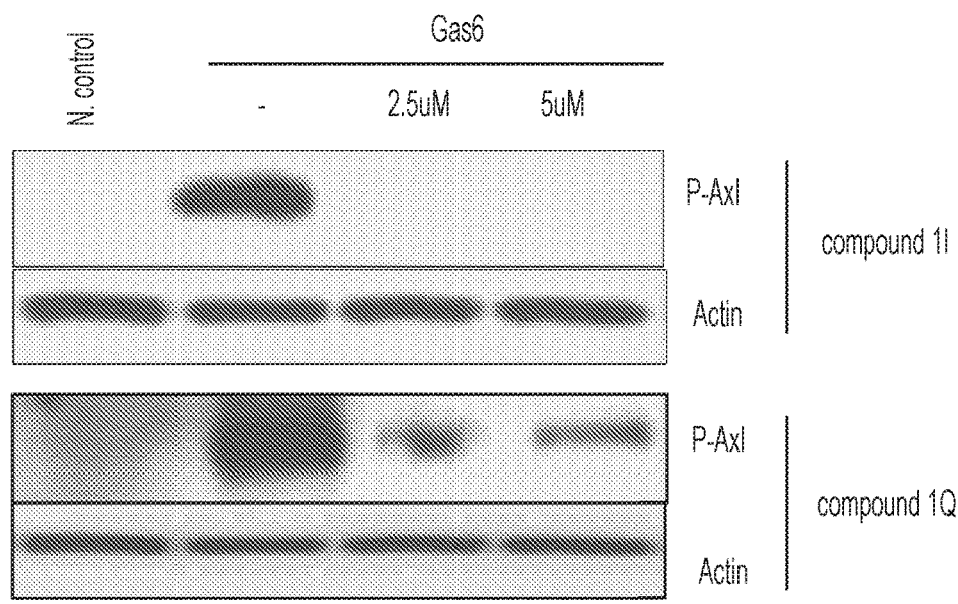
FIG. 5A illustrates that compounds inhibit the activation (phosphorylation) of native Axl in Axl-positive human breast cancer cell line MBA-MD-231.
Figure 5B:
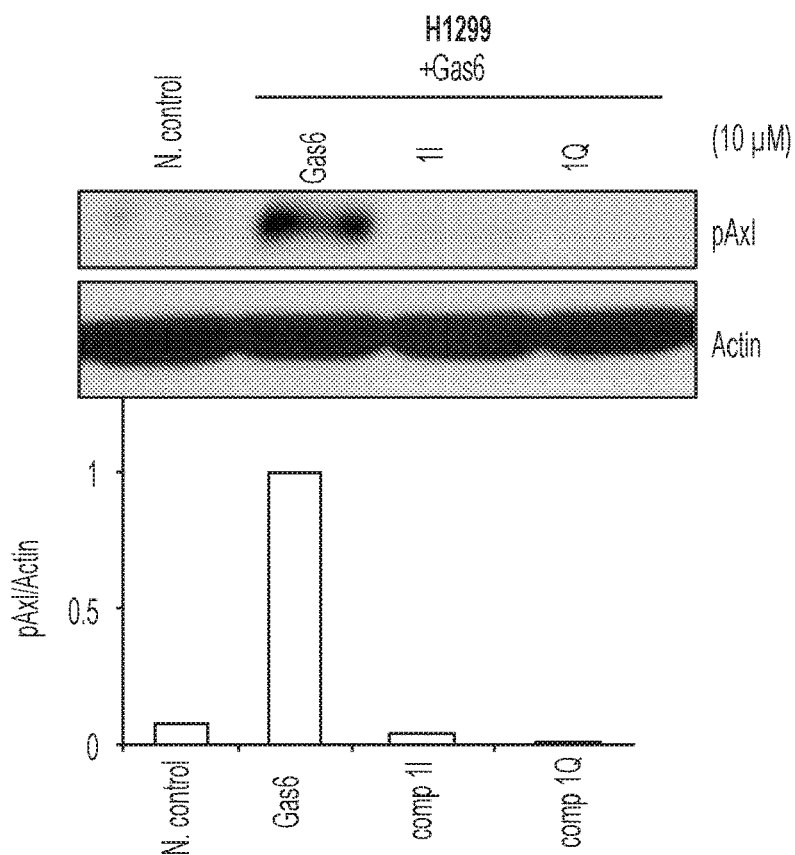
FIG. 5B illustrates that compounds inhibit the activation (phosphorylation) of native Axl in Axl-positive human lung cancer cell line H1299.
Figure 6A:
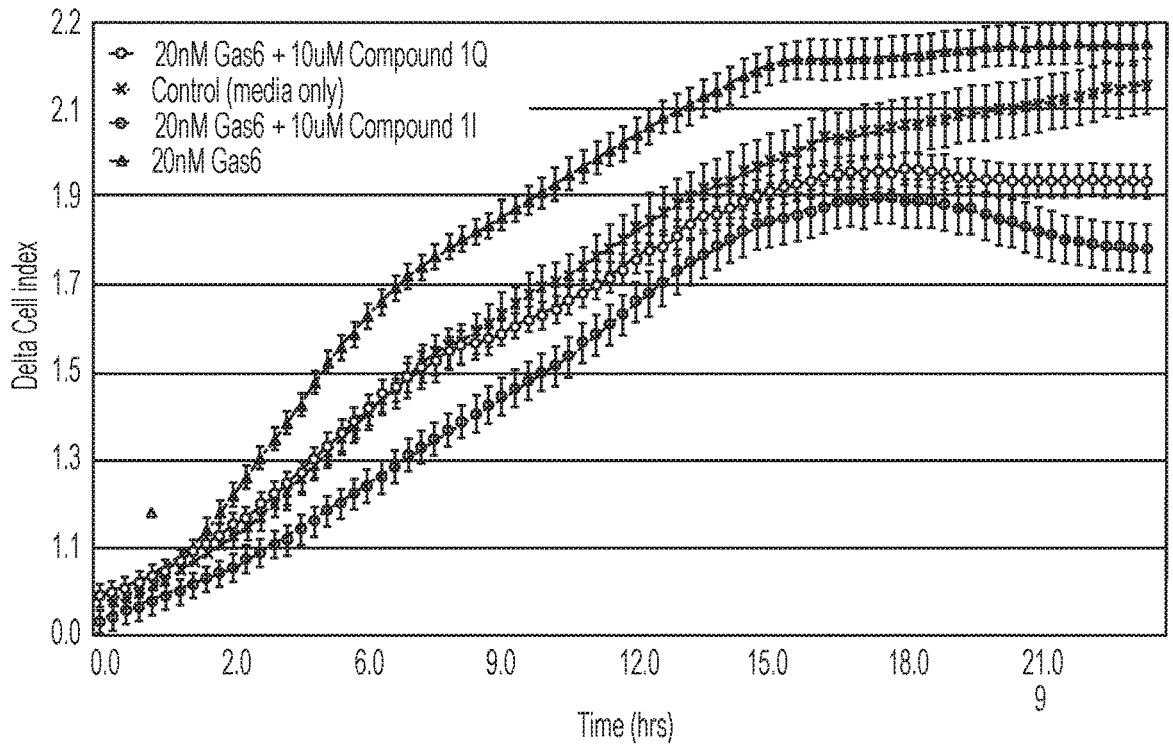
FIG. 6A shows plots that reveal the ability of compounds 1Q and 1I to suppress migration of MDA-MB-231 cancer cells.
Figure 6B:
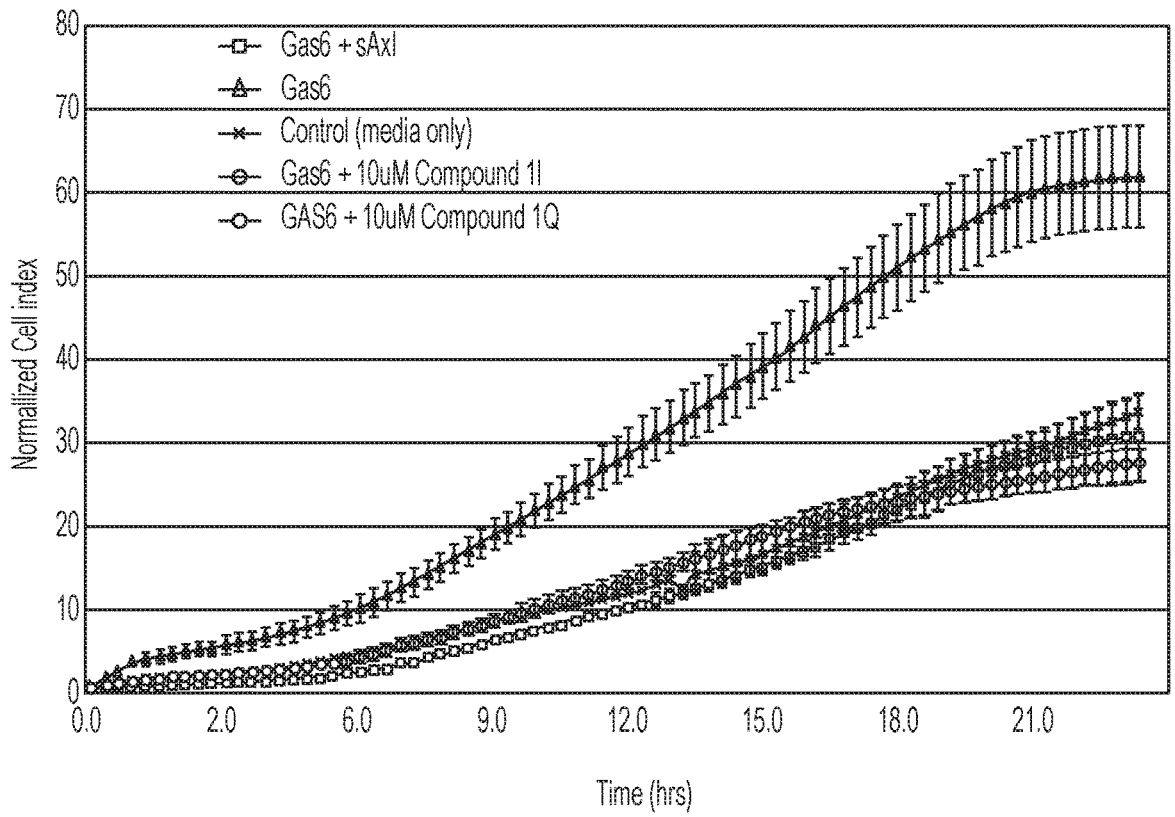
FIG. 6B shows plots that reveal the ability of compounds 1Q and 1I, compared with soluble Axl (sAxl), to suppress migration of H1299 cancer cells.

Next, to translate results obtained using chimeric Axl receptor cell lines into the biology of native Axl receptor activation, an array of cell lines was screened to identify cancer cell lines that (i) overexpressed Axl, and (ii) responded in an inducible manner to exogenous Gas6. Consistent with previous reports, some cell lines were identified that had constitutive Axl activation as well as other cell lines that had inducible Axl activation, most notably the triple-negative breast adenocarcinoma MDA-MB-231, the lung adenocarcinoma H1299, and the lung adenocarcinoma Calu-3. Compounds 1I and 1Q exhibited potent inhibition of activation (phosphorylation) of Axl in native cancer cell lines, as shown for both Axl-positive MBA-MD-231 breast cancer (FIG. 5A) and H1299 lung cancer (FIG. 5B) cell lines. Upon pre-treatment of cells with 10 μM compound 1I or compound 1Q, both Gas6-inducible phosphorylation of native Axl (pAxl) and Gas6-inducible Akt phosphorylation (a known substrate Axl) were abrogated. The observed effects with compound 1I and 1Q were as effective as sAxl Ig1/Ig2 fusion protein, a biologic that sequesters Gas6 away from the native Axl receptor (FIGS. 6A-6B).

Figure 6C:
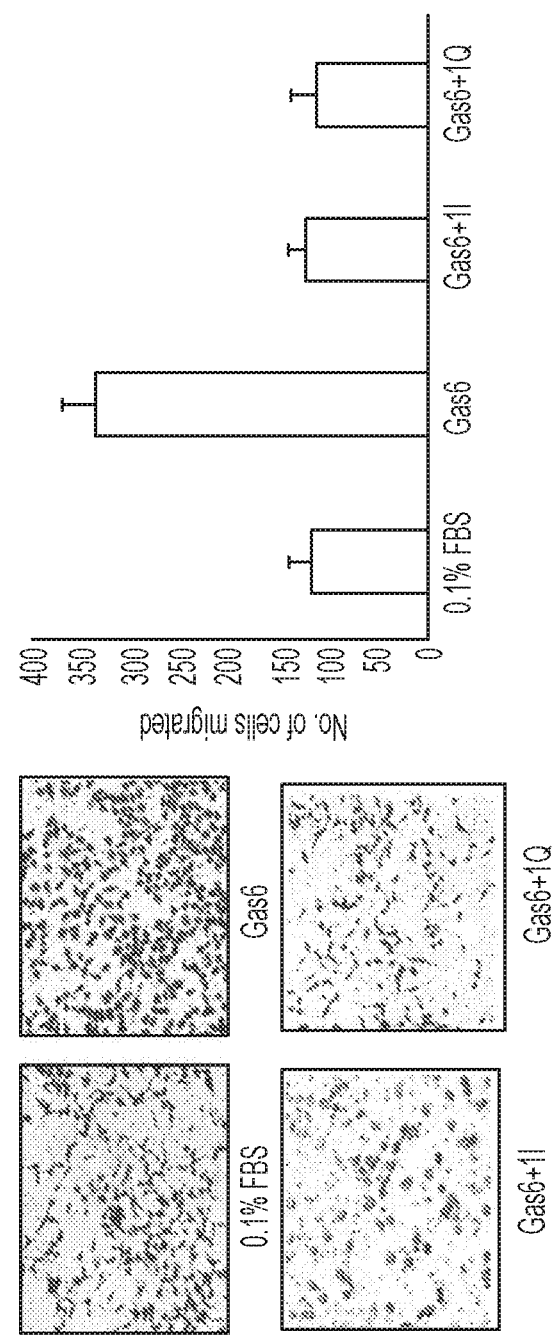
FIG. 6C shows that pretreatment of H1299 cells with compounds 1I or 1Q strongly suppressed Gas6-inducible motility through an 8 mm pore (transwell).
Figure 6D:
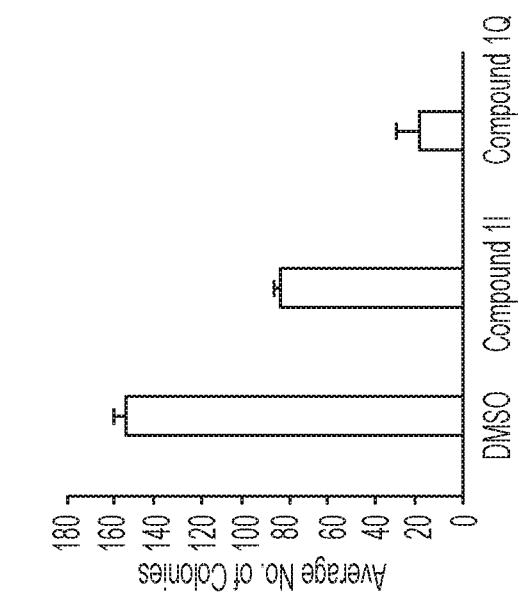
FIG. 6D shows that pretreatment of H1299 cells with compounds 1I or 1Q strongly suppressed clonogenic growth.
Figure 6D:
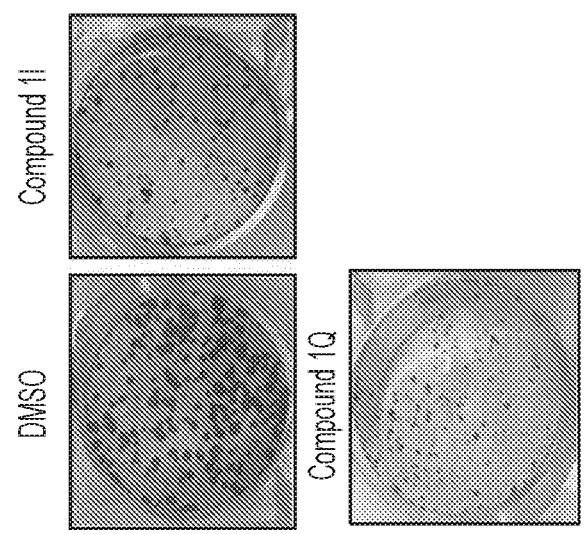
Figure 7A:
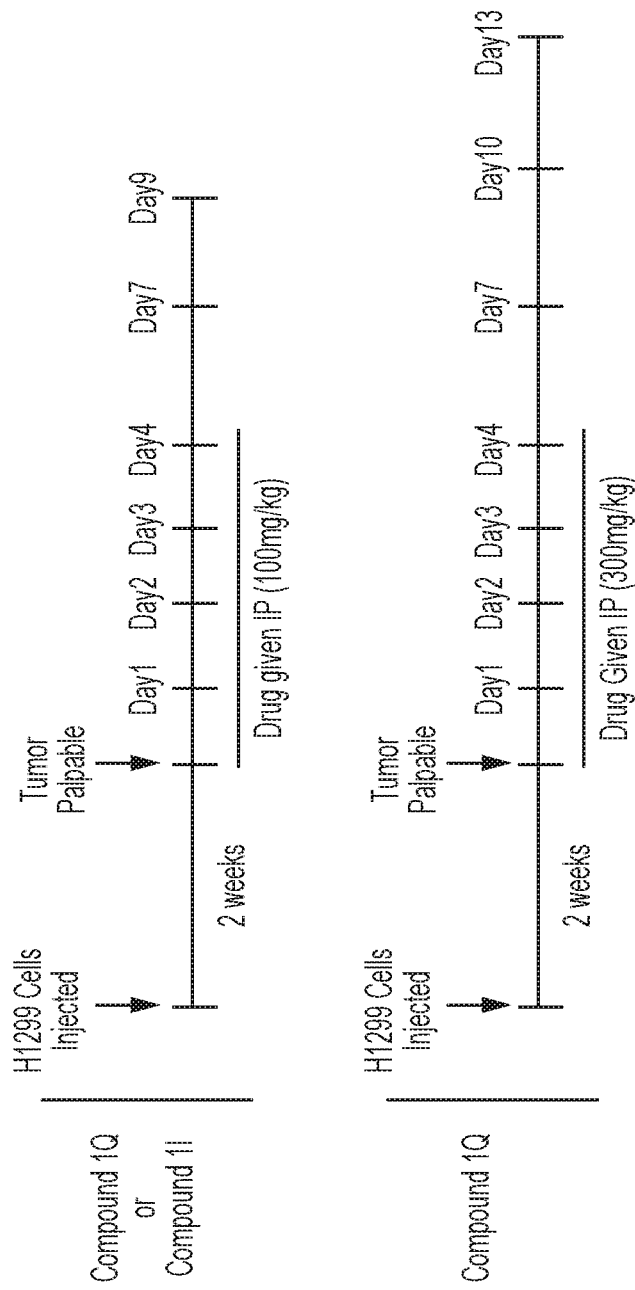
FIG. 7A depicts the dosing schedule for mice employed in toxicity and efficacy studies.
Figure 7B:
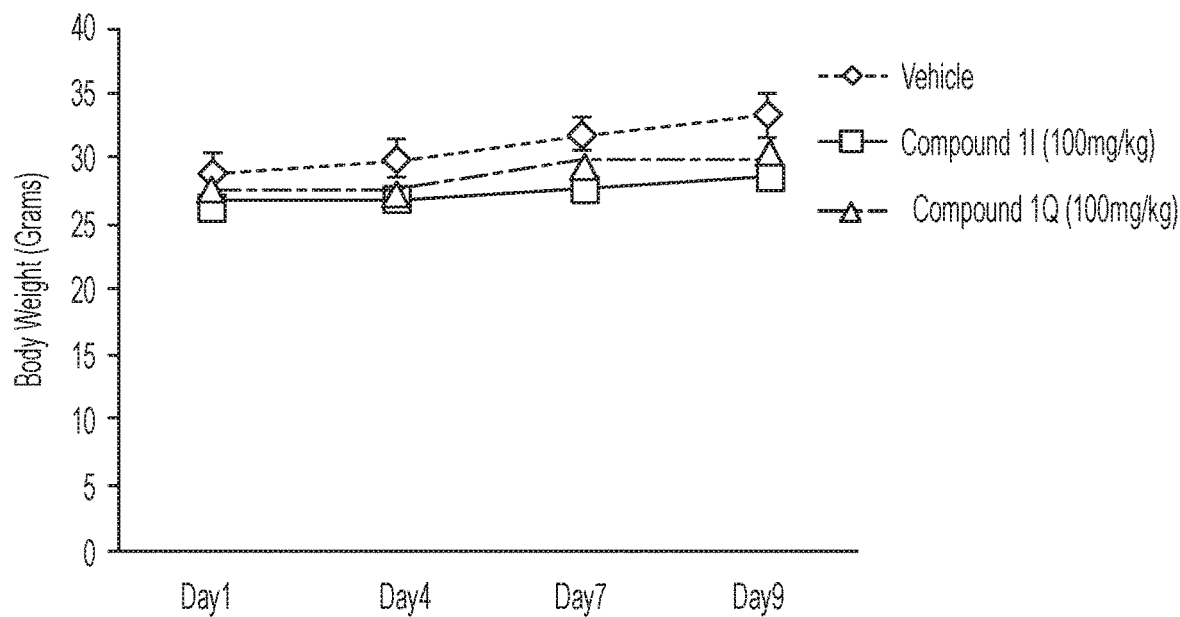
FIG. 7B shows the effect of compound 1I or 1Q, dosed at 100 mg/kg IP, on body weight of mice. Absence of effect relative to vehicle is an indicator that compound is non-toxic.
Figure 7C:
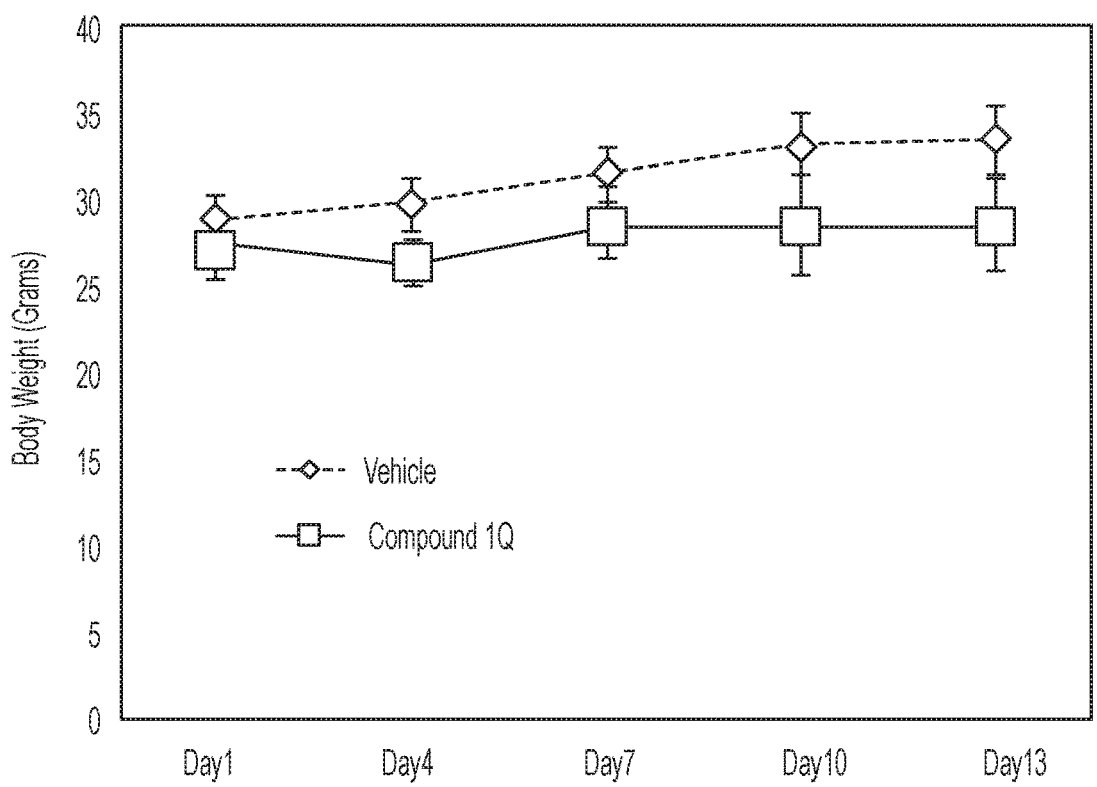
FIG. 7C shows the effect of compound 1Q, dosed at 300 mg/kg IP, on body weight of mice. Absence of effect relative to vehicle is an indicator that compound is non-toxic.
Figure 7D:
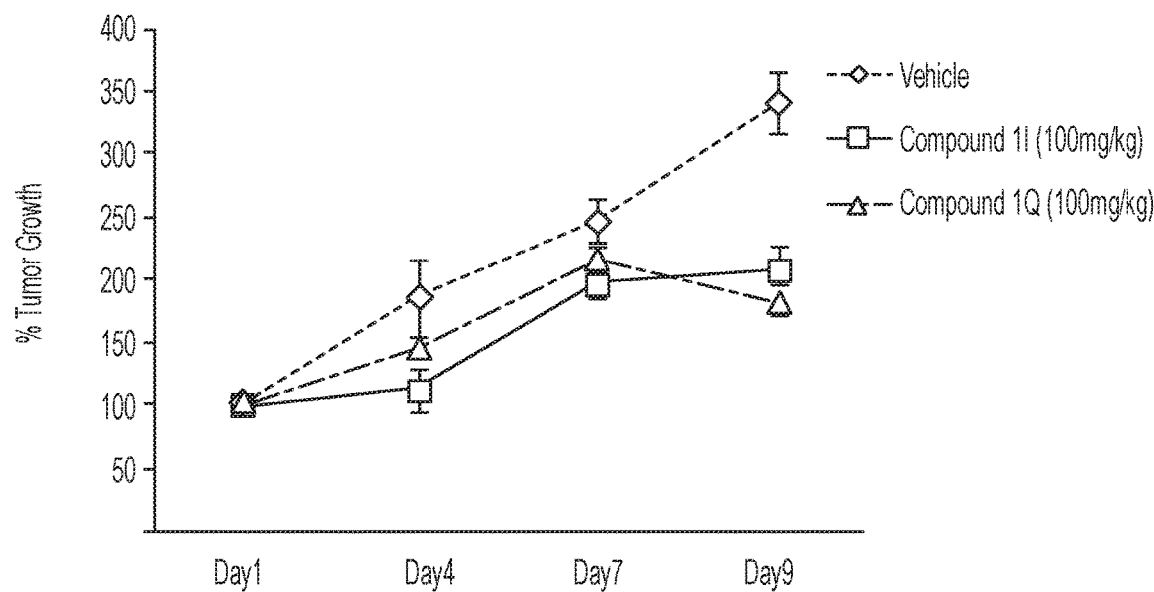
FIG. 7D demonstrates the ability of compound 1Q or 1I, dosed at 100 mg/kg IP, to suppress tumor growth (volume) in mice.
Figure 7E:
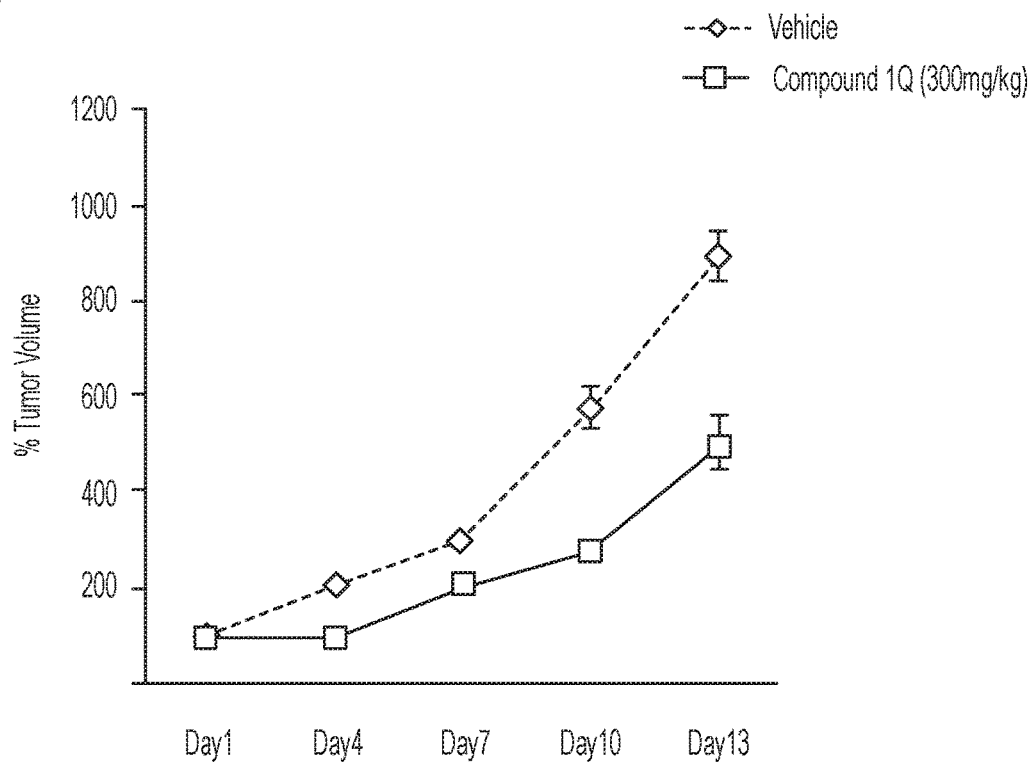
FIG. 7E demonstrates the ability of compound 1Q, dosed at 300 mg/kg IP, to suppress tumor growth (volume) in mice.
Figure 8:
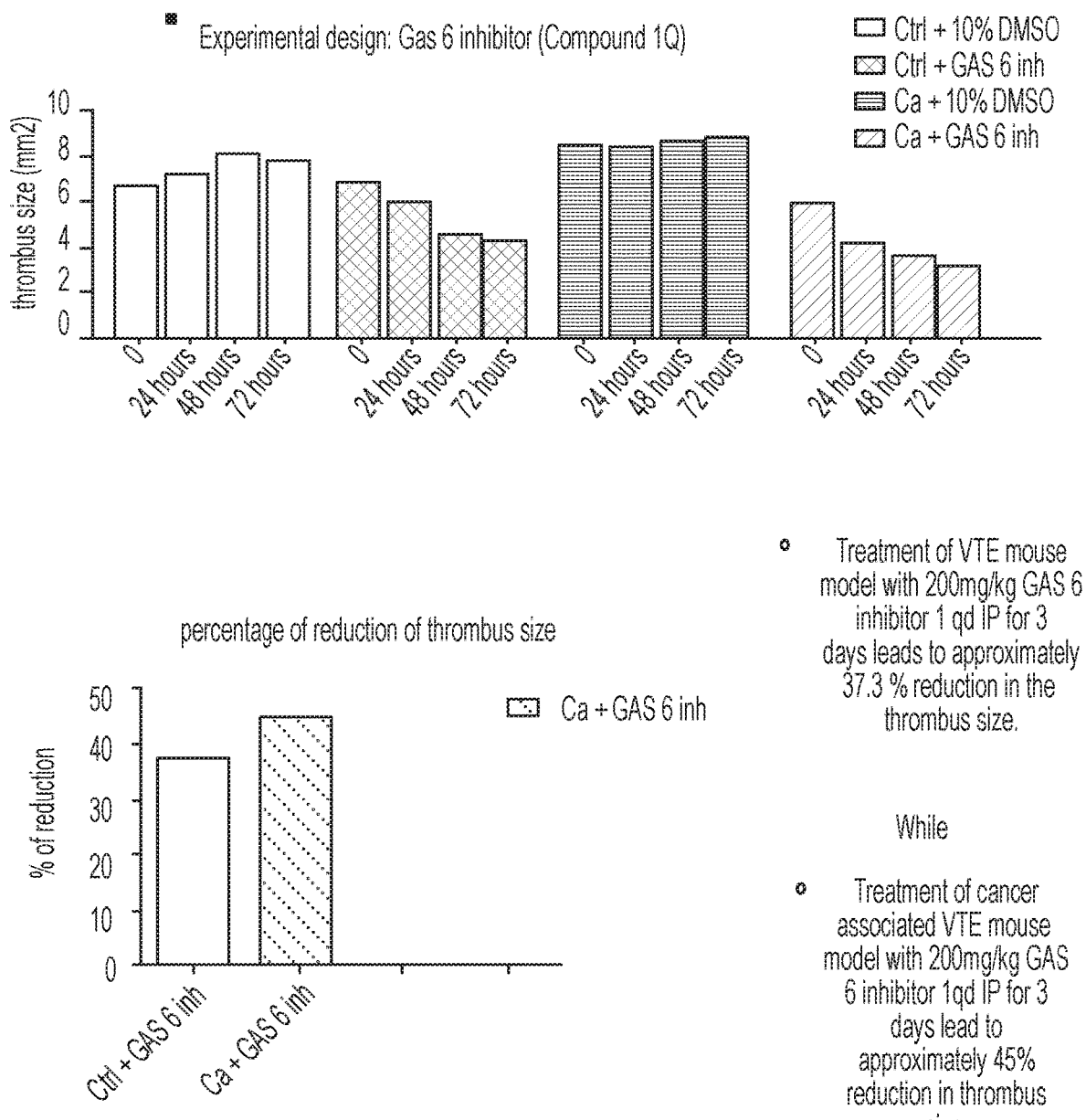
FIG. 8 demonstrates that treatment with compound 1Q dosed at 200 mg/kg qd IP for three days leads to approximately 37.3% reduction in thrombus size in venous thromboembolism (VTE) mouse model and 45% reduction in thrombus size in cancer associated VTE mouse model.

To access functional outcomes of Ig1 inhibitors, their effects on Gas6-inducible oncogenic features in Axl-expressing tumor cell lines were examined, as well as their effects on tumorigenicity when H1299 cells were transplanted into a NOD-SCID in vivo mouse model. Pretreatment of H1299 cells with compound 1I or compound 1Q strongly suppressed Gas6-inducible motility through an 8 μm pore (FIG. 6C), as well as suppressed clonogenic growth when cultured in the presence of Gas6 (FIG. 6D). Furthermore, to assess effects of compound 1I and compound 1Q on the early kinetics of motility, these parameters were studied in real-time using Xcelligence technology (FIGS. 6A, 6B). These compounds suppressed motility in both Gas6-inducible H1299 and MDA-MB-231 cells, and notably their effects were similar to the inhibition observed in sAxl ligand traps (FIG. 6B).

Finally, based on the promising in vitro and cell culture experiments showing anti-Axl activity of certain compounds, the in vivo efficacies of compound 1I and compound 1Q using a murine SCID/human H1299 lung cancer xenograft model was investigated (FIG. 7A-E). As indicated, SCID mice were subcutaneously injected with 250,000 tumor cells in the hind flanks with human H1299 cells until palpable tumors were present. Subsequently, mice were injected every two days with vehicle, compound 1I or compound 1Q at a concentration of 100 mg/kg for up to 2 weeks. As indicated, both compound 1I and compound 1Q significantly suppressed growth of tumor (measured in terms of tumor volume), while body weights were not significantly different. Neither compound 1I nor compound 1Q showed notable toxicity in cell culture or in vivo even at the highest dose tested 300 mg/kg IP (FIG. 7C), and both inhibitor molecules displayed good bioavailability with a half-life ($t_{1/2}$) of ~8 hours (not shown). Taken together, these studies support the further development of TAM Ig1 inhibitors as anti-cancer therapeutics (FIGS. 7A-E).

Discussion

A novel first-in-class TAM receptor antagonist that interferes with the binding of Gas6 to the Ig1 domain of TAMs in the extracellular region was developed and characterized. These small molecule compounds show promising therapeutic potential, and can block Axl and signaling at low-to-sub micromolar concentrations. Moreover, pre-clinical studies support their utility in both cell lines and in vivo, and suggest they have minimal toxicity and good bioavailability when administered to mice. Furthermore, to assess the effects of these compounds on the early kinetics of motility, we investigated these parameters in real-time using Xcelligence technology (FIGS. 6A, 6B). As indicated, these compounds suppressed motility in both Gas6-inducible H1299 and MDA-MB-231 cells, and notably their effects were similar to the inhibition observed in sAxl ligand traps (FIG. 6B). These studies establish proof-of-concept that, in addition to the continued development of TKIs, therapeutic monoclonal antibodies (mAbs), and Fc-TAM extracellular soluble traps (e.g., sAxl) as TAM therapeutics, compounds that block the major grove between the Axl Ig1 and the Gas6 LG1 domain should be considered as a therapeutic strategy. By targeting a binding site in the extracellular domain, the subject compounds would likely impart advantages over TKIs pertaining to cellular uptake and subsequent efflux pump-mediated and mutational resistance. More fundamentally, molecular modeling suggests that these inhibitors effectively block the functionally critical protein:protein interaction (PPI) between the Ig1 domain of Axl and the LG domain of Gas6. The development of inhibitors of PPIs represents a significant challenge in drug development (Reviewed in Azzarito V1, et al., Inhibition of α-helix-mediated protein-protein interactions using designed molecules. *Nat Chem.* 2013; 5(3): 161-73; Jin L., et al., Targeting protein-protein interaction by small molecules. *Annu Rev Pharmacol Toxicol.* 2014; 54:435-56).

In recent years, over-expression of TAM receptors has been reported in a wide range of human cancers, an axis that is associated with aggressive cancer phenotypes, emergence of drug resistance, immune escape, and overall poor patient survival. In tumor cells, activation of Axl has been associated with the activation of proliferation and survival pathways such as Erk and Akt (Keating A K, et al., *Molecular Cancer Therapeutics* 2010 May; 9(5): 1298-1307; Knubel K. H., et al., *Oncotarget* 2014 Mar. 15; 5(5): 1338-1351; Schlegel J., et al., *The Journal of Clinical Investigation* 2013 May 1; 123(5): 2257-2267), emergence of drug resistance via the direct phosphorylation of other tyrosine kinases such as MET and EGFR (Bansal N., et al., *Oncotarget* 2015 Jun. 20; 6(17): 15321-15331), and epithelial to mesenchymal transition (EMT) via the up-regulation of TWIST and SLUG (Asiedu M. K., et al., *Oncogene* 2014 Mar. 6; 33(10): 1316-1324; Ji W., et al., *BMC Cancer* 2013; 13: 606; Wu F., et al., *Int J Clin Exp Pathol* 2014; 7(10): 6653-6661. Finally, Gas6, the main ligand for Mer and Axl, is also concomitantly overexpressed in human solid cancers, establishing an autocrine loop that constitutively activates TAMs on tumor cells (Kirane A., et al, *Cancer Research* 2015 Sep. 15; 75(18): 3699-3705; Rankin E. B., et al., *Proceedings of the National Academy of Sciences of the United States of America* 2014 Sep. 16; 111(37): 13373-13378).

Besides the intrinsic activation of TAMs in non-resectable solid cancers, TAMs also contribute to tumor progression via their expression on infiltrating myeloid-suppressor cells, macrophages, and NK cells where they also contribute to immune escape. For example, the infiltration of Mer-expressing NK and M2 macrophages is associated with suppression of anti-tumor immune responses (Cook R. S., et al., *The Journal of Clinical Investigation* 2013 Aug. 1; 123(8): 3231-3242; Paolino M., et al., *Nature* 2014 Mar. 27; 507 (7493): 508-512). This places TAMs as unique oncogenic proteins that, besides activating conventional oncogenic pathways alluded to above, also contribute to tumorigenesis in an unconventional manner by blocking signals necessary for immunogenic death and thereby promoting tolerance and immune suppression in the tumor microenvironment (Rothlin C. V., et al., *Annual Review of Immunology* 2015; 33: 355-391). As such, generalized antagonists that act as pan-TAM inhibitors and target the binding site between Gas6 and TAMs may exhibit opportunistic pleiotrophic effects for multiple effector cells that coordinately improve outcomes in tumor patients. Further studies that investigate TAM Ig1 inhibitors in immune-competent mouse models will shed more light on these queries, particularly whether and how these drugs induce immunogenic anti-tumor responses, when combined with therapeutics such as anthracyclines that induce immunogenic death.

To date, three main types of TAM inhibitors have been considered that include; (i) small molecule tyrosine kinase inhibitors (TKIs), (ii) antagonistic monoclonal antibodies (mAbs), and (iii) Fc-TAM soluble decoy receptors (Kariolis M. S., et al., *Nature Chemical Biology* 2014 November; 10(11):977-83; Graham D. K., et al., *Nature reviews Cancer* 2014 December; 14(12): 769-785). All three approaches show therapeutic promise, and each has strengths and weaknesses. Small molecule TAM TKIs can show robust inhibitory activities in vitro, but most are not TAM specific, and show considerable off-target profiles which could give rise to adverse drug reactions. For example, the Axl specific TKI inhibitor BGB324 (previously known as R428) has reported an IC50 activity of 14 nM for Axl (compared with 700 nM and 1400 nM IC50s for Mer and Tyro3). However, BGB324 also has off-target effects on VEGFR, Abl, Tie-2 and MET kinases. Likewise, UNC569 and UNC1666, which have preferred specificity for Mer over Axl and Tyro3, also have off-target effects on Flt3 and RET. Similarly, although both Fc-TAM receptor traps and mAbs for Axl and Mer are also in clinical development, both receptors are highly glycosylated, potentially masking antigenic epitopes. The class of pan-TAM antagonists described here that target the Ig1 domain of TAMs and prevent Gas6 binding may offer unique advantages in the existing arsenal of TAM inhibitors, by simultaneously inhibiting Axl and Mer in the extracellular tumor microenvironment. Inhibitors that target binding sites located in the unique extracellular region of TAMs may offer additional advantages by virtue of the fact that they obviate the requirement for cell influx and subsequent efflux. This feature may confer improved and more efficient exposure of the drug to the target receptor, reduced likelihood of drug resistance, and fewer and less severe adverse effects.

One embodiment of the current study is aimed at therapeutics including anti-cancer therapeutics in the form of TAM ligand antagonists. Additionally, the interaction of Gas6 with TAMs recently has been shown to have important consequences in arterial thrombosis formation (Gould W. R., et al., *J Thromb Haemost* 2005 April; 3(4): 733-741; Saller F., et al., *Blood Cells Mol Dis* 2006 May-June; 36(3): 373-378). Levels of Gas6 are elevated in thrombotic platelets and knockout of Gas6 blocks experimental thrombosis (Blostein M. D., et al., *J Thromb Thrombolysis October;* 32(3): 272-278; Cosemans J. M., et al., *J Thromb Haemost* August; 8(8): 1797-1808). Accordingly, inhibitors of Gas6 binding to TAMs may be useful to benefit high-risk patients prone to platelet aggregation and thrombosis. TAM inhibitors may also be therapeutically relevant as antiviral agents, especially against so-called enveloped viruses which include ebola, zika, dengue, Marburg, West Nile, and HIV. For example, HIV is an enveloped RNA virus that buds from the host plasma membrane in the latter stages of the infectious cycle. In doing so, HIV virus has high concentration of phosphatidylserine (PS) associated with the envelope, enabling HIV to act as an apoptotic cell mimic (Callahan M. K., et al., *Journal of Immunology* 2003 May 1; 170(9): 4840-4845; Trommeshauser D., et al., *Chem Phys Lipids* 2000 September; 107(1): 83-92). Binding of HIV to TAMs receptors on macrophages or dendritic cells is expected to induce immune suppression and tolerance. Accordingly, TAM inhibitors may be useful to stimulate immune responses in HIV in combination with inhibitors to block replication. Finally, the TAM receptors represent potential targets for therapeutic intervention in inflammatory CNS diseases and neurodegenerative disorders such as Parkinson's disease (Fourgeaud L, et al., *Nature*. 2016 Apr. 14; 532(7598):240-4; Pierce A M and Keating A K. *Brain Research*. 2014 Jan. 13; 1542:206-20).

Example 2. Preparation of Compound 2

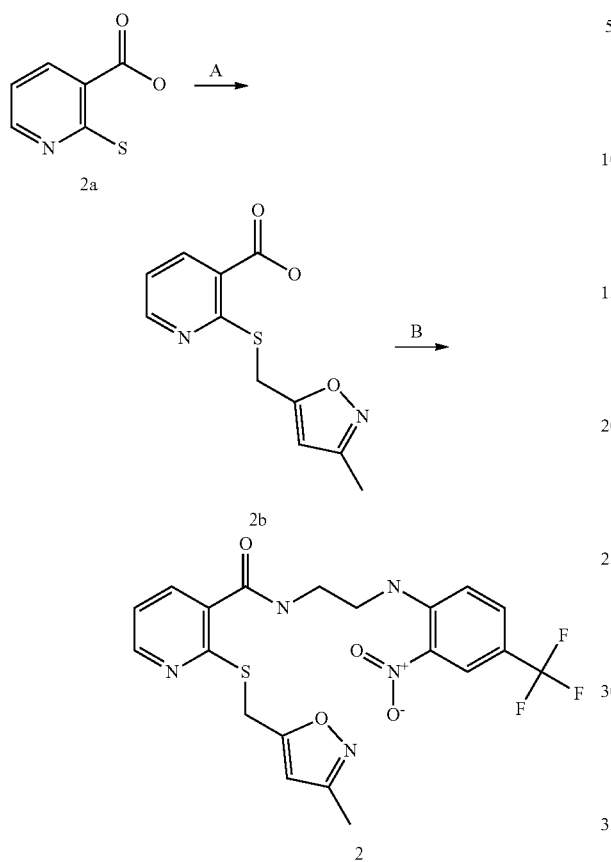

Step A:

A mixture of 2-mercapto-nicotinic acid 1a (1.24 g, 8.00 mmol), NaI (0.12 g, 0.80 mmol) and 5-chloromethyl-3-methyl-isoxazole (1.15 g, 8.80 mmol) in 10% NaOH methanol solution (8 mL) was stirred for 2 hours at 40° C. Then the solvent was evaporated, the residue was dissolved in water (30 mL) and the solution was acidified to pH-2 with 10% aqueous HCl. The precipitate formed was filtered, washed with water (2×20 mL) and dried to obtain 1.4 g (5.60 mmol, 70%) of compound 2b.

Step B:

To a cooled to 0° C. solution of compound 2b (0.260 g, 1.04 mmol), N*1*-(2-nitro-4-trifluoromethyl-phenyl)-ethane-1,2-diamine (0.259 g, 1.04 mmol) and HOBt (0.191 g, 1.25 mmol) in DMF (2 mL) EDC (0.219 g, 1.14 mmol) was added and the mixture was stirred overnight at room temperature. Then water (4 mL) was added, and the resulting precipitate was filtered, washed with water and dried to yield 0.170 g (0.35 mmol, 34%) of compound 2.

$^1$H NMR (DMSO-d$_6$, 400 MHz, ppm), δ=2.13 (s, 3H, CH$_3$), 3.49 (m, 2H, CH$_2$), 3.63 (m, 2H, CH$_2$), 4.44 (s, 2H, CH$_2$), 6.14 (s, 1H, Ar), 7.22 (m, 1H, Ar), 7.33 (d, 1H, $^3J_{H,H}$=9.1 Hz, Ar), 7.56 (d, 1H, $^3J_{H,H}$=9.1 Hz, Ar), 7.82 (d, 1H, $^3J_{H,H}$=7.2 Hz, Ar), 8.29 (s, 1H, Ar), 8.55 (d, 1H, $^3J_{H,H}$=3.5 Hz, Ar), 8.63 (t, 1H, $^3J_{H,H}$=5.4 Hz, Ar), 8.77 (t, 1H, $^3J_{H,H}$=5.4 Hz, Ar).

$^{13}$C NMR (DMSO-d$_6$, 125 MHz, ppm), δ=11.4, 24.8, 38.6, 42.3, 103.8, 114.9, 115.3, 115.6, 115.9, 116.4, 119.8, 119.9, 120.3, 122.9, 124.5, 124.6, 125.7, 128.3, 129.2, 130.8, 132.3, 132.5, 136.2, 147.5, 150.8, 156.3, 160.0, 166.8, 170.1.

Example 3. Preparation of Compound 3

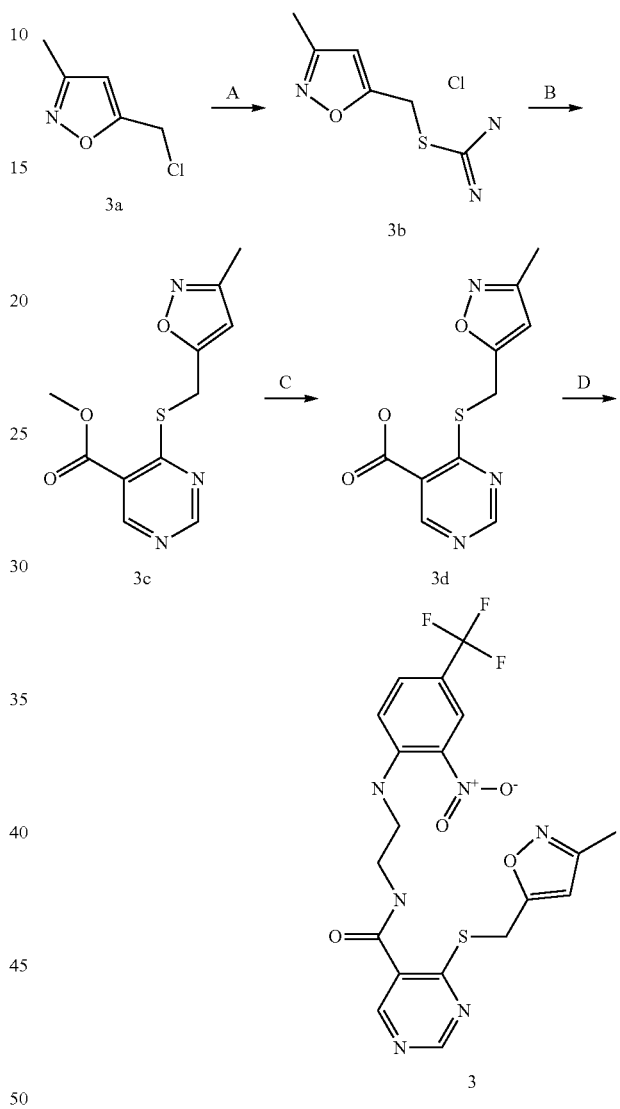

Steps A-C:

A solution of 5-chloromethyl-3-methyl-isoxazole 2a (1.50 g, 11.5 mmol) and thiourea (0.900 g, 11.8 mmol) in methanol (20 mL) was stirred overnight at 50° C. Then KOH (2.50 g, 44.6 mmol) was added, and the mixture was stirred for 30 min at room temperature. Next, 4-chloro-pyrimidine-5-carboxylic acid methyl ester (1.85 g, 10.8 mmol) was added and the reaction was stirred at 50° C. for 2 hours. Then 10% aqueous KOH solution (10 mL) was added and the mixture was stirred overnight at room temperature. The liquids were evaporated, the residue was dissolved in water (30 mL) and the resunting solution was acidified with 10% HCl until pH-2-3. The precipitate formed was filtered, washed with water (2×20 mL) and dried to yield 1.6 g (6.37 mmol, 60%) of compound 3d.

Steps D:

To a cooled to 0° C. solution of compound 3d (0.260 g, 1.04 mmol), N*1*-(2-nitro-4-trifluoromethyl-phenyl)-ethane-1,2-diamine (0.259 g, 1.04 mmol) and HOBt (0.191 g, 1.25 mmol) in DMF (2 mL) EDC (0.219 g, 1.14 mmol) was added and the mixture was stirred overnight at room temperature. Then water (4 mL) was added, and the resulting precipitate was filtered, washed with water and dried to yield 0.335 g (0.695 mmol, 67%) compound 3.

$^1$H NMR (DMSO-d$_6$, 400 MHz, ppm), δ=2.15 (s, 3H, CH$_3$), 3.51 (m, 2H, CH$_2$), 3.64 (m, 2H, CH$_2$), 4.5 (s, 2H, CH$_2$), 6.23 (s, 1H, Ar), 7.33 (d, 1H, $^3J_{H,H}$=6.1 Hz, Ar), 7.76 (d, 1H, $^3J_{H,H}$=6.1 Hz, Ar), 8.30 (s, 1H, Ar), 8.65 (br s, 1H, NH), 7.81 (s, 1H, Ar), 8.95 (br s, 1H, NH), 9.05 (s, 1H, Ar).

$^{13}$C NMR (DMSO-d$_6$, 125 MHz, ppm), δ=11.5, 24.2, 38.7, 42.3, 104.3, 115.2, 115.5, 115.7, 116.0, 116.4, 121.2, 123.3, 124.6, 124.7, 125.5, 126.2, 127.6, 131.1, 132.4, 147.5, 154.6, 158.7, 160.3, 164.9, 167.9, 169.2.

Example 4. Preparation of Compound 4

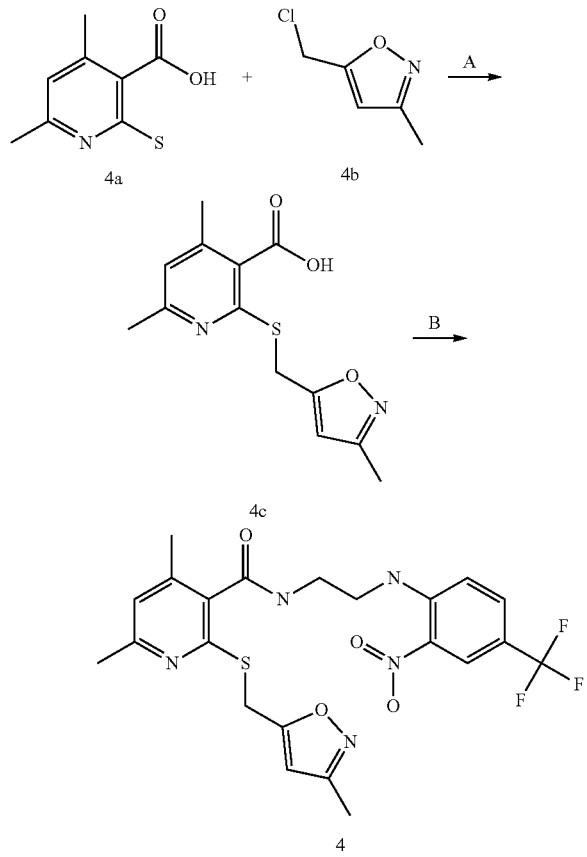

Step A:

A mixture of 2-mercapto-4,6-dimethyl-nicotinic acid 3a (0.982 g, 5.37 mmol), NaI (0.08 g, 0.537 mmol) and 5-chloromethyl-3-methyl-isoxazole (0.774 g, 5.91 mmol) in 10% NaOH methanol solution (8 mL) was stirred for 2 hours at 40° C. Then the solvent was evaporated, the residue was dissolved in water (30 mL) and the solution was acidified to pH-2 with 10% aqueous HCl. The precipitate formed was filtered, washed with water (2×20 mL) and dried to obtain 1 g (3.60 mmol, 67%) of compound 4c.

Step B:

To a cooled to 0° C. solution of compound 4c (0.272 g, 0.98 mmol), N*1*-(2-nitro-4-trifluoromethyl-phenyl)-ethane-1,2-diamine (0.244 g, 0.98 mmol) and HOBt (0.180 g, 1.18 mmol) in DMF (2 mL) EDC (0.205 g, 1.08 mmol) was added and the mixture was stirred overnight at room temperature. Then water (4 mL) was added, and the resulting precipitate was filtered, washed with water and dried to yield 0.400 g (0.786 mmol, 80%) of compound 4.

$^1$H NMR (DMSO-d$_6$, 400 MHz, ppm), δ=2.11 (s, 3H, CH$_3$), 2.14 (s, 3H, CH$_3$), 2.42 (s, 3H, CH$_3$), 3.50 (m, 2H, CH$_2$), 3.62 (m, 2H, CH$_2$), 4.46 (s, 2H, CH$_2$), 6.13 (s, 1H, Ar), 6.93 (s, 1H, Ar), 7.36 (d, 1H, $^3J_{H,H}$=8.7 Hz, Ar), 7.80 (d, 1H, $^3J_{H,H}$=8.7 Hz, Ar), 8.31 (s, 1H, Ar), 8.56 (t, 1H, $^3J_{H,H}$=5.5 Hz, Ar), 8.68 (t, 1H, $^3J_{H,H}$=5.5 Hz, Ar)

$^{13}$C NMR (DMSO-d$_6$, 125 MHz, ppm), δ=11.5, 18.8, 24.1, 24.2, 38.2, 42.6, 103.9, 115.3, 115.6, 115.8, 116.1, 116.4, 121.2, 121.5, 123.3, 124.6, 124.7, 125.5, 127.7, 129.9, 131.0, 132.5, 132.6, 145.1, 147.3, 152.1, 157.8, 160.0, 166.9, 169.9.

The compounds of Examples 5-28 were prepared in similar manner to that discussed in Example 4, step B.

Example 5. Preparation of Compound 5

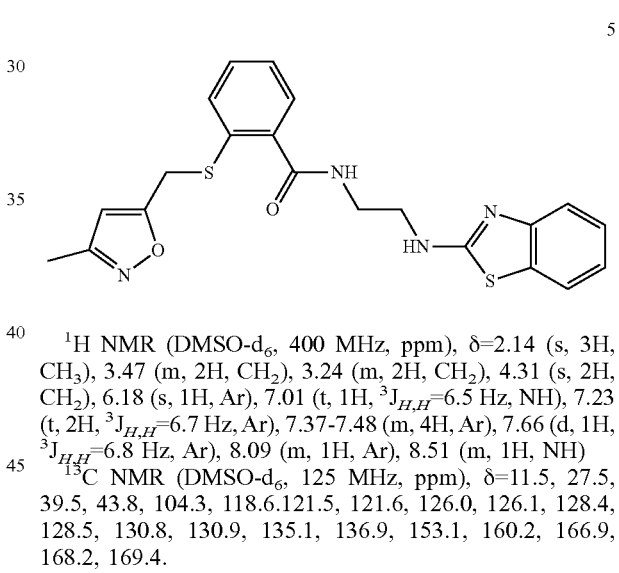

$^1$H NMR (DMSO-d$_6$, 400 MHz, ppm), δ=2.14 (s, 3H, CH$_3$), 3.47 (m, 2H, CH$_2$), 3.24 (m, 2H, CH$_2$), 4.31 (s, 2H, CH$_2$), 6.18 (s, 1H, Ar), 7.01 (t, 1H, $^3J_{H,H}$=6.5 Hz, NH), 7.23 (t, 2H, $^3J_{H,H}$=6.7 Hz, Ar), 7.37-7.48 (m, 4H, Ar), 7.66 (d, 1H, $^3J_{H,H}$=6.8 Hz, Ar), 8.09 (m, 1H, Ar), 8.51 (m, 1H, NH)

$^{13}$C NMR (DMSO-d$_6$, 125 MHz, ppm), δ=11.5, 27.5, 39.5, 43.8, 104.3, 118.6.121.5, 121.6, 126.0, 126.1, 128.4, 128.5, 130.8, 130.9, 135.1, 136.9, 153.1, 160.2, 166.9, 168.2, 169.4.

Example 6. Preparation of Compound 6

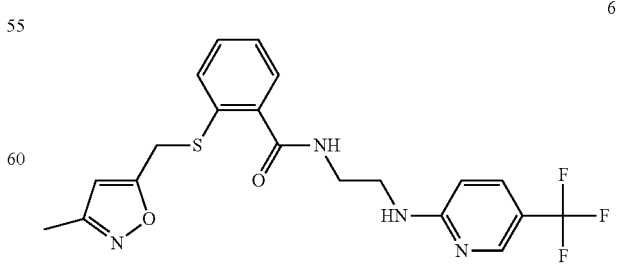

$^1$H NMR (DMSO-d$_6$, 400 MHz, ppm), δ=2.14 (s, 3H, CH$_3$), 3.38 (m, 2H, CH$_2$), 3.47 (m, 2H, CH$_2$), 4.32 (s, 2H, CH$_2$), 6.18 (s, 1H, Ar), 6.59 (d, 1H, $^3J_{H,H}$=8.0 Hz, Ar), 7.22 (t, 1H, $^3J_{H,H}$=6.0 Hz, NH), 7.24-7.45 (m, 4H, Ar), 7.62 (d, 1H, 3J$_{H,H}$=7.5 Hz, Ar), 8.29 (m, 1H, Ar), 8.44 (m, 1H, NH)

$^{13}$C NMR (DMSO-d$_6$, 125 MHz, ppm), δ=11.5, 27.5, 39.3, 56.6, 104.3, 108.9, 112.8, 113.1, 113.3, 113.6, 122.5, 124.7, 126.0, 126.8, 128.4, 128.5, 130.8, 134.0, 134.9, 137.0, 146.0, 146.1, 160.2, 161.3, 168.3, 169.4.

Example 7. Preparation of Compound 7

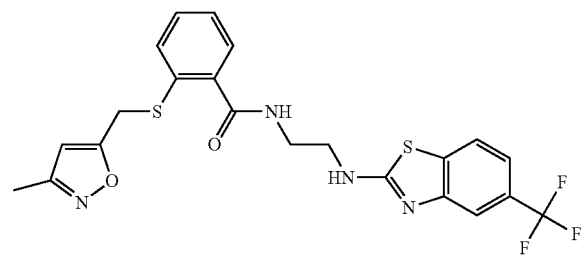

7

$^1$H NMR (DMSO-d$_6$, 400 MHz, ppm), δ=2.14 (s, 3H, CH$_3$), 3.49 (m, 2H, CH$_2$), 3.58 (m, 2H, CH$_2$), 4.32 (s, 2H, CH$_2$), 6.18 (s, 1H, Ar), 7.21 (m, 1H, NH), 7.34-7.47 (m, 4H, Ar), 7.63 (s, 1H, Ar), 7.90 (d, 1H, $^3J_{H,H}$=7.5 Hz, Ar), 8.43 (m, 1H, Ar), 8.43 (m, 1H, NH)

$^{13}$C NMR (DMSO-d$_6$, 100 MHz, ppm), δ=11.4, 27.3, 39.2, 43.8, 104.2, 114.3, 114.4, 117.50, 117.54, 121.1, 122.3, 123.7, 125.8, 126.5, 126.6, 126.9, 127.2, 127.5, 128.3, 128.4, 129.2, 130.7, 134.9, 135.5, 136.7, 153.1, 160.0, 168.2, 168.4, 169.2.

Example 8. Preparation of Compound 8

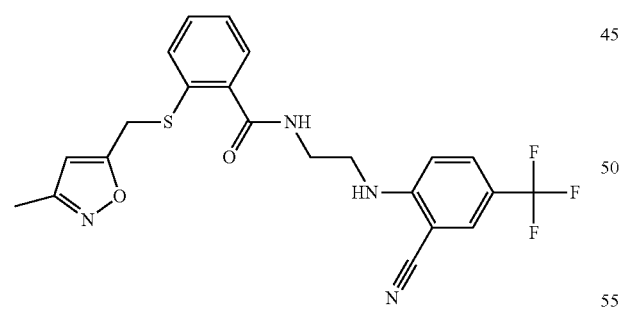

8

$^1$H NMR (DMSO-d$_6$, 400 MHz, ppm), δ=2.16 (s, 3H, CH$_3$), 3.33 (m, 2H, CH$_2$), 3.44 (m, 2H, CH$_2$), 4.34 (s, 2H), 6.18 (s, 1H, Ar), 6.92 (s, 1H, NH), 7.07 (m, 1H, Ar), 7.42 (s, 1H, Ar), 7.48 (m, 3H, Ar), 7.71 (m, 1H, Ar), 7.89 (m, 1H, Ar), 8.53 (m, 1H, NH)

$^{13}$C NMR (DMSO-d$_6$, 125 MHz, ppm), δ=11.5, 27.6, 38.7, 42.4, 94.8, 104.2, 111.8, 116.1, 116.3, 116.6, 116.9, 117.3, 121.5, 123.6, 125.8, 126.1, 127.9, 128.3, 128.6, 130.8, 131.6, 131.8, 131.9, 137.0, 153.2, 160.1, 168.6, 169.3.

Example 9. Preparation of Compound 9

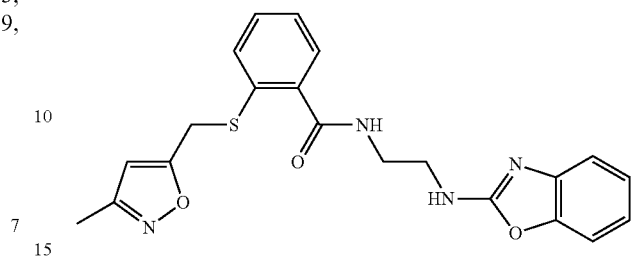

9

$^1$H NMR (DMSO-d$_6$, 400 MHz, ppm), δ=2.15 (s, 3H, CH$_3$), 3.30 (m, 2H, CH$_2$), 3.48 (m, 2H, CH$_2$), 4.32 (s, 2H, CH$_2$), 6.19 (s, 1H, Ar), 6.98 (m, 1H, NH), 7.13 (m, 1H, Ar), 7.34 (m, 2H, Ar), 7.40-7.48 (m, 4H, Ar), 8.00 (m, 1H, Ar), 8.53 (m, 1H, NH)

$^{13}$C NMR (DMSO-d$_6$, 125 MHz, ppm), δ=11.5, 27.5, 39.3, 42.4, 104.3, 109.1, 116.0, 120.7, 124.2, 126.0, 128.4, 128.5, 130.8, 134.9, 136.9, 143.8, 148.7, 160.2, 162.9, 168.2, 169.4.

Example 10. Preparation of Compound 10

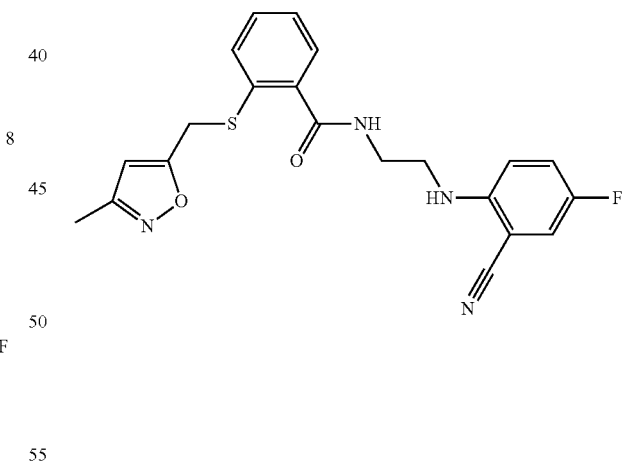

10

$^1$H NMR (DMSO-d$_6$, 400 MHz, ppm), δ=2.19 (s, 3H, CH$_3$), 3.40 (m, 2H, CH$_2$), 3.45 (m, 2H, CH$_2$), 4.22 (s, 2H, CH$_2$), 5.97 (m, 1H, NH), 6.05 (s, 1H, Ar), 6.90 (m, 1H, Ar), 7.19-7.27 (m, 3H, Ar), 7.35-7.44 (m, 3H, Ar), 8.38 (m, 1H, NH)

$^{13}$C NMR (DMSO-d$_6$, 125 MHz, ppm), δ=11.5, 27.5, 38.8, 42.8, 94.7, 94.8, 104.3, 113.0, 113.1, 117.5, 117.6, 119.2, 119.3, 122.8, 123.0, 126.1, 128.3, 128.6, 130.8, 134.8, 137.0, 148.3, 152.3, 154.1, 160.2, 168.5, 169.3.

Example 11. Preparation of Compound 11

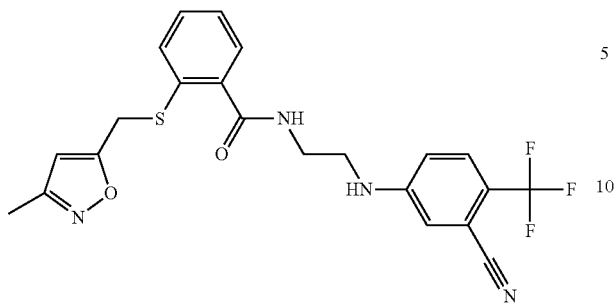

11

¹H NMR (DMSO-d₆, 400 MHz, ppm), δ=2.18 (s, 3H, CH₃), 3.44-3.47 (m, 4H, 2CH₂), 4.22 (s, 2H, CH₂), 6.04 (m, 1H, NH), 6.06 (s, 1H, Ar), 6.96 (d, 1H, ³J$_{H,H}$=7.5 Hz, Ar), 7.24 (t, 1H, ³J$_{H,H}$=6.8 Hz, Ar), 7.31 (s, 1H, Ar), 7.35-7.42 (m, 3H, Ar), 7.51 (d, 1H, ³J$_{H,H}$=8.0 Hz, Ar), 8.38 (m, 1H, NH)

¹³C NMR (DMSO-d₆, 125 MHz, ppm), δ=11.5, 27.6, 38.4, 42.8, 104.2, 115.3, 115.4, 115.5, 115.7, 116.0, 116.9, 118.4, 118.9, 121.4, 123.5, 125.7, 126.1, 127.9, 128.2, 128.3, 128.7, 130.8, 134.8, 137.0, 146.2, 160.1, 168.7, 169.3.

Example 12. Preparation of Compound 12

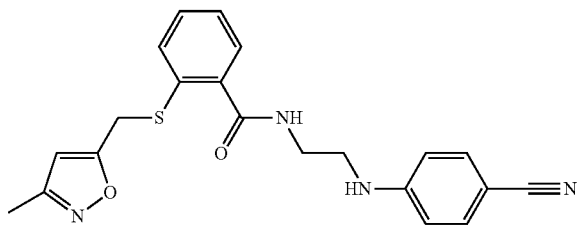

12

¹H NMR (DMSO-d₆, 400 MHz, ppm), δ=2.19 (s, 3H, CH₃), 3.30 (m, 2H, CH₂), 3.46 (m, 2H, CH₂), 4.22 (s, 2H, CH₂), 6.06 (s, 1H, Ar), 6.50 (t, 1H, ³J$_{H,H}$=5.4 Hz, NH), 6.66 (d, 2H, ³J$_{H,H}$=8.4 Hz, Ar), 7.26 (t, 1H, ³J$_{H,H}$=7.2 Hz, Ar), 7.36-7.44 (m, 5H, Ar), 8.32 (t, 1H, ³J$_{H,H}$=5.5 Hz, NH)

¹³C NMR (DMSO-d₆, 125 MHz, ppm), δ=11.5, 27.5, 38.9, 41.1, 96.3, 104.3, 112.4, 121.2, 126.0, 128.4, 128.5, 130.8, 134.0, 134.9, 136.8, 152.7, 160.2, 168.3, 169.3.

Example 13. Preparation of Compound 13

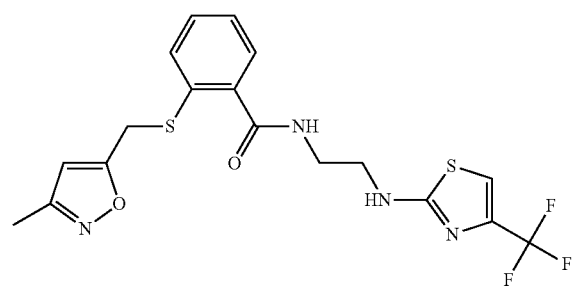

13

¹H NMR (DMSO-d₆, 400 MHz, ppm), δ=2.19 (s, 3H, CH₃), 3.48 (m, 4H, CH₂), 4.22 (s, 2H, CH₂), 6.07 (s, 1H, Ar), 7.03 (s, 1H, Ar), 7.25 (t, 1H, ³J$_{H,H}$=6.8 Hz, Ar), 7.38 (m, 2H, Ar), 7.46 (d, 1H, ³J$_{H,H}$=7.8 Hz, Ar), 7.94 (m, 1H, NH), 8.30 (m, 1H, NH)

¹³C NMR (DMSO-d₆, 125 MHz, ppm), δ=11.5, 27.6, 39.1, 44.4, 104.2, 110.00, 110.04, 110.07, 118.0, 120.2, 122.3, 124.5, 126.0, 128.5, 130.8, 132.6, 135.0, 136.9, 138.7, 139.0, 139.4, 139.6, 160.1, 168.2, 169.3, 170.7.

Example 14. Preparation of Compound 14

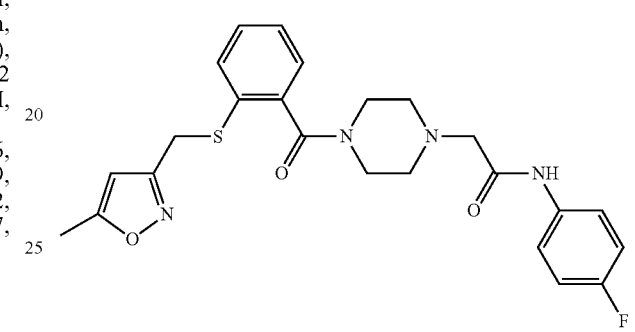

14

¹H NMR (DMSO-d₆, 400 MHz, ppm), δ=2.33 (s, 3H, CH₃), 2.43 (m, 2H, CH₂), 2.59 (m, 2H, CH₂), 3.12 (m, 2H, CH₂), 3.16 (s, 2H, CH₂), 3.71 (m, 2H, CH₂), 4.22 (s, 2H, CH₂), 6.14 (s, 1H, Ar), 4.15 (m, 2H, Ar), 7.21 (d, 1H, ³J$_{H,H}$=7.8 Hz, Ar), 7.29 (t, 1H, ³J$_{H,H}$=7.1 Hz, Ar), 7.39 (t, 1H, ³J$_{H,H}$=7.1 Hz, Ar), 7.53 (d, 1H, ³J$_{H,H}$=7.1 Hz, Ar), 7.66 (m, 2H, Ar), 9.80 (s, 1H, NH)

¹³C NMR (DMSO-d₆, 125 MHz, ppm), δ=12.2, 27.6, 41.4, 46.7, 52.7, 53.1, 61.7, 102.2, 115.5, 115.7, 121.8, 121.9, 126.9, 127.1, 129.7, 132.1, 135.4, 137.9, 157.4, 159.8, 161.4, 167.4, 168.4, 170.1.

Example 15. Preparation of Compound 15

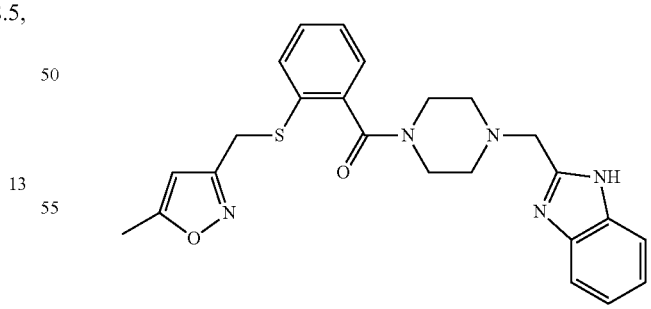

15

¹H NMR (DMSO-d₆, 400 MHz, ppm), δ=2.32 (s, 3H, CH₃), 2.39 (m, 2H, CH₂), 2.54 (m, 2H, CH₂), 3.08 (m, 2H, CH₂), 3.67 (m, 2H, CH₂), 3.76 (s, 2H, CH₂), 4.21 (m, 2H, CH₂), 6.12 (s, 1H, Ar), 7.13 (m, 2H, Ar), 7.20 (d, 1H, ³J$_{H,H}$=6.5 Hz, Ar), 7.28 (t, 1H, ³J$_{H,H}$=6.5 Hz, Ar), 7.39 (t, 1H, ³J$_{H,H}$=6.5 Hz, Ar), 7.50-7.53 (m, 3H, Ar), 12.10 broad (s, 1H, NH)

$^{13}$C NMR (DMSO-d$_6$, 125 MHz, ppm), δ=12.3, 27.8, 41.6, 46.8, 52.9, 53.4, 56.0, 102.3, 122.0, 127.0, 127.1, 127.2, 129.3, 129.8, 129.9, 131.9, 132.2, 138.1, 151.9, 161.5, 167.6, 170.2.

Example 16. Preparation of Compound 16

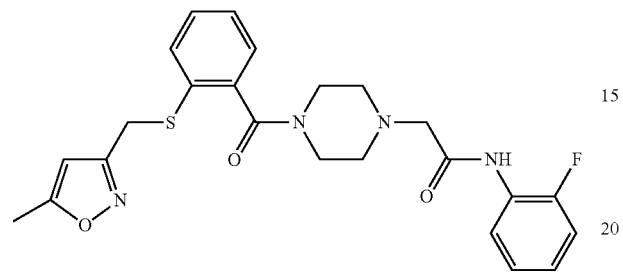

$^1$H NMR (DMSO-d$_6$, 400 MHz, ppm), δ=2.37 (s, 3H, CH$_3$), 2.54 (m, 2H, CH$_2$), 2.70 (m, 2H, CH$_2$), 3.21 (m, 4H, CH$_2$), 3.76 (m, 2H, CH$_2$), 4.12 (s, 2H, CH$_2$), 6.05 (s, 1H, Ar), 7.06-7.21 (m, 4H, Ar), 7.30 (t, 1H, $^3J_{H,H}$=7.8 Hz, Ar), 7.38 (t, 1H, $^3J_{H,H}$=7.8 Hz, Ar), 7.46 (t, 1H, $^3J_{H,H}$=7.8 Hz, Ar), 8.11 (d, 1H, $^3J_{H,H}$=10 Hz, Ar), 9.46 (s, 1H, NH)

$^{13}$C NMR (DMSO-d$_6$, 125 MHz, ppm), δ=12.3, 27.8, 41.7, 41.0, 47.0, 52.8, 53.2, 61.4, 115.8, 116.0, 124.5, 125.0, 125.1, 125.8, 125.9, 126.3, 126.4, 127.1, 127.2, 129.8, 129.9, 132.2, 138.0, 153.0, 155.0, 161.5, 167.6, 168.8, 170.2.

Example 17. Preparation of Compound 17

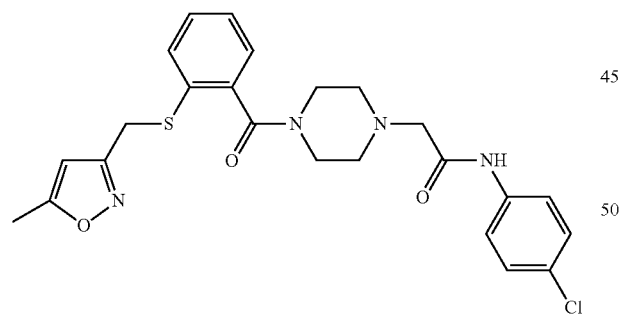

$^1$H NMR (DMSO-d$_6$, 400 MHz, ppm), δ=2.37 (s, 3H, CH$_3$), 2.49 (m, 2H, CH$_2$), 2.66 (m, 2H, CH$_2$), 3.15 (s, 2H, CH$_2$), 3.19 (m, 2H, CH$_2$), 3.76 (s, 2H, CH$_2$), 4.12 (s, 2H, CH$_2$), 6.05 (s, 1H, Ar), 7.19 (s, 1H, Ar), 7.23 (d, 2H, $^3J_{H,H}$=7.8 Hz, Ar), 7.30 (t, 1H, $^3J_{H,H}$=8.9 Hz, Ar), 7.36 (t, 1H, 7.8 $^3J_{H,H}$=Hz, Ar), 7.48 (d, 1H, $^3J_{H,H}$=7.8 Hz, Ar), 7.65 (d, 2H, $^3J_{H,H}$=7.8 Hz, Ar), 9.67 (s, 1H, NH)

$^{13}$C NMR (DMSO-d$_6$, 125 MHz, ppm), δ=12.2, 27.7, 41.4, 46.7, 52.7, 53.1, 61.8, 102.2, 121.6, 127.0, 127.1, 129.0, 129.7, 132.1, 137.9, 138.0, 161.4, 167.4, 168.7, 170.1.

Example 18. Preparation of Compound 18

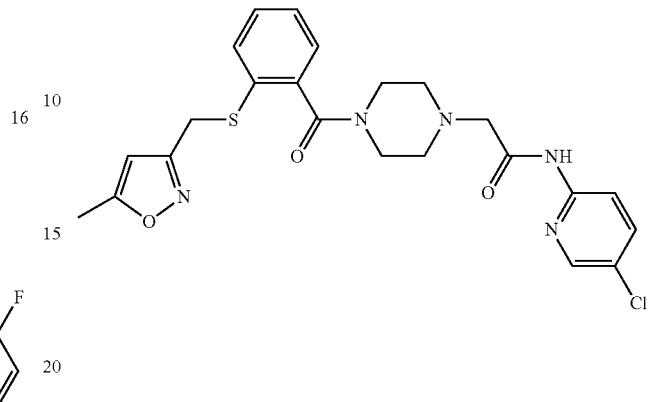

$^1$H NMR (DMSO-d$_6$, 400 MHz, ppm), δ=2.33 (s, 3H, CH$_3$), 2.44 (m, 2H, CH$_2$), 2.62 (m, 2H, CH$_2$), 3.08 (m, 2H, CH$_2$), 3.26 (s, 2H, CH$_2$), 3.67 (m, 2H, CH$_2$), 4.22 (s, 2H, CH$_2$), 6.14 (s, 1H, Ar), 7.20 (d, 1H, $^3J_{H,H}$=7.8 Hz, Ar), 7.30 (t, 1H, $^3J_{H,H}$=7.8 Hz, Ar), 7.40 (t, 1H, $^3J_{H,H}$=7.8 Hz, Ar), 7.35 (d, 1H, $^3J_{H,H}$=7.8 Hz, Ar), 7.91 (d, 1H, $^3J_{H,H}$=8.7 Hz, Ar), 8.13 (d, 1H, $^3J_{H,H}$=8.7 Hz, Ar), 8.37 (s, 1H, Ar), 10.22 (s, 1H, NH)

$^{13}$C NMR (DMSO-d$_6$, 125 MHz, ppm), δ=12.3, 27.8, 41.6, 46.9, 52.7, 53.1, 61.3, 102.3, 114.9, 125.9, 127.1, 127.2, 129.8, 129.9, 132.2, 138.0, 138.6, 147.0, 150.5, 161.5, 167.5, 169.5, 170.2.

Example 19. Preparation of Compound 19

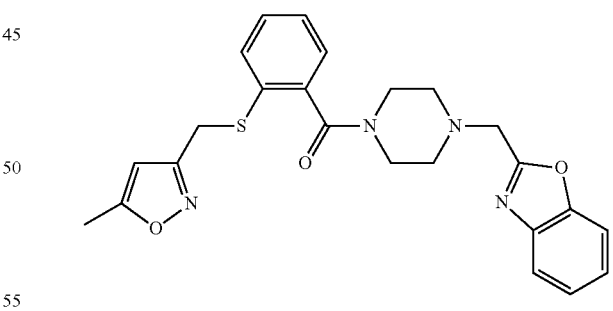

$^1$H NMR (DMSO-d$_6$, 400 MHz, ppm), δ=2.32 (s, 3H, CH$_3$), 2.44 (m, 2H, CH$_2$), 2.62 (m, 2H, CH$_2$), 3.06 (m, 2H, CH$_2$), 3.65 (m, 2H, CH$_2$), 3.91 (s, 2H, CH$_2$), 4.19 (m, 2H, CH$_2$), 6.10 (s, 1H, Ar), 7.20 (d, 1H, $^3J_{H,H}$=7.6 Hz, Ar), 7.27 (t, 1H, $^3J_{H,H}$=7.6 Hz, Ar), 7.35-7.45 (m, 4H, Ar), 7.51 (d, 1H, $^3J_{H,H}$=7.6 Hz, Ar), 7.71 (t, 1H, $^3J_{H,H}$=Hz, Ar)

$^{13}$C NMR (DMSO-d$_6$, 125 MHz, ppm), δ=12.3, 27.79, 41.57, 46.8, 52.4, 52.9, 54.6, 102.3, 111.4, 120.3, 125.0, 125.8, 127.1, 127.2, 129.8, 129.9, 132.2, 138.0, 141.1, 150.8, 161.5, 163.6, 167.5, 170.2.

Example 20. Preparation of Compound 20

Example 22. Preparation of Compound 22

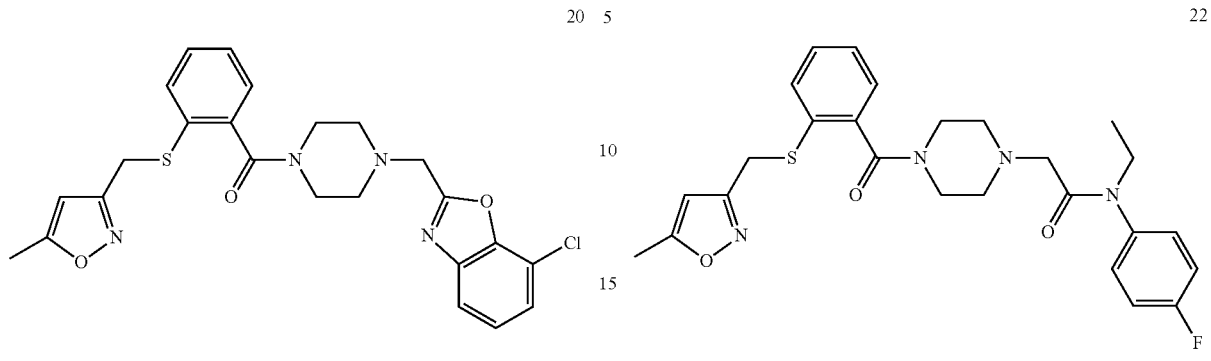

1H NMR (DMSO-d$_6$, 400 MHz, ppm), δ=2.32 (s, 3H, CH$_3$), 2.47 (m, 2H, CH$_2$), 2.65 (m, 2H, CH$_2$), 3.07 (m, 2H, CH$_2$), 3.66 (m, 2H, CH$_2$), 3.95 (s, 2H, CH$_2$), 4.19 (m, 2H, CH$_2$), 6.10 (s, 1H, Ar), 7.20 (d, 1H, $^3J_{H,H}$=7.1 Hz, Ar), 7.27 (t, 1H, $^3J_{H,H}$=7.1 Hz, Ar), 7.39 (m, 4H, Ar), 7.52 (d, 2H, $^3J_{H,H}$=6.8 Hz, Ar), 7.72 (d, 1H, $^3J_{H,H}$=7.1 Hz, Ar)

$^{13}$C NMR (DMSO-d$_6$, 125 MHz, ppm), δ=12.2, 27.6, 41.4, 46.7, 52.3, 52.7, 54.3, 102.2, 115.0, 119.3, 125.9, 126.2, 126.9, 127.0, 129.7, 129.8, 132.1, 137.9, 142.4, 147.2, 161.4, 164.2, 167.5, 170.1.

$^1$H NMR (DMSO-d$_6$, 400 MHz, ppm), δ=1.06 (t, 3H, $^3J_{H,H}$=7.0 Hz), 2.29 (m, 2H, CH$_2$), 2.37 (s, 3H, CH$_3$), 2.44 (m, 2H, CH$_2$), 2.84 (s, 2H, CH$_2$), 3.05 (s, 2H, CH$_2$), 3.64 (m, 4H, 2CH$_2$), 4.08 (s, 2H, CH$_2$), 6.03 (s, 1H, Ar), 7.15 (m, 4H, Ar), 7.22-7.34 (m, 4H, Ar), 7.44 (d, 1H, $^3J_{H,H}$=7.8 Hz, Ar)

$^{13}$C NMR (DMSO-d$_6$, 125 MHz, ppm), δ=12.3, 13.3, 27.8, 41.6, 43.9, 46.8, 52.4, 52.8, 59.7, 102.3, 116.6, 116.7, 127.0, 127.1, 129.8, 129.9, 131.0, 131.1, 132.2, 138.2, 138.4, 160.7, 161.5, 162.6, 167.5, 168.4, 170.1.

Example 21. Preparation of Compound 21

Example 23. Preparation of Compound 23

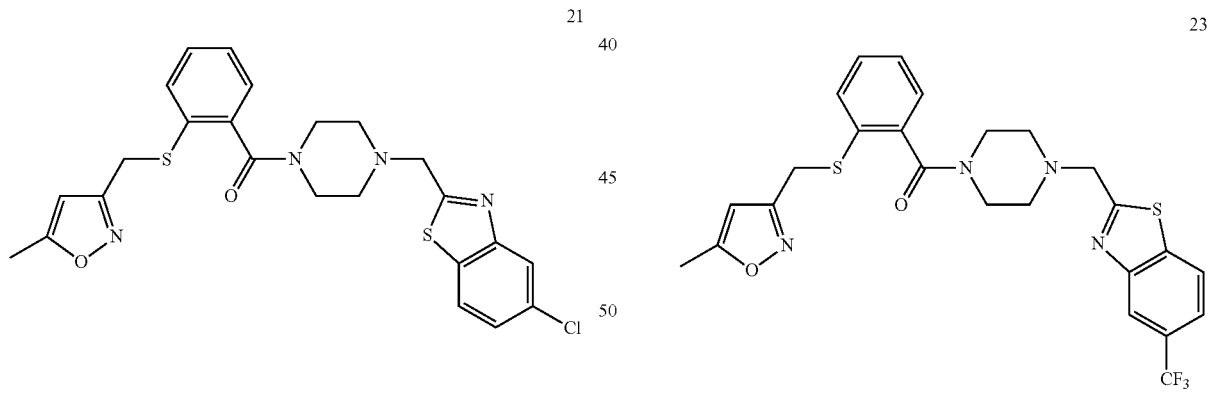

$^1$H NMR (DMSO-d$_6$, 400 MHz, ppm), δ=2.33 (s, 3H, CH$_3$), 2.47 (m, 2H, CH$_2$), 2.65 (m, 2H, CH$_2$), 3.10 (m, 2H, CH$_2$), 3.69 (m, 2H, CH$_2$), 4.01 (s, 2H, CH$_2$), 4.22 (m, 2H, CH$_2$), 6.14 (s, 1H, Ar), 7.31 (d, 1H, $^3J_{H,H}$=7.6 Hz, Ar), 7.35 (t, 1H, $^3J_{H,H}$=7.6 Hz, Ar), 7.39 (t, 1H, $^3J_{H,H}$=7.6 Hz, Ar), 7.43 (dd, 1H, $^3J_{H,H}$=8.6 Hz, $^4J_{H,H}$=1.9 Hz, Ar), 7.56 (d, 1H, $^3J_{H,H}$=7.6 Hz, Ar), 8.01 (d, 1H, $^4J_{H,H}$=1.9 Hz, Ar), 8.11 (d, 1H, $^3J_{H,H}$=8.6 Hz, Ar)

$^{13}$C NMR (DMSO-d$_6$, 125 MHz, ppm), δ=12.4, 27.8, 41.7, 47.0, 53.0, 53.4, 59.6, 102.3, 122.4, 124.4, 125.6, 127.1, 127.2, 129.91, 129.97, 131.3, 132.2, 134.2, 138.0, 154.1, 161.6, 167.6, 170.2, 175.5.

$^1$H NMR (DMSO-d$_6$, 400 MHz, ppm), δ=2.33 (s, 3H, CH$_3$), 2.47 (m, 2H, CH$_2$), 2.66 (m, 2H, CH$_2$), 3.11 (m, 2H, CH$_2$), 3.69 (m, 2H, CH$_2$), 4.05 (s, 2H, CH$_2$), 4.22 (m, 2H, CH$_2$), 6.15 (s, 1H, Ar), 7.21 (d, 1H, $^3J_{H,H}$=7.6 Hz, Ar), 7.30 (t, 1H, $^3J_{H,H}$=6.7 Hz, Ar), 7.39 (t, 1H, $^3J_{H,H}$=7.6 Hz, Ar), 7.54 (d, 1H, $^3J_{H,H}$=7.6 Hz, Ar), 7.77 (d, 1H, $^3J_{H,H}$=6.7 Hz, Ar), 8.28 (s, 1H, Ar), 8.34 (d, 1H, $^3J_{H,H}$=7.6 Hz, Ar)

$^{13}$C NMR (DMSO-d6, 125 MHz, ppm), δ=12.3, 27.9, 41.7, 47.0, 53.0, 53.4, 59.5, 102.3, 119.8, 121.6, 123.8, 124.3, 126.0, 127.1, 127.25, 127.29, 127.4, 127.6, 129.2, 129.9, 130.0, 132.2, 138.1, 139.7, 153.2, 161.2, 167.6, 170.2, 176.0.

Example 24. Preparation of Compound 24

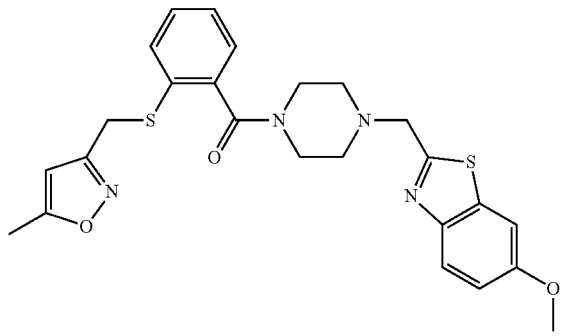

24

¹H NMR (DMSO-d₆, 400 MHz, ppm), δ=2.37 (s, 3H, CH₃), 2.54 (m, 2H, CH₂), 2.69 (m, 2H, CH₂), 3.17 (m, 2H, CH₂), 3.74 (m, 2H, CH₂), 3.85 (s, 3H, CH₃), 3.92 (s, 2H, CH₂), 4.11 (m, 2H, CH₂), 6.04 (s, 1H, Ar), 7.00 (dd, 1H, $^3J_{H,H}$=8.7 Hz, $^4J_{H,H}$=2.2 Hz, Ar), 7.19 (d, 1H, $^3J_{H,H}$=6.7 Hz, Ar), 7.27 (t, 1H, $^3J_{H,H}$=7.6 Hz, Ar), 7.33 (t, 1H, $^3J_{H,H}$=7.6 Hz, Ar), 7.43 (d, 1H, $^4J_{H,H}$=2.2 Hz, Ar), 7.46 (d, 1H, $^3J_{H,H}$=7.6 Hz, Ar), 7.73 (d, 1H, $^3J_{H,H}$=8.7 Hz, Ar), 8.10 (s, 1H, Ar)

¹³C NMR (DMSO-d6, 125 MHz, ppm), δ=12.3, 27.8, 41.7, 46.9, 52.9, 53.4, 56.3, 59.7, 102.3, 105.4, 115.7, 123.5, 127.1, 127.2, 129.90.129.97, 132.2, 136.9, 138.1, 147.7, 157.6, 161.6, 167.6, 169.3, 170.2.

Example 25. Preparation of Compound 25

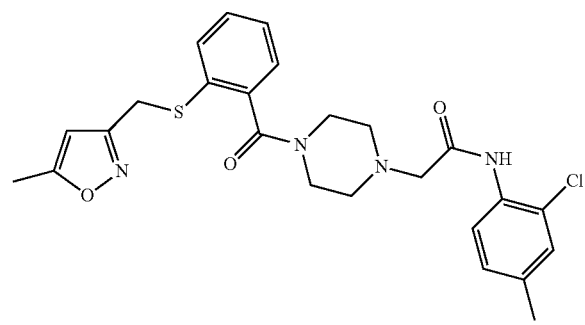

25

¹H NMR (DMSO-d₆, 400 MHz, ppm), δ=2.28 (s, 3H, CH₃), 2.33 (s, 3H, CH₃), 2.43 (m, 2H, CH₂), 2.65 (m, 2H, CH₂), 3.13 (m, 2H, CH₂), 3.20 (s, 2H, CH₂), 3.72 (m, 2H, CH₂), 4.23 (m, 2H, CH₂), 6.14 (s, 1H, Ar), 7.15 (d, 1H, $^3J_{H,H}$=8.1 Hz, Ar), 7.21 (d, 1H, $^3J_{H,H}$=7.8 Hz, Ar), 7.19 (t, 1H, $^3J_{H,H}$=7.8 Hz, Ar), 7.39 (m, 2H, Ar), 7.24 (d, 1H, $^3J_{H,H}$=7.8 Hz, Ar), 8.03 (d, 1H, $^3J_{H,H}$=7.8 Hz, Ar), 9.75 (s, 1H, NH)

¹³C NMR (DMSO-d₆, 125 MHz, ppm), δ=12.3, 20.7, 27.8, 41.82, 41.84, 47.1, 52.9, 53.3, 61.5, 102.3, 122.4, 123.8, 127.1, 127.2, 128.9, 129.94, 129.98, 132.2, 132.4, 135.5, 138.0, 161.5, 167.6, 168.5, 170.2.

Example 26. Preparation of Compound 26

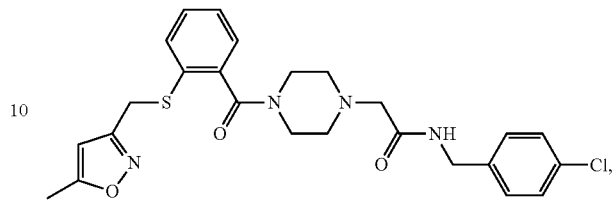

26

¹H NMR (DMSO-d₆, 400 MHz, ppm), δ=2.32 (s, 3H, CH₃), 2.35 (m, 2H, CH₂), 3.01 (m, 2H, CH₂), 2.50 (m, 2H, CH₂), 3.08 (m, 2H, CH₂), 3.67 (m, 2H, CH₂), 4.21 (m, 2H, CH₂), 4.27 (d, 2H, $^3J_{H,H}$=6.0 Hz, Ar), 6.12 (s, 1H, Ar), 7.20 (d, 1H, $^3J_{H,H}$=7.5 Hz, Ar), 7.29 (m, 3H, Ar), 7.40 (m, 3H, Ar), 7.51 (d, 1H, $^3J_{H,H}$=7.5 Hz, Ar), 8.40 (t, 1H, $^3J_{H,H}$=6.0 Hz, NH)

¹³C NMR (DMSO-d6, 125 MHz, ppm), δ=12.3, 27.8, 41.4, 41.8, 46.7, 53.0, 53.4, 61.3, 102.3, 127.1, 127.2, 128.8, 128.9, 129.6, 129.82, 129.88, 129.9, 131.8, 132.2, 138.1, 139.3, 161.5, 167.5, 169.7, 170.2.

Example 27. Preparation of Compound 27

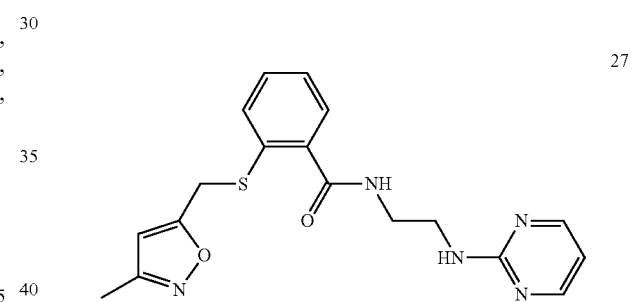

27

¹H NMR (DMSO-d6, 500 MHz, ppm), δ=1.75 (s, 3H, CH₃), 3.50 (m, 4H, 2CH₂), 4.45 (s, 2H, CH₂), 6.14 (s, 1H, Ar), 6.51 (m, 1H, Ar), 7.11 (m, 1H, Ar), 7.26 (m, 1H, Ar), 7.49 (m, 3H, Ar), 8.50 (m, 2H, NH, Ar), 8.95 (m, 1H, NH).

¹³C NMR (DMSO-d6, 125 MHz, ppm), δ=11.5, 27.6, 38.7, 49.7, 104.3, 110.8, 120.8, 126.1, 128.4, 128.6, 130.7, 134.8, 137.2, 158.6, 160.2, 162.9, 168.2, 169.4.

Example 28. Preparation of Compound 28

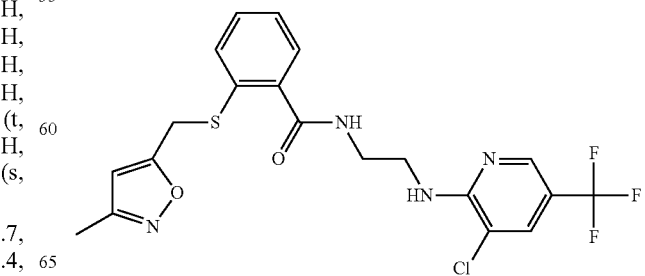

28

$^1$H NMR (DMSO-d$_6$, 500 MHz, ppm), δ=1.75 (s, 3H, CH$_3$), 3.48 (s, 2H, CH$_2$), 3.55 (s, 2H, CH$_2$), 4.45 (s, 2H, CH$_2$), 6.14 (s, 1H, Ar), 7.17 (s, 1H, Ar), 7.47 (m, 4H, Ar), 7.99 (s, 1H, Ar), 8.27 (s, 1H, NH), 8.50 (m, 1H, NH).

$^{13}$C NMR (DMSO-d6, 125 MHz, ppm), δ=11.5, 27.6, 39.0, 41.4, 104.3, 113.7, 113.9, 114.2, 114.5, 114.9, 126.0, 128.4, 128.5, 130.7, 133.4, 134.8, 137.1, 144.3, 144.3, 156.7, 160.1, 168.4, 169.4.

Example 29. Experimental Inhibitory Activity of Inhibitor Compounds at 10 µM in the Reporter Cell Line Assay Stable hAxl/IFN-γR1 CHO reporter cell lines (contain human Axl extracellular domains and transmembrane and intracellular domains of human IFN-γR1) were serum starved for 5 hrs±small molecule inhibitors and then stimulated with human GAS6 conditioned media±small molecule inhibitors for 30 minutes.

(** Values of the inhibitory activity of compounds are normalized to a 0-1 scale, where 0.0-0.1 corresponds to the negative control (100% inhibition) and 1.0 corresponds to positive control (0% inhibition)).

| Compound No. | Reporter Cell Line Activity at 10 uM** |
|---|---|
| Negative control | 0.10 |
| Positive control | 1.00 |
| 1A | 0.60 |
| 1B | 0.70 |
| 1C | 0.60 |
| 1D | 0.50 |
| 1E | 0.60 |
| 1F | 0.20 |
| 1H | 0.20 |
| 1I | 0.20 |
| 1K | 0.80 |
| 1L | 0.20 |
| 1M | 0.20 |
| 1N | 0.30 |
| 1O | 0.40 |
| 1P | 1.00 |
| 1Q | 0.10 |
| 1R | 0.40 |
| 2 | 0.57 |
| 3 | 0.26 |
| 4 | 0.83 |
| 5 | 0.13 |
| 6 | 0.06 |
| 7 | 0.33 |
| 8 | 0.09 |
| 9 | 0.20 |
| 10 | 0.14 |
| 11 | 0.29 |
| 12 | 0.16 |
| 13 | 0.06 |
| 14 | 1.10 |
| 15 | 1.41 |
| 16 | 1.09 |
| 17 | 0.79 |
| 18 | 0.46 |
| 19 | 0.41 |
| 20 | 0.55 |
| 21 | 0.08 |
| 22 | 1.08 |
| 23 | 0.08 |
| 24 | 0.90 |
| 25 | 0.27 |
| 26 | 0.54 |
| 27 | 0.16 |
| 28 | 0.06 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

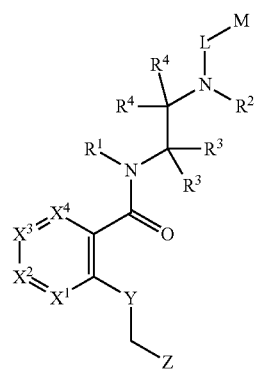

wherein:
(a) $X^1$ is N or $CR^{a1}$, $X^2$ is N or $CR^{a2}$, $X^3$ is N or $CR^{a3}$, $X^4$ is N or $CR^{a4}$, wherein:
 (i) no more than two of $X^1$, $X^2$, $X^3$, or $X^4$ is N;
 (ii) each $R^{a1}$, $R^{a2}$, $R^{a3}$, and $R^{a4}$ is independently hydrogen, halogen, (C$_1$-C$_4$)alkyl, (C$_1$-C$_4$)haloalkyl, —O(C$_1$-C$_4$)alkyl, or —O(C$_1$-C$_4$)haloalkyl;
(b) Y is S, S(=O), S(=O)$_2$, or O;
(c) Z is a 5-membered heteroaryl or 6-membered heteroaryl, wherein any 5-membered heteroaryl or 6-membered heteroaryl of Z is optionally substituted with one or more halogen, NO$_2$, CN, —OH, (C$_1$-C$_4$) alkyl, (C$_1$-C$_4$)haloalkyl, —O(C$_1$-C$_4$)alkyl, or —O(C$_1$-C$_4$)haloalkyl;
(d) $R^1$ is hydrogen or (C$_1$-C$_4$)alkyl, $R^2$ is hydrogen or (C$_1$-C$_4$)alkyl and L is absent;
(e) each $R^3$ is independently hydrogen or (C$_1$-C$_4$)alkyl;
(f) each $R^4$ is independently hydrogen or (C$_1$-C$_4$)alkyl;
(g) M is an aryl or a 5-10-membered heteroaryl, wherein any aryl or 5-10-membered heteroaryl of M is optionally substituted with one or more halogen, NO$_2$, CN, —OH, (C$_1$-C$_4$)alkyl, (C$_1$-C$_4$)haloalkyl, —O(C$_1$-C$_4$) alkyl, or —O(C$_1$-C$_4$)haloalkyl;
or a salt thereof;
provided the compound is not
2-[[(2-methyl-4-thiazolyl)methyl]thio]-N-[2-[[3-(trifluoromethyl)-2-pyridinyl]amino]ethyl]-benzamide;
N-[2-[(2-cyano-3-fluorophenyl)amino]ethyl]-2-[(3-thienylmethyl)thio]-benzamide;
N-[2-[[3-chloro-5-(trifluoromethyl)-2-pyridinyl]amino] ethyl]-2-[[(2-methyl-4-thiazolyl)methyl]thio]-benzamide;
2-[[(3-methyl-5-isoxazolyl)methyl]thio]-N-[2-[[2-nitro-4-(trifluoromethyl)phenyl]amino]ethyl]-benzamide;
N-[2-[(3-cyano-2-pyridinyl)amino]ethyl]-2-[(2-thienylmethyl)thio]-benzamide;
2-[[(5-methyl-3-isoxazolyl)methyl]thio]-N-[2-[(2- nitrophenyl)amino]ethyl]-3-pyridinecarboxamide;
N-[2-[(3,5-dichloro-2-pyridinyl)amino]ethyl]-2-[[(3-methyl-1,2,4-oxadiazol-5-yl)methyl]thio]-benzamide;
2-[[(2-methyl-4-thiazolyl)methyl]thio]-N-[2-[(4-nitrophenyl)amino]ethyl]-benzamide;

N-[2-(2-benzothiazolylamino)ethyl]-2-[(2-thienylmethyl)thio]-benzamide;
N-[2-[(3-cyano-2-pyridinyl)amino]ethyl]-2-[(4-thiazolylmethyl)thio]-benzamide;
2-[[(3-methyl-5-isoxazolyl)methyl]thio]-N-[2-[(6-methyl-3-pyridazinyl)amino]ethyl]-benzamide;
2-[[(3,5-dimethyl-4-isoxazolyl)methyl]thio]-N-[2-[[3-(trifluoromethyl)-2-pyridinyl]amino]ethyl]-3-pyridinecarboxamide;
2-[[(3-methyl-5-isoxazolyl)methyl]thio]-N-[2-[(2-nitrophenyl)amino]ethyl]-benzamide;
N-[2-[(2-nitrophenyl)amino]ethyl]-2-[(3-thienylmethyl)thio]-benzamide;
2-[[(3,5-dimethyl-4-isoxazolyl)methyl]thio]-N-[1-methyl-2-(methylphenylamino)ethyl]-3-pyridinecarboxamide;
N-[2-[(2-cyano-3-fluorophenyl)amino]ethyl]-2-[[(5-methyl-1,2,4-oxadiazol-3-yl)methyl]thio]-benzamide;
N-[2-[ethyl(2-methylphenyl)amino]ethyl]-2-[[(5-methyl-3-isoxazolyl)methyl]thio]-3-pyridinecarboxamide;
2-[[(3-methyl-1,2,4-oxadiazol-5-yl)methyl]thio]-N-[2-[(2-nitrophenyl)amino]ethyl]-benzamide;
2-[[(2-methyl-4-thiazolyl)methyl]thio]-N-[2-(2-pyrazinylamino)ethyl]-benzamide;
N-[2-[ethyl(2-methylphenyl)amino]ethyl]-2-[[(3-methyl-1,2,4-oxadiazol-5-yl)methyl]thio]-benzamide;
N-[1-methyl-2-(methylphenylamino)ethyl]-2-[(2-thienylmethyl)thio]-benzamide;
2-[[(3,5-dimethyl-4-isoxazolyl)methyl]thio]-N-[2-[ethyl(2-methylphenyl)amino]ethyl]-3-pyridinecarboxamide;
2-[[(5-methyl-3-isoxazolyl)methyl]thio]-N-[2-(methylphenylamino)propyl]-3-pyridinecarboxamide;
2-[[(2-methyl-4-thiazolyl)methyl]thio]-N-[2-(4-quinazolinylamino)ethyl]-benzamide;
2-[[(3,5-dimethyl-4-isoxazolyl)methyl]thio]-N-[2-(2-pyrimidinylamino)ethyl]-benzamide;
2-[[(3,5-dimethyl-4-isoxazolyl)methyl]thio]-N-[2-[[2-nitro-4-(trifluoromethyl)phenyl]amino]ethyl]-3-pyridinecarboxamide;
N-[2-(methylphenylamino)propyl]-2-[(4-thiazolylmethyl)thio]-benzamide;
N-[2-[(3,5-dichloro-2-pyridinyl)amino]ethyl]-2-[(4-thiazolylmethyl)thio]-benzamide;
N-[2-[ethyl(3-methylphenyl)amino]ethyl]-2-[[(3-methyl-1,2,4-oxadiazol-5-yl)methyl]thio]-benzamide;
2-[[(5-methyl-1,2,4-oxadiazol-3-yl)methyl]thio]-N-[2-[(4-nitrophenyl)amino]ethyl]-benzamide;
N-[2-[(2-cyano-3-fluorophenyl)amino]ethyl]-2-[[(3-methyl-1,2,4-oxadiazol-5-yl)methyl]thio]-benzamide;
2-[[(3,5-dimethyl-4-isoxazolyl)methyl]thio]-N-[2-[(5-methyl[1,2,4]triazolo[1,5-a]pyrimidin-7-yl)amino]ethyl]-benzamide;
N-[2-(methylphenylamino)propyl]-2-[(2-thienylmethyl)thio]-benzamide;
2-[[(5-methyl-1,2,4-oxadiazol-3-yl)methyl]thio]-N-[2-[(2-nitrophenyl)amino]ethyl]-benzamide;
2-[[(5-methyl-1,2,4-oxadiazol-3-yl)methyl]thio]-N-[2-(methylphenylamino)propyl]-benzamide;
2-[[(3-methyl-5-isoxazolyl)methyl]thio]-N-[2-[(4-nitrophenyl)amino]ethyl]-benzamide;
N-[2-[(2-cyano-3-fluorophenyl)amino]ethyl]-2-[[(3,5-dimethyl-4-isoxazolyl)methyl]thio]—3-pyridinecarboxamide;
2-[[(2-methyl-4-thiazolyl)methyl]thio]-N-[2-[(2-nitrophenyl)amino]ethyl]-benzamide;
N-[2-[(3-cyano-2-pyridinyl)amino]ethyl]-2-[(5-methyl-1,2,4-oxadiazol-3-yl)methoxy]-benzamide;
2-[(3,5-dimethyl-4-isoxazolyl)methoxy]-N-[2-[(4-nitrophenyl)amino]ethyl]-benzamide;
2-[(3,5-dimethyl-4-isoxazolyl)methoxy]-N-[2-[ethyl(2-methylphenyl)amino]ethyl]-benzamide;
2-[(3,5-dimethyl-4-isoxazolyl)methoxy]-N-[2-[ethyl(3-methylphenyl)amino]ethyl]-benzamide;
N-[2-[(3-cyano-2-pyridinyl)amino]ethyl]-2-[(3,5-dimethyl-4-isoxazolyl)methoxy]-benzamide;
N-[2-[[3-chloro-5-(trifluoromethyl)-2-pyridinyl]amino]ethyl]-2-[(3,5-dimethyl-4-isoxazolyl)methoxy]-benzamide;
N-[2-(methylphenylamino)ethyl]-2-(4-thiazolylmethoxy)-benzamide;
N-[2-(methylphenylamino)propyl]-2-(4-thiazolylmethoxy)-benzamide
2-[(5-methyl-1,2,4-oxadiazol-3-yl)methoxy]-N-[2-[(2-nitrophenyl)amino]ethyl] benzamide;
2-[(3,5-dimethyl-4-isoxazolyl)methoxy]-N-[2-(2-pyrimidinylamino)ethyl]-benzamide;
2-[(3,5-dimethyl-4-isoxazolyl)methoxy]-N-[1-methyl-2-(methylphenylamino)ethyl]-benzamide;
2-[(3,5-dimethyl-4-isoxazolyl)methoxy]-N-[2-[(6-methyl-3-pyridazinyl)amino]ethyl]-benzamide; or
2-[(2-methyl-4-thiazolyl)methoxy]-N-[2-[[2-nitro-4-(trifluoromethyl)phenyl]amino]ethyl]-benzamide;
or a salt thereof.

2. The compound of claim 1, wherein the compound of formula I is a compound of formula Ic:

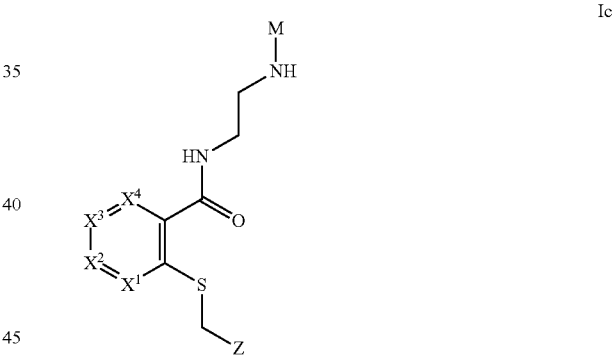

or a salt thereof, wherein.

3. The compound of claim 1, wherein Z is:

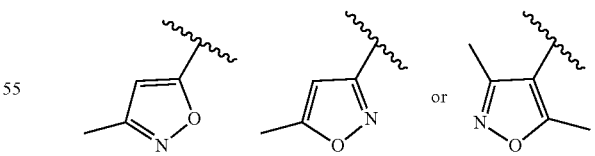

4. The compound of claim 1, wherein M is selected from the group consisting of phenyl, benzothiazolyl, pyridinyl, benzoxazolyl, thiazolyl, benzoimidazolyl, and pyrimidinyl, wherein any phenyl, benzothiazolyl, pyridinyl, benzoxazolyl, thiazolyl, benzoimidazolyl, or pyrimidinyl of M is optionally substituted with one or more halogen, $NO_2$, CN, —OH, $(C_1-C_4)$alkyl, $(C1 C_4)$haloalkyl, —O$(C_1-C_4)$alkyl, or —O$(C_1-C_4)$haloalkyl.

5. The compound of claim 1, wherein M is:
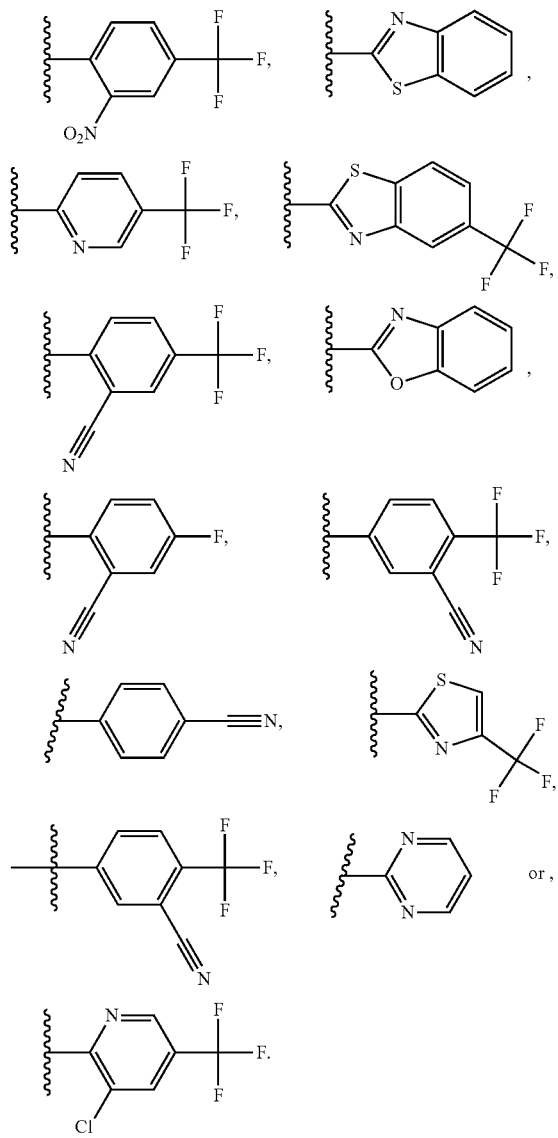
6. The compound of claim 1, wherein the
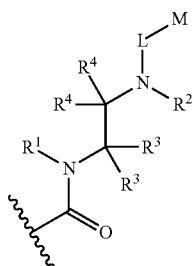
residue of formula I is:
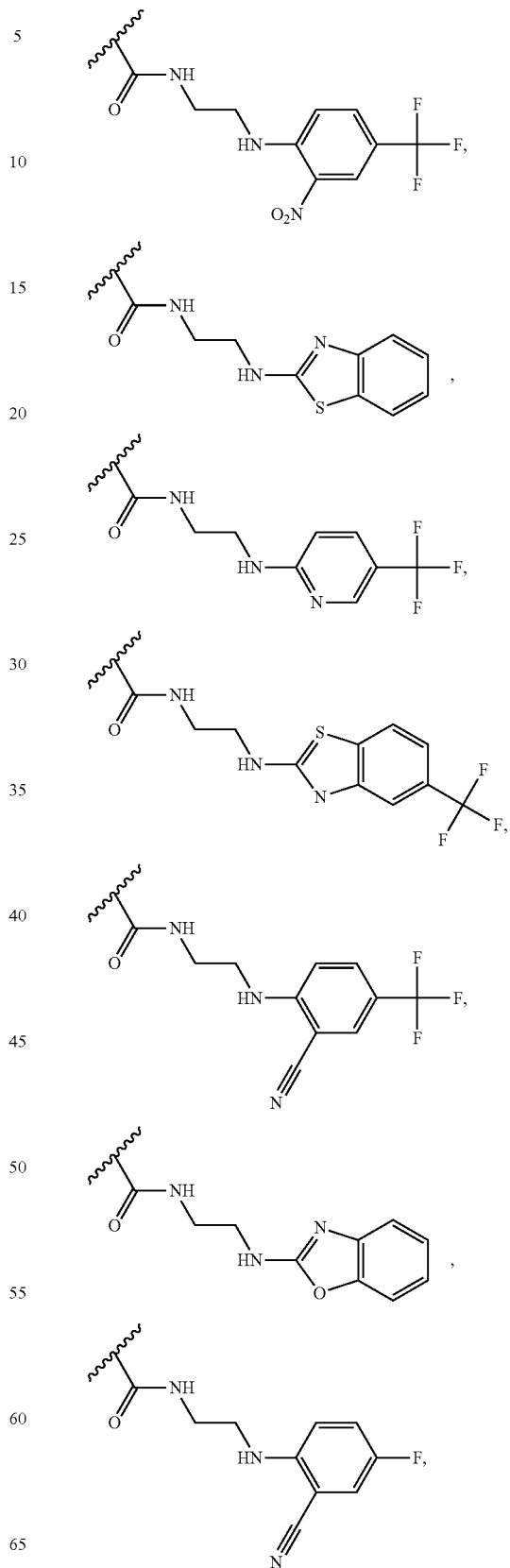

149
-continued
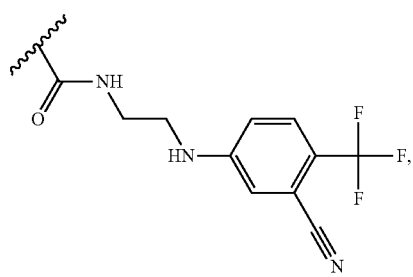
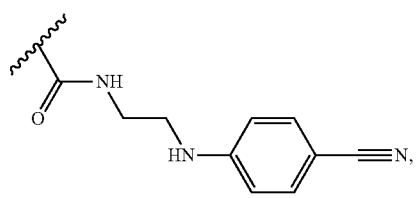
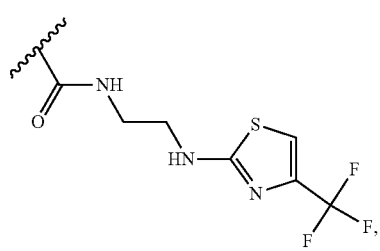
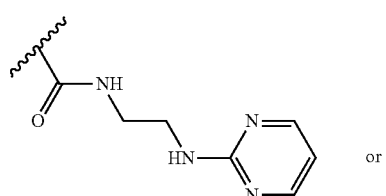
or
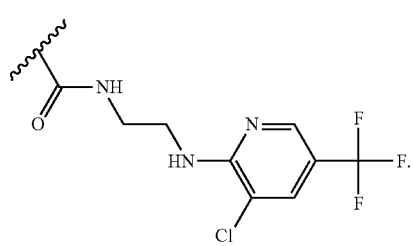
7. A compound that is:
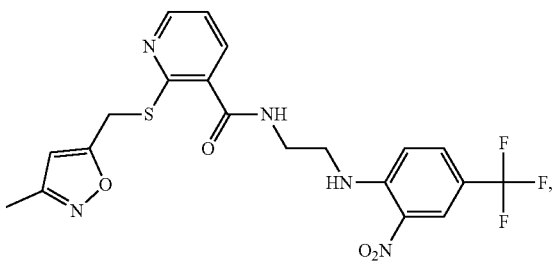
150
-continued
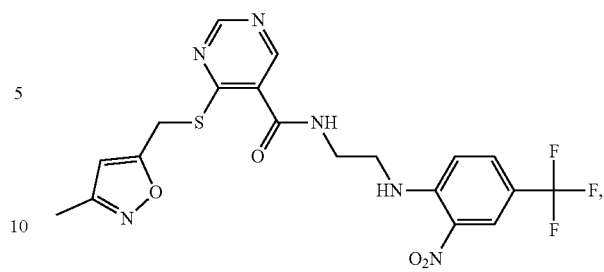
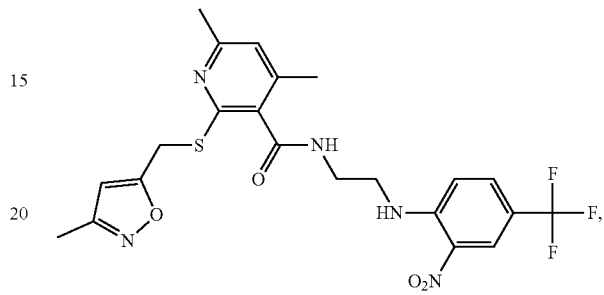
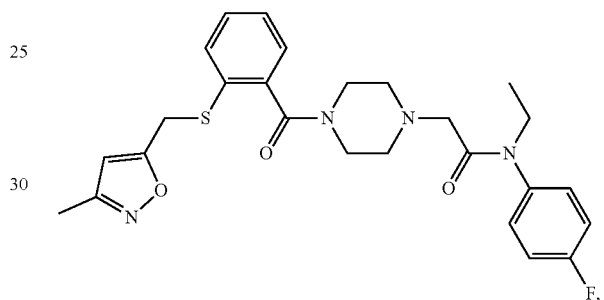
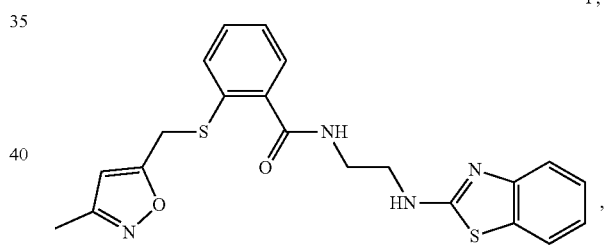
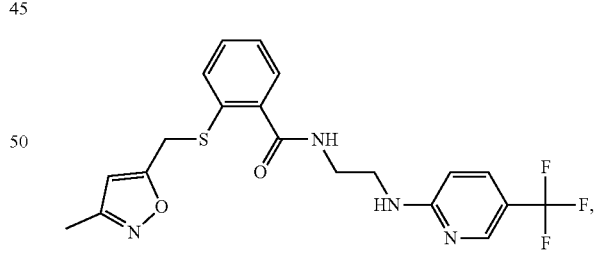
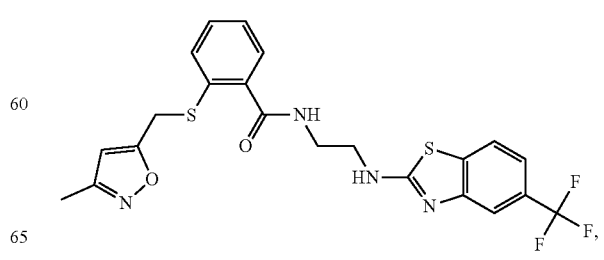

151
-continued
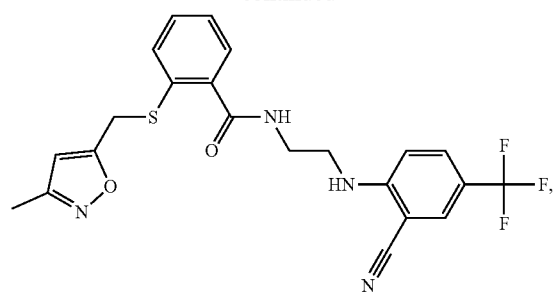
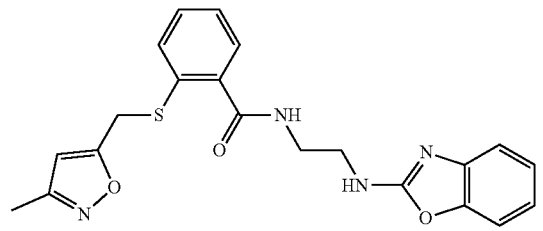
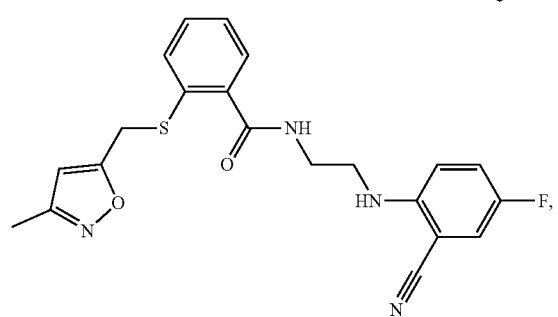
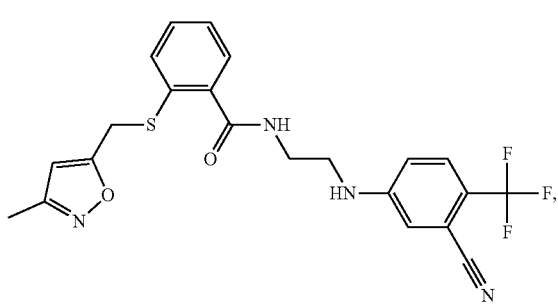
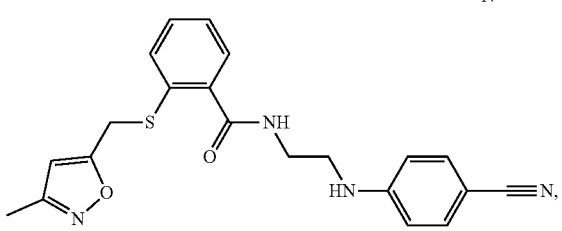
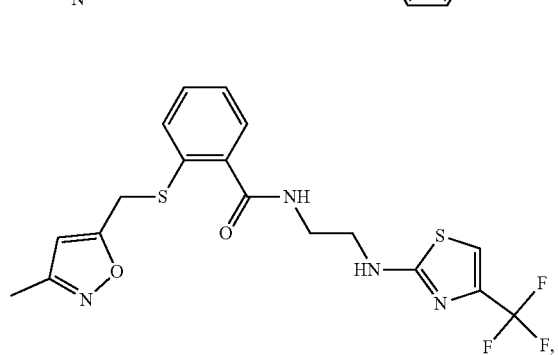
152
-continued
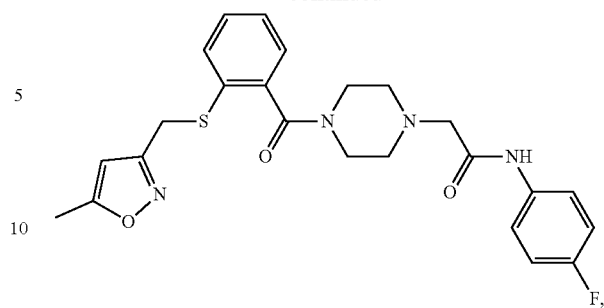
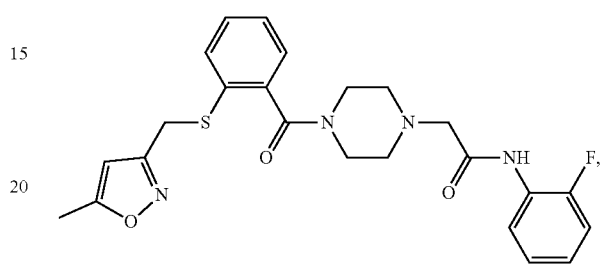
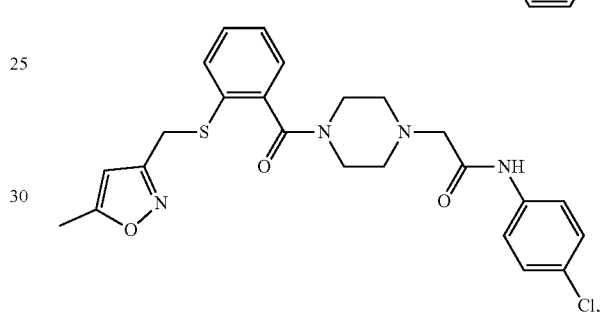
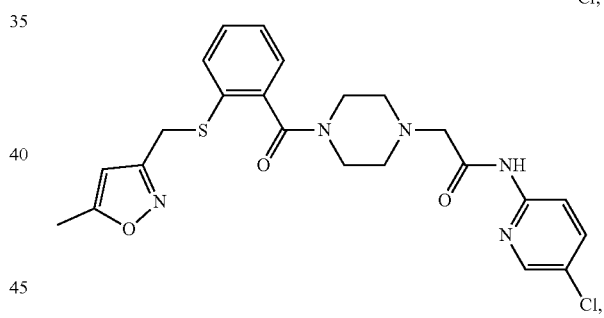
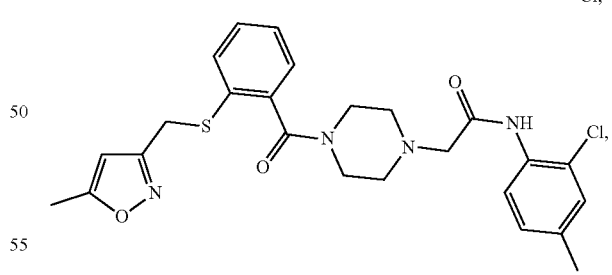
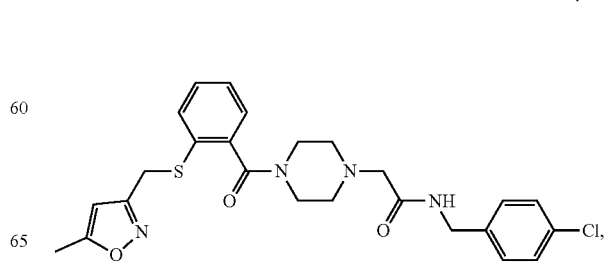

or

or a salt thereof.

8. A method of treating breast cancer or non-small cell lung cancer in a mammal in need thereof, comprising administering to the mammal a therapeutically effective amount of a compound of formula I:

formula I

wherein:
(a) $X^1$ is N or $CR^{a1}$, $X^2$ is N or $CR^{a2}$, $X^3$ is N or $CR^{a3}$, $X^4$ is N or $CR^{a4}$, wherein:
 (i) no more than two of $X^1$, $X^2$, $X^3$, or $X^4$ is N;
 (ii) each $R^{a1}$, $R^{a2}$, $R^{a1}$, and $R^{a4}$ is independently hydrogen, halogen, $(C_1$-$C_4)$alkyl, $(C_1$-$C_4)$haloalkyl, —O$(C_1$-$C_4)$alkyl, or —O$(C_1$-$C_4)$haloalkyl;
(b) Y is S, S(=O), S(=O)$_2$, or O;
(c) Z is a 5 membered heteroaryl or 6-membered heteroaryl wherein any 5 membered heteroaryl or 6-membered heteroaryl of Z is optionally substituted with one or more halogen, NO$_2$, CN, —OH, $(C_1$-$C_4)$alkyl, $(C_1$-$C_4)$haloalkyl, —O$(C_1$-$C_4)$alkyl, or —O$(C_1$-$C_4)$haloalkyl;
(d) $R^1$ is hydrogen or $(C_1$-$C_4)$alkyl and $R^2$ is hydrogen or $(C_1$-$C_4)$alkyl;
(e) each $R^3$ is independently hydrogen or $(C_1$-$C_4)$alkyl;
(f) each $R^4$ is independently hydrogen or $(C_1$-$C_4)$alkyl;
(g) L is absent
and
(h) M is an aryl, a 5-10-membered heteroaryl, or a 5-10-membered heterocycle wherein any aryl, 5-10-membered heteroaryl, or 5-10-membered heterocycle of M is optionally substituted with one or more halogen, NO$_2$, CN, —OH, $(C_1$-$C_4)$alkyl, $(C_1$-$C_4)$haloalkyl, —O$(C_1$-$C_4)$alkyl, or —O$(C_1$-$C_4)$haloalkyl;

or a pharmaceutically acceptable salt thereof.

9. The method according to claim 8, wherein the compound of formula I is a compound of formula Ic:

formula Ic

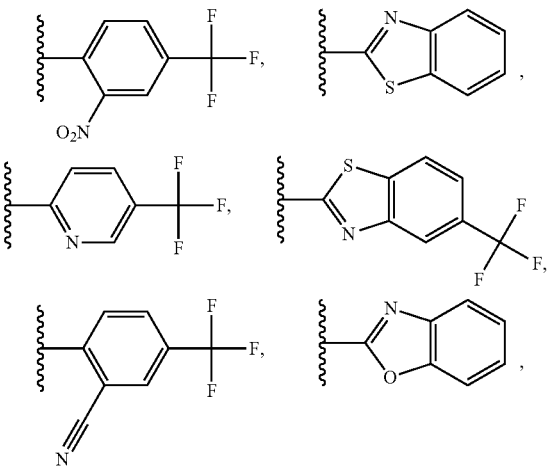

or a salt thereof.

10. The method according to claim 8, wherein Z is:

11. The method according to claim 8, wherein M is selected from the group consisting of phenyl, benzothiazolyl, pyridinyl, benzoxazolyl, thiazolyl, benzoimidazolyl, and pyrimidinyl, wherein any phenyl, benzothiazolyl, pyridinyl, benzoxazolyl, thiazolyl, benzoimidazolyl, or pyrimidinyl of M is optionally substituted with one or more halogen, NO$_2$, CN, —OH, $(C_1$-$C_4)$alkyl, $(C_1$-$C_4)$haloalkyl, —O$(C_1$-$C_4)$alkyl, or —O$(C_1$-$C_4)$haloalkyl.

12. The method according to claim 8, wherein M is:

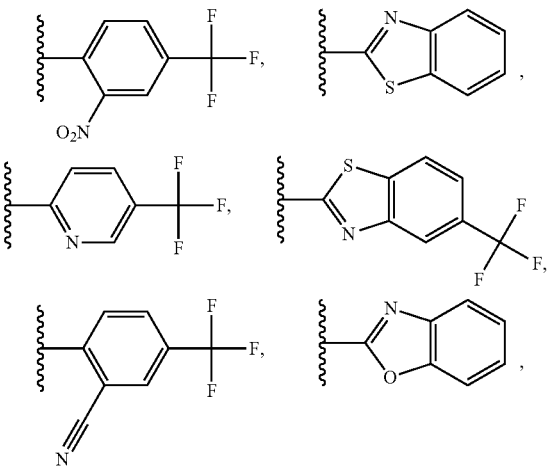

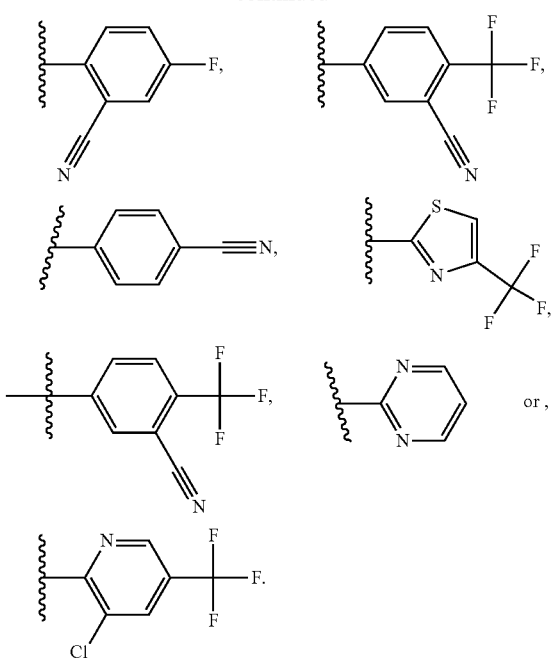
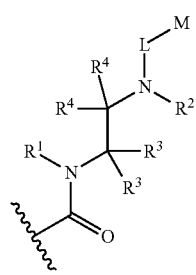
or,
13. The method according to claim 8, wherein the
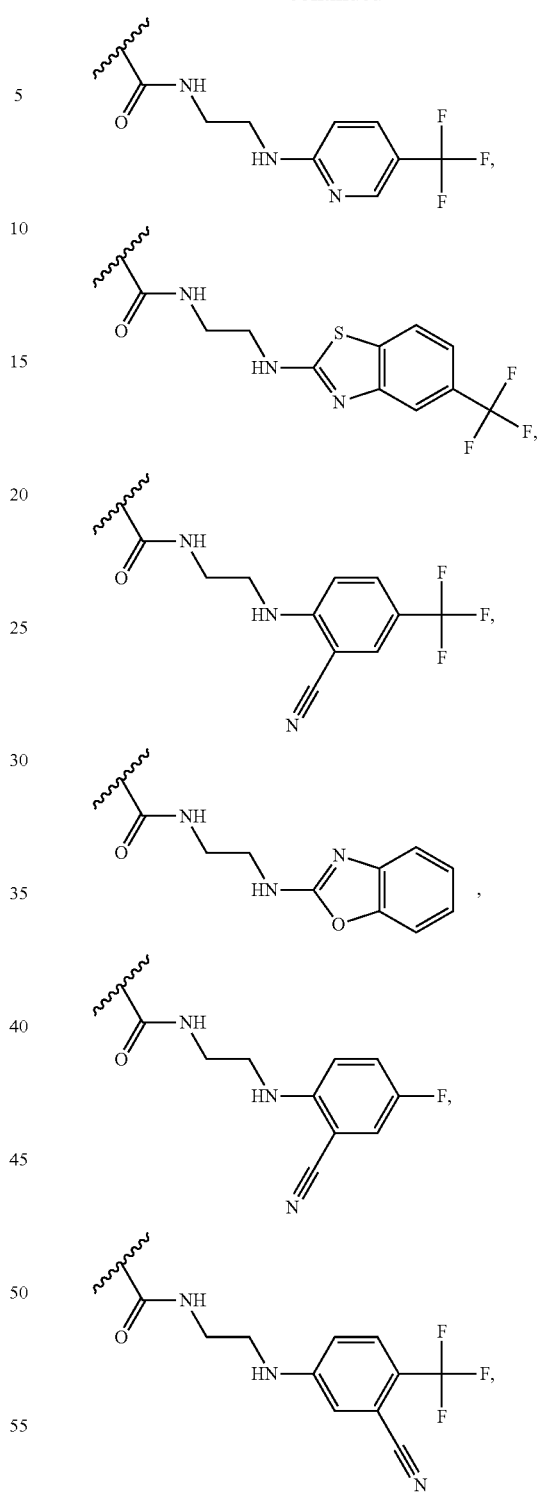
residue of formula I is:
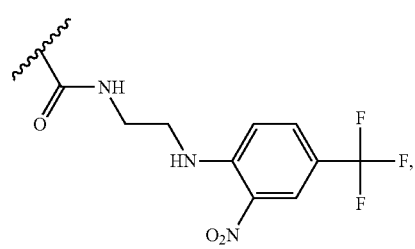
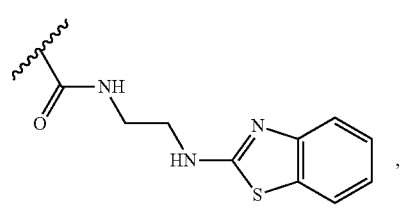
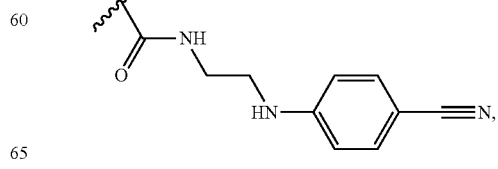

-continued
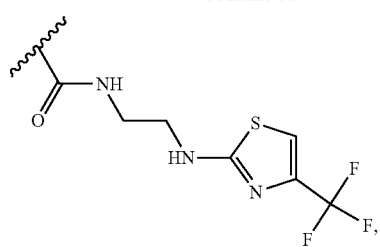
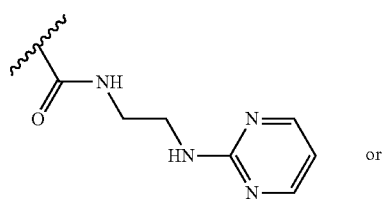
or
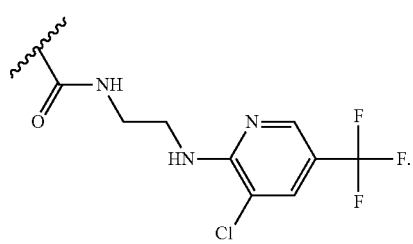
14. The method of claim 8, wherein the compound of formula I is:
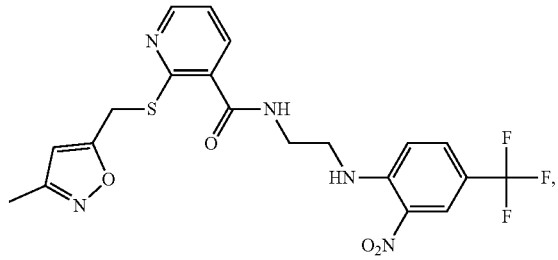
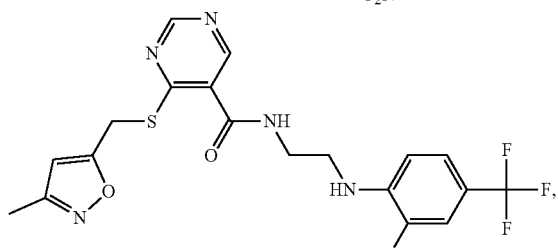
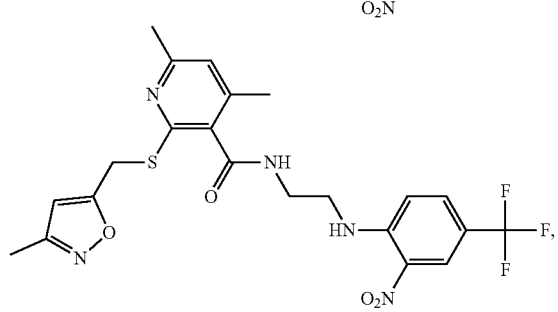
-continued
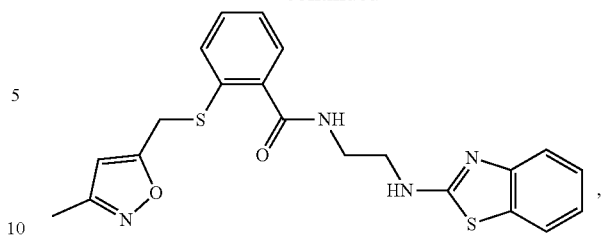
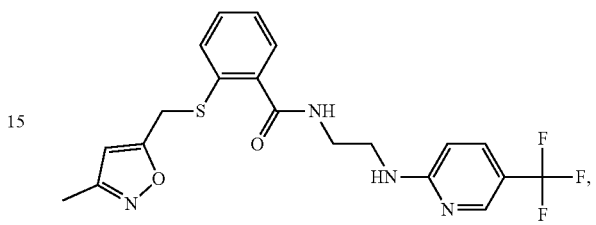
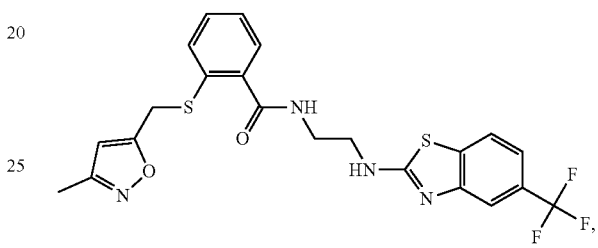
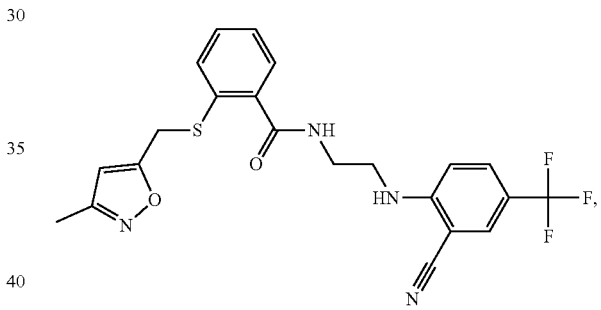
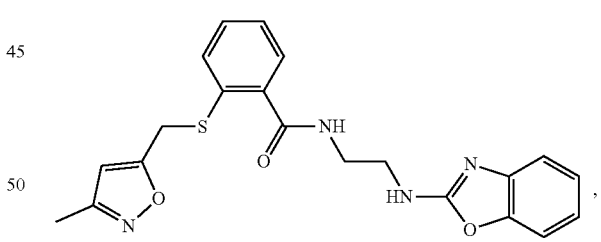
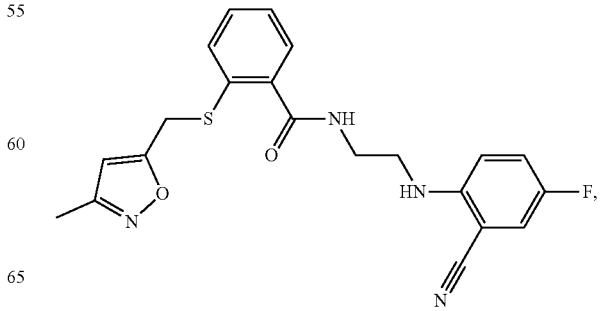

-continued

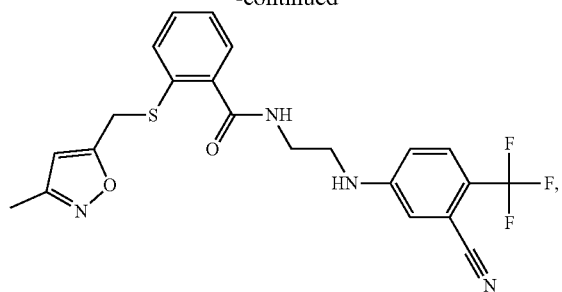

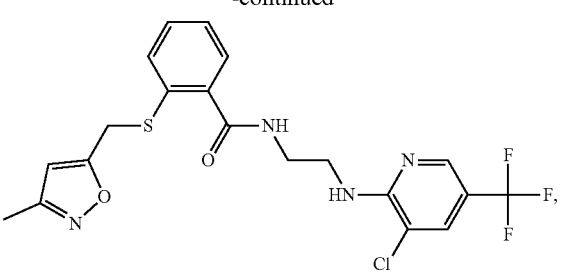

or a salt thereof.

15. A pharmaceutical composition comprising a compound as described in claim 1 or a pharmaceutically acceptable salt thereof.

16. A pharmaceutical composition comprising a compound as described in claim 7 or a pharmaceutically acceptable salt thereof and a pharmaceutically acceptable carrier, excipient, or adjuvant.

17. A method of treating breast cancer or non-small cell lung cancer in a mammal in need thereof, comprising administering to the mammal a therapeutically effective amount of a compound as described in claim 1 or a pharmaceutically acceptable salt thereof.

18. A method of treating breast cancer or non-small cell lung cancer in a mammal in need thereof, comprising administering to the mammal a therapeutically effective amount of a compound as described in claim 7 or a pharmaceutically acceptable salt thereof.

* * * * *

UNITED STATES PATENT AND TRADEMARK OFFICE
CERTIFICATE OF CORRECTION

PATENT NO. : 10,851,096 B2
APPLICATION NO. : 16/311136
DATED : December 1, 2020
INVENTOR(S) : Welsh et al.

Page 1 of 1

It is certified that error appears in the above-identified patent and that said Letters Patent is hereby corrected as shown below:

In the Claims

Column 146, Line 48, Claim 2, please delete "or a salt thereof, wherein" and insert -- or a salt thereof. --

Column 146, Line 66, Claim 4, please delete ", (C1 C$_4$)haloalkyl," and insert -- , (C$_1$-C$_4$)haloalkyl, --

Column 160, Lines 23, Claim 15, please delete "salt thereof." and insert -- salt thereof and a pharmaceutically acceptable carrier, excipient, or adjuvant. -- therefor Signed and Sealed this
Twenty-eighth Day of June, 2022

Katherine Kelly Vidal
*Director of the United States Patent and Trademark Office*